US011286257B2

(12) United States Patent
Ambrosi et al.

(10) Patent No.: US 11,286,257 B2
(45) Date of Patent: Mar. 29, 2022

(54) PROCESSES FOR PREPARING TOLL-LIKE RECEPTOR MODULATOR COMPOUNDS

(71) Applicant: Gilead Sciences, Inc., Foster City, CA (US)

(72) Inventors: Andrea Ambrosi, Oakland, CA (US); Florence J. Bachrach, Foster City, CA (US); Pavel R. Badalov, Edmonton (CA); Stephen P. Lathrop, Lake Bluff, IL (US); Jeffrey E. Merit, Foster City, CA (US); Beau P. Pritchett, San Francisco, CA (US); Christopher S. Regens, San Francisco, CA (US); Tiago Vieira, Edmonton (CA); Adam B. Weinstein, Belmont, CA (US); Todd A. Wenderski, Hayward, CA (US); Zehua Zheng, Burnaby (CA)

(73) Assignee: Gilead Sciences, Inc., Foster City, CA (US)

( * ) Notice: Subject to any disclaimer, the term of this patent is extended or adjusted under 35 U.S.C. 154(b) by 21 days.

(21) Appl. No.: 16/911,643

(22) Filed: Jun. 25, 2020

(65) Prior Publication Data

US 2021/0017170 A1    Jan. 21, 2021

Related U.S. Application Data

(60) Provisional application No. 62/868,662, filed on Jun. 28, 2019.

(51) Int. Cl.
*C07D 471/04* (2006.01)
*C07D 213/81* (2006.01)
*C07D 413/04* (2006.01)

(52) U.S. Cl.
CPC ......... *C07D 471/04* (2013.01); *C07D 213/81* (2013.01); *C07D 413/04* (2013.01)

(58) Field of Classification Search
None
See application file for complete search history.

(56) References Cited

U.S. PATENT DOCUMENTS

| | | | |
|---|---|---|---|
| 2,512,572 A | 6/1950 | Smith, Jr. et al. |
| 2,581,889 A | 1/1952 | Timmis |
| 2,665,275 A | 1/1954 | Campbell et al. |
| 2,667,486 A | 1/1954 | Cain |
| 2,740,784 A | 4/1956 | Sletzinger et al. |
| 2,939,882 A | 6/1960 | Mecorney |
| 2,940,972 A | 6/1960 | Roch |
| 3,071,587 A | 1/1963 | Curran et al. |
| 3,081,230 A | 3/1963 | Weinstock et al. |
| 3,122,546 A | 2/1964 | Osdene |
| 3,159,628 A | 12/1964 | Pechter et al. |
| 3,162,635 A | 12/1964 | Schroeder |
| 3,475,425 A | 10/1969 | Roch |
| 3,843,791 A | 10/1974 | McFarland |
| 3,859,287 A | 1/1975 | Parish et al. |
| 4,438,128 A | 3/1984 | Wiedemann |
| 4,608,383 A | 8/1986 | Wiedemann |
| 5,047,405 A | 9/1991 | Gennari |
| 5,064,833 A | 11/1991 | Ife et al. |
| 5,281,603 A | 1/1994 | Venkatesan et al. |
| 5,300,509 A | 4/1994 | Block et al. |
| 5,354,776 A | 10/1994 | Chandraratna |
| 5,380,724 A | 1/1995 | Zubovics et al. |
| 5,500,428 A | 3/1996 | Block et al. |
| 5,534,518 A | 7/1996 | Henrie |
| 5,641,783 A | 6/1997 | Klein et al. |
| 5,665,772 A | 9/1997 | Cottens et al. |
| 5,707,998 A | 1/1998 | Takase et al. |
| 5,780,462 A | 7/1998 | Lee et al. |
| 5,843,943 A | 12/1998 | Carson et al. |
| 5,866,572 A | 2/1999 | Barker et al. |
| 5,929,046 A | 7/1999 | McMurry et al. |
| 5,955,464 A | 9/1999 | Barker et al. |
| 5,992,713 A | 11/1999 | Manabat |
| 6,043,228 A | 3/2000 | McMurray et al. |
| 6,203,723 B1 | 3/2001 | Hsu |
| 6,331,547 B1 | 12/2001 | Zhu et al. |
| 6,440,991 B1 | 8/2002 | Zhu et al. |
| 6,559,149 B1 | 5/2003 | Matsuoka et al. |
| 6,844,343 B1 | 1/2005 | Ptleiderer et al. |
| 6,946,465 B2 | 9/2005 | Waer et al. |
| 7,074,801 B1 | 7/2006 | Yoshida et al. |
| 7,276,506 B2 | 10/2007 | Waer et al. |
| 7,501,513 B2 | 3/2009 | Waer et al. |
| 7,928,111 B2 | 4/2011 | Tachdjian et al. |

(Continued)

FOREIGN PATENT DOCUMENTS

| | | |
|---|---|---|
| CH | 231852 | 7/1944 |
| CN | 1583747 | 2/2005 |

(Continued)

OTHER PUBLICATIONS

Kumar et al., "Synthesis and Molecular Docking Studies of Novel 2-(2-Amino-6-Phenyl-4-Pyrimidinylamino) Ethanol Derivatives: Using Ring-Opening Reactions of Cyclic Ketene-N,O-Acetal", Oriental Journal of Chemistry, vol. 33., No. 3, Jun. 28, 2017, pp. 1555-1562.
Huang et al., "Facilitating the Transmetalation Step with Aryl-Zincates in Nickel-Catalyzed Enantioselective Arylation of Secondary Benzylic Halides", ChemRxiv (2019) 1-22, 2019, Feb. 27, 2019, pp. 1-24.
European Patent Office, International Search Report and Written Opinion for PCT/US2020/039501 dated Nov. 18, 2020, 17 pages.
Kujime et al., Regioselective Preparation of Pterin 6-Triflate and Its Application to 6-Substituted Pterin Synthesis, Heterocycles, 2007, pp. 1841-1850, vol. 57.
Ypakob et al., Tavtomepnr, 1994, pp. 37-41.

(Continued)

*Primary Examiner* — Heidi Reese
(74) *Attorney, Agent, or Firm* — Mintz, Levin, Cohn, Ferris, Glovsky and Popeo, P.C.

(57) ABSTRACT

The present disclosure provides methods for preparing (R)-2-((2-amino-7-fluoropyrido[3,2-d]pyrimidin-4-yl)amino)-2-methylhexan-1-ol or a salt thereof and related key intermediates.

30 Claims, 10 Drawing Sheets

(56) References Cited

U.S. PATENT DOCUMENTS

| | | |
|---|---|---|
| 8,143,394 B2 | 3/2012 | Watkins et al. |
| 8,232,278 B2 | 7/2012 | De Jonghe et al. |
| 8,338,435 B2 | 12/2012 | Herdewijn et al. |
| 8,367,670 B2 | 2/2013 | Desai et al. |
| 8,536,187 B2 | 9/2013 | Canales et al. |
| 8,541,421 B2 | 9/2013 | Tachdjian et al. |
| 8,633,186 B2 | 1/2014 | Tachdjian et al. |
| 8,637,531 B2 | 1/2014 | Bondy et al. |
| 8,673,929 B2 | 3/2014 | Gao et al. |
| 8,729,089 B2 | 5/2014 | Bondy et al. |
| 8,901,133 B2 | 12/2014 | Ren et al. |
| 8,916,575 B2 | 12/2014 | McGowan et al. |
| 8,969,363 B2 | 3/2015 | Castro et al. |
| 9,181,276 B2 | 11/2015 | Tachdjian et al. |
| 9,259,426 B2 | 2/2016 | Gao et al. |
| 9,603,848 B2 | 3/2017 | Servant et al. |
| 9,670,205 B2 | 6/2017 | Aktoudianakis et al. |
| 10,144,736 B2 | 12/2018 | Herdewijn et al. |
| 10,285,990 B2 | 5/2019 | Aktoudianakis et al. |
| 10,370,342 B2 | 8/2019 | Chin et al. |
| 10,640,499 B2 | 5/2020 | Chin et al. |
| 10,882,851 B2 | 1/2021 | Gao et al. |
| 11,124,487 B2 | 9/2021 | Chin et al. |
| 2003/0236255 A1 | 12/2003 | Waer et al. |
| 2004/0030156 A1 | 2/2004 | Maul |
| 2004/0038856 A1 | 2/2004 | Chakravarty et al. |
| 2004/0102447 A1 | 5/2004 | Bonnert et al. |
| 2004/0167121 A1 | 8/2004 | Aronov et al. |
| 2004/0167198 A1 | 8/2004 | Wrasidlo et al. |
| 2005/0054626 A1 | 3/2005 | Carter et al. |
| 2005/0054653 A1 | 3/2005 | Eisenbrand et al. |
| 2005/0191238 A1 | 9/2005 | Casebier et al. |
| 2005/0282814 A1 | 12/2005 | Wrasidlo et al. |
| 2006/0116371 A1 | 6/2006 | Martyres et al. |
| 2007/0004721 A1 | 1/2007 | Waer et al. |
| 2007/0043000 A1 | 2/2007 | Waer et al. |
| 2007/0054916 A1 | 3/2007 | Patel et al. |
| 2007/0287704 A1 | 12/2007 | Dollinger et al. |
| 2008/0004285 A1 | 1/2008 | De Jonghe et al. |
| 2008/0027062 A1 | 1/2008 | Doblhofer et al. |
| 2008/0096883 A1 | 4/2008 | Caravatti et al. |
| 2008/0112884 A1 | 5/2008 | Casebier et al. |
| 2008/0182870 A1 | 7/2008 | Bondy et al. |
| 2008/0234251 A1 | 9/2008 | Doherty et al. |
| 2008/0306053 A1 | 12/2008 | Tachdjian et al. |
| 2008/0306093 A1 | 12/2008 | Servant et al. |
| 2008/0312227 A1 | 12/2008 | De Jong he et al. |
| 2009/0036430 A1 | 2/2009 | De Jonghe et al. |
| 2009/0131414 A1 | 5/2009 | De Jonghe et al. |
| 2009/0253696 A1 | 10/2009 | Herdewijn et al. |
| 2009/0318456 A1 | 12/2009 | Herdewijn et al. |
| 2010/0029585 A1 | 2/2010 | Howbert et al. |
| 2010/0143299 A1 | 6/2010 | Gao et al. |
| 2010/0143301 A1 | 6/2010 | Desai et al. |
| 2010/0305117 A1 | 12/2010 | HerdewiLn et al. |
| 2011/0098248 A1 | 4/2011 | Halcomb et al. |
| 2011/0224155 A1 | 9/2011 | Zoller |
| 2011/0230502 A1 | 9/2011 | Tachdjian et al. |
| 2012/0122838 A1 | 5/2012 | Ren et al. |
| 2012/0238587 A1 | 9/2012 | Lee et al. |
| 2013/0029982 A1 | 1/2013 | Castro et al. |
| 2013/0109693 A1 | 5/2013 | Routier et al. |
| 2014/0235623 A1 | 8/2014 | Tachdjian et al. |
| 2016/0289229 A1 | 10/2016 | Aktoudianakis et al. |
| 2017/0071944 A1 | 3/2017 | Geleziunas et al. |
| 2019/0152974 A1 | 5/2019 | Herdewijn et al. |
| 2020/0017451 A1 | 1/2020 | Chin et al. |
| 2020/0345738 A1 | 11/2020 | Asselin et al. |
| 2020/0347051 A1 | 11/2020 | Asselin et al. |
| 2021/0017170 A1 | 1/2021 | Aktoudianakis et al. |
| 2021/0276988 A1 | 9/2021 | Gao et al. |

FOREIGN PATENT DOCUMENTS

| | | |
|---|---|---|
| DE | 19 21 308 | 1/1971 |
| DE | 267 495 | 5/1989 |
| DE | 40 09 941 | 10/1991 |
| EP | 0042593 A1 | 12/1981 |
| EP | 0 108 890 | 5/1984 |
| EP | 0 134 922 | 3/1985 |
| EP | 0 185 259 | 6/1986 |
| EP | 0 290 819 | 11/1988 |
| EP | 0322133 A1 | 6/1989 |
| EP | 0 362 645 | 4/1990 |
| EP | 0404322 A1 | 12/1990 |
| EP | 0404355 A1 | 12/1990 |
| EP | 0 544 445 | 6/1993 |
| EP | 0 574 906 | 12/1993 |
| EP | 0837063 A1 | 4/1998 |
| EP | 0 956 855 | 11/1999 |
| EP | 1 144 412 | 10/2001 |
| EP | 1382603 A1 | 1/2004 |
| EP | 1 479 682 | 11/2004 |
| EP | 1724268 A1 | 11/2006 |
| EP | 3097102 B1 | 10/2017 |
| EP | 2709989 B1 | 12/2017 |
| EP | 3321265 A1 | 5/2018 |
| GB | 677342 | 8/1952 |
| GB | 763044 | 12/1956 |
| GB | 785353 | 10/1957 |
| GB | 1301319 A | 12/1972 |
| GB | 2 143 232 | 2/1985 |
| GB | 2 405 793 | 3/2005 |
| JP | H07138238 A | 5/1995 |
| JP | 2000038350 A | 2/2000 |
| JP | 2000053653 A | 2/2000 |
| JP | 2000053654 A | 2/2000 |
| WO | WO-1993007124 A1 | 4/1993 |
| WO | WO-199325712 | 12/1993 |
| WO | WO-199406431 | 3/1994 |
| WO | WO-199411001 | 5/1994 |
| WO | WO-199414065 | 6/1994 |
| WO | WO-199422449 | 10/1994 |
| WO | WO-1994022855 A1 | 10/1994 |
| WO | WO-1994027439 A1 | 12/1994 |
| WO | WO-199513075 | 5/1995 |
| WO | WO-199531469 | 11/1995 |
| WO | WO-199531987 | 11/1995 |
| WO | WO-199532203 | 11/1995 |
| WO | WO-199610568 | 4/1996 |
| WO | WO-1996016960 A1 | 6/1996 |
| WO | WO-1996020710 | 7/1996 |
| WO | WO-1997023616 | 7/1997 |
| WO | WO-1997030034 A1 | 8/1997 |
| WO | WO-1997031920 | 9/1997 |
| WO | WO-1997039358 | 10/1997 |
| WO | WO-1998004558 | 2/1998 |
| WO | WO-1998008516 | 3/1998 |
| WO | WO-1998052948 | 11/1998 |
| WO | WO-1999050264 A1 | 10/1999 |
| WO | WO-2000039129 A1 | 7/2000 |
| WO | WO-2000045800 | 8/2000 |
| WO | WO-2001019825 | 3/2001 |
| WO | WO-2001021619 A1 | 3/2001 |
| WO | WO-2002032507 | 4/2002 |
| WO | WO-2003001887 A2 | 1/2003 |
| WO | WO-2003031406 A2 | 4/2003 |
| WO | WO-2003062240 | 7/2003 |
| WO | WO-2004026307 A1 | 4/2004 |
| WO | WO-2004065392 A1 | 8/2004 |
| WO | WO-2004072033 A2 | 8/2004 |
| WO | WO-2004104005 | 12/2004 |
| WO | WO-2005020899 A2 | 3/2005 |
| WO | WO-2005021003 A1 | 3/2005 |
| WO | WO-2005025574 | 3/2005 |
| WO | WO-2005028444 A1 | 3/2005 |
| WO | WO-2005039587 | 5/2005 |
| WO | WO-2005046698 | 5/2005 |
| WO | WO-2005063752 | 7/2005 |
| WO | WO-2005073204 | 8/2005 |
| WO | WO-2005079391 A2 | 9/2005 |

(56) References Cited

FOREIGN PATENT DOCUMENTS

| | | |
|---|---|---|
| WO | WO-2005080377 A1 | 9/2005 |
| WO | WO-2005105761 A1 | 11/2005 |
| WO | WO-2006015859 A1 | 2/2006 |
| WO | WO-2006039718 A2 | 4/2006 |
| WO | WO-2006050843 A1 | 5/2006 |
| WO | WO-2006058867 A2 | 6/2006 |
| WO | WO-2006058869 A2 | 6/2006 |
| WO | WO-2006069805 A2 | 7/2006 |
| WO | WO-2006120251 | 11/2006 |
| WO | WO-2006135993 A1 | 12/2006 |
| WO | WO-2007093901 A1 | 8/2007 |
| WO | WO-2007135026 | 11/2007 |
| WO | WO-2007135027 | 11/2007 |
| WO | WO-2008003149 A1 | 1/2008 |
| WO | WO-2008009076 A1 | 1/2008 |
| WO | WO-2008009077 A2 | 1/2008 |
| WO | WO-2008009078 A2 | 1/2008 |
| WO | WO-2008009079 A2 | 1/2008 |
| WO | WO-2008009706 A1 | 1/2008 |
| WO | WO-2008024977 A2 | 2/2008 |
| WO | WO-2008030455 A2 | 3/2008 |
| WO | WO-2008077649 A1 | 7/2008 |
| WO | WO-2008077651 A1 | 7/2008 |
| WO | WO-2008154221 A2 | 12/2008 |
| WO | WO-2009003669 A2 | 1/2009 |
| WO | WO-2010002877 A2 | 1/2010 |
| WO | WO-2010002998 A1 | 1/2010 |
| WO | WO-2010042489 A2 | 4/2010 |
| WO | WO-2010046639 A1 | 4/2010 |
| WO | WO-2010092340 A1 | 8/2010 |
| WO | WO-2011057148 A1 | 5/2011 |
| WO | WO-2011072275 A1 | 6/2011 |
| WO | WO-2011097607 A1 | 8/2011 |
| WO | WO-2011135259 A1 | 11/2011 |
| WO | WO-2012058601 A | 5/2012 |
| WO | WO-2012136834 A1 | 10/2012 |
| WO | WO-2012156498 A1 | 11/2012 |
| WO | WO-2013060881 A | 5/2013 |
| WO | WO-2013090840 A1 | 6/2013 |
| WO | WO-2013117615 A1 | 8/2013 |
| WO | WO-2013174947 A1 | 11/2013 |
| WO | WO-2014116755 A1 | 1/2014 |
| WO | WO-2014023813 A1 | 2/2014 |
| WO | WO-2014056953 A1 | 4/2014 |
| WO | WO-2014076221 A1 | 5/2014 |
| WO | WO-2014078778 A2 | 5/2014 |
| WO | WO-2014120995 A2 | 7/2014 |
| WO | WO-2014128189 A1 | 8/2014 |
| WO | WO-2015014815 A1 | 2/2015 |
| WO | WO-2015168269 A1 | 11/2015 |
| WO | WO-2015191752 A1 | 12/2015 |
| WO | WO-2016141092 A1 | 9/2016 |
| WO | WO-2017048727 A1 | 3/2017 |
| WO | WO-2018002319 A1 | 1/2018 |
| WO | WO-2018045144 A1 | 3/2018 |
| WO | WO-2018045150 A1 | 3/2018 |
| WO | WO-2020214652 A1 | 10/2020 |
| WO | WO-2020214663 A1 | 10/2020 |

OTHER PUBLICATIONS

Dominican Patent Office, Office Action for DO Application No. P2017-0203, dated Oct. 8, 2020, with English translation, 4 pages.
European Patent Office, International Search Report and Written Opinion for International Application No. PCT/US2016/020499, dated Jul. 25, 2019, 18 pages.
European Patent Office, International Search Report and Written Opinion for PCT/US2020/028237, dated Jun. 30, 2020, 8 pages.
European Patent Office, International Search Report and Written Opinion for PCT/US2020/028257, dated Jun. 26, 2020, 8 pages.
Gulf Cooperation Council Patent Office, Examination Report for GC Application No. GC 2016-30932, dated Jul. 6, 2020, 4 pages.
Israel Patent Office, Office Action for IL Application No. 254164, dated Sep. 21, 2020, 2 pages.
Mexico Patent Office, Notice of Allowance for MX Application No. MX/a/2017011307, dated Oct. 14, 2020, 2 pages.
Ukraine Patent Office, Notice of Allowance for UA Application No. a210708923, dated Nov. 5, 2020, 17 pages.
Schlaepfer et al., "TLR8 Activates HIV from Latently Infected Cells of Myeloid-monocytic Origin Directly via the MAPK Pathway and from Latently Infected CD4+ T Cells Indirectly via TNF-α", Journal of Immunology, 2011, 186(7):4314-4324.
Wikipedia, entries for Anthistamine, Autoimmunity, List of Autoimmune Diseases, Lupus Erythematosus, and Sjogren's Syndrome, retrieved Dec. 28, 2006 from http://en.wikipedia.org, 23 pages.
Abou-Hedeed et al., Pteridines CVIII Reactions of 6, 7-Dichloro-1, 3-Dimethyllumazine with Sulfur-Nucleophiles, Pteridines, 1996, pp. 113-122, vol. 7.
Armarego et al., Quinazolines. Part IX. Covalent hydration in the neutral species of substituted quinazolines, J. Chem. Soc. B: Phys. Org., 1967, pp. 449-454.
Baba et al., Synergistic Antiviral Effects of Antiherpes Compounds and Human Leukocyte Interferon on Varicella-Zoster Virus in Vitro, Antimicrob. Agents Chemother., 1984, pp. 515-517, vol. 25.
Banker et al. (eds.), Modern Pharmaceutics: Third Edition, Revised and Expanded, Marcel Dekker, Inc., 1996, pp. 451 and 596.
Barl et al., The Halogen/Magnesium-Exhange using iPrMgCl•LiCl and related exchange reagents, Hetercycles, 2014, pp. 827-844.
Beers et al. (eds), The Merck Manual of Diagnosis and Therapy, Merck Research Laboratories: Whitehouse Station, N.J., Leukemias, 1999, pp. 953-954, Chapter 138.
Beers et al. (eds), The Merck Manual of Diagnosis and Therapy, Merck Research Laboratories: Whitehouse Station, N.J., Neurologic Disorders, 1999, pp. 1474-1476, Sec. 14.
Bennett et al., Cecil Textbook of Medicine, 20th Ed., 1996, pp. 1004-1010, vol. 1.
Bennett et al., Cecil Textbook of Medicine, 20th Ed., 1996, pp. 1992-1996, vol. 2.
Bennett et al., Cecil Textbook of Medicine, 20th Ed., 1996, pp. 2050-2057, vol. 2.
Bigorgne et al., TLRs in Hepatic Cellular Crosstalk, Gastroenterology Research and Practice, 2010, pp. 1-7, Article ID 618260.
Black et al., Agents that Block TNF-a Synthesis or Activity, 1997, Ann. Rep. Med. Chem., pp. 241-250, vol. 32.
Boon, Pteridines. Part IV., Derivatives of 2:4-Diaminopteridine and Related Compounds, J. Chem. Soc., 1957, pp. 21462158.
Brown et al., Pteridine Studies. Part XIV. Methylation of 2-Amino-4-hydroxypteridine and Related Compounds, J. Chem. Soc., 1961, pp. 869:4413-869:4420.
Buitendijk et al., Toll-like Receptor Agonists are Potent Inhibitors of Human Immunodeficiency Virus-Type 1 Replication in Peripheral Blood Mononuclear Cells, AIDS Research and Human Retroviruses, May 1, 2014, pp. 457-467, vol. 30, No. 5.
Bundgaard (ed.). Design of Prodrugs, 1985, p. 1.
Buu-Hoi et al., Phthalonimides (1,3,4-Trioxo-1,2,3,4-Tetrahydroisoquinolines) of Potential Biological Interest, J. Heretocyclic Chem., 1968, pp. 545-546, vol. 5.
Cairo, Immunology Lecture #20: Transplantation, Columbia University [online] 2003, Retrieved Jul. 12, 2005 from http://healthsciences.columbia.edu/dept/ps/2007/immuno/2006/IM20.pdf (6 pages).
Cervantes et al., TLR8: the forgotten relatuve revindicated, Cellular & Molecular Immunology, 2012, pp. 434-438, vol. 9.
Chantry, Tumour Necrosis Factor Antagonists, Exp. Op. Emerging Drugs, 1999, pp. 5-13, Ch. 1.
Chapman et al., Synthethic Antimalarials. Part XVI. 4-Dialkylaminoalkylaminoquinazolines. Variation of Substituents in the 6- and 7-Positions, Journal of the Chemical Society, 1947, pp. 890-899.
Cho, Synthesis and antiviral activity of a series of 1'-substituted 4-aza-7,9-dideazaadenosince C-nucleosides, Bioorganic & Medicinal Chemistry Letters, 2012, pp. 2705-2707.
Chou et al., Quantitative Analysis of Dose-Effect Relationships: The Combined Effects of Multiple Drugs or Enzyme Inhibitors, Adv. Enzyme ReguL, 1984, pp. 27-55.
Cohen, The Development and Therapeutic Potential of Protein Kinase Inhibitors, Chemical Biology, 1999, pp. 459-465.

(56) References Cited

OTHER PUBLICATIONS

Colonna et al., Plasmacytoid dendritic cells in immunity, Nature Immunology, 2004, 5(12)0:1219-1226.
Cottam et al., Substituted Xanthines, Pteridinediones and Related Compounds as Potential Anti-Inflammatory Agents. Synthesis and Biological Evaluation of Inhibitors of Tumor Necrosis Factor Alpha, J. Med. Chem. 1996, pp. 2-9, vol. 39.
Database Beilstein, Accession No. 1184281, Beilstein Institute for Organic Chemistry, ZA Pat No. 6706096, 1968. (XP-002324247, 2 pages).
Database Beilstein, Accession No. 7216143, Beilstein Institute for Organic Chemistry, HTCYAM Heterocycles EN 41:7811-788, 1995. (XP-002296937, 3 pages).
Database Beilstein, Accession No. 7928670, Beilstein Institute for Organic Chemistry, HTCYAM Heterocycles EN 48:1255-1274, 1998. (XP-002296938, 2 pages).
Database Beilstein, Accession Nos. 285496, 252276, and 250719, Beilstein Institute for Organic Chemistry, Angew. Chem. 73:695, 704, 1961; Ber. Bunsen-Ges. Phys. Chem. 69:458, 462, 465, 1965; Chem. Ber. 90:2631, 2633, 2635, 1957; Chem. Ber. 95:755, 762, 1962; Chem. Ber. 106:3203, 3205, 1973; Chem. Ber. 114:699-706, 1981; Heterocycles 24:1565-1566, 1986; Heterocycles 41:781-788, 1995; J. Chem. Soc. Perkin Trans. 2:35-36, 1979; Justus Liebigs Ann. Chem. 547:180, 183, 1941; Liebigs Ann. Chem. 11:11798-1814, 1984; Zh. Org. Khim. RU 32:455-460, 1996. (XP-002296934, 22 pages).
Database Beilstein, Accession Nos. 533693 and 540145, Beilstein Institute for Organic Chemistry, CHBEAM Chem. Ber. 93: 2668, 2671, 1960. (XP-002296935, 4 pages).
Database Beilstein, Accession Nos. 6337777 and 6373242, Beilstein Institute for Organic Chemistry, KGSSAQ Khim. Geterotsikt Soedin. RU9: 1202-1207, 1992. (XP-002296933, 6 pages).
Database Beilstein, Accession Nos. 9571456 and 9570157, Beilstein Institute for Organic Chemistry, IASKEA Izv. Akad. Nauk. Ser. Khim. RU6:1328-1334, 2003. (XP-002296936, 11 pages).
Database WPI Week 2005, Feb. 23, 2005, Thompson Scientific, London, GB (XP002498175).
Dempcy et al., Regioselective synthesis of imidazo[4,5-g]quinazoline quinone nucleosides and quinazoline amino nucleosides. Studies of their xanthine oxidase and purine nucleoside phosphorylase substrate activity, J. Org. Chem., 1991, 776-85, vol. 56.
Dermer, Another Anniversary for the War on Cancer, Bio/Technology, Mar. 12, 1994, p. 320, vol. 12.
Deuis, Pharmacological characterization of the highly Nav1.7 selective spider venom peptide Pn3a, Scientific Reports, 2017, pp. 1-18.
Dimauro et al., Microwave-assisted preparation of fused bicyclic heteroaryl boronates: application in one-pot Suzuki couplings, J. Org. Chem., 2006, pp. 3959-3962.
Ding et al, Parallel Synthesis of Pteridine Derivatives as Potent Inhibitors for Hepatitis C Virus NS5B RNA-Dependent RNA Polymerase, Bioorg Med. Chem. Lett., 2005, pp. 675-678, vol. 15.
Elion et al., Antagonists of Nucleic Acid Derivatives. VIII. Synergism in Combinations of Biochemically Related Antimetabolites, J. Biol. Chem., 1954, pp. 477-488.
Elliott et al., Synthesis of N-10-Methyl-4-Thiofolic Acid and Related Compounds, J. Med. Chem., 1975, pp. 492-496, vol. 18.
Freshney, Culture of Animal Cells, 1983, pp. 1-6, Chapter 1, Alan R. Liss, Inc.
Frohlich et al., Inhibition of Neuronal Nitric Oxide Synthase by 4-Amino Pteridine Derivatives: Structure-Activity Relationship of Antagonists of (6R)-5, 6, 7, 8-Tetrahydrobiopterin Cofactor, J. Med. Chem., 1999, pp. 4108-4121, vol. 42.
Ganellin, Final Report on the Activities of the Medicinal Chemistry Section, 2002, Retrieved Jun. 2, 2004 from www.iupac.org/divisions/VII/VII.M/VIIM-ReportDec2001.pdf (4 pages).
Gerlach et al., Influence of Pyrimidopyrimidine and Pteridine Derivatives on Phosphate and Adenosine Permeability in Human Erythrocytes, Arzneimittelforschung, 1965, pp. 558-563, vol. 15 (English Abstract).
Giori et al., Reactivity of 3H-Pyrimido[5, 4-c] [1, 2, 5] Oxadiazin-3-One Towards Carbanions: Synthesis of Pteridine-2, 4-Diones, J. Heterocyclic Chem., 1986, pp. 1661-1665, vol. 23.
Golub et al., Molecular Classification of Cancer: Class Discovery and Class Prediction by Gene Expression Monitoring, Science, Oct. 15, 1999, pp. 531-537, vol. 286.
Gonzalez-Rodriguez et al., Synergistic combinations of the dual enkephalinase inhibitor PL265 given orally with various analgesic compounds acting on different targets, in a murine model of cancer-induced bone pain, Scand J Pain, 2017, pp. 25-38.
Guillermo et al., Targeting cell cycle kinases for cancer therapy, Current Medicinal Chemistry, Apr. 1, 2007, pp. 969-985, vol. 14.
Hayakawa et al., Synthesis and Biological Evaluation of 4-Morpholino-2-Phenylquinazolines and Related Derivatives as Novel PI3 Kinase p110alpha Inhibitors, Bioorg. Med. Chem., 2006, pp. 6847-6858, vol. 14.
Hayden, Antimicrobial Agents (Continued) Antiviral Agents (Nonretroviral), Goodman and Gilman's The Pharmacological Basis for Therapeutics, 10th Edition, 2001, pp. 1313-1315, Chapter 50.
Higuchi et al., A Disproportionation of 6-Amino-5-Benzylideneamino-1,3-dimethyluracils in Formamide. Formation of 6,7-Diaryl-1,3-dimethyllumazines and Theophylline, Heterocycles, 1976, pp. 977-980, vol. 4.
Horner et al., Analogs of 3-amino-7-chloro-1,2,4-benzotriazine 1-oxide as antimalarial agents, J. Med. Chem., 1968, pp. 946-949, vol. 11.
Illei et al., Novel, Non-Antigen-Specific Therapeutic Approaches to Autoimmune/Inflammatory Diseases, Curr. Op. Immunol., 2000, pp. 712-718, vol. 12.
Isensee, Synergistic regulation of serotonin and opioid signaling contribute to pain insensitivity in Nav1.7 knockout mice, Neuroscience, Science Signaling, 2017, 11 pages.
Israel et al., Pyrimidine Derivatives. VII. Some Condensed Derivatives of 2, 4, 5-Triamino-6-Methylthiopyrimidine, J. Pharm. Sci., 1965, pp. 1626-1632, vol. 54.
Iwagaki et al., Decreased Serum Tryptophan In Patients With Cancer Cachexia Correlates With Increased Serum Neopterin, Immunot Investig., 1995, pp. 467-478, vol. 24.
Jackson et al., 6, 7-Disubstituted 2, 4-Diaminoteridines: Novel Inhibitors of Pneumocystis carinii and Toxoplasma gondii Dihydrofolate Reductase, Antimicrob. Agents Chemother., 1996, pp. 1371-1375, vol. 40.
Jo, et al., Toll Like Receptor 8 Agonist and Bacteria Trigger Potent Activation of Innate Immune Cells in Human Liver, PLOS Pathogens, Jun. 2014, 13 pages.
Kaczanowska et al. (2013) "TLR agonists: our best frenemy in cancer immunotherapy" Journal of Leukocyte Biology 93(6):847-863.
Kaldrikyan et al., "Pteridine Derivatives. I. Synthesis of Some Substituted 6,7-Diarylpteridines," Armyanskii Khimicheskii Zhumat, 1976, vol. 29., pp. 337-341.
Kandror et al., Radical Arylation of N-Substituted Carboxylic Acid Thioamides and Cyclic Thioamides, Russ. Chem. Bull., 1982, pp. 1873-1876, vol. 31 (Abstract only).
Kikelj, From 2-Aminobenzonitriles and Carbon Dioxide, Carbon Monoxide, Carbon Disulfide, or Potassium 0-Ethyl Dithiocarbonate, Science of Synthesis, 2004, pp. 573-749, 2004.
Landauer et al., A Convenient Synthesis of Some 4-Substituted 5-Aminopyrimidines, J. Chem. Soc., 1953, pp. 3721-3722.
Landry et al., Pharmacologie Des Cibles Vers L'Indication Therapeutique, Cours et Exercices, 2003, p. 177.
Leguen, Pain management by a new series of dual inhibitors of enkephalin degrading enzymes: long lasting antinociceptive properties and potentiation by CCK2 antagonist or methadone, Pain, 2002, 139-148.
Lensink, Synthesis and structure of sulfonamido cyclopentadiene titanium complexes: X-ray structure, Journal of Organometallic Chemistry 553, 1998, pp. 387-392.
Lin et al., Use of the Methylxanthine Derivative A802715 in Transplantation Immunology, I. Strong in Vitro Inhibitory Effects on CD28-Costimulated T Cell Activities, Transplantation, 1997, p. 1813, vol. 63.

(56) References Cited

OTHER PUBLICATIONS

Lin et al., Use of the Methylxanthine Derivative A802715 in Transplantation Immunology, I. Strong in Vitro Inhibitory Effects on CD28-Costimulated T Cell Activities, Transplantation, 1997, pp. 1734-1738, vol. 63.

Magnus et al., Neural Stem Cells in Inflammatory CNS Diseases: Mechanisms and Therapy, J. Cell. MoL Med., 2005, pp. 303-319, vol. 9.

Matter et al., Structural Requirements for Inhibition of the Neuronal Nitric Oxide Synthase (NOS-I): 3D-QSAR Analysis of 4-Oxo- and 4-Amino-Pteridine-Based Inhibitors, Med. Chem., 2002, pp. 2923-2941, vol. 45.

Merz et al. Synthesis of 7-Benzylamino-6-chloro-2-piperazino-4-pyrrolidinopteridine and Novel Derivatives Free of Positional Isomers. Potent Inhibitors of cAMP-Specific Phosphodiesterase and of Malignant Tumor Cell Growth, J. Med. Chem., 1996, pp. 4733-4743, vol. 41.

Minett, Endogenous opioids contribute to insensitivity to pain in humans and mice lacking sodium channel Nav1.7, Nature Communciations, 2015, 8 pages.

Mohr et al., Pteridines. Part XCVII. Synthesis and Properties of 6-thioxanthopterine and 7-thioisoxanthopterin, Helv. Chim. Acta, 1992, pp. 2317-2326, vol. 75.

Moody, et al., Toll-Like Receptor 7/8 (TLR7/8) and TLR9 Agonists Cooperate to Enhance HIV-1 Envelope Antibody Responses in Rhesus Macaques. Journal of Virology, Mar. 15, 2014, pp. 3329-3339, vol. 88, No. 6.

Moreb et al., The Therapeutic Potential of Interleukin-1 and Tumor Necrosis Factor on Hematopoietic Stem Cells, Leuk, Lymphoma, 1992, pp. 267-275, vol. 8, Abstract Only.

Murata et al., A Facile Method for Regioselective 6,7-Disubstitution of Pleridine, Heterocycles, 2000, pp. 1259-1262, vol. 53.

Neilsen et al., Unequivocal Syntheses of 6-Methykl- and 6-Phenylisoxanthoterin, J. Heterocyclic Chem., 1987, pp. 1621-1628, vol. 24.

Nicolaus, Symbiotic Approach to Drug Design, in Decision Making in Drug Research, 1983, pp. 173-186, Gross (Ed.) Raven Press: New York.

Novis et al., Reactivation of latent HIV-1 in central memory CD4+ T cells through TLR-1/2 stimulation, Retrovirology, 2013, 15 pages, vol. 10, No. 119.

Obach, Drug-drug Interactions: An Important Negative Attribute in Drugs, Drugs Today, 2003, pp. 301-338, vol. 39.

Ochoa et al., Application of Neural Networks to the Study of Structure-Activity Relationships of 6.7-Diarylpteridines as Nematocides, Med. Chem. Res., 1997, pp. 530-545, vol. 7.

Ohto et al., Structure and Function of Toll-like Receptor 8, Microbes and Infection, Feb. 8, 2014, 1 page, vol. 16.

O'Neill et al, The history of Toll-like receptors—redefining innate immunity, Nature Reviews/immunology, 2013, pp. 453-460, vol. 13.

Patani et al., Bioisosterism: A Rational Approach in Drug Design, Chem. Rev., 1996, pp. 3147-3176, vol. 96.

Peng et al., Toll-Like Receptor 8-Mediated Reversal of CD4+ Regulatory T Cell Function, Science, Aug. 26, 2005, pp. 1380-1384.

Pfleiderer et al., Pteridine, XII: Synthese von 2-Amino-4-Alkoxy-Pteridinen, Chem. Ber., 1961, pp. 12-18, vol. 94.

Ramu et al, Circumvention of Adriamycin Resistance by Dipyridamole Analogues: A Structure-activity Relationship Study, Int. J. Cancer, 1989, pp. 487-491, vol. 43.

Rodrigues et al., Co/SiO2 Catalysts for Selective Hydrogenation of Crotonaldehyde III. Promoting Effect of Zinc, Appl. Catalysis A: Gen., 2004, pp. 201-211, 257.

Roethle et al., Identification and Optimization of Pteridinone Toll-Like Receptor 7 (TLR7) Agonists for the Oral Treatment of Viral Hepatitis, Journal of Medicinal Chemistry, 2013, pp. 7324-7333.

Rosowsky et al., Structure-activity and structure-selectivity studies on Diaminoquinozolines and other inhibitors of Pneumocystis carnii and Toxoplasma gondii Dihydrofolate Reductase, Antimicrobial Agents and Chemotherapy, 1995, pp. 78-86, vol. 39, No. 1.

Sasse, A simple new method for preparation of 2-substituted quinazolines, Sythesis., 1978, pp. 379-382.

Sato et al., Studies on Pyrazines. Part 37. Synthesis of 6-Propionylpteridine-2.4 (1 H,3H)-dione and its 1- and/or 3-Methyl Derivatives from Marine Natural Products, J. Chem. Soc., 2000, pp. 89-95, vol. 1.

Sielecki et al., Quinazolines as cyclin dependent kinase inhibitors, Bioorg. Med. Chem. Lett., 2001, pp. 1157-1160, vol. 9.

Spickett et al, The Synthesis of Compounds With Potential Anti-Folic Acid Activity. Part I 7-Amino- And 7-Hydroxy-Pteridines, J. Chem. Soc., 1954, pp. 2887-2891.

Sugimoto et al., Regioselective Arylation of 1,3-Dimethyllumazine and Its 5-Oxide by Diazonium Salts, Pteridines, 1997, pp. 188-194, vol. 8.

Sun, Inhibitors of voltage-gated sodium channel Nav1.7: patent applications since 2010, Pharmaceutical Patent Analyst, 2014, pp. 509-521.

Taghavi-Moghadam et al., A New, General, and Regioselective Method for the Synthesis of 2, 6-Disubstituted 4-Aminopteridines, Tetrahedron Lett., 1997, pp. 6835-6836, vol. 38.

Taylor Jr. et al., Opioid antagonists for pain, Expert Opinion on Investigational Drugs, 2013, pp. 517-525.

Ulrich, Kirk-Othmer Encyclopedia of Chemical Technology, Wiley, Chapter 4: Crystallization, 2002 (7 pages).

Ankylosing Spondylitis, Retrieved Online on Jul. 27, 2007 from http://www.nlm.nih.gov/medicineplus/print/ankylosingspondylitis.html, 3 pages.

FDA mulls drug to slow late-stage Alzheimer's, Retrieved from CNN.com, Sep. 24, 2003, 2 pages.

Vema et al., Design of EGFR Kinase Inhibitors: A Ligand-Based Approach and its Confirmation with Structure-Based Studies, Boorg. Med. Chem., 2003, pp. 4643-4653, vol. 11.

Vinot, Etude de Pteridiones-2,4 III Orientation de la Reaction de Condensation D'a-dicetones Avec le Diamino-4,5 Dimethyl-1,3 Uracile, Bulletin de la Societe Chimique de France, 1972, pp. 2752-5722, No. 9-10.

Vippagunta et al., Crystalline Solids, Adv. Drug Del. Rev., 2001, pp. 3-26, vol. 48.

Wang et al., Organic Letters, 2004, pp. 2793-2796, vol. 6.

Warren, Therapeutic efficacy of the small molecule GS-5734 against Ebola virus in rhesus monkeys, Nature, 2016, 19 pages.

Watashi, et al., Interleukin-1 and Tumor Necrosis Factor Triggeer Restriction of Hepatitis B Virus Infection Via a Cytidine Deaminase Activation-induced Cytidine Deaminase (AID), The Journal of Biological Chemistry, Nov. 1, 2013, pp. 31715-31727, vol. 288, No. 44.

Weinstock et al. Pteridines. XII. Structure-Activity Relationships of Some Pteridine Diuretics, J. Med. Chem., 1968, pp. 573-579, vol. 11.

West, Solid State Chemistry and its Applications, Wiley, pp. 358, 365, 1988.

Wille-Reece et al., Toll-like receptor agonists influence the magnitude and quality of memory T cell responses after prime-boost immunization in nonhuman primates, The Journal of Experimental Medicine, May 15, 2006, pp. 1249-1258.

Wolff (ed.) Burger's Medicinal Chemistry and Drug Discovery: Fifth Edition, Principles and Practice, 1995, pp. 783-802, vol. 1.

Wolff (ed.) Burger's Medicinal Chemistry and Drug Discovery: Fifth Edition, Principles and Practice, 1995, pp. 975-977, vol. 1.

Xagorari, Toll-Like Receptors and Viruses: Induction of Innate Antiviral Immune Responses, The Open Microbiology Journal, 2008, pp. 49-59, vol. 2.

Yao et al., Pteridines. Protection of Pteridines, Helv. Chim. Acta., 2003, pp. 1-12, vol. 86.

Yin et al., Synthesis of 2,4-Diaminoquinazolines and Tricyclis Quinazolines by Cascade Reductive Cyclization of Methyl N-Cyano-2-notrobenzimidates, The Journal of Organic Chemistry, 2012, pp. 2649-2658, vol. 77.

Yu et al., Dual Character of Toll-like Receptor Signaling: Protumorigenic Effects and Anti-tumor Functions, Biochimica et Biophysica Acta, 2013, 1 page, Abstract only.

Zhao et al., Toll-like Receptors and Prostate Cancer, Frontiers in Immunology, Jul. 23, 2014, 1 page, vol. 5.

(56) References Cited

OTHER PUBLICATIONS

Australian Patent Office, Examination Report No. 1 for Australian Patent Application No. 2016216673 dated Sep. 5, 2016.
Australian Patent Office, Examination Report No. 2 for Australian Patent Application No. 2016216673 dated Nov. 14, 2016.
Australian Patent Office, Examination Report No. 1 for Australian Patent Application No. 2016322763 dated Nov. 28, 2018.
Chilean Patent Office, Official Action for CL Application No. 201702225, dated Nov. 9, 2018, (11 pages).
European Patent Office, Examination Report dated Nov. 29, 2016 for EP Patent Application No. 16711723.3.
European Patent Office, International Preliminary Report on Patentability dated Apr. 7, 2009 for International Application No. PCT/BE2007/000092, International filing date Jul. 20, 2007.
European Patent Office, International Preliminary Report on Patentability dated Jan. 20, 2009 for International Application No. PCT/BE2007/000091.
European Patent Office, International Search Report and Written Opinion dated Dec. 8, 2016 for International Application No. PCT/US2016/051545, 13 pages.
European Patent Office, International Preliminary Report on Patentability for PCT International Patent Application No. PCT/US2017/049562, dated Mar. 14, 2019, 8 pages.
European Patent Office, International Search Report and Written Opinion for International Application No. PCT/US2017/049562, dated Nov. 14, 2017, 11 pages.
European Patent Office, International Search Report and Written Opinion for International Application No. PCT/US2017/049573, dated Oct. 25, 2017, 12 pages.
European Patent Office, International Search Report and Written Opinion for International Application No. PCT/BE2007/000091, dated Nov. 11, 2008 (9 pages).
European Patent Office, International Search Report for PCT/US2016/020499 dated Jul. 25, 2016.
Korean Patent Office, Notice of Preliminary Rejection for Korean Patent Application No. 10-2016-7023289.
Korean Patent Office, Search Report for Korean Patent Application 10-2016-7023289 dated Aug. 25, 2016 with English translation.
USPTO, Office Action dated Dec. 27, 2016 for U.S. Appl. No. 15/264,401, 11 pages.
USPTO, Office Action for U.S. Appl. No. 12/374,242 dated Apr. 9, 2012 (20 pages).

Step 14　　　　Step 15　　　　Step 16

Step 17

PROCESSES FOR PREPARING TOLL-LIKE RECEPTOR MODULATOR COMPOUNDS

CROSS-REFERENCES TO RELATED APPLICATIONS

This application claims priority to U.S. Provisional Application No. 62/868,662, filed Jun. 28, 2019, which is incorporated herein in its entirety for all purposes.

BACKGROUND OF THE DISCLOSURE

Toll-like receptor (TLR) family plays a fundamental role in pathogen recognition and activation of innate immunity. Toll-like receptor 8 (TLR-8) is predominantly expressed by myeloid immune cells and activation of this receptor stimulates a broad immunological response. Agonists of TLR-8 activate myeloid dendritic cells, monocytes, monocyte-derived dendridic cells and Kupffer cells leading to the production of proinflammatory cytokines and chemokines, such as interleukin-18 (IL-18), interleukin-12 (IL-12), tumor necrosis factor-alpha (TNF-a), and interferongamma (IFN-γ). Such agonists also promote the increased expression of co-stimulatory molecules such as $CD^{8+}$ cells, major histocompatibility complex molecules (MAIT, NK cells), and chemokine receptors.

Collectively, activation of these innate and adaptive immune responses induces an immune response and provides a therapeutic benefit in various conditions involving autoimmunity, inflammation, allergy, asthma, graft rejection, graft versus host disease (GvHD), infection, cancer, and immunodeficiency. For example, with respect to hepatitis B, activation of TLR8 on professional antigen presenting cells (pAPCs) and other intrahepatic immune cells is associated with induction of IL-12 and proinflammatory cytokines, which is expected to augment HBV-specific T cell responses, activate intrahepatic NK cells and drive reconstitution of antiviral immunity. See e.g. Wille-Reece, U. et al., *J Exp Med* 203, 1249-1258 (2006); Peng, G. et al., *Science* 309, 1380-1 384 (2005); Jo, J. et al., *PLoS Pathogens* 10, e1004210 (2014) and Watashi, K. et al., *J Biol Chem* 288, 317 15-3 1727 (2013).

Given the potential to treat a wide array of diseases, potent and selective modulators of TLR-8 that have reduced potential for off target liabilities are particularly desirable. Toll-like receptor modulator compounds, such as diamino pyrido[3,2-d] pyrimidine compounds and methods of making them have been disclosed in WO 2016/141092. However, there remains a need for methods of preparing diamino pyrido[3,2-d] pyrimidine compounds.

BRIEF SUMMARY OF THE DISCLOSURE

In one embodiment, the present disclosure provides a method for preparing a compound of Formula I:

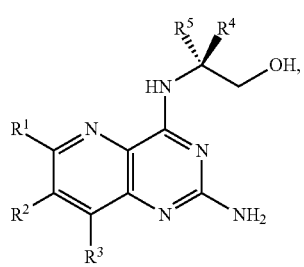

(I)

or a salt thereof, the method including:

a) forming a first reaction mixture including a compound of Formula III:

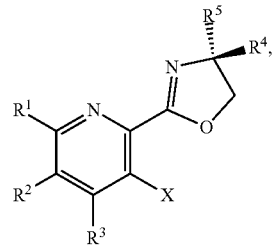

(III)

or a salt thereof, a compound having the formula PG-NHC(=NH)NH₂ or a salt thereof, a first base, and a first solvent to form a compound of Formula II:

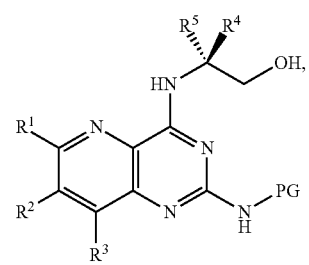

(II)

or a salt thereof, and b) forming a second reaction mixture including the compound of Formula II or the salt thereof, a deprotecting agent, and a second solvent to provide the compound of Formula I or the salt thereof, wherein $R^1$, $R^2$, and $R^3$ are each independently hydrogen, F, Cl, CN, $CF_3$, $C_{1-3}$ alkyl, or $C_{1-3}$ alkoxy; $R^4$ is hydrogen or methyl; $R^5$ is $C_{3-6}$ alkyl; X is F, Cl, Br, I, or OTs; and PG is an amino protecting group.

In another embodiment, the present disclosure provides a method for preparing a compound of Formula I:

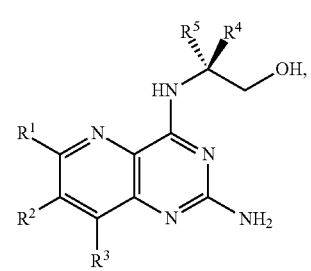

(I)

or a salt thereof, the method including:

a) forming a first reaction mixture including a compound of Formula III:

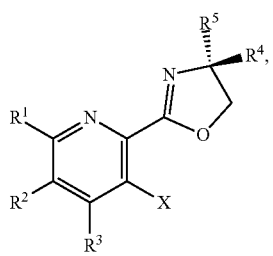

(III)

or a salt thereof, a compound having the Formula PG-NHC(=NH)NH$_2$ or a salt thereof, a first transition-metal catalyst, a first base, and a first solvent to form a compound of Formula II:

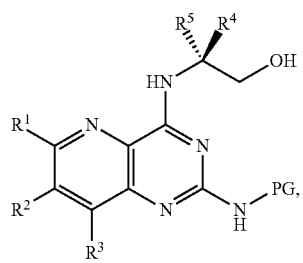

(II)

or a salt thereof, and b) forming a second reaction mixture including the compound of Formula II or the salt thereof, a deprotecting agent, and a second solvent to provide the compound of Formula I or the salt thereof, wherein R$^1$, R$^2$, and R$^3$ are each independently hydrogen, F, Cl, CN, CF$_3$, C$_{1-3}$ alkyl, or C$_{1-3}$ alkoxy; R$^4$ is hydrogen or methyl; R$^5$ is C$_{3-6}$ alkyl; X is Cl, Br, I, or OTs; and PG is an amino protecting group.

In another embodiment, the present disclosure provides a method for preparing a compound of Formula Ib:

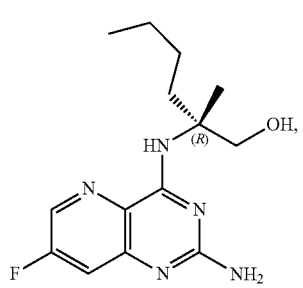

(Ib)

or a salt thereof, the method including:

a4) forming a seventh reaction mixture including a compound of Formula VIIIb:

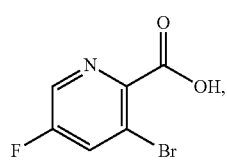

(VIIIb)

or a salt thereof, oxalyl chloride, N,N-dimethylformamide, 2-methyltetrahydrofuran to form a compound of Formula VIIb:

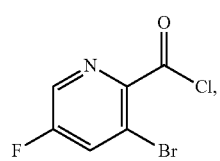

(VIIb)

or a salt thereof, a3) forming a sixth reaction mixture including the compound of Formula VIIb or the salt thereof, a compound of Formula VIb:

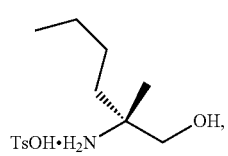

(VIb)

aqueous potassium carbonate, 2-methyltetrahydrofuran, and water to form a compound of Formula Vb:

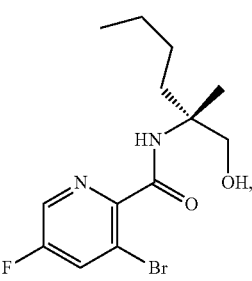

(Vb)

or a salt thereof, a2) forming a fourth reaction mixture including the compound of Formula Vb or the salt thereof, thionyl chloride, and 2-methyltetrahydrofuran to form a compound of Formula IVb-1:

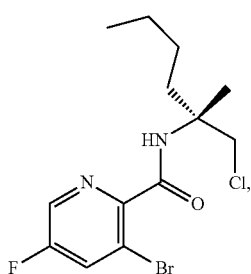

(IVb-1)

or a salt thereof, a1) forming a third reaction mixture including the compound of Formula IVb-1 or the salt thereof, aqueous sodium hydroxide, tetra-n-butylammonium hydrogensulfate, and 2-methyltetrahydrofuran to form a compound of Formula IIIb:

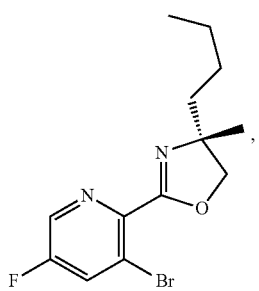

(IIIb)

or a salt thereof, a) forming a first reaction mixture including the compound of Formula IIIb or the salt thereof, a compound a compound of Formula IXa wherein n is from 0 to 1:

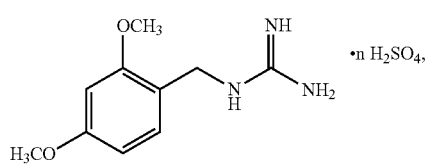

(IXa)

Cu(II) acetate, potassium phosphate tribasic, cysteine, 2-methyltetrahydrofuran, and acetonitrile to form a compound of Formula IIb:

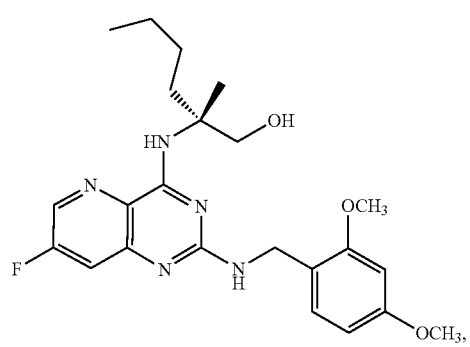

(IIb)

or a salt thereof, b) forming a second reaction mixture including the compound of Formula Ib or the salt thereof, trifluoroacetic acid, and dichloromethane to prepare a trifluoroacetic acid salt of the compound of Formula Ib:

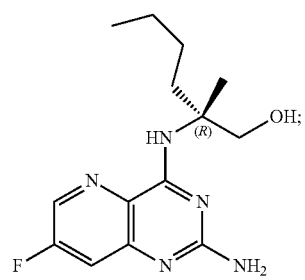

(Ib)

c) forming a ninth reaction mixture including the trifluoroacetic acid salt of the compound of Formula Ib, sodium hydroxide, ethanol, and water to provide the compound of Formula Ib in a neutral form.

In some embodiments, the present disclosure provides a method for preparing a compound of Formula II:

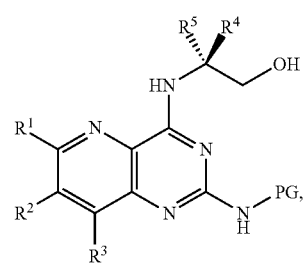

(II)

or a salt thereof, the method including:

a) forming a first reaction mixture including a compound of Formula V:

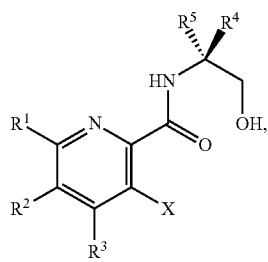

(V)

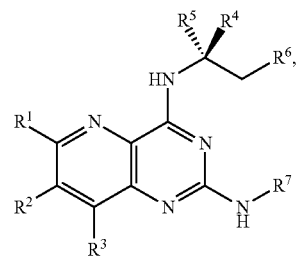

(XVIII)

or a salt thereof, a compound having the Formula PG-NHC(=NH)NH$_2$ or a salt thereof, a first transition-metal catalyst, a first base, and a first solvent to form the compound of Formula II, or a salt thereof, wherein $R^1$, $R^2$, and $R^3$ can each independently be hydrogen, F, Cl, CN, CF$_3$, C$_{1-3}$ alkyl, or C$_{1-3}$ alkoxy; $R^4$ can be hydrogen or methyl; $R^5$ can be C$_{3-6}$ alkyl; X can be F, Cl, Br, I, or OTs; and PG can be an amino protecting group.

In another embodiment, the present disclosure provides a method for preparing a compound of Formula I:

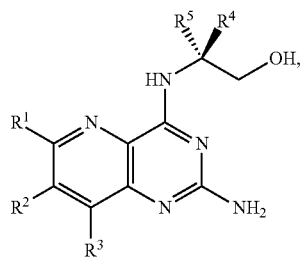

(I)

or a salt thereof, comprising:

a) forming a first reaction mixture comprising a compound of Formula III:

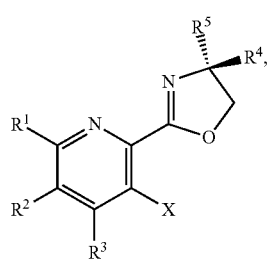

(III)

a compound having the Formula H$_2$NC(=NH)NH$_2$ or a salt thereof, a first base, and a first solvent to form the compound of Formula I or the salt thereof, wherein $R^1$, $R^2$, and $R^3$ can each independently be hydrogen, F, Cl, CN, CF$_3$, C$_{1-3}$ alkyl, or C$_{1-3}$ alkoxy; $R^4$ can be hydrogen or methyl; $R^5$ can be C$_{3-6}$ alkyl; and X can be F, Cl, Br, I, or OTs.

In another embodiment, the present disclosure provides a method for preparing a compound of Formula XVIII:

or a salt thereof, comprising:

a) forming a first reaction mixture comprising a compound of Formula XV:

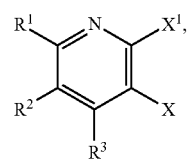

(XV)

a compound of Formula XVI-1:

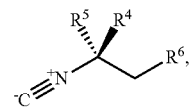

(XVI-1)

or a salt thereof, a compound having the Formula R$^7$—NHC(=NH)NH$_2$ or a salt thereof, a first transition-metal catalyst, a first base, and a first solvent, to form the compound of Formula XVIII or the salt thereof, wherein $R^1$, $R^2$, and $R^3$ are each independently hydrogen, F, Cl, CN, CF$_3$, C$_{1-3}$ alkyl, or C$_{1-3}$ alkoxy; $R^4$ is hydrogen or methyl; $R^5$ is C$_{1-6}$ alkyl; $R^6$ is hydrogen, OH, or O-PG1; $R^7$ is hydrogen or PG; X and X$^1$ are each independently F, Cl, Br, I, or OTs; PG is an amino protecting group; and PG1 is a hydroxy protecting group.

In another embodiment, the present disclosure provides a method for preparing a compound of Formula I:

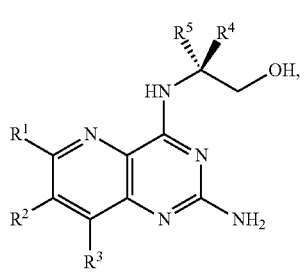

(I)

or a salt thereof, the method including:

a) forming a first reaction mixture including a compound of Formula XI:

(XI)

[Structure of Formula XI: pyrido-pyrimidine with R¹, R², R³ substituents and two Cl groups]

or a salt thereof, a compound of Formula VI:

(VI)

[Structure of Formula VI: H₂N-C(R⁴)(R⁵)-CH₂OH]

or a salt thereof, a first base, and a first solvent to form a compound of Formula X:

(X)

[Structure of Formula X]

or a salt thereof, b) forming a second reaction mixture including the compound of Formula IX or the salt thereof, a compound of PG-NH₂ or a salt thereof, a second base, and a second solvent to form a compound of Formula II:

(II)

[Structure of Formula II]

or a salt thereof, and b) forming a third reaction mixture including the compound of Formula II or the salt thereof, a deprotecting agent, and a third solvent to provide the compound of Formula I or the salt thereof, wherein $R^1$, $R^2$, and $R^3$ are each independently hydrogen, F, Cl, CN, $CF_3$, $C_{1-3}$ alkyl, or $C_{1-3}$ alkoxy; $R^4$ is hydrogen or methyl; $R^5$ is $C_{3-6}$ alkyl; and PG is an amino protecting group.

In another embodiment, the present disclosure provides a method for preparing a compound of Formula Ib:

(Ib)

[Structure of Formula Ib]

or a salt thereof, the method comprising:

a) forming a first reaction mixture comprising a compound of Formula XIb:

(XIb)

[Structure of Formula XIb]

or a salt thereof, a compound of Formula VIb:

(VIb)

[Structure of Formula VIb: TsOH·H₂N-...-OH]

N,N-diisopropylethylamine, 2-methyltetrahydrofuran, and isopropyl acetate to form a compound of Formula Xb:

(Xb)

[Structure of Formula Xb]

or a salt thereof, b) forming a second reaction mixture comprising the compound of Formula Xb or the salt thereof, 2,4-dimethoxybenzylamine, potassium carbonate, 2-methyltetrahydrofuran, and isopropyl acetate to form a compound of Formula IIb:

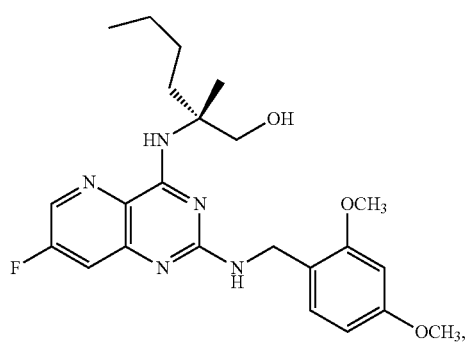

(IIb)

or a salt thereof, and c) forming a third reaction mixture comprising the compound of Formula Ib or the salt thereof, trifluoroacetic acid, and dichloromethane to prepare a trifluoroacetic acid salt of the compound of Formula Ib:

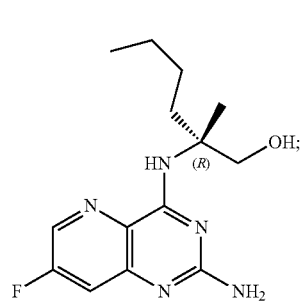

(Ib)

and d) forming a fourth reaction mixture comprising the trifluoroacetic acid salt of the compound of Formula Ib, sodium hydroxide, ethanol, and water to provide the compound of Formula Ib in a salt-free form.

In another embodiment, the present disclosure provides a compound of Formula III:

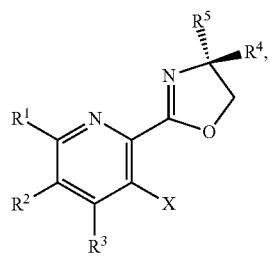

(III)

or a salt thereof, wherein $R^1$, $R^2$, and $R^3$ are each independently hydrogen, F, Cl, CN, $CF_3$, $C_{1-3}$ alkyl, or $C_{1-3}$ alkoxy; $R^4$ is hydrogen or methyl; $R^5$ is $C_{3-6}$ alkyl; and X is Cl, Br, I, or OTs.

In another embodiment, the present disclosure provides a compound of Formula IV:

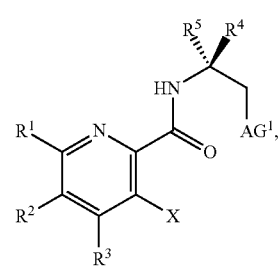

(IV)

or a salt thereof, wherein $R^1$, $R^2$, and $R^3$ are each independently hydrogen, F, Cl, CN, $CF_3$, $C_{1-3}$ alkyl, or $C_{1-3}$ alkoxy; $R^4$ is hydrogen or methyl; $R^5$ is $C_{3-6}$ alkyl; X is F, Cl, Br, I, or OTs; and $AG^1$ is Cl, Br, $OSO_3H$, $OSO_3$, OMs, OTs, or OTf.

In another embodiment, the present disclosure provides a compound of Formula IV:

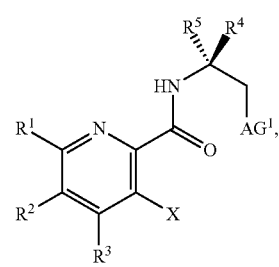

(IV)

or a salt thereof, wherein $R^1$, $R^2$, and $R^3$ are each independently hydrogen, F, Cl, CN, $CF_3$, $C_{1-3}$ alkyl, or $C_{1-3}$ alkoxy; $R^4$ is hydrogen or methyl; $R^5$ is $C_{3-6}$ alkyl; X is F, Cl, Br, I, or OTs; and $AG^1$ is Cl, Br, OMs, OTs, or OTf.

In another embodiment, the present disclosure provides a compound of Formula V:

13

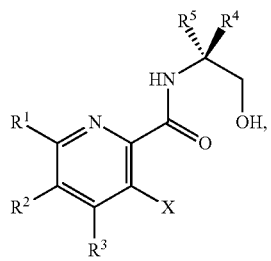
(V)

or a salt thereof, wherein $R^1$, $R^2$, and $R^3$ are each independently hydrogen, F, Cl, CN, $CF_3$, $C_{1-3}$ alkyl, or $C_{1-3}$ alkoxy; $R^4$ is hydrogen or methyl; $R^5$ is $C_{3-6}$ alkyl; and X is F, Cl, Br, I, or OTs, provided that the compound of Formula V is not 3-bromo-N-(1-hydroxy-3-methylbutan-2-yl)picolinamide, 3-bromo-N-(1-hydroxy-3,3-dimethylbutan-2-yl)picolinamide, 3-bromo-N-(1-hydroxy-4-methylpentan-2-yl)picolinamide, 3-bromo-N-(1-hydroxy-4-methylpentan-2-yl)picolinamide, 3,6-dichloro-N-(1-hydroxy-3-methylbutan-2-yl)picolinamide, 3,6-dichloro-N-(1-hydroxy-4-methylpentan-2-yl)picolinamide, 3,4,5-trichloro-N-(1-hydroxy-3-methylbutan-2-yl)picolinamide, 3,6-dichloro-N-(1-hydroxy-4,4-dimethylpentan-2-yl)picolinamide, or 3,4,5-trichloro-N-(1-hydroxy-4-methylpentan-2-yl)picolinamide.

In another embodiment, the present disclosure provides a compound of Formula V:

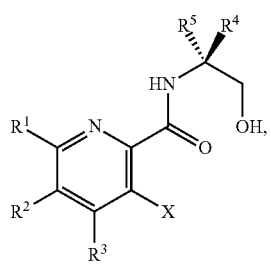
(V)

or a salt thereof, wherein R, $R^2$, and $R^3$ are each independently hydrogen, F, Cl, CN, $CF_3$, $C_{1-3}$ alkyl, or $C_{1-3}$ alkoxy; $R^4$ is hydrogen or methyl; $R^5$ is $C_{3-6}$ alkyl; and X is Cl, Br, I, or OTs, provided that the compound of Formula V is not 3-bromo-N-(1-hydroxy-3-methylbutan-2-yl)picolinamide, 3-bromo-N-(1-hydroxy-3,3-dimethylbutan-2-yl)picolinamide, 3-bromo-N-(1-hydroxy-4-methylpentan-2-yl)picolinamide, 3-bromo-N-(1-hydroxy-4-methylpentan-2-yl)picolinamide, 3,6-dichloro-N-(1-hydroxy-3-methylbutan-2-yl)picolinamide, 3,6-dichloro-N-(1-hydroxy-4-methylpentan-2-yl)picolinamide, 3,4,5-trichloro-N-(1-hydroxy-3-methylbutan-2-yl)picolinamide, 3,6-dichloro-N-(1-hydroxy-4,4-dimethylpentan-2-yl)picolinamide, or 3,4,5-trichloro-N-(1-hydroxy-4-methylpentan-2-yl)picolinamide.

In another embodiment, the present disclosure provides a compound of Formula XII:

14

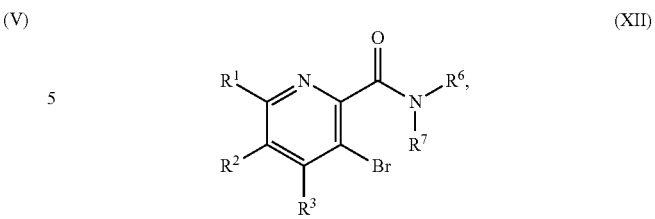
(XII)

or a salt thereof, wherein $R^1$, $R^2$, and $R^3$ are each independently hydrogen, F, Cl, CN, $CF_3$, $C_{1-3}$ alkyl, or $C_{1-3}$ alkoxy; and $R^6$ and $R^7$ are each independently hydrogen, $C_{1-4}$ alkyl, or $C_{3-6}$ cycloalkyl, or $R^6$ and $R^7$ are combined to form a 3-6 membered N-linked heterocycloalkyl, optionally having an additional 1-2 heteroatoms selected from O and S, provided that at least one of $R^1$, $R^2$, and $R^3$ is F, Cl, CN, $CF_3$, $C_{1-3}$ alkyl, or $C_{1-3}$ alkoxy.

DETAILED DESCRIPTION OF THE DISCLOSURE

I. General

Figure 1:
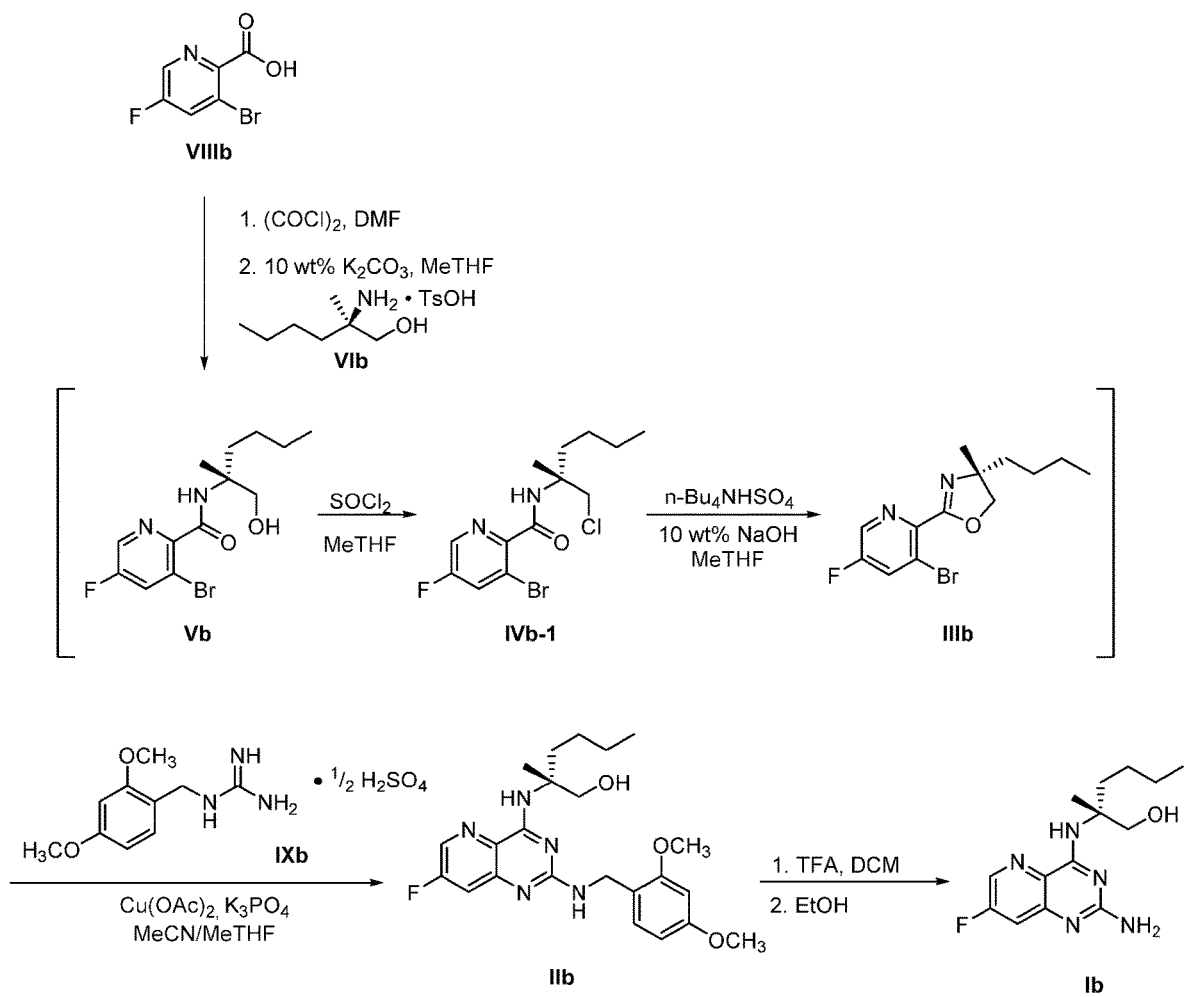
FIG. 1 shows the preparation of the compound of Formula Ib via a transition-metal mediated coupling reaction of (R)-2-(3-bromo-5-fluoropyridin-2-yl)-4-butyl-4-methyl-4,5-dihydrooxazole (Ib) with a protected guanidine compound provides (R)-2-((2-((3,4-dimethylbenzyl)amino)-7-fluoropyrido[3,2-d]pyrimidin-4-yl)amino)-2-methylhexan-1-ol (Ib), which is then deprotected to form (R)-2-((2-amino-7-fluoropyrido[3,2-d]pyrimidin-4-yl)amino)-2-methylhexan-1-ol (Ib).
Figure 2:
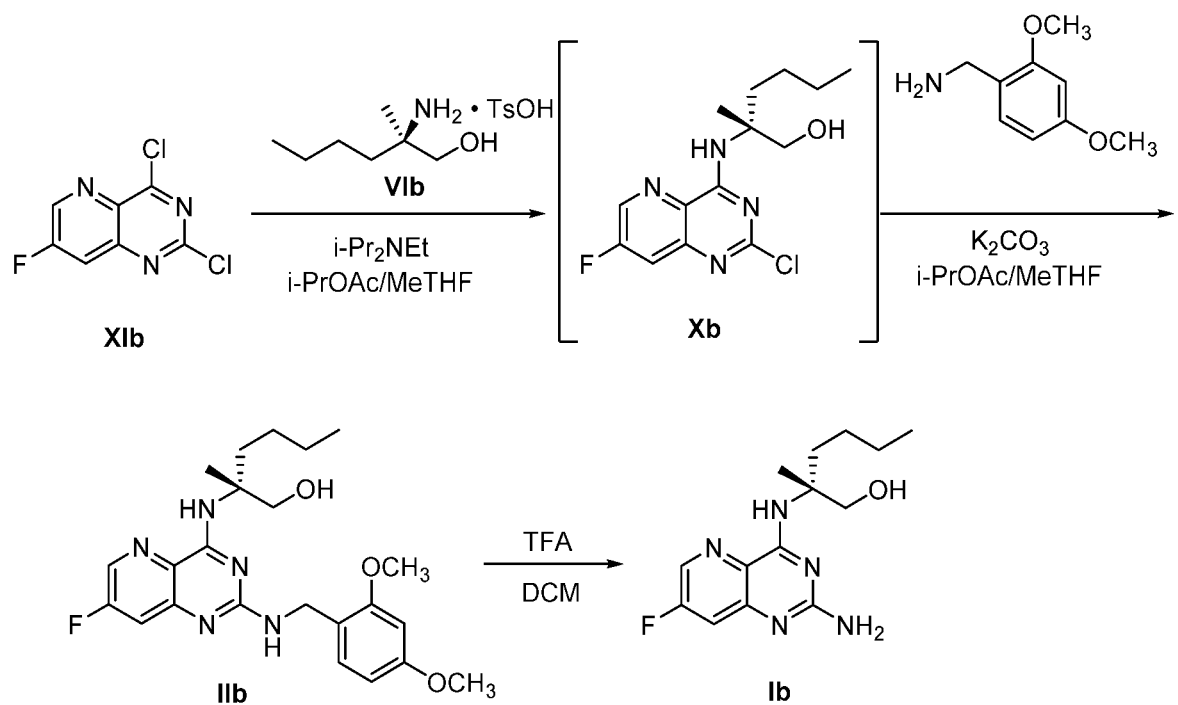
FIG. 2 shows the preparation of the compound of Formula Ib via two sequential nucleophilic aromatic substitution reactions of 2,4-dichloro-7-fluoropyrido[3,2-d]pyrimidine (XIb) to provide (R)-2-((2-((3,4-dimethylbenzyl)amino)-7-fluoropyrido[3,2-d]pyrimidin-4-yl)amino)-2-methylhexan-1-ol (Ib), which is then deprotected to form (R)-2-((2-amino-7-fluoropyrido[3,2-d]pyrimidin-4-yl)amino)-2-methylhexan-1-ol (Ib).

The present disclosure provides methods for preparing compounds of Formula I or a salt thereof, in particular (R)-2-((2-amino-7-fluoropyrido[3,2-d]pyrimidin-4-yl)amino)-2-methylhexan-1-ol. The present disclosure also provides methods for preparing compounds of Formula III, IV, V, VI, VII, VIII, IX, and X. In addition, the present disclosure provides compounds of Formula III, IV, V, and XI.

II. Definitions

The abbreviations used herein have their conventional meaning within the chemical and biological arts.

"Alkyl" refers to a straight or branched, saturated, aliphatic radical having the number of carbon atoms indicated (i.e., $C_{1-6}$ means one to six carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, n-propyl, isopropyl, n-butyl, isobutyl, sec-butyl, tert-butyl, n-pentyl, isopentyl, hexyl, etc.

"Alkoxy" refers to an alkyl group having an oxygen atom that connects the alkyl group to the point of attachment: alkyl-O—. Alkoxy groups can have any suitable number of carbon atoms, such as $C_1$-$C_6$. Alkoxy groups include, for example, methoxy, ethoxy, n-propoxy, iso-propoxy, butoxy, 2-butoxy, iso-butoxy, sec-butoxy, tert-butoxy, pentoxy, hexoxy, etc.

"Cycloalkyl" refers to a saturated or partially unsaturated, monocyclic, fused bicyclic or bridged polycyclic ring assembly containing from 3 to 12 carbon ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_3$-$C_5$ cycloalkyl, exemplary groups include, but are not limited to, cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to, cyclopropyl, cyclobutyl, cyclopentyl, and cyclohexyl.

"N-linked heterocycloalkyl" or "nitrogen-linked heterocycloalkyl" refers to the heterocycloalkyl group linked via N-position on the ring. For example, N-linked aziridinyl is aziridin-1-yl, N-linked azetidinyl is azetidin-1-yl, N-linked pyrrolidinyl is pyrrolidin-1-yl, N-linked piperidinyl is piperidin-1-yl, N-linked pyrazolidinyl is pyrazolidin-1-yl or pyrazolidin-2-yl, N-linked imidazolidinyl can be imidazolidin-1-yl or imidazolidin-3-yl, N-linked piperazinyl is piperazin-1-yl or piperazin-4-yl, N-linked oxazolidinyl is oxazolidin-3-yl, N-linked isoxazolidiny is isoxazolidin-2-yl, N-linked thiazolidinyl is thiazolidin-3-yl, N-linked isothiazolidinyl is isothiazolidin-2-yl, and N-linked morpholinyl is 4-morpholinyl.

"OMs" refers to methanesulfonate; "OTs" refers to p-toluenesulfonate; and "OTf" refers to trifluoromethanesulfonate.

"Forming a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

"Acid" refers to a compound that is capable of donating a proton (H+) under the Bronsted-Lowry definition, or is an electron pair acceptor under the Lewis definition. Acids useful in the present disclosure are Brønsted-Lowry acids that include, but are not limited to, alkanoic acids or carboxylic acids (formic acid, acetic acid, citric acid, lactic acid, oxalic acid, etc.), fluorinated carboxylic acids (trifluoroacetic acid), sulfonic acids and mineral acids, as defined herein. Mineral acids are inorganic acids such as hydrogen halides (hydrofluoric acid, hydrochloric acid, hydrobromic acid, etc.), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, triflouromethanesulfonic acid, among others.

"Lewis Acid" refers to a compound or ionic species which can accept an electron pair from a donor compound. The Lewis acids useful in the present disclosure include, but are not limited to, boron trifluoride diethyl etherate, lithium chloride, zinc chloride, titanium tetrachloride, silicon tetrachloride, aluminum chloride, samarium(II) iodide, cerium (III) chloride, and lanthanum(III) chloride lithium chloride complex.

"Base" refers to a functional group that deprotonates water to produce a hydroxide ion. Bases useful in the present disclosure include organic bases and inorganic bases. Exemplary organic bases include amines, carboxylates, alkali alkoxides, metal amides, and alkyl or alkenyl-metal compounds, as defined herein. Exemplary inorganic bases include alkali bicarbonates, alkali carbonates, alkali phosphates tribasic, alkali phosphate dibasic, alkali hydroxides, and alkali hydride, as defined herein. Amines useful in the present disclosure as bases include tertiary amines, aromatic amine bases, and amidine-based compounds, as defined herein.

"Tertiary amine" refers to a compound having formula $N(R)_3$ wherein the R groups can be alkyl, aryl, heteroalkyl, heteroaryl, among others, or two R groups together form a N-linked heterocycloalkyl. The R groups can be the same or different. Non-limiting examples of tertiary amines include triethylamine, tri-n-butylamine, N,N-diisopropylethylamine, N-methylpyrrolidine, N-methylmorpholine, dimethylaniline, diethylaniline, 1,8-bis(dimethylamino)naphthalene, quinuclidine, and 1,4-diazabicylo[2.2.2]-octane (DABCO).

"Aromatic amine base" refers to a N-containing 5- to 10-membered heteroaryl compound or a tertiary amine having formula $N(R)_3$ wherein at least one R group is an aryl or heteroaryl. Aromatic amine bases useful in the present application include, but are not limited to, pyridine, lutidines (e.g., 2,6-lutidine, 3,5-lutidine, and 2,3-lutidine), collidines (e.g., 2,3,4-collidine, 2,3,5-collidine, 2,3,6-collidine, 2,4,5-collidine, 2,4,6-collidine, and 3,4,5-collidine), 4-dimethylaminopyridine, imidazole, dimethylaniline, and diethylaniline.

"Amidine-based compounds" herein refers to a class of chemical compounds that include, but are not limited to, 1,8-diazabicyclo[5.4.0]undec-7-ene (DBU) and 1,5-diazabicyclo[4.3.0]non-5-en (DBN).

"Carboxylates" refers to a class of chemical compounds which are composed of an alkali metal cation or a phosphonium and the carboxylate anion ($RC(O)O^-$) where the R group can be alkyl or aryl. Carboxylates useful in the present disclosure include, but are not limited to, lithium acetate ($LiOC(O)CH_3$), sodium acetate ($NaOC(O)CH_3$), potassium acetate ($KOC(O)CH_3$), cesium acetate ($CsOC(O)CH_3$), potassium trimethylacetate ($KOC(O)C(CH_3)_3$), and tetrabutylphosphonium malonate.

"Alkali bicarbonate" refers to a class of chemical compounds which are composed of an alkali metal cation and the hydrogencarbonate anion ($HCO_3^-$). Alkali carbonates useful in the present disclosure include lithium bicarbonate ($LiHCO_3$), sodium bicarbonate ($NaHCO_3$), potassium bicarbonate ($KHCO_3$), and cesium bicarbonate ($CsHCO_3$).

"Alkali carbonate" refers to a class of chemical compounds which are composed of an alkali metal cation and the carbonate anion ($CO_3^{2-}$). Alkali carbonates useful in the present disclosure include lithium carbonate ($Li_2CO_3$), sodium carbonate ($Na_2CO_3$), potassium carbonate ($K_2CO_3$), and cesium carbonate ($Cs_2CO_3$).

"Alkali phosphate tribasic" refers to a class of chemical compounds which are composed of an alkali metal cation and the phosphate anion ($PO_4^{3-}$). Alkali phosphates tribasic useful in the present disclosure include sodium phosphate tribasic ($Na_3PO_4$) and potassium phosphate tribasic ($K_3PO_4$).

"Alkali phosphate dibasic" refers to a class of chemical compounds which are composed of an alkali metal cation and the hydrogenphosphate anion ($HPO_4^{2-}$). Alkali phosphates dibasic useful in the present disclosure include sodium phosphate dibasic ($Na_2HPO_4$) and potassium phosphate dibasic ($K_2HPO_4$).

"Alkali hydroxide" refers to a class of chemical compounds which are composed of an alkali metal cation and the hydroxide anion ($OH^-$). Alkali hydroxides useful in the present disclosure include lithium hydroxide (LiOH), sodium hydroxide (NaOH), potassium hydroxide (KOH), and cesium hydroxide (CsOH).

"Alkali alkoxide" refers to a class of chemical compounds which are composed of an alkali metal cation and the alkoxide anion ($RO^-$), wherein R is $C_{1-4}$ alkyl. Alkali alkoxides useful in the present disclosure include, but are not limited to, sodium isopropoxide, sodium methoxide, sodium tert-butoxide, potassium tert-butoxide, and potassium isopropoxide.

"Metal amide" refers to a class of coordination compounds composed of a metal center with amide ligands of the form —$NR_2$, wherein R is alkyl, cycloalkyl, or silyl. Metal amides useful in the present disclosure include, but are not limited to, lithium diisopropylamide, lithium bis(trimethylsilyl)amide, potassium bis(trimethylsilyl)-amide, lithium 2,2,6,6-tetramethylpiperidide, 2,2,6,6-tetramethylpiperidinylmagnesium chloride, bis(2,2,6,6-tetramethylpiperidinyl)magnesium, and di-n-butyllithium(2,2,6,6-tetramethylpiperidinyl)magnesate).

"Alkyl- and alkenylmetal compound" refers to a class of chemical compounds composed of a metal center bond to alkyl or alkenyl. Alkyl- and alkenylmetal compounds useful in the present disclosure include, but are not limited to, n-butyllithium, isopropylmagnesium chloride, tri-n-butyllithium magnesate, di-n-butylmagnesium, di-sec-butylmagnesium, and ethyl n-butylmagnesium.

"Alkali hydride" refers to a class of chemical compounds composed of an alkali metal cation and the hydride anion ($H^-$). Alkali hydrides useful in the present disclosure include lithium hydride, sodium hydride and potassium hydride.

"Protecting group" refers to a compound that renders a functional group unreactive to a particular set of reaction conditions, but that is then removable in a later synthetic step so as to restore the functional group to its original state. Such protecting groups are well known to one of ordinary skill in the art and include compounds that are disclosed in "Protective Groups in Organic Synthesis", 4th edition, T. W. Greene and P. G. M. Wuts, John Wiley & Sons, New York, 2006, which is incorporated herein by reference in its entirety.

"Amino protecting group" refers to a protecting group that is used to protect an amino group. "Amino" as used herein, and unless otherwise specified, refers to —$NH_2$. Exemplary amino protecting groups include, but are not limited to, a carbobenzyloxy (Cbz) group, p-methoxybenzyl carbonyl (Moz or MeOZ) group, tert-Butyloxycarbonyl (BOC) group, 9-fluorenylmethyloxycarbonyl (Fmoc) group, acetyl (Ac) group, benzoyl (Bz) group, benzyl (Bn) group, carbamate group, p-methoxybenzyl (PMB), 3,4-dimethoxybenzyl (DMB), p-methoxyphenyl (PMP), Tosyl (Ts) group, Troc (trichloroethyl chloroformate) group, and other sulfonamides (Nosyl & Nps) groups.

"Deprotecting agent" refers to one or more chemicals or agents that remove the protecting group as defined above so that the functional group is restored to its original state.

"Metal" refers to elements of the periodic table that are metallic and that can be neutral, or negatively or positively charged as a result of having more or fewer electrons in the valence shell than is present for the neutral metallic element. Metals useful in the present disclosure include the alkali metals and transition metals. Alkali metals in the present disclosure include alkali metal cations. Alkali metal cations useful in the present disclosure include $Li^+$, $Na^+$, $K^+$, and $Cs^+$. Transition metals useful in the present disclosure include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Transition metals useful in the present disclosure include transition metal cations, for example, $Cd^{2+}$, $Co^{2+}$, $Co^+$, $Cr^{2+}$, $Cr^+$, $Cu^+$ (i.e., Cu(I)), $Cu^{2+}$ (i.e., Cu(II)), $Fe^{2+}$, Fe, $Mn^{2+}$, $Mn^+$, $Ni^{2+}$, $Ni^+$, $Pd^{2+}$ (i.e., Pd(II)), and $Zn^{2+}$.

"Catalyst" refers to a substance that increases the rate of a chemical reaction by reducing the activation energy, but which is left unchanged by the reaction. Catalysts may be classified as either homogeneous or heterogeneous. A homogeneous catalyst is one whose molecules are dispersed in the same phase as the reactant molecules. A heterogeneous catalyst is one whose molecules are not in the same phase as the reactants, which are typically gases or liquids that are adsorbed onto the surface of the solid catalyst. Catalysts useful in the present disclosure are both homogeneous catalysts and heterogeneous catalysts.

"Transition-metal catalyst" refers to a compound that is composed of a transition metal as defined above that can be neutral or positively charged.

"Ligand" refers to a molecule (functional group) that binds to a central metal atom to form a coordination complex. The bonding with the metal generally involves formal donation of one or more of the ligand's electron pairs. The nature of metal-ligand bonding can range from covalent to ionic. Furthermore, the metal-ligand bond order can range from one to three. In general, ligands are viewed as electron donors and the metals as electron acceptors. Exemplary ligands in the present disclosure are tertiary amines as defined above, polypyridyl ligands as defined herein, and amino acids as defined herein.

"Polypyridyl ligand" refers to a class of compounds containing at least two pyridine moieties, which are either connected by a bond (e.g., 2,2'-bipyridine compounds) or a part of a fused tricyclic aromatic ring assembly containing 14 ring atoms (e.g., 1,10-phenanthroline compounds). Exemplary polypyridyl ligands include, but are not limited to, 2,2'-bipyridine, 1,10-phenanthroline, 4,4'-dimethyl-2,2'-bipyridine, 6,6'-dimethyl-2,2'-bipyridine, 4,4'-di-tert-butyl-2,2-bipyridine, and 2,2'-bipyridine-4,4'-dicarboxylic acid.

"Amino acid" refers to naturally occurring and synthetic amino acids, as well as amino acid analogs that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

"Phase-transfer agent" or "phase-transfer catalyst (PTC)" refers to a catalyst that facilitates the migration of a reactant from one phase into another phase where reaction occurs. Phase-transfer catalysis is a special form of heterogeneous catalysis. Ionic reactants are often soluble in an aqueous phase but insoluble in an organic phase in the absence of the phase-transfer catalyst. The catalyst functions like a detergent for solubilizing the salts into the organic phase. By using a PTC process, one can achieve faster reactions, obtain higher conversions or yields, make fewer byproducts, eliminate the need for expensive or dangerous solvents that will dissolve all the reactants in one phase, eliminate the need for expensive raw materials and/or minimize waste problems. PTC is not limited to systems with hydrophilic and hydrophobic reactants. PTC is sometimes employed in liquid/solid and liquid/gas reactions. As the name implies, one or more of the reactants are transported into a second phase which contains both reactants. Phase-transfer catalysts for anionic reactants are often quaternary ammonium salts, as defined herein.

"Quaternary ammonium salt" refers to a salt of a quaternary ammonium cation, as defined herein. Quaternary ammonium cation, also known as quat, refers to a positively charged compound having the formula $NR_4^+$ where R groups can be alkyl, aryl, or a combination thereof. Unlike the ammonium ion ($NH_4^+$) and the primary, secondary, or tertiary ammonium cations, the quaternary ammonium cations are permanently charged, independent of the pH of their solution.

"Activating agent" refers to a reagent capable of converting a less reactive functional group to a more reactive functional group in the molecule, which has an increased propensity to undergo a specified chemical reaction. In some embodiments, for example, the activating agents convert the —OH group in the compound of Formula V to a reactive function group (e.g., —Cl, —OMs, —OTs, or —OTf). In some embodiments, the activating agents are peptide coupling agents known in the art that activate the —C(O)OH group (e.g., the compound of Formula VIII) and then react with an amine to form an amide (e.g., the compound of Formula V). Additional non-limiting examples of a reactive function group include $OSO_3H$ and $—OSO_3^-$.

"Chlorinating agent" refers to a reagent capable of adding a chloro group, —Cl, to a compound. Representative chlorinating agents include, but are not limited to, phosphorous oxychloride, thionyl chloride, oxalyl chloride and sulfuryl chloride.

"Brominating agent" refers to a reagent capable of adding a bromo group, —Br, to a compound. Representative brominating agents include, but are not limited to, bromine, N-bromosuccinimide, triphenylphosphine dibromide, tetrabutylammonium tribromide, trimethylphenylammonium tribromide, N-bromoacetamide, pyridinium tribromide, dibromodimethylhydantoin, tribromoisocyanuric acid, N-bromosaccharin, and 1,2-dibromo-1,1,2,2-tetrachloroethane.

"Sulfonating agent" refers to a reagent capable of adding a sulfonate group, $—OSO_3^-$, to a compound. Representative sulfonating agents include, but are not limited to, sulfur trioxide, sulfur trioxide complexes (e.g., dioxane, pyridine, polyvinylpyridine, trimethylamine, triethylamine, dimethylaniline, thioxane, bis(2-chloroethyl)ether, 2-methylpyridine, quinoline, N,N'-dimethylformamide, tri-n-propylamine, tri-n-butylamine, N-alkylmorpholines (methyl, ethyl, n-butyl), pentamethylguanidine, 4'-methylacetanilide, N,N'-diethyl-4-toluenesulfonamide, tetramethylurea, tetramethyladipamide, N,N'-dimethylurethane, formylmorpholide, N,N'-dimethylbenzamide, dimethylcyanamide, n-propylpiperidine, n-isoamylpiperidine, N-benzylpiperidine, trimethylphosphine oxide, tetrahydrofuran, diethylsulfide, anthraquinone, benzanthrone, benzonapthone, or 2,6-dimethyl-γ-pyrone), chlorosulfonic acid, and sulfur dioxide.

"Promoter" refers to a substance added to a reactant (e.g., a chlorinating agent as defined above) to improve its performance in a chemical reaction (e.g., a formation of acyl chloride of Formula VII from an acid of Formula VIII). By itself the promoter has little or no catalytic effect in the reaction.

"Cyclization agent" or "cyclization agents" refer to one or more reagents (when used in a combination) capable of promoting a cyclization reaction (e.g., the 4,5-dihydrooxazole formation from the compound of Formula V) via reactions known in the art.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, tetrahydrofuran, methyltetrahydrofuran, diethyl ether, 1,4-dioxane, acetone, ethyl acetate, dimethylformamide, acetonitrile and dimethyl sulfoxide. Representative non-polar solvents include alkanes (pentanes, hexanes, etc.), cycloalkanes (cyclopentane, cyclohexane, etc.), benzene, and toluene. Other solvents are useful in the present disclosure.

Solvents can also be grouped based on their chemical structures, for example, ethers (e.g., diethyl ether, methyl tert-butyl ether, tetrahydrofuran, 2-methyltetrahydrofuran, 1,4-dioxane, etc.), ketones (e.g., acetone, methyl isobutyl ketone, etc.), esters (ethyl acetate, butyl acetate, isobutyl acetate, etc.), aromatic solvents (e.g., benzene, toluene, xylenes, etc.), chlorinated solvents (e.g., dichloromethane, 1,2-dichloroethane, etc.), hydrocarbons (n-heptane, hexanes, cyclohexane, methylcyclohexane, etc.), alcohols (methanol, ethanol, propanol, isopropanol, etc.), or acids (e.g., formic acid, acetic acid, etc.).

"Salt" refers to acid or base salts of the compounds used in the methods of the present disclosure. Salts useful in the present disclosure include, but are not limited to, hemisulfate, sulfate, chloride, bromide, carbonate, nitrate, and acetate salts. A hemisulfate salt refers a compound in which only one of two basic groups is formed a salt with sulfuric acid. A carbonate salt includes a hydrogencarbonate (or bicarbonate) salt. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

III. Methods of Preparing Compounds

The present disclosure includes several methods of preparing the compounds of Formula I.

A. Method of Preparing Compounds of Formula I from Formula III

1. Preparation of Formula I from Formula III

In some embodiments, the present disclosure provides a method for preparing a compound of Formula I:

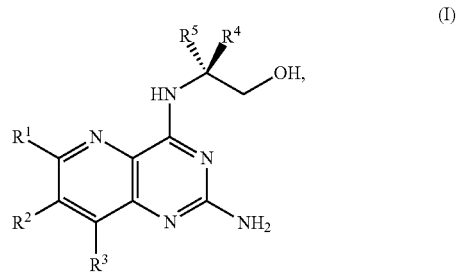

or a salt thereof, the method including:

a) forming a first reaction mixture including a compound of Formula III:

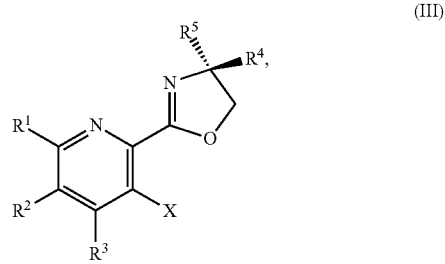

or a salt thereof, a compound having the Formula PG-NHC(=NH)NH$_2$ or a salt thereof, a first base, and a first solvent to form a compound of Formula II:

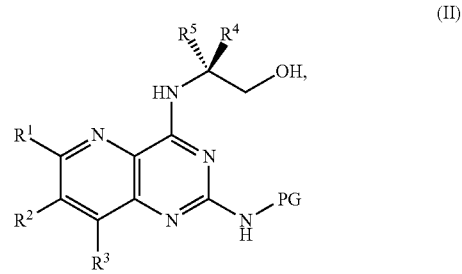

or a salt thereof, and b) forming a second reaction mixture including the compound of Formula II or the salt thereof, a deprotecting agent, and a second solvent to provide the compound of Formula I or the salt thereof, wherein $R^1$, $R^2$, and $R^3$ can each independently be hydrogen, F, Cl, CN, CF$_3$, C$_{1-3}$ alkyl, or C$_{1-3}$ alkoxy; $R^4$ can be hydrogen or methyl; $R^5$ can be C$_{3-6}$ alkyl; X can be F, Cl, Br, I, or OTs; and PG can be an amino protecting group.

In one embodiment, the present disclosure provides a method for preparing a compound of Formula I:

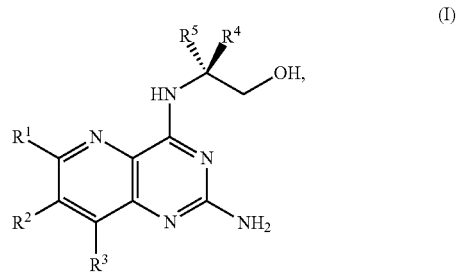

or a salt thereof, the method including:

a) forming a first reaction mixture including a compound of Formula III:

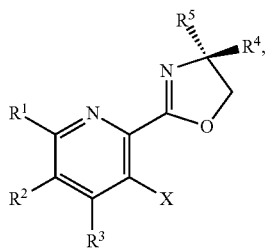

or a salt thereof, a compound having the formula PG-NHC(=NH)NH$_2$ or a salt thereof, a first transition-metal catalyst, a first base, and a first solvent to form a compound of Formula II:

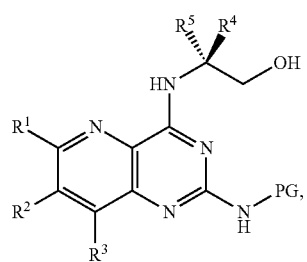

or a salt thereof, and b) forming a second reaction mixture including the compound of Formula II or the salt thereof, a deprotecting agent, and a second solvent to provide the compound of Formula I or the salt thereof, wherein $R^1$, $R^2$, and $R^3$ can each independently be hydrogen, F, Cl, CN, CF$_3$, C$_{1-3}$ alkyl, or C$_{1-3}$ alkoxy; $R^4$ can be hydrogen or methyl; $R^5$ can be C$_{3-6}$ alkyl; X can be F, Cl, Br, I, or OTs; and PG can be an amino protecting group.

In one embodiment, the present disclosure provides a method for preparing a compound of Formula I:

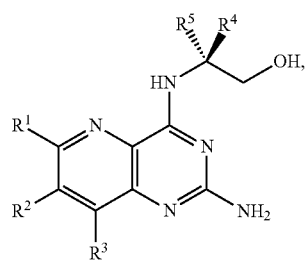

or a salt thereof, the method including:

a) forming a first reaction mixture including a compound of Formula III:

or a salt thereof, a compound having the formula PG-NHC(=NH)NH$_2$ or a salt thereof, a first transition-metal catalyst, a first base, and a first solvent to form a compound of Formula II:

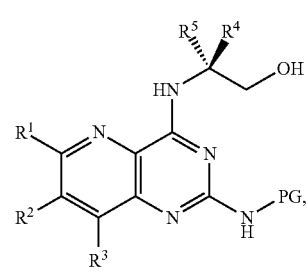

or a salt thereof, and b) forming a second reaction mixture including the compound of Formula II or the salt thereof, a deprotecting agent, and a second solvent to provide the compound of Formula I or the salt thereof, wherein $R^1$, $R^2$, and $R^3$ can each independently be hydrogen, F, Cl, CN, CF$_3$, C$_{1-3}$ alkyl, or C$_{1-3}$ alkoxy; $R^4$ can be hydrogen or methyl; $R^5$ can be C$_{3-6}$ alkyl; X can be Cl, Br, I, or OTs; and PG can be an amino protecting group.

The compound having the formula PG-NHC(=NH)NH$_2$ can be in any suitable form. In some embodiments, the compound having the formula PG-NHC(=NH)NH$_2$ can be in a neutral form. In some embodiments, the compound having the formula PG-NHC(=NH)NH$_2$ can be in a salt form. In some embodiments, the compound having the formula PG-NHC(=NH)NH$_2$ can be a hemisulfate, a sulfate, a chloride, a bromide, a carbonate, a nitrate, or an acetate salt thereof. In some embodiments, the compound having the formula PG-NHC(=NH)NH$_2$ can be of Formula IX:

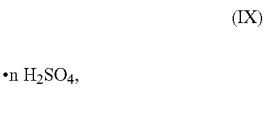

wherein n can be from 0 to 1. In some embodiments, the compound of Formula IX can be a hemisulfate salt wherein n can be ½, a sulfate salt wherein n can be 1, or a combination thereof. In some embodiments, the compound of Formula IX can be a hemisulfate salt wherein n can be ½.

PG can be an amino protecting group. Suitable amino protecting groups include, but are not limited to, a carbobenzyloxy (Cbz) group, a p-methoxybenzyl carbonyl (Moz or MeOZ) group, a tert-Butyloxycarbonyl (BOC) group, a 2-trimethylsilylethyoxymethyl (SEM) group, a 9-fluorenylmethyloxycarbonyl (Fmoc) group, an acetyl (Ac) group, a benzoyl (Bz) group, a benzyl (Bn) group, a carbamate group, a p-methoxybenzyl (PMB) group, a 2,4-dimethoxybenzyl group (DMB), a 1-(2,4-dimethoxyphenyl)ethyl, a 3,4-dimethoxybenzyl (DMPB) group, a p-methoxyphenyl (PMP) group, a tosyl (Ts) group, a Troc (trichloroethyl chloroformate) group, and other sulfonamides (Nosyl & Nps) groups. In some embodiments, PG can be 2,4-dimethoxybenzyl.

In some embodiments, the compound of Formula IX can be of Formula IXa:

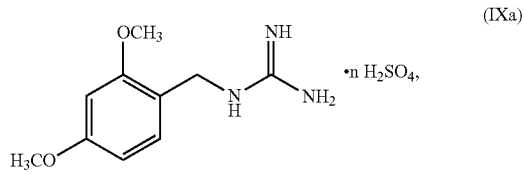 [SMILES: COc1ccc(CNC(=N)N)c(OC)c1]

(IXa)

wherein n can be from 0 to 1. In some embodiments, the compound of Formula IXa can be a hemisulfate salt wherein n can be ½, a sulfate salt wherein n can be 1, or a combination thereof. In some embodiments, the compound of Formula IXa can be a hemisulfate salt having Formula IXb:

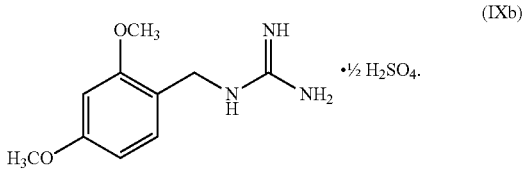 [SMILES: COc1ccc(CNC(=N)N)c(OC)c1]

(IXb)

The first transition-metal catalyst can be a compound that includes one or more transition metals or transition metal cations. Suitable transition metals include, but are not limited to, Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Suitable transition metal cations include, but are not limited to, $Cd^{2+}$, $Co^{2+}$, $Co^+$, $Cr^{2+}$, $Cr^+$, $Cu^+$ (i.e., Cu(I)), $Cu^{2+}$ (i.e., Cu(II)), $Fe^{2+}$, Fe, $Mn^{2+}$, $Mn^+$, $Ni^{2+}$, $Ni^+$, $Pd^{2+}$ (i.e., Pd(II)), and $Zn^{2+}$. In some embodiments, the first transition-metal catalyst includes a copper metal, a copper oxide, a copper (I) salt, a copper (II) salt, or combinations thereof. In some embodiments, the first transition-metal catalyst includes a copper (I) salt. In some embodiments, the first transition-metal catalyst includes a copper (II) salt. In some embodiments, the first transition-metal catalyst can be Cu(I) iodide, Cu(I) bromide, Cu(I) chloride, Cu(I) acetate, Cu(I) carbonate, Cu(I) nitrate, Cu(I) sulfate, Cu(I) phosphate, Cu(I) 3-methylsalicylate, Cu(I) thiophene-2-carboxylate, Cu(I) oxide, Cu(II) iodide, Cu(II) bromide, Cu(II) chloride, Cu(II) acetate, Cu(II) carbonate, Cu(II) nitrate, Cu(II) sulfate, Cu(II) pyrophosphate, Cu(II) phosphate, Cu(II) tartrate, Cu(II) oxide, or combinations thereof. In some embodiments, the first transition-metal catalyst can be Cu(II) iodide, Cu(II) bromide, Cu(II) chloride, Cu(II) acetate, Cu(II) carbonate, Cu(II) nitrate, Cu(II) sulfate, Cu(II) pyrophosphate, Cu(II) phosphate, Cu(II) tartrate, Cu(II) oxide, or combinations thereof. In some embodiments, the first transition-metal catalyst includes Cu(II) acetate. In some embodiments, the first transition-metal catalyst can be Cu(II) acetate.

The first base can be an alkali carbonate, an alkali bicarbonate, an alkali phosphate tribasic, a carboxylate, an amidine-based compound, or combinations thereof. Suitable alkali carbonates include lithium carbonate, sodium carbonate, potassium carbonate, and cesium carbonate. Suitable alkali bicarbonates include lithium bicarbonate, sodium bicarbonate, and potassium bicarbonate. Suitable alkali phosphates tribasic include sodium phosphate tribasic and potassium phosphate tribasic. Suitable carboxylates include, but are not limited to, lithium acetate, sodium acetate, potassium acetate, cesium acetate, potassium trimethylacetate, and tetrabutylphosphonium malonate. Suitable amidine-based compounds include, but are not limited to, 1,8-diazabicyclo[5.4.0]undec-7-ene (DBU) and 1,5-diazabicyclo[4.3.0]non-5-en (DBN). In some embodiments, the first base can be lithium carbonate, sodium carbonate, potassium carbonate, cesium carbonate, lithium bicarbonate, sodium bicarbonate, potassium bicarbonate, sodium phosphate tribasic, potassium phosphate tribasic, potassium acetate, potassium trimethylacetate, tetrabutylphosphonium malonate, 1,8-diazabicyclo[5.4.0]undec-7-ene, 1,5-diazabicyclo[4.3.0]non-5-en, or combinations thereof. In some embodiments, the first base includes potassium phosphate tribasic. In some embodiments, the first base can be potassium phosphate tribasic.

The first solvent can be any suitable polar or non-polar, protic or aprotic solvent. In some embodiments, the first solvent can be acetonitrile, propionitrile, N,N-dimethylacetamide, N-methyl-2-pyrrolidinone, dimethylsulfoxide, tetrahydrofuran, 2-methyltetrahydrofuran, 1,4-dioxane, cyclopentyl methyl ether, isopropanol, 2-methylbutan-2-ol, ethyl acetate, isopropyl acetate, methyl isobutyl ketone, toluene, trifluorotoluene, xylenes, or combinations thereof. In some embodiments, the first solvent includes 2-methyltetrahydrofuran. In some embodiments, the first solvent includes acetonitrile. In some embodiments, the first solvent includes 2-methyltetrahydrofuran and acetonitrile. In some embodiments, the first solvent can be 2-methyltetrahydrofuran and acetonitrile.

In some embodiments, the first reaction mixture further includes a first ligand. In some embodiments, the first ligand can be an amino acid, a polypyridyl ligand, or a tertiary amine. Suitable amino acids include naturally occurring and synthetic amino acids, as well as amino acid analogs that function in a manner similar to the naturally occurring amino acids. Suitable polypyridyl ligands include, but are not limited to, 2,2'-bipyridine, 1,10-phenanthroline, 4,4'-dimethyl-2,2'-bipyridine, 6,6'-dimethyl-2,2'-bipyridine, 4,4'-di-tert-butyl-2,2-bipyridine, 2,2'-bipyridine-4,4'-dicarboxylic acid and 2,2':6'2"-terpyridine. Suitable tertiary amines include, but are not limited to, triethylamine, tri-n-butylamine, N,N-diisopropylethylamine, N-methylpyrrolidine, N-methylmorpholine, 1,4-diazabicylo[2.2.2]-octane, and N,N,N',N'-tetramethylethylenediamine. In some embodiments, the first ligand can be arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, α-(methylamino)isobutyric acid, (4-methyl-1-piperazinyl)acetic acid, N-acetyl-cysteine, 2,2'-bipyridine, 1,10-phenanthroline, 4,4'-dimethyl-2,2'-bipyridine, 6,6'-dimethyl-2,2'-bipyridine, 4,4'-di-tert-butyl-2,2-bipyridine, 2,2'-bipyridine-4,4'-dicarboxylic acid, N,N,N',N'-tetramethylethylenediamine, or combinations thereof. In some embodiments, the first ligand includes cysteine, selenocysteine, N-acetyl-cysteine, or homocysteine. In some embodiments, the first ligand includes cysteine. In some embodiments, the first ligand includes L-cysteine. In some embodiments, the first ligand can be cysteine, selenocysteine, N-acetyl-cysteine, or homocysteine. In some embodiments, the first ligand can be cysteine. In some embodiments, the first ligand can be L-cysteine.

In general, the first reaction (i.e., step a)) can be performed at an ambient to an elevated temperature. For example, the first reaction mixture can be at a temperature of from 30° C. to 110° C. or heated to reflux. In some embodiments, the first reaction mixture can be at a temperature of from 40° C. to 100° C., from 50° C. to 100° C., from 50° C. to 90° C., from 60° C. to 90° C., from 70° C. to 90° C., or about 80° C. In some embodiments, the first reaction mixture can be at a temperature of from 55° C. to a reflux temperature. In some embodiments, the first reaction mixture can be heated to reflux.

Once the first reaction is complete, the first transition metal catalyst can be removed from the reaction mixture by a second ligand, for example, ethylenediaminetetraacetic acid (EDTA) or EDTA disodium salt. In some embodiments, upon completion of the first reaction, the first transition metal catalyst can be removed from the first reaction mixture using a second ligand. In some embodiments, the second ligand includes ethylenediaminetetraacetic acid or a salt thereof. In some embodiments, upon completion of the first reaction, the first transition metal catalyst can be removed from the first reaction mixture using ethylenediaminetetraacetic acid or a salt thereof. In some embodiments, upon completion of the first reaction, Cu(II) can be removed from the first reaction mixture using ethylenediaminetetraacetic acid disodium salt.

The compound of Formula II can be deprotected by various methods known in the art to provide the compound of Formula I or a salt thereof. When PG is 2,4-dimethoxybenzyl, the compound of Formula II can be deprotected by various methods, for example, under acidic, reductive (hydrogenolysis), or oxidative conditions to provide the compound of Formula I or the salt thereof.

In some embodiments, the deprotecting agent can be an acid. In some embodiments, the acid can be trifluoroacetic acid, trichloroacetic acid, acetic acid, formic acid, hydrochloric acid, sulfuric acid, phosphoric acid, or combinations thereof. In some embodiments, the acid includes trifluoroacetic acid. In some embodiments, the acid can be trifluoroacetic acid.

In some embodiments, the deprotecting agent can be a hydrogen source and the second reaction mixture further includes a second transition-metal catalyst. In some embodiments, the hydrogen source can be ammonium formate, formic acid, hydrogen gas, or combinations thereof. In some embodiments, the hydrogen source includes hydrogen gas. In some embodiments, the hydrogen source includes ammonium formate. In some embodiments, the hydrogen source includes formic acid. In some embodiments, the second transition-metal catalyst can be palladium hydroxide on carbon, palladium on carbon, or platinum oxide. In some embodiments, the second transition-metal catalyst includes palladium hydroxide on carbon. In some embodiments, the second transition-metal catalyst includes palladium on carbon. In some embodiments, the second transition-metal catalyst includes platinum oxide. In some embodiments, the deprotecting agent can be hydrogen gas and the second reaction mixture further includes palladium hydroxide on carbon, palladium on carbon, or platinum oxide. In some embodiments, the deprotecting agent includes ammonium formate and the second reaction mixture further includes palladium hydroxide on carbon, palladium on carbon, or platinum oxide. In some embodiments, the deprotecting agent includes formic acid and the second reaction mixture further includes palladium hydroxide on carbon, palladium on carbon, or platinum oxide. In some embodiments, the deprotecting agent includes formic acid and the second solvent includes formic acid.

In some embodiments, the hydrogen source can be hydrogen gas. In some embodiments, the hydrogen source can be ammonium formate. In some embodiments, the hydrogen source can be formic acid. In some embodiments, the second transition-metal catalyst can be palladium hydroxide on carbon. In some embodiments, the second transition-metal catalyst can be palladium on carbon. In some embodiments, the second transition-metal catalyst can be platinum oxide. In some embodiments, the deprotecting agent can be ammonium formate and the second reaction mixture further includes palladium hydroxide on carbon, palladium on carbon, or platinum oxide. In some embodiments, the deprotecting agent can be formic acid and the second reaction mixture further includes palladium hydroxide on carbon, palladium on carbon, or platinum oxide. In some embodiments, the deprotecting agent can be formic acid and the second solvent can be formic acid.

In some embodiments, the deprotecting agent can be boron tribromide, 2,3-dichloro-5,6-dicyano-1,4-benzoquinone, ceric ammonium nitrate, or a combination of trifluoromethanesulfonic acid and 1,3-dimethoxybenzene.

The second solvent can be any suitable polar or non-polar, protic or aprotic solvent. In some embodiments, the second solvent can be ethyl acetate, isopropyl acetate, butyl acetate, isobutyl acetate, tetrahydrofuran, 2-methyltetrahydrofuran, 1,4-dioxane, toluene, benzene, xylenes, trifluorotoluene, anisole, dimethylsulfoxide, propionitrile, butyronitrile, dichloromethane, 1,2-dichloroethane, chlorobenzene, methanol, ethanol, isopropanol, water, formic acid, acetic acid, trichloroacetic acid, or combinations thereof. In some embodiments, the second solvent includes formic acid. In some embodiments, the second solvent includes dichloromethane. In some embodiments, the second solvent can be formic acid. In some embodiments, the second solvent can be dichloromethane.

In general, the second reaction (i.e., step b)) can be performed at any suitable temperature, for example, at a temperature of from −10° C. to 80° C. In some embodiments, the second reaction mixture can be at a temperature of from −10° C. to 80° C., from 0° C. to 50° C., from 10° C. to 50° C., from 20° C. to 50° C., or from 20° C. to 40° C. In some embodiments, the second reaction mixture can be at a temperature of from 20° C. to 40° C. In some embodiments, the second reaction mixture can be at a temperature of about 30° C. In some embodiments, the second reaction mixture can be at a temperature of about 40° C. In some embodiments, the second solvent includes dichloromethane, and the second reaction mixture can be heated to reflux. In some embodiments, the second solvent can be dichloromethane, and the second reaction mixture can be heated to reflux.

2. Preparation of Formula III from Formula IV

In some embodiments, the method further includes prior to step a):
  a1) forming a third reaction mixture including a compound of Formula IV:

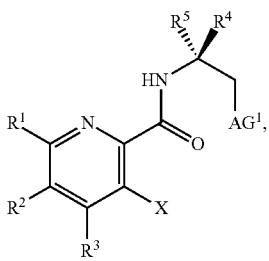

(IV)

or a salt thereof, a second base, and a third solvent to form the compound of Formula III, or the salt thereof, wherein $AG^1$ is Cl, Br, $OSO_3H$, $OSO_3^-$, OMs, OTs, or OTf.

In some embodiments, the method further includes prior to step a):

a1) forming a third reaction mixture including a compound of Formula IV:

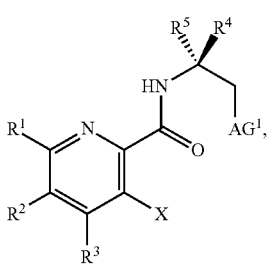

(IV)

or a salt thereof, a second base, and a third solvent to form the compound of Formula III, or the salt thereof, wherein $AG^1$ is Cl, Br, OMs, OTs, or OTf.

The second base can be a tertiary amine, an aromatic amine base, an alkali carbonate, an alkali bicarbonate, an alkali phosphate tribasic, an alkali hydroxide, or combinations thereof.

Suitable tertiary amines include, but are not limited to, triethylamine, tri-n-butylamine, N,N-diisopropylethylamine, N-methylpyrrolidine, and N-methylmorpholine. Suitable aromatic amine bases include, but are not limited to, pyridine, lutidines (e.g., 2,6-lutidine, 3,5-lutidine, and 2,3-lutidine), collidines (e.g., 2,3,4-collidine, 2,3,5-collidine, 2,3,6-collidine, 2,4,5-collidine, 2,4,6-collidine, and 3,4,5-collidine), and 4-dimethylaminopyridine. Suitable alkali carbonates include lithium carbonate, sodium carbonate, potassium carbonate, and cesium carbonate. Suitable alkali bicarbonates include lithium bicarbonate, sodium bicarbonate, and potassium bicarbonate. Suitable alkali phosphates tribasic include sodium phosphate tribasic and potassium phosphate tribasic. Suitable alkali hydroxides includes lithium hydroxide, sodium hydroxide, potassium hydroxide, and cesium hydroxide. In some embodiments, the second base can be triethylamine, tri-n-butylamine, N,N-diisopropylethylamine, N-methylpyrrolidine, N-methylmorpholine, pyridine, 2,6-lutidine, 2,4,6-collidine, 4-dimethylaminopyridine, sodium carbonate, potassium carbonate, cesium carbonate, sodium bicarbonate, potassium bicarbonate, potassium phosphate tribasic, sodium hydroxide, potassium hydroxide, or combinations thereof. The second base can be in an aqueous solution. In some embodiments, the second base includes an aqueous solution of sodium hydroxide. In some embodiments, the second base can be an aqueous solution of sodium hydroxide.

The third solvent can be any suitable polar aprotic solvent or non-polar solvent. In some embodiments, the third solvent can be tetrahydrofuran, 2-methyltetrahydrofuran, methyl tert-butyl ether, 1,4-dioxane, dichloromethane, 1,2-dichloroethane, benzene, toluene, xylenes, or combinations thereof. In some embodiments, the third solvent includes 2-methyltetrahydrofuran. In some embodiments, the third solvent can be 2-methyltetrahydrofuran.

The third reaction (i.e., step a1)) can be performed with or without a phase-transfer agent. In some embodiments, the third reaction mixture further includes a phase-transfer agent. In some embodiments, the phase-transfer agent can be a quaternary ammonium salt. In some embodiments, the quaternary ammonium salt can be tetra-n-butylammonium hydrogensulfate, tetra-n-butylammonium bromide, tetra-n-butylammonium chloride, benzyltributylammonium bromide, benzyltriethylammonium chloride, benzalkonium chloride, or dodecylethyldimethylammonium bromide. In some embodiments, the quaternary ammonium salt includes tetra-n-butylammonium hydrogensulfate. In some embodiments, the quaternary ammonium salt can be tetra-n-butylammonium hydrogensulfate. In some embodiments, the phase-transfer agent can be tetra-n-butylammonium hydrogensulfate.

In general, the third reaction (i.e., step a1)) can be performed at any suitable temperature. For example, the third reaction mixture can be at a temperature of from 0° C. to 80° C. In some embodiments, the third reaction mixture can be at a temperature of from 0° C. to 80° C., from 10° C. to 60° C., from 10° C. to 50° C., from 15° C. to 50° C., from 20° C. to 50° C., or about 35° C. In some embodiments, the third reaction mixture can be at a temperature of from 15° C. to 50° C. In some embodiments, the third reaction mixture can be at a temperature of about 35° C.

In some embodiments, the compound of Formula IV has the formula:

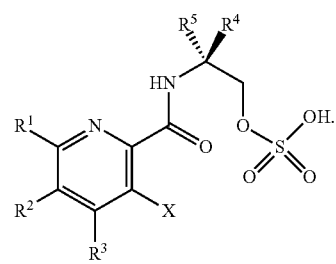

In some embodiments, the compound of Formula IV has the formula:

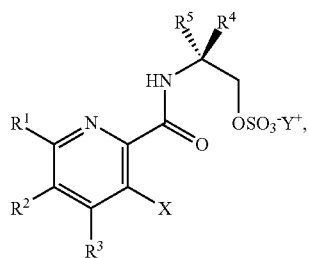

wherein Y⁺ is a metal ion M⁺, or ammonium salt HA⁺. Any suitable metal ion M⁺ can be used, including, but not limited to, lithium, sodium, potassium, calcium, or cesium. Any suitable ammonium salt HA⁺ can be used, including, but not limited to trimethylammonium, triethylammonium, or dicyclohexylammonium. In some embodiments, Y⁺ is sodium. In some embodiments, Y⁺ is $HNMe_3^+$. In some embodiments, the compound of Formula IV has the formula:

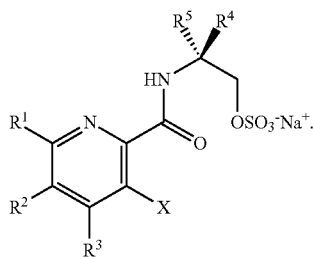

In some embodiments, the third solvent includes acetonitrile, propionitrile, butyronitrile, N,N-dimethylacetamide, N-methyl-2-pyrrolidinone, dimethylsulfoxide, 2-methyltetrahydrofuran, tetrahydrofuran, 1,4-dioxane, cyclopentyl methyl ether, toluene, trifluorotoluene, xylenes, benzonitrile, dichloromethane, 1,2-dichloroethane, chlorobenzene, methanol, ethanol, n-butanol, 1-hexanol, 2-propanol, 2-methyl-2-butanol. In some embodiments, the third solvent includes 2-methyl-2-butanol. In some embodiments, the third solvent can be 2-methyl-2-butanol.

In some embodiments, the third reaction mixture further includes an additive. Suitable additives include, but are not limited to, thionyl chloride, oxalyl chloride, phosphorus(V) oxychloride, phosphorus(V) pentachloride, methanesulfonyl chloride, para-toluenesulfonic acid, methanesulfonic anhydride, trifluoromethanesulfonic anhydride, water, acetic anhydride, 4-dimethylamino pyridine, or a tetra-butylammonium salt (e.g., hydrogen sulfate, chloride, bromide, or iodide salt). In some embodiments, the additive is absent.

3. Preparation of Formula IV from Formula V

In some embodiments, the method further includes prior to step a1):

a2) forming a fourth reaction mixture including a compound of Formula V:

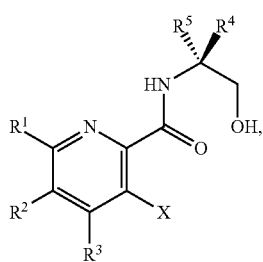

or a salt thereof, a first activating agent, and a fourth solvent to form the compound of Formula IV:

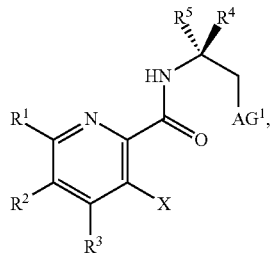

or the salt thereof.

In some embodiments, AG¹ can be Cl; and the first activating agent can be a first chlorinating agent. The first chlorinating agent can be any suitable chlorinating agent capable of converting the —OH group of Formula V to a corresponding —Cl group (i.e., AG¹ can be Cl in Formula IV). In some embodiments, the first chlorinating agent can be oxalyl chloride, thionyl chloride, phosphorus oxychloride, phosphorus pentachloride, or chlorosulfonic acid. In some embodiments, the first chlorinating agent includes oxalyl chloride. In some embodiments, the first chlorinating agent includes thionyl chloride. In some embodiments, the first chlorinating agent can be oxalyl chloride. In some embodiments, the first chlorinating agent is thionyl chloride.

In some embodiments, AG¹ can be Br; and the first activating agent can be a brominating agent. The brominating agent can be any suitable brominating agent capable of converting the —OH group of Formula V to a corresponding —Br group (i.e., AG¹ can be Br in Formula IV). In some embodiments, the brominating agent can be triphenylphosphine dibromide or tribromoisocyanuric acid.

In some embodiments, AG¹ can be OMs, OTs, or OTf; and the first activating agent can be methanesulfonyl chloride, methanesulfonic anhydride, para-toluenesulfonyl chloride, para-toluenesulfonic acid, para-toluenesulfonic anhydride, or trifluoromethanesulfonic anhydride. In some embodiments, AG¹ can be OMs; and the first activating agent can be methanesulfonyl chloride or methanesulfonic anhydride. In some embodiments, AG¹ can be OMs; and the first activating agent includes methanesulfonyl chloride. In some embodiments, AG¹ can be OTs; and the first activating agent includes para-toluenesulfonyl chloride. In some embodiments, AG¹ can be OTf; and the first activating agent includes trifluoromethanesulfonic anhydride. In some embodiments, AG¹ can be OTs; and the first activating agent can be para-toluenesulfonyl chloride. In some embodiments, AG¹ can be OTf; and the first activating agent can be trifluoromethanesulfonic anhydride.

The fourth solvent can be any suitable polar aprotic solvent and/or non-polar solvents. In some embodiments, the fourth solvent can be tetrahydrofuran, 2-methyltetrahydrofuran, methyl tert-butyl ether, 1,4-dioxane, dichloromethane, 1,2-dichloroethane, benzene, toluene, xylenes, or combinations thereof. In some embodiments, the fourth solvent includes 2-methyltetrahydrofuran. In some embodiments, the fourth solvent can be 2-methyltetrahydrofuran.

In general, when the first activating agent can be the first chlorinating agent, the fourth reaction (i.e., step a2)) can be performed at any suitable temperature. For example, the fourth reaction mixture can be at a temperature of from 0° C. to 80° C. In some embodiments, the fourth reaction mixture can be at a temperature of from 0° C. to 80° C., from 10° C. to 80° C., from 20° C. to 70° C., from 30° C. to 60° C., from 40° C. to 60° C., from 15° C. to 50° C., or about 50° C. In some embodiments, the fourth reaction mixture can be at a temperature of from 15° C. to 50° C. In some embodiments, the fourth reaction mixture can be at a temperature of about 50° C.

In some embodiments, the method further includes prior to step a1):

a2) forming a fourth reaction mixture including a compound of Formula V:

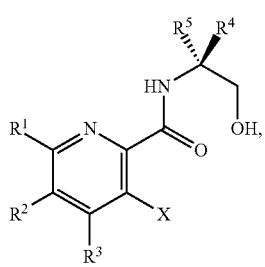

or a salt thereof, a first activating agent, and a fourth solvent to form a compound of Formula IV-2:

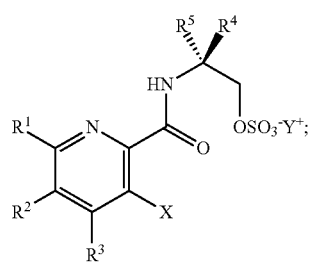

and treating the compound of Formula IV-2 or the salt thereof with an ion-exchange reagent in the fourth solvent to form the compound of Formula IV:

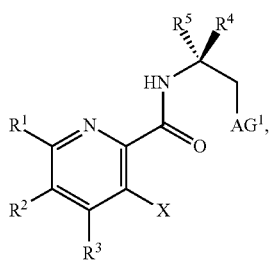

or the salt thereof, wherein $AG^1$ is $OSO_3H$ or $OSO_3^-$.

In some embodiments, $AG^1$ can be $OS_3H$ or $OSO_3^-$; and the first activating agent can be a sulfonating agent. The sulfonating agent can be any suitable sulfonating agent capable of converting the —OH group of Formula V to a corresponding —$OS_3H$ or $OSO_3^-$. In some embodiments, the sulfonating agent can be sulfur trioxide, chlorosulfonic acid, sulfur dioxide, or a sulfur trioxide complex. In some embodiments, the sulfur trioxide complex can be sulfur trioxide complexed with dioxane, pyridine, polyvinylpyridine, trimethylamine, triethylamine, dimethylaniline, thioxane, bis(2-chloroethyl)ether, 2-methylpyridine, quinoline, N,N'-dimethylformamide, tri-n-propylamine, tri-n-butylamine, N-alkylmorpholines (methyl, ethyl, n-butyl), pentamethylguanidine, 4'-methylacetanilide, N,N'-diethyl-4-toluenesulfonamide, tetramethylurea, tetramethyladipamide, N,N'-dimethylurethane, formylmorpholide, N,N'-dimethylbenzamide, dimethylcyanamide, n-propylpiperidine, n-isoamylpiperidine, N-benzylpiperidine, trimethylphosphine oxide, tetrahydrofuran, diethylsulfide, anthraquinone, benzanthrone, benzonapthone, or 2,6-dimethyl-γ-pyrone. In some embodiments, the sulfonating agent includes a sulfur trioxide trimethylamine complex. In some embodiments, the sulfonating agent can be a sulfur trioxide trimethylamine complex.

In some embodiments of the compound of Formula IV-2, wherein $Y^+$ is hydrogen, pyridinium, trimethylammonium, triethylammonium, methylpyridinium, quinolinium, tri-n-propylammonium, tri-n-butylammonium, a morpholinium optionally substituted with methyl, ethyl, or n-butyl, petamethylguanidinium, N,N'-dimethylethylenediammonium, dimethylcyanamide, or benzylpiperidinium. In some embodiments of Formula IV-2, $Y^+$ is trimethylammonium.

In some embodiments, the ion exchange reagent can bean ion exchange resin (e.g., Ion exchanger I, II, III, IV, or V; Amberlite® IR-120, e.g., $H^+$ form, $Na^+$ form, IRA-67, IRA-402, IRA-410, 15; and Dowex®, e.g., 50 WX 4, 50W-XZ8, 1-X8); a mineral acid (e.g., hydrochloric acid, or hydrobromic acid); a carboxylate (e.g., disodium sebacate, sodium hexanoate, sodium 2-ethylhexanoate, calcium 2-ethylhexanoate, or potassium 2-ethylhexanoate); a hydroxide or an alkoxide (e.g., lithium tert-butoxide, sodium tert-pentoxide, potassium tert-pentoxide, potassium tert-butoxide, sodium tert-butoxide, sodium hydroxide, potassium hydroxide, or cesium hydroxide); an amine (e.g., dicyclohexylamine, or N-methylcyclohexylamine); or others (e.g., sodium tetrafluoroborate, potassium phosphate dibasic, calcium sulfate, or ferrocyanic acid). In some embodiments, the ion exchange reagent includes sodium 2-ethylhexanoate. In some embodiments, the ion exchange reagent can be sodium 2-ethylhexanoate.

In some embodiments, the compound of Formula IV is in an acid form having the formula:

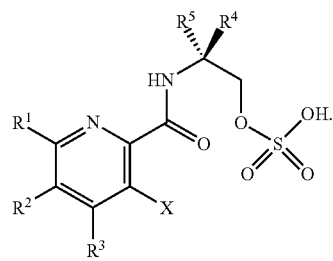

In some embodiments, the compound of Formula IV is in a salt form having the formula:

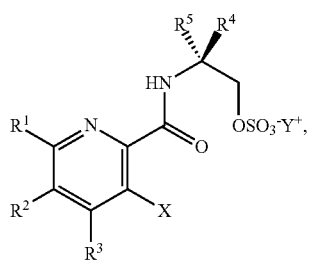

wherein Y⁺ is a metal ion M⁺, or ammonium salt HA⁺. Any suitable metal ion M⁺ can be used, such as, but not limited to, lithium, sodium, potassium, calcium, or cesium. Any suitable ammonium salt HA⁺ can be used, such as, but not limited to, trimethylammonium, triethylammonium, or dicyclohexylammonium. In some embodiments, Y⁺ is sodium. In some embodiments, the compound of Formula IV has the formula:

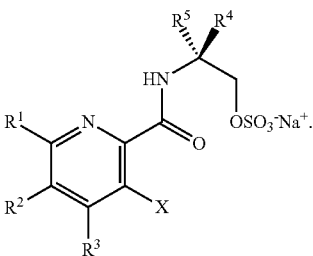

In some embodiments, the fourth solvent can be any suitable polar aprotic solvent and/or non-polar solvents. In some embodiments, the fourth solvent can be acetonitrile, propionitrile, butyronitrile, N,N-dimethylacetamide, N-methyl-2-pyrrolidinone, dimethylsulfoxide, 2-methyltetrahydrofuran, tetrahydrofuran, 1,4-dioxane, cyclopentyl methyl ether, isopropyl acetate, ethyl acetate, butyl acetate, isobutyl acetate, acetone, methyl isobutyl ketone, toluene, trifluorotoluene, xylenes, benzonitrile, dichloromethane, 1,2-dichloroethane, chlorobenzene, or combinations thereof. In some embodiments, the fourth solvent includes acetonitrile, 2-methyltetrahydrofuran, or a combination thereof. In some embodiments, the fourth solvent includes acetonitrile and 2-methyltetrahydrofuran. In some embodiments, the fourth solvent can be acetonitrile, 2-methyltetrahydrofuran, or a combination thereof. In some embodiments, the fourth solvent can be acetonitrile and 2-methyltetrahydrofuran.

In general, the sulfonating and ion-exchange steps of the fourth reaction (i.e., step a2) can be performed at any suitable temperature. For example, the sulfonating reaction mixture can be at a temperature of from 0° C. to 100° C. In some embodiments, the sulfonating reaction mixture can be at a temperature of from 20° C. to 100° C., from 30° C. to 100° C., from 40° C. to 100° C., from 40° C. to 100° C., from 50° C. to 100° C., from 60° C. to 100° C., from 60° C. to 90° C., or from 60° C. to 80° C. In some embodiments, the sulfonating reaction mixture can be at a temperature of from 60° C. to 80° C. For example, the ion-exchange reaction mixture can be at a temperature of from 0° C. to 50° C. In some embodiments, the ion-exchange reaction mixture can be at a temperature of from 10° C. to 40° C., from 15° C. to 40° C., from 15° C. to 30° C., or about 20° C. In some embodiments, the ion-exchange reaction mixture can be at a temperature of about 20° C.

4. Preparation of Formula III from Formula V

In some embodiments, the method further includes prior to step a):

a1-2) forming a fifth reaction mixture including a compound of Formula V:

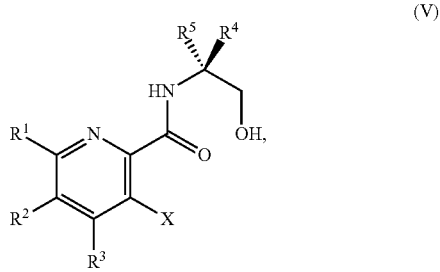

or a salt thereof, one or more cyclizing agents, and a fifth solvent to form the compound of Formula III or the salt thereof.

The one or more cyclizing agents can be any suitable reagents capable of forming the 4,5-dihydrooxazole moiety from the compound of Formula V via cyclization. The one or more cyclizing agents can be a reagent in combination with triphenylphosphine, for example, 2,3-dichloro-5,6-dicyano-p-benzoquinone (DDQ)/triphenylphosphine, diethyl azodicarboxylate (DEAD)/triphenylphosphine, diisopropyl azodicarboxylate (DIAD)/triphenylphosphine, or carbon tetrabromide/triphenylphosphine. The one or more cyclizing agents can be a dehydrating reagent used alone, for example, methyl N-(triethylammoniosulfonyl)-carbamate (also known as Burgess reagent). The one or more cyclizing agents can be diethylaminosulfur trifluoride (DAST) that mediates the cyclization to form the 4,5-dihydrooxazole moiety. In some embodiments, the one or more cyclizing agents are a combination of 2,3-dichloro-5,6-dicyano-p-benzoquinone and triphenylphosphine, a combination of diethyl azodicarboxylate and triphenylphosphine, a combination of diisopropyl azodicarboxylate and triphenylphosphine, a combination of carbon tetrabromide and triphenylphosphine, methyl N-(triethylammoniosulfonyl)-carbamate, or diethylaminosulfur trifluoride.

The fifth solvent can be any suitable polar aprotic solvent and/or non-polar solvent. In some embodiments, the fifth solvent can be tetrahydrofuran, 2-methyltetrahydrofuran, methyl tert-butyl ether, 1,4-dioxane, dichloromethane, 1,2-dichloroethane, benzene, toluene, xylenes, or combinations thereof. In some embodiments, the fifth solvent includes 2-methyltetrahydrofuran.

In some embodiments, the fifth solvent can be 2-methyltetrahydrofuran.

5. Preparation of Formula V from Formula VII and Formula VI

In some embodiments, the method further includes prior to step a) or a1-2):

a3) forming a sixth reaction mixture including a compound of Formula VII:

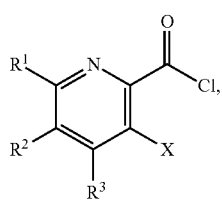

(VII)

or a salt thereof, a compound of Formula VI:

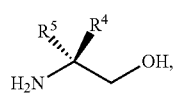

(VI)

or a salt thereof, a third base, and a sixth solvent to form the compound of Formula V or the salt thereof.

The compound of Formula VI can be in any suitable form. In some embodiments, the compound of Formula VI can be in a neutral form. In some embodiments, the compound of Formula VI can be in a salt form. In some embodiments, the compound of Formula VI can be a tosylate salt thereof.

The third base can be a tertiary amine, an aromatic amine base, an alkali carbonate, an alkali bicarbonate, an alkali phosphate tribasic, an alkali hydroxide, or combinations thereof. Suitable tertiary amines include, but are not limited to, triethylamine, tri-n-butylamine, N,N-diisopropylethylamine, N-methylpyrrolidine, and N-methylmorpholine. Suitable aromatic amine bases include, but are not limited to, pyridine, lutidines (e.g., 2,6-lutidine, 3,5-lutidine, and 2,3-lutidine), collidines (e.g., 2,3,4-collidine, 2,3,5-collidine, 2,3,6-collidine, 2,4,5-collidine, 2,4,6-collidine, and 3,4,5-collidine), and 4-dimethylaminopyridine. Suitable alkali carbonates include lithium carbonate, sodium carbonate, potassium carbonate, and cesium carbonate. Suitable alkali bicarbonates include lithium bicarbonate, sodium bicarbonate, and potassium bicarbonate. Suitable alkali phosphates tribasic include sodium phosphate tribasic and potassium phosphate tribasic. Suitable alkali hydroxides include lithium hydroxide, sodium hydroxide, potassium hydroxide, and cesium hydroxide. In some embodiments, the third base can be triethylamine, tri-n-butylamine, N,N-diisopropylethylamine, N-methylpyrrolidine, N-methylmorpholine, pyridine, 2,6-lutidine, 2,4,6-collidine, 4-dimethylaminopyridine, sodium carbonate, potassium carbonate, cesium carbonate, sodium bicarbonate, potassium bicarbonate, potassium phosphate tribasic, sodium hydroxide, potassium hydroxide, or combinations thereof. In some embodiments, the third base can be in an aqueous solution. In some embodiments, the third base includes potassium carbonate. In some embodiments, the third base includes an aqueous solution of potassium carbonate. In some embodiments, the third base can be potassium carbonate. In some embodiments, the third base can be an aqueous solution of potassium carbonate.

The sixth solvent can be any suitable polar aprotic solvent and/or non-polar solvent. In some embodiments, the sixth solvent further includes water. In those embodiments, the sixth reaction (i.e., step a3)) can be a biphasic reaction. In some embodiments, the sixth solvent can be tetrahydrofuran, 2-methyltetrahydrofuran, methyl tert-butyl ether, 1,4-dioxane, dichloromethane, 1,2-dichloroethane, benzene, toluene, xylenes, water, or combinations thereof. In some embodiments, the sixth solvent includes 2-methyltetrahydrofuran. In some embodiments, the sixth solvent includes 2-methyltetrahydrofuran and water. In some embodiments, the sixth solvent can be 2-methyltetrahydrofuran. In some embodiments, the sixth solvent can be 2-methyltetrahydrofuran and water.

In general, the sixth reaction (i.e., step a3)) can be performed at any suitable temperature. For example, the fourth reaction mixture can be at a temperature of from 0° C. to 60° C. In some embodiments, the fourth reaction mixture can be at a temperature of from 0° C. to 60° C., from 10° C. to 50° C., from 10° C. to 40° C., from 20° C. to 40° C., from 20° C. to 30° C., or about 20° C. In some embodiments, the third reaction mixture can be at a temperature of from 20° C. to 30° C. In some embodiments, the third reaction mixture can be at a temperature of about 20° C.

6. Preparation of Formula VII from Formula VIII

In some embodiments, the method further includes prior to step a3):

a4) forming a seventh reaction mixture including a compound of Formula VIII:

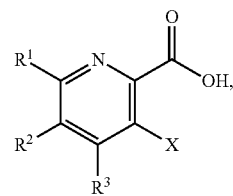

(VIII)

or a salt thereof, a second chlorinating agent, a promoter, and a seventh solvent to form the compound of Formula VII or the salt thereof.

The second chlorinating agent can be any suitable chlorinating agent capable of converting the —C(O)OH group of Formula VIII to the —C(O)Cl group of Formula VII. In some embodiments, the second chlorinating agent can be oxalyl chloride, thionyl chloride, phosphorus oxychloride, phosphorus pentachloride, or (chloromethylene)dimethyliminium chloride. In some embodiments, the second chlorinating agent includes oxalyl chloride. In some embodiments, the second chlorinating agent includes thionyl chloride. In some embodiments, the second chlorinating agent can be oxalyl chloride. In some embodiments, the second chlorinating agent can be thionyl chloride.

In some embodiments, the promoter can be N,N-dimethylformamide, N,N-dimethylacetamide, or dichloromethylene-dimethyliminium chloride. In some embodiments, the promoter includes N,N-dimethylformamide. In some embodiments, the promoter can be N,N-dimethylformamide.

The seventh solvent can be any suitable polar aprotic solvent and/or non-polar solvent. In some embodiments, the seventh solvent can be tetrahydrofuran, 2-methyltetrahydrofuran, methyl tert-butyl ether, 1,4-dioxane, dichloromethane, 1,2-dichloroethane, benzene, toluene, xylenes, or combinations thereof. In some embodiments, the seventh solvent includes 2-methyltetrahydrofuran. In some embodiments, the seventh solvent can be 2-methyltetrahydrofuran.

In general, the seventh reaction (i.e., step a4)) can be performed at any suitable temperature. For example, the seventh reaction mixture can be at a temperature of from 0° C. to 60° C. In some embodiments, the seventh reaction mixture can be at a temperature of from 0° C. to 60° C., from 10° C. to 50° C., from 10° C. to 40° C., from 20° C. to 40° C., from 20° C. to 30° C., or about 20° C. In some embodiments, the seventh reaction mixture can be at a temperature of from 20° C. to 30° C. In some embodiments, the seventh reaction mixture can be at a temperature of about 20° C.

7. Preparation of Formula V from Formula VIII and Formula VI

In some embodiments, the method further includes prior to step a2) or a1-2):

a3-1) forming an eighth reaction mixture including a compound of Formula VIII:

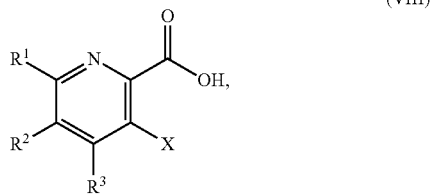

(VIII)

or a salt thereof, a compound of Formula VI:

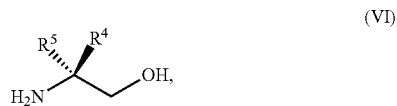

(VI)

or a salt thereof, a second activating agent, a fourth base, and an eighth solvent to form the compound of Formula V or the salt thereof.

The compound of Formula VI can be in any suitable form. In some embodiments, the compound of Formula VI can be in a neutral form. In some embodiments, the compound of Formula VI can be in a salt form. In some embodiments, the compound of Formula VI can be a tosylate salt thereof.

The second activating agent can be any peptide coupling reagent capable of activating an acid group (e.g., the acid group of Formula III), thereby reacting with an amine (e.g., the compound of Formula VI) to form an amide bond (e.g., the amide group of formula V). The peptide coupling reagents include isobutyl chloroformate, 1,1'-carbonyldiimidazole (CDI), dicyclohexylcarbodiimide (DCC), diisopropylcarbodiimide (DIC), 1-ethyl-3-(3-dimethylaminopropyl) carbodiimide (EDCI), O-(benzotriazol-1-yl)-N,N,N',N'-tetramethyluronium hexafluorophosphate (HBTU), 0-(7-azabenzotriazol-1-yl)-N,N,N',N'-tetramethyluronium hexafluorophosphate (HATU), hydroxybenzotriazole (HOBt), and 1-hydroxy-7-azabenzotriazole (HOAt). In some embodiments, the second activating agent can be isobutyl chloroformate or 1,1'-carbonyldiimidazole.

The fourth base can be a tertiary amine, an aromatic amine base, or a combination thereof. Suitable tertiary amines include, but are not limited to, triethylamine, tri-n-butylamine, N,N-diisopropylethylamine, N-methylpyrrolidine, and N-methylmorpholine. Suitable aromatic amine bases include, but are not limited to, pyridine, lutidines (e.g., 2,6-lutidine, 3,5-lutidine, and 2,3-lutidine), collidines (e.g., 2,3,4-collidine, 2,3,5-collidine, 2,3,6-collidine, 2,4,5-collidine, 2,4,6-collidine, and 3,4,5-collidine), and 4-dimethylaminopyridine. In some embodiments, the fourth base can be triethylamine, tri-n-butylamine, N,N-diisopropylethylamine, N-methylpyrrolidine, N-methylmorpholine, pyridine, 2,6-lutidine, 2,4,6-collidine, 4-dimethylaminopyridine, or combinations thereof. In some embodiments, the fourth base includes N,N-diisopropylethylamine. In some embodiments, the fourth base can be N,N-diisopropylethylamine.

The eighth solvent can be any suitable polar aprotic solvent and/or non-polar solvent. In some embodiments, the eighth solvent can be N,N-dimethylformamide, N,N-dimethylacetamide, N-methyl-2-pyrrolidinone, dimethyl sulfoxide, acetonitrile, ethyl acetate, tetrahydrofuran, 2-methyltetrahydrofuran, methyl tert-butyl ether, 1,4-dioxane, dichloromethane, 1,2-dichloroethane, benzene, toluene, xylenes, or combinations thereof. In some embodiments, the eighth solvent includes N,N-dimethylformamide. In some embodiments, the eighth solvent includes 2-methyltetrahydrofuran. In some embodiments, the eighth solvent includes N,N-dimethylformamide and 2-methyltetrahydrofuran. In some embodiments, the eighth solvent can be N,N-dimethylformamide. In some embodiments, the eighth solvent can be 2-methyltetrahydrofuran. In some embodiments, the eighth solvent can be N,N-dimethylformamide and 2-methyltetrahydrofuran.

The compound of Formula I in a neutral form can be generated by contacting the salt of the compound of Formula I with a base. In some embodiments, the method further includes c) forming a ninth reaction mixture including the salt of the compound of Formula I, a fifth base, and a ninth solvent to provide the compound of Formula I in a neutral form.

The fifth base can be an alkali carbonate or alkali hydroxide. Suitable alkali carbonates include sodium carbonate and potassium carbonate. Suitable alkali hydroxides include sodium hydroxide and potassium hydroxide. In some embodiments, the fifth base can be sodium hydroxide or potassium hydroxide. In some embodiments, the fifth base includes sodium hydroxide. In some embodiments, the fifth base can be in an aqueous solution. In some embodiments, the fifth base includes an aqueous solution of sodium hydroxide. In some embodiments, the fifth base can be sodium hydroxide. In some embodiments, the fifth base can be an aqueous solution of sodium hydroxide.

The ninth solvent can be any suitable alcohol solvent, ester solvent, and/or water. In some embodiments, the ninth solvent can be methanol, ethanol, isopropanol, ethyl acetate, isopropyl acetate, water, or combinations thereof. In some embodiments, the ninth solvent includes i) ethanol and water or ii) ethyl acetate and water. In some embodiments, the ninth solvent includes ethanol and water. In some embodiments, the ninth solvent includes ethyl acetate and water. In some embodiments, the ninth solvent can be i) ethanol and water or ii) ethyl acetate and water. In some embodiments, the ninth solvent can be ethanol and water. In some embodiments, the ninth solvent can be ethyl acetate and water.

When the ninth solvent includes an ester solvent (e.g., ethyl acetate or isopropyl acetate), upon completion of the reaction, the reaction mixture after partition can be further treated with an aqueous solution of sodium bicarbonate.

In general, the ninth reaction (i.e., step c)) can be performed at any suitable temperature. For example, the ninth reaction mixture can be at a temperature of from 0° C. to 60° C. In some embodiments, the ninth reaction mixture can be at a temperature of from 0° C. to 60° C., from 10° C. to 60° C., from 10° C. to 50° C., or from 20° C. to 40° C. In some embodiments, the ninth reaction mixture can be at a temperature of from 20° C. to 40° C. In some embodiments, the ninth reaction mixture can be at a temperature of about 20°

C. In some embodiments, the ninth reaction mixture can be at a temperature of about 40° C. 8. Preparation of Formula II from Formula III In some embodiments, the present disclosure provides a method for preparing a compound of Formula II:

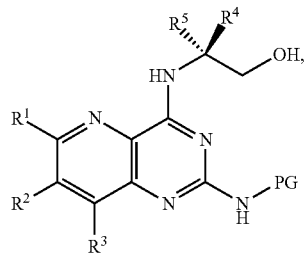
(II)

or a salt thereof, the method including:
a) forming a first reaction mixture including a compound of Formula III:

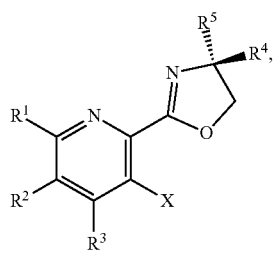
(III)

or a salt thereof, a compound having the Formula PG-NHC(=NH)NH$_2$ or a salt thereof, and a first solvent to form the compound of Formula II:

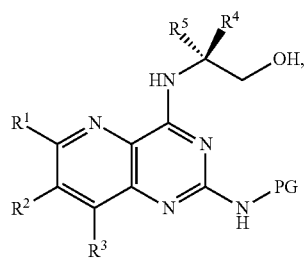
(II)

or the salt thereof,
wherein R$^1$, R$^2$, and R$^3$ can each independently be hydrogen, F, Cl, CN, CF$_3$, C$_{1-3}$ alkyl, or C$_{1-3}$ alkoxy; R$^4$ can be hydrogen or methyl; R$^5$ can be C$_{3-6}$ alkyl; X can be F; and PG can be an amino protecting group.

The compound having the Formula PG-NHC(=NH)NH$_2$ can be in any suitable form. In some embodiments, the compound having the Formula PG-NHC(=NH)NH$_2$ can be in a neutral form. In some embodiments, the compound having the Formula PG-NHC(=NH)NH$_2$ can be in a salt form. In some embodiments, the compound having the Formula PG-NHC(=NH)NH$_2$ can be a hemisulfate, a sulfate, a chloride, a bromide, a carbonate, a nitrate, or an acetate salt thereof. In some embodiments, the compound having the Formula PG-NHC(=NH)NH$_2$ can be of Formula IXc:

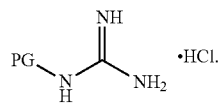
(IXc)

In some embodiments, PG can be an amino protecting group. Suitable amino protecting groups include, but are not limited to, tert-butyloxycarbonyl, 9-fluorenylmethoxycarbonyl, benzyloxylcarbonyl, allyloxycarbonyl, acetyl, trifluoroacetyl, 2,2,5,7,8-Pentamethyl-chromane-6-sulfonyl chloride, para-toluenesulfonyl, 4-methoxy-2,3,6-trimethylbenzenesulfonyl, 2,4-dimethoxybenzyl, 4-methoxybenzyl, or 2-chlorobenzyl. In some embodiments, PG can be 2,4-dimethoxybenzyl.

In some embodiments, the first reaction mixture further comprises a first base. The first base can be a carbonate (e.g., cesium carbonate, lithium carbonate, sodium carbonate, potassium carbonate, rubidium carbonate, magnesium carbonate, calcium carbonate, strontium carbonate, barium carbonate, nickel carbonate, zinc carbonate, silver carbonate, or ammonium carbonate), a metal oxide (e.g., magnesium oxide), a hydroxide (e.g., potassium hydroxide, sodium hydroxide, lithium hydroxide, cesium hydroxide, barium hydroxide, ammonium hydroxide, or tetra-n-butylammonium hydroxide), an alkoxide (e.g., lithium phenoxide), a silanolate (e.g., potassium trimethylsilanolate, sodium trimethylsilanolate, lithium silanolate, or sodium dimethylphenylsilanolate), a phosphate (e.g. potassium phosphate tribasic, calcium phosphate tribasic, magnesium phosphate tribasic, sodium phosphate tribasic, sodium phosphate dibasic, or potassium phosphate dibasic), a hydride (e.g., sodium hydride or potassium hydride), an amine (e.g., N,N-diisopropylethyl amine, triethylamine, N,N,N',N'-tetramethylethylenediamine, 1,4-diazabicyclo[2.2.2]octane, 1-azabicyclo[2.2.2]octane, 1,8-diaza[5.4.0] undec-7-ene, 1,5-diazabicyclo[4.3.0]non-5-ene pyridine, 1,1,3,3-tetramethylguanidine, 4-methylmorpholine, 2-tert-buty-1,1,3,3-tetramethylguanidine, 1,3,4,6,7,8-hexahydro-1-methyl-2H-pyrimido[1,2-a]pyrimidine, 1,8-bis(dimethylamino) naphthalene, or N,N,N'N'-tetramethyl-1,8-napthalenediamine), an amide (e.g., lithium bis (trimethylsilyl)amide, sodium bis(trimethylsilyl)amide, potassium bis(trimethylsilyl)amide, lithium diisopropyl amide, sodium diisopropyl amide, or lithium dicyclohexylamide), an alkylmetal (e.g., n-butyllithium, tert-butyllithium, methyllithium, phenyllithium, lithium naphthalenide, or sodium naphthalenide), an alkoxide (e.g., magnesium tert-butoxide, potassium tert-butoxide, sodium tert-butoxide, sodium tert-pentoxide, or potassium tert-pentoxide), a phosphorane (e.g., tert-butylimino-tri(pyrrolidino) phosphorene, 2-tert-butylimino-tri(pyrrolidino)phosphorene, or 2-tert-butylimino-2-diethylamino-1,3-dimethylperhydro-1,3,2-diazaphorene), or combinations thereof. In some embodiments, the first base includes cesium carbonate. In some embodiments, the first base can be cesium carbonate.

The first solvent can be any suitable polar or non-polar, protic or aprotic solvent. The first solvent can be a polar aprotic solvent (e.g., N,N'-dimethylformamide, N,N'-dimethylacetamide, N-methylpyrrolidinone, dimethylsulfoxide, sulfolane, acetonitrile, propionitrile, butyronitrile, nitromethane, or nitroethane), an ether (tetrahydrofuran, 2-methyltetrahydrofuran, 1,4-dioxane, dibutyl ether, methyl tert-butyl ether, or cyclopentyl methyl ether), an alcohol (e.g., methanol, ethanol, n-butanol, 2-butanol, tert-butanol, 2-methylbutan-2-ol, 2,2,2-trifluoroethanol, or hexafluoro-2-propanol), a ketone (e.g, methyl isobutyl ketone, or methyl ethyl ketone), an ester (e.g., isopropyl acetate, or n-butylacetate), a chlorinate solvent (e.g., 1,2-dichloroethane, chlorobenzene, or trifluorotoluene), an aromatic solvent (e.g., toluene, xylenes, or anisole), water, or combinations thereof. In some embodiments, the first solvent includes 2-methyltetrahydrofuran. In some embodiments, the first solvent can be 2-methyltetrahydrofuran.

In some embodiments, the first reaction mixture further includes an additive. The additive can be 4-dimethylaminopyridine, 4-piperidinopyridine, 4-pyrolidinopyridine, imidazole, N-methylimidazole, or 9-azajulolidine. In some embodiments, the additive is absent.

In general, the first reaction (i.e., step a)) can be performed at an ambient to an elevated temperature. For example, the first reaction mixture can be at a temperature of from 30° C. to 150° C. In some embodiments, the first reaction mixture can be at a temperature of from 40° C. to 100° C., from 40° C. to 90° C., from 40° C. to 80° C., or about 80° C. In some embodiments, the first reaction mixture can be at a temperature of from 40° C. to 80° C. In some embodiments, the first reaction mixture can be at a temperature of about 80° C.

In some embodiments, the method further includes prior to step a):

a1) forming a third reaction mixture including a compound of Formula IV:

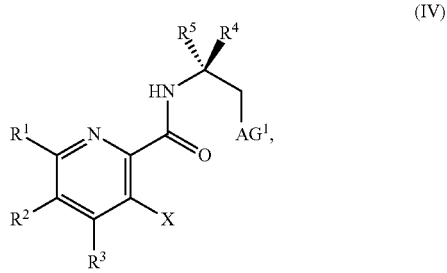

or a salt thereof, a second base, and a third solvent to form the compound of Formula III, or the salt thereof, wherein X is F; and $AG^1$ is Cl.

The second base can be an aprotic amine (e.g., triethylamine, tri-n-butylamine, N,N'-diisopropylethylamine, N-methylpyrrolidine, or N-methylmorpholine), an aromatic amine (e.g., pyridine, 2,6-lutidine, or collidine), an inorganic base (e.g., sodium carbonate, sodium bicarbonate, potassium hydroxide, potassium carbonate, cesium carbonate, or potassium phosphate). The second base can be in an aqueous solution. In some embodiments, the second base includes an aqueous solution of sodium hydroxide. In some embodiments, the second base can be an aqueous solution of sodium hydroxide.

The third solvent can be any suitable polar aprotic solvent or non-polar solvent. The third solvent can be an ether (e.g., tetrahydrofuran, 2-methyltetrahydrofuran, methyl tert-butyl ether, or 1,4-dioxane), a halogenated solvent (e.g., dichloromethane, or 1,2-dichloroethane), an aromatic solvent (benzene, toluene, or xylenes), water, or combinations thereof. In some embodiments, the third solvent includes 2-methyltetrahydrofuran. In some embodiments, the third solvent includes 2-methyltetrahydrofuran and water. In some embodiments, the third solvent can be 2-methyltetrahydrofuran. In some embodiments, the third solvent can be 2-methyltetrahydrofuran and water.

The third reaction (i.e., step a1)) can be performed with or without a phase-transfer agent. In some embodiments, the third reaction mixture further includes a phase-transfer agent. The phase-transfer agent can be an ammonium salt (e.g., tetra-n-butylammonium bisulfate, tetra-n-butylammonium chloride, tetra-n-butylammonium bromide, benzalkonium chloride, or dodecylethyldimethylammonium bromide). In some embodiments, the phase-transfer agent includes tetra-n-butylammonium bisulfate. In some embodiments, the phase-transfer agent can be tetra-n-butylammonium bisulfate.

In general, the third reaction (i.e., step a1)) can be performed at any suitable temperature. For example, the third reaction mixture can be at a temperature of from 20° C. to 80° C. In some embodiments, the third reaction mixture can be at a temperature of from 20° C. to 70° C., from 20° C. to 60° C., from 20° C. to 50° C., or from 20° C. to 40° C. In some embodiments, the third reaction mixture can be at a temperature of from 20° C. to 40° C.

In some embodiments, the method further includes prior to step a1):

a2) forming a fourth reaction mixture including a compound of Formula V:

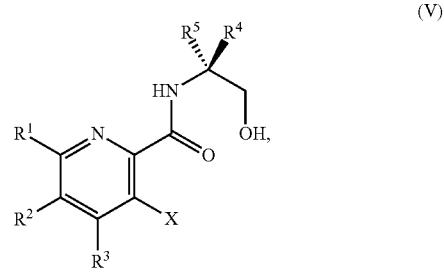

or a salt thereof, a first activating agent, and a fourth solvent to form the compound of Formula IV:

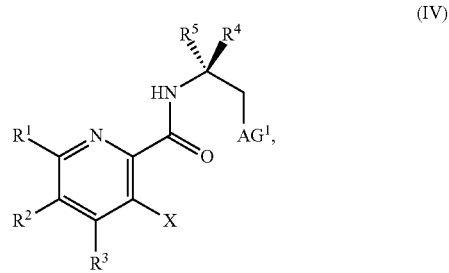

or the salt thereof, wherein X is F; and $AG^1$ is Cl.

In some embodiments, the first activating agent can be a first chlorinating agent. The first chlorinating agent can be any suitable chlorinating agent capable of converting the —OH group of Formula V to a corresponding —Cl group (i.e., $AG^1$ can be Cl in Formula IV). In some embodiments, the first chlorinating agent can be thionyl chloride, oxalyl chloride, phosphorus(V) oxychloride, phosphorus(V) pentachloride, methanesulfonyl chloride, para-toluenesulfonic acid, methanesulfonic anhydride, trifluoromethanesulfonic anhydride, or chlorosulfonic acid. In some embodiments, the first chlorinating agent includes oxalyl chloride. In some embodiments, the first chlorinating agent includes thionyl chloride. In some embodiments, the first chlorinating agent can be oxalyl chloride. In some embodiments, the first chlorinating agent can be thionyl chloride.

The fourth solvent can be any suitable polar aprotic solvent and/or non-polar solvents. The fourth solvent can be an ether (e.g., tetrahydrofuran, 2-methyltetrahydrofuran, methyl tert-butyl ether, or 1,4-dioxane), a halogenated solvent (e.g, dichloromethane, or 1,2-dichloroethane), an aromatic solvent (e.g., benzene, toluene, or xylenes), or combinations thereof. In some embodiments, the fourth solvent includes 2-methyltetrahydrofuran. In some embodiments, the fourth solvent can be 2-methyltetrahydrofuran.

In general, the fourth reaction (i.e., step a2)) can be performed at any suitable temperature. For example, the fourth reaction mixture can be at a temperature of from 0° C. to 80° C. In some embodiments, the fourth reaction mixture can be at a temperature of from 20° C. to 80° C., from 30° C. to 80° C., from 40° C. to 80° C., from 50° C. to 80° C., or from 50° C. to 70° C. In some embodiments, the fourth reaction mixture can be at a temperature of from 50° C. to 70° C.

In some embodiments, the method further includes prior to step a2) or a1-2):

a3) forming a sixth reaction mixture including a compound of Formula VII:

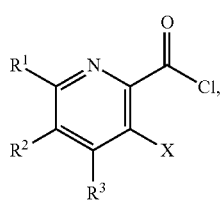

(VII)

or a salt thereof, a compound of Formula VI:

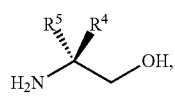

(VI)

or a salt thereof, a third base, and a sixth solvent to form the compound of Formula V or the salt thereof, wherein X is F.

The compound of Formula VI can be in any suitable form. In some embodiments, the compound of Formula VI can be in a neutral form. In some embodiments, the compound of Formula VI can be in a salt form. In some embodiments, the compound of Formula VI can be a tosylate salt thereof.

The third base can be a tertiary amine (e.g., triethylamine, tri-n-butylamine, N,N-diisopropylethylamine, N-methylpyrrolidine, or N-methylmorpholine), an aromatic amine (e.g., pyridine, 2,6-lutidine, or collidine), or an inorganic base (e.g., sodium carbonate, sodium bicarbonate, sodium hydroxide, potassium hydroxide, potassium carbonate, cesium carbonate, or potassium phosphate tribasic). In some embodiments, the third base can be in an aqueous solution. In some embodiments, the third base includes potassium carbonate. In some embodiments, the third base includes an aqueous solution of potassium carbonate. In some embodiments, the third base can be potassium carbonate. In some embodiments, the third base can be an aqueous solution of potassium carbonate.

The sixth solvent can be any suitable polar aprotic solvent and/or non-polar solvent. In some embodiments, the sixth solvent further includes water. In some embodiments, the sixth reaction (i.e., step a3)) can be a biphasic reaction. In some embodiments, the sixth solvent can be an ether (e.g., tetrahydrofuran, 2-methyltetrahydrofuran, methyl tert-butyl ether, or 1,4-dioxane), a halogenated solvent (e.g., dichloromethane, or 1,2-dichloroethane), an aromatic solvent (e.g., benzene, toluene, or xylenes), water, or combinations thereof. In some embodiments, the sixth solvent includes 2-methyltetrahydrofuran. In some embodiments, the sixth solvent includes 2-methyltetrahydrofuran and water. In some embodiments, the sixth solvent can be 2-methyltetrahydrofuran. In some embodiments, the sixth solvent can be 2-methyltetrahydrofuran and water.

In general, the sixth reaction (i.e., step a3)) can be performed at any suitable temperature. For example, the sixth reaction mixture can be at a temperature of from 0° C. to 60° C. In some embodiments, the sixth reaction mixture can be at a temperature of from 0° C. to 60° C., from 10° C. to 50° C., from 10° C. to 40° C., from 20° C. to 40° C., from 20° C. to 30° C., or about 20° C. In some embodiments, the sixth reaction mixture can be at a temperature of from 20° C. to 30° C. In some embodiments, the sixth reaction mixture can be at a temperature of about 20° C.

In some embodiments, the method further includes prior to step a3):

a4) forming a seventh reaction mixture including a compound of Formula VIII:

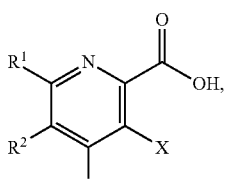

(VIII)

or a salt thereof, a second chlorinating agent, a promoter, and a seventh solvent to form the compound of Formula VII or the salt thereof, wherein X is F.

The second chlorinating agent can be any suitable chlorinating agent capable of converting the —C(O)OH group of Formula VIII to the —C(O)Cl group of Formula VII. In some embodiments, the second chlorinating agent can be oxalyl chloride, thionyl chloride, phosphorus(V) oxychloride, phosphorus(V) pentachloride, (chloromethylene)dimethyliminium chloride, 1,1'-carbonyldiimidazole, or isobutyl chloroformate. In some embodiments, the second chlorinating agent includes oxalyl chloride. In some embodiments, the second chlorinating agent includes thionyl chloride. In some embodiments, the second chlorinating agent can be oxalyl chloride. In some embodiments, the second chlorinating agent can be thionyl chloride.

In some embodiments, the promoter can be N,N-dimethylformamide or dichloromethylene-dimethyliminium chloride. In some embodiments, the promoter includes N,N-dimethylformamide. In some embodiments, the promoter can be N,N-dimethylformamide.

The seventh solvent can be any suitable polar aprotic solvent and/or non-polar solvent. In some embodiments, the seventh solvent can be an ether (e.g., tetrahydrofuran, 2-methyltetrahydrofuran, methyl tert-butyl ether, or 1,4-dioxane), a halogenated solvent (e.g., dichloromethane, or 1,2-dichloroethane), an aromatic solvent (e.g., benzene, toluene, or xylenes), water, or combinations thereof. In some embodiments, the seventh solvent includes 2-methyltetrahydrofuran. In some embodiments, the seventh solvent can be 2-methyltetrahydrofuran.

In general, the seventh reaction (i.e., step a4)) can be performed at any suitable temperature. For example, the seventh reaction mixture can be at a temperature of from 0° C. to 60° C. In some embodiments, the seventh reaction mixture can be at a temperature of from 0° C. to 60° C., from 10° C. to 50° C., from 10° C. to 40° C., from 20° C. to 40° C., from 20° C. to 30° C., or about 20° C. In some embodiments, the seventh reaction mixture can be at a temperature of from 20° C. to 30° C. In some embodiments, the seventh reaction mixture can be at a temperature of about 20° C.

The compound of Formula II can be deprotected by various methods known in the art to provide the compound of Formula I or a salt thereof. In some embodiments, when PG is 2,4-dimethoxybenzyl, the compound of Formula II can be deprotected by various methods, for example, under acidic, reductive (hydrogenolysis), or oxidative conditions to provide the compound of Formula I or the salt thereof, as described herein.

9. Embodiments of Formula I, II, III, IV, V, VII, and VIII

In some embodiments of any one of formulae I, II, III, IV, V, VII, and VIII, $R^2$ can be Cl, F, CN, $CF_3$, $C_{1-3}$ alkyl, or $C_{1-3}$ alkoxy; and $R^1$ and $R^3$ can each independently be hydrogen, F, Cl, CN, $CF_3$, $C_{1-3}$ alkyl, or $C_{1-3}$ alkoxy. The $C_{1-3}$ alkyl can be methyl, ethyl, n-propyl, or isopropyl. The $C_{1-3}$ alkoxy can be methoxy, ethoxy, n-propoxy, or isopropoxy. In some embodiments of any one of formulae I, II, III, IV, V, VII, and VIII, $R^2$ can be Cl, F, CN, $CF_3$, methyl, ethyl, n-propyl, isopropyl, methoxy, ethoxy, n-propoxy, or isopropoxy; and $R^1$ and $R^3$ can each independently be hydrogen, F, Cl, CN, $CF_3$, methyl, ethyl, n-propyl, isopropyl, methoxy, ethoxy, n-propoxy, or isopropoxy. In some embodiments of any one of formulae I, II, III, IV, V, VII, and VIII, $R^2$ can be Cl, F, CN, $CF_3$, methyl, ethyl, n-propyl, isopropyl, methoxy, ethoxy, n-propoxy, or isopropoxy; and $R^1$ and $R^3$ can each be hydrogen. In some embodiments of any one of formulae I, II, III, IV, V, VII, and VIII, $R^2$ can be F, and $R^1$ and $R^3$ can each be hydrogen.

In some embodiments of any one of formulae I, II, III, IV, V, and VI, $R^4$ can be hydrogen. In some embodiments of any one of formulae I, II, III, IV, V, and VI, $R^4$ can be methyl.

In some embodiments of any one of formulae I, II, III, IV, V, and VI, $R^5$ can be $C_{3-6}$ alkyl. In some embodiments of any one of formulae I, II, III, IV, V, and VI, $R^5$ can be n-propyl, isopropyl, n-butyl, isobutyl, sec-butyl, tert-butyl, n-pentyl, isopentyl, or hexyl. In some embodiments of any one of formulae I, II, III, IV, V, and VI, $R^5$ can be n-butyl.

In some embodiments of any one of formulae I, II, III, IV, V, and VI, $R^4$ can be methyl; and $R^5$ can be $C_{3-6}$ alkyl. In some embodiments of any one of formulae I, II, III, IV, V, and VI, $R^4$ can be methyl; and $R^5$ can be n-propyl, isopropyl, n-butyl, isobutyl, sec-butyl, tert-butyl, n-pentyl, isopentyl, or hexyl. In some embodiments of any one of formulae I, II, III, IV, V, and VI, $R^4$ can be methyl; and $R^5$ can be n-butyl.

In some embodiments of any one of formulae III, IV, V, VII, and VIII, X can be F, Br, I, or OTs. In some embodiments of any one of formulae III, IV, V, VII, and VIII, X can be Br. In some embodiments of any one of formulae III, IV, V, VII, and VIII, X can be F.

In some embodiments, the compound of Formula I can be of Formula Ia:

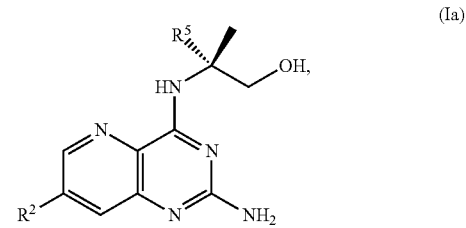

(Ia)

or a salt thereof, wherein $R^2$ and $R^5$ are defined and described herein.

In some embodiments, the compound of Formula I can be of Formula Ib:

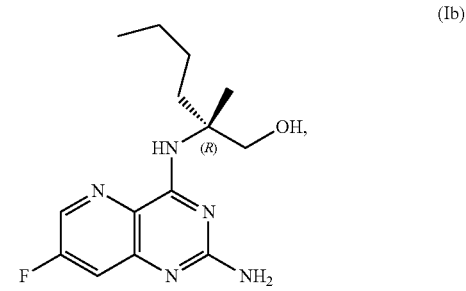

(Ib)

or a salt thereof.

In some embodiments, the compound of Formula II can be of Formula IIa:

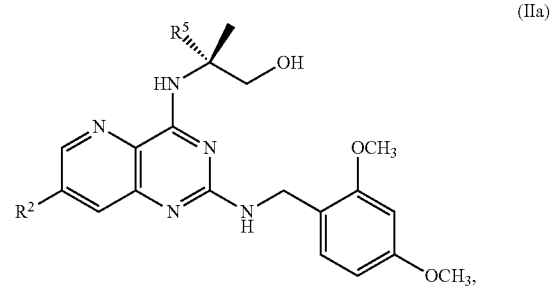

(IIa)

or a salt thereof, wherein $R^2$ and $R^5$ are defined and described herein.

In some embodiments, the compound of Formula II can be of Formula IIb:

(IIb)

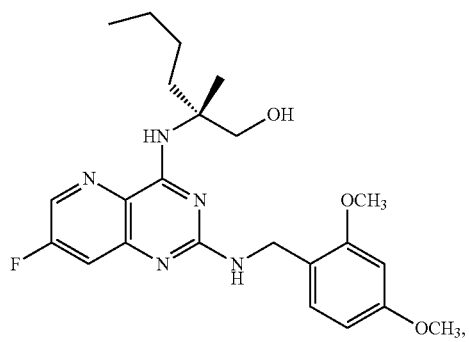

or a salt thereof.

In some embodiments, the compound of Formula III can be of Formula IIIa:

(IIIa)

or a salt thereof, wherein $R^2$ and $R^5$ are defined and described herein.

In some embodiments, the compound of Formula III can be of Formula IIIa-1:

(IIIa-1)

or a salt thereof, wherein $R^2$ and $R^5$ are defined and described herein.

In some embodiments, the compound of Formula III can be of Formula IIIb:

(IIIb)

or a salt thereof.

In some embodiments, the compound of Formula III can be of Formula IIIb-1:

(IIIb-1)

or a salt thereof.

In some embodiments, the compound of Formula IV can be of Formula IV-1:

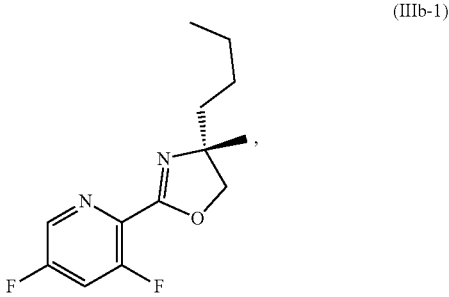 [SMILES: CCCC[C@]1(C)COC(c2ncc(F)cc2F)=N1]

or a salt thereof, wherein $R^1$, $R^2$, $R^3$, $R^4$, $R^5$, and X are defined and described herein.

In some embodiments, the compound of formula IV-1 can be of Formula IVa-1:

(IVa-1)

or a salt thereof, wherein $R^2$ and $R^5$ are defined and described herein.

In some embodiments, the compound of formula IV-1 can be of Formula IVa-2:

(IVa-2)

or a salt thereof, wherein $R^2$ and $R^5$ are defined and described herein.

In some embodiments, the compound of Formula IV-1 can be of Formula IVb-1:

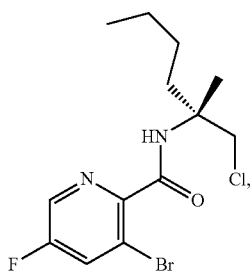

(IVb-1)

or a salt thereof.

In some embodiments, the compound of Formula IV-1 can be of Formula IVb-2:

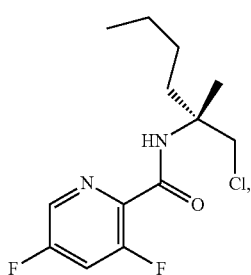

(IVb-2)

or a salt thereof.

In some embodiments, the compound of Formula V can be of Formula Va:

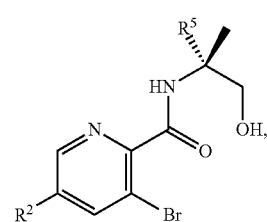

(Va)

or a salt thereof, wherein $R^2$ and $R^5$ are defined and described herein.

In some embodiments, the compound of Formula V can be of Formula Va-1:

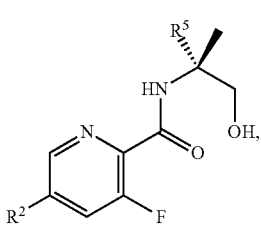

(Va-1)

or a salt thereof, wherein $R^2$ and $R^5$ are defined and described herein.

In some embodiments, the compound of Formula V can be of Formula Vb:

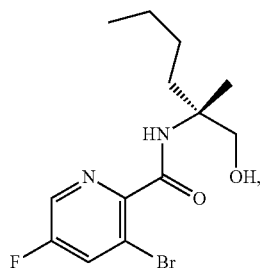

(Vb)

or a salt thereof.

In some embodiments, the compound of Formula V can be of Formula Vb-1:

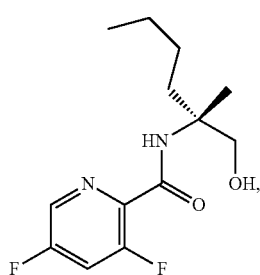

(Vb-1)

or a salt thereof.

In some embodiments, the compound of Formula VI can be of Formula VIa:

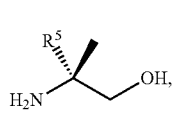

(VIa)

or a salt thereof, wherein $R^5$ are defined and described herein.

In some embodiments, the compound of Formula VI can be of Formula VIb:

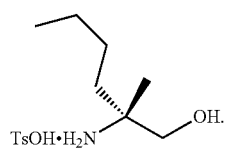

(VIb)

In some embodiments, the compound of Formula VII can be of Formula VIIa:

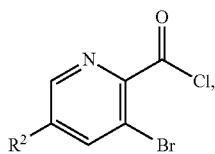
(VIIa)

or a salt thereof, wherein $R^2$ are defined and described herein.

In some embodiments, the compound of Formula VII can be of Formula VIIa-1:

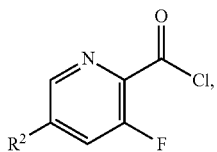
(VIIa-1)

or a salt thereof, wherein $R^2$ are defined and described herein.

In some embodiments, the compound of Formula VII can be of Formula VIIb:

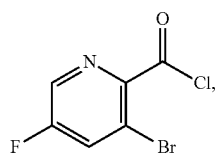
(VIIb)

or a salt thereof.

In some embodiments, the compound of Formula VII can be of Formula VIIb-1:

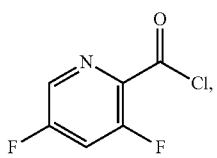
(VIIb-1)

or a salt thereof.

In some embodiments, the compound of Formula VIII can be of Formula VIIIa:

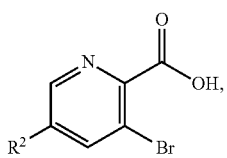
(VIIIa)

or a salt thereof, wherein $R^2$ is defined and described herein.

In some embodiments, the compound of Formula VIII can be of Formula VIIIa-1:

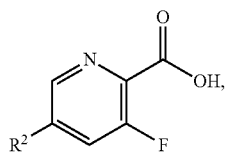
(VIIIa-1)

or a salt thereof, wherein $R^2$ is defined and described herein.

In some embodiments, the compound of Formula VIII can be of Formula VIIIb:

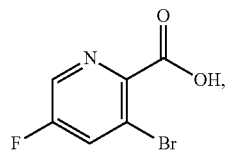
(VIIIb)

or a salt thereof.

In some embodiments, the compound of Formula VIII can be of Formula VIIIb-1:

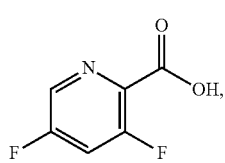
(VIIIb-1)

or a salt thereof.

In some embodiments, the present disclosure provides a method for preparing a compound of Formula Ib:

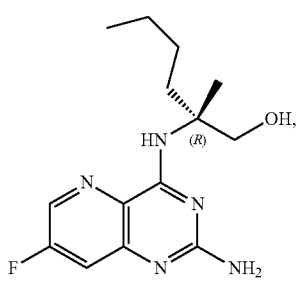
(Ib)

or a salt thereof, the method including:

a4) forming a seventh reaction mixture including a compound of Formula VIIIb:

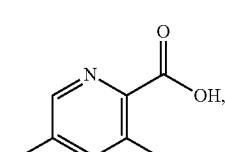
(VIIIb)

or a salt thereof, oxalyl chloride, N,N-dimethylformamide, 2-methyltetrahydrofuran to form a compound of Formula VIIb:

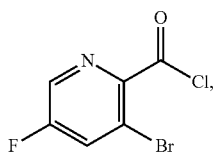
(VIIb)

or a salt thereof, a3) forming a sixth reaction mixture including the compound of Formula VIIb or the salt thereof, a compound of Formula VIb:

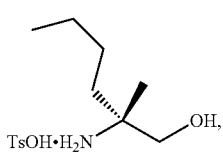
(VIb)

aqueous potassium carbonate, 2-methyltetrahydrofuran, and water to form a compound of Formula Vb:

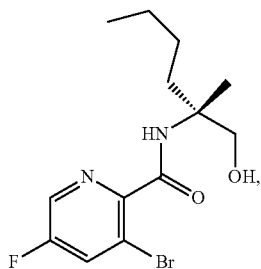
(Vb)

or a salt thereof, a2) forming a fourth reaction mixture including the compound of Formula Vb or the salt thereof, thionyl chloride, and 2-methyltetrahydrofuran to form a compound of Formula IVb-1:

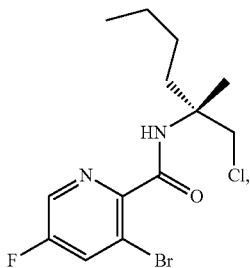
(IVb-1)

or a salt thereof, a1) forming a third reaction mixture including the compound of Formula IVb-1 or the salt thereof, aqueous sodium hydroxide, tetra-n-butylammonium hydrogensulfate, and 2-methyltetrahydrofuran to form a compound of Formula IIIb:

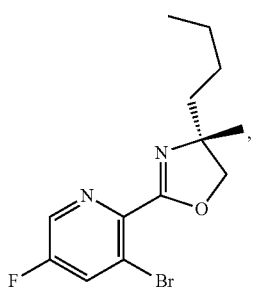
(IIIb)

or a salt thereof, a) forming a first reaction mixture including the compound of Formula IIIb or the salt thereof, a compound of Formula IXa wherein n is from 0 to 1:

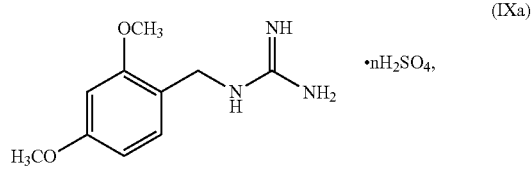 [SMILES: COc1ccc(CNC(=N)N)c(OC)c1]
(IXa)

Cu(II) acetate, potassium phosphate tribasic, cysteine, 2-methyltetrahydrofuran, and acetonitrile to form a compound of Formula IIb:

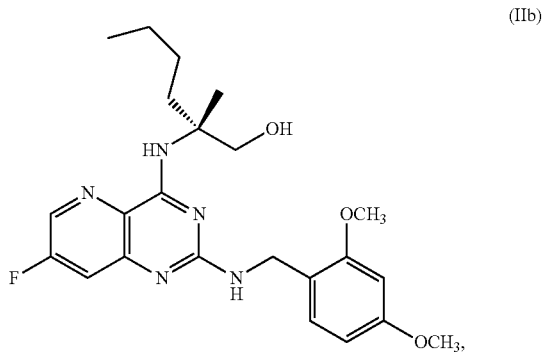 [SMILES: CCCC[C@](C)(CO)Nc1nc(NCc2ccc(OC)cc2OC)nc2cc(F)cnc12]
(IIb)

or a salt thereof, b) forming a second reaction mixture including the compound of Formula Ib or the salt thereof, trifluoroacetic acid, and dichloromethane to prepare a trifluoroacetic acid salt of the compound of Formula Ib:

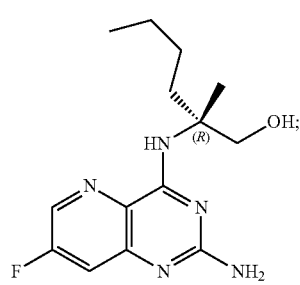
(Ib)

and c) forming a ninth reaction mixture including the trifluoroacetic acid salt of the compound of Formula Ib, sodium hydroxide, ethanol, and water to provide the compound of Formula Ib in a neutral form.

In some embodiments, the compound of Formula IXa can be of Formula IXb:

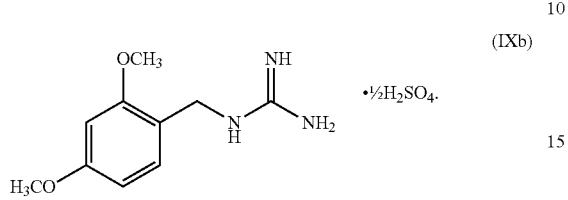
(IXb)

In some embodiments, the present disclosure provides a method for preparing a compound of Formula Ib:

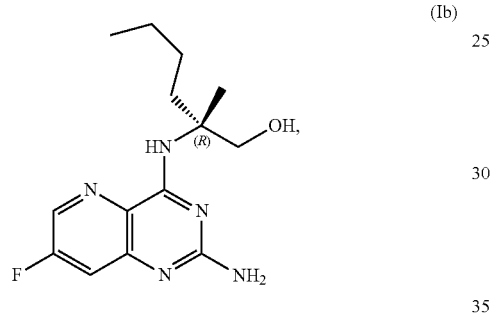
(Ib)

or a salt thereof, the method including:

a4) forming a seventh reaction mixture including a compound of Formula VIIIb-1:

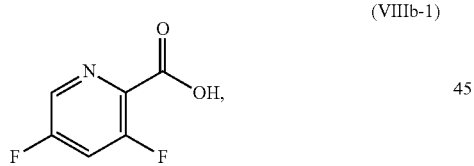
(VIIIb-1)

or a salt thereof, oxalyl chloride, N,N-dimethylformamide, 2-methyltetrahydrofuran to form a compound of Formula VIIb-1:

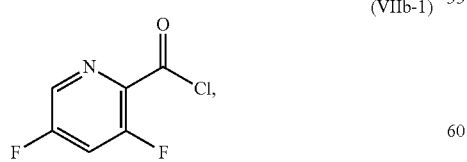
(VIIb-1)

or a salt thereof;

a3) forming a sixth reaction mixture including the compound of Formula VIIb-1 or the salt thereof, a compound of Formula VIb:

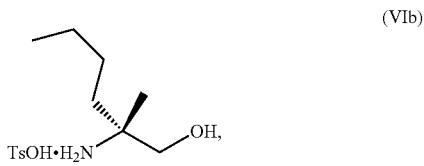
(VIb)

aqueous potassium carbonate, 2-methyltetrahydrofuran, and water to form a compound of Formula Vb-1:

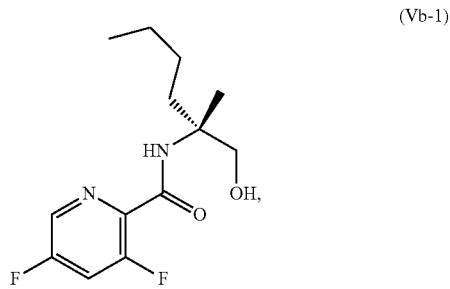 [SMILES: CCCC[C@](C)(CO)NC(=O)c1ncc(F)cc1F]
(Vb-1)

or a salt thereof;

a2) forming a fourth reaction mixture including the compound of Formula Vb-1 or the salt thereof, thionyl chloride, and 2-methyltetrahydrofuran to form a compound of Formula IVb-2:

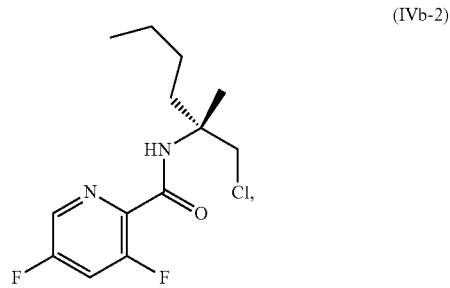 [SMILES: CCCC[C@](C)(CCl)NC(=O)c1ncc(F)cc1F]
(IVb-2)

or a salt thereof;

a1) forming a third reaction mixture including the compound of Formula IVb-2 or the salt thereof, aqueous sodium hydroxide, tetra-n-butylammonium hydrogensulfate, and 2-methyltetrahydrofuran to form a compound of Formula IIIb-1:

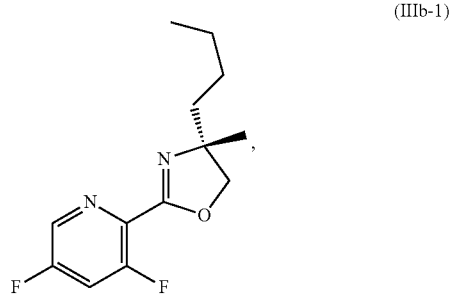 [SMILES: CCCC[C@]1(C)COC(c2ncc(F)cc2F)=N1]
(IIIb-1)

or a salt thereof, a) forming a first reaction mixture including the compound of Formula IIIb-1 or the salt thereof, a compound of Formula IXc:

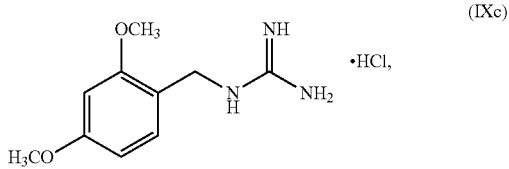 [SMILES: COc1ccc(CNC(=N)N)c(OC)c1]

cesium carbonate, and 2-methyltetrahydrofuran to form a compound of Formula IIb:

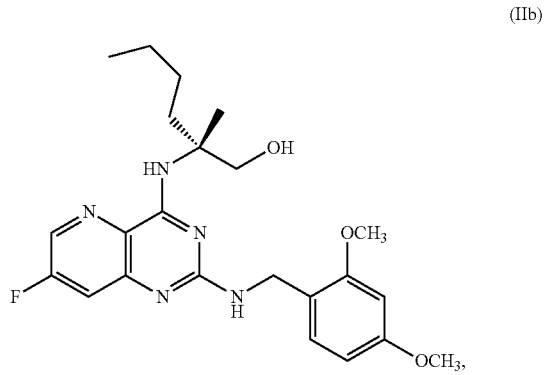 [SMILES: CCCC[C@](C)(CO)Nc1nc(NCc2ccc(OC)cc2OC)nc2cc(F)cnc12]

or a salt thereof, b) forming a second reaction mixture including the compound of Formula Ib or the salt thereof, trifluoroacetic acid, and dichloromethane to prepare a trifluoroacetic acid salt of the compound of Formula Ib:

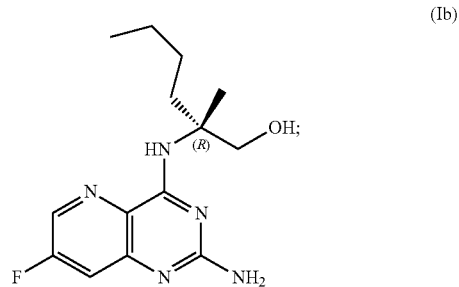

and c) forming a ninth reaction mixture including the trifluoroacetic acid salt of the compound of Formula Ib, sodium hydroxide, ethanol, and water to provide the compound of Formula Ib in a neutral form.

In some embodiments, the compound of Formula Vb or Vb-1, or the salt thereof can be isolated in a solution including 2-methyltetrahydrofuran and used in the following step a2) without purification and/or removal of the 2-methyltetrahydrofuran. In some embodiments, the compound of Formula IVb-1 or IVb-2, or the salt thereof can be isolated in a solution including 2-methyltetrahydrofuran and used in the following step a1) without purification and/or removal of the 2-methyltetrahydrofuran. In some embodiments, the compound of Formula IIIb or IIIb-1, or the salt thereof can be isolated in a solution including 2-methyltetrahydrofuran and used in the following step a) without purification and/or removal of the 2-methyltetrahydrofuran. In some embodiments, the compound of Formula Vb or b-1, or the salt thereof, the compound of Formula IVb-1 or IVb-2, or the salt thereof, and the compound of Formula IIIb or IIIb-1, or the salt thereof can each be isolated in a solution including 2-methyltetrahydrofuran and used in the following step without purification and/or removal of 2-methyltetrahydrofuran. In some embodiments, the compound of Formula Vb or b-1, or the salt thereof can be isolated in a solution including 2-methyltetrahydrofuran and used in the following step a2) without removal of the 2-methyltetrahydrofuran. In some embodiments, the compound of Formula IVb-1 or IVb-2, or the salt thereof can be isolated in a solution including 2-methyltetrahydrofuran and used in the following step a1) without removal of the 2-methyltetrahydrofuran. In some embodiments, the compound of Formula IIIb or IIIb-1, or the salt thereof can be isolated in a solution including 2-methyltetrahydrofuran and used in the following step a) without removal of the 2-methyltetrahydrofuran. In some embodiments, the compound of Formula Vb or Vb-1, or the salt thereof, the compound of Formula IVb-1 or IVb-2, or the salt thereof, and the compound of Formula IIIb or IIIb-1, or the salt thereof can each be isolated in a solution including 2-methyltetrahydrofuran and used in the following step without removal of 2-methyltetrahydrofuran.

In some embodiments, the compound of Formula Vb or the salt thereof can be isolated in a solution including 2-methyltetrahydrofuran and used in the following step a2) without purification and/or removal of the 2-methyltetrahydrofuran. In some embodiments, the compound of Formula IVb-1 or the salt thereof can be isolated in a solution including 2-methyltetrahydrofuran and used in the following step a1) without purification and/or removal of the 2-methyltetrahydrofuran. In some embodiments, the compound of Formula IIIb or the salt thereof can be isolated in a solution including 2-methyltetrahydrofuran and used in the following step a) without purification and/or removal of the 2-methyltetrahydrofuran. In some embodiments, the compound of Formula Vb or the salt thereof, the compound of Formula IVb-1 or the salt thereof, and the compound of Formula IIIb or the salt thereof can each be isolated in a solution including 2-methyltetrahydrofuran and used in the following step without purification and/or removal of 2-methyltetrahydrofuran. In some embodiments, the compound of Formula Vb or the salt thereof can be isolated in a solution including 2-methyltetrahydrofuran and used in the following step a2) without removal of the 2-methyltetrahydrofuran. In some embodiments, the compound of Formula IVb-1 or the salt thereof can be isolated in a solution including 2-methyltetrahydrofuran and used in the following step a1) without removal of the 2-methyltetrahydrofuran. In some embodiments, the compound of Formula IIIb or the salt thereof can be isolated in a solution including 2-methyltetrahydrofuran and used in the following step a) without removal of the 2-methyltetrahydrofuran. In some embodiments, the compound of Formula Vb or the salt thereof, the compound of Formula IVb-1 or the salt thereof, and the compound of Formula IIIb or the salt thereof can each be isolated in a solution including 2-methyltetrahydrofuran and used in the following step without removal of 2-methyltetrahydrofuran.

In some embodiments, the compound of Formula VIIb or VIIb-1, or the salt thereof can be formed in situ and used in the following step a3) without purification and/or removal of 2-methyltetrahydrofuran. In some embodiments, the compound of Formula VIIb or VIIb-1, or the salt thereof can be formed in situ and used in the following step a3) without removal of 2-methyltetrahydrofuran.

In some embodiments, the compound of Formula VIIb or the salt thereof can be formed in situ and used in the following step a3) without purification and/or removal of 2-methyltetrahydrofuran. In some embodiments, the compound of Formula VIIb or the salt thereof can be formed in situ and used in the following step a3) without removal of 2-methyltetrahydrofuran.

In some embodiments, the compound of Formula VIIb or VIIb-1, or the salt thereof, the compound of Formula Vb or Vb-1, or the salt thereof, the compound of Formula IVb-1 or IVb-2, or the salt thereof, and the compound of Formula IIIb or IIIb-1, or the salt thereof can each be isolated in a solution including 2-methyltetrahydrofuran and used in the following step without purification and/or removal of 2-methyltetrahydrofuran. In some embodiments, the compound of Formula VIIb or VIIb-1, or the salt thereof, the compound of Formula Vb or Vb-1, or the salt thereof, the compound of Formula IVb-1 or IVb-2, or the salt thereof, and the compound of Formula IIIb or IIIb-1, or the salt thereof can each be isolated in a solution including 2-methyltetrahydrofuran and used in the following step without removal of 2-methyltetrahydrofuran.

In some embodiments, the compound of Formula VIIb or the salt thereof, the compound of Formula Vb or the salt thereof, the compound of Formula IVb-1 or the salt thereof, and the compound of Formula IIIb or the salt thereof can each be isolated in a solution including 2-methyltetrahydrofuran and used in the following step without purification and/or removal of 2-methyltetrahydrofuran. In some embodiments, the compound of Formula VIb or the salt thereof, the compound of Formula Vb or the salt thereof, the compound of Formula IVb-1 or the salt thereof, and the compound of Formula IIIb or the salt thereof can each be isolated in a solution including 2-methyltetrahydrofuran and used in the following step without removal of 2-methyltetrahydrofuran.

B. Method of Preparing Compounds of Formula I from Formula V

In some embodiments, the present disclosure provides a method for preparing a compound of Formula II:

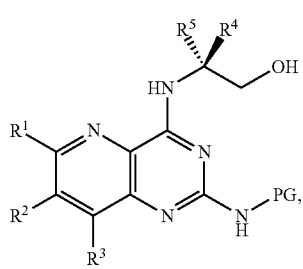

(II)

or a salt thereof, the method including:
 a) forming a first reaction mixture including a compound of Formula V:

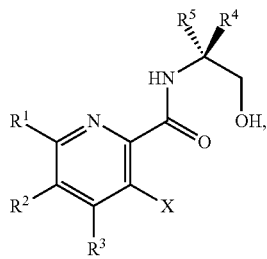

(V)

or a salt thereof, a compound having the Formula PG-NHC(=NH)NH$_2$ or a salt thereof, a first transition-metal catalyst, a first base, and a first solvent to form the compound of Formula II, or a salt thereof, wherein $R^1$, $R^2$, and $R^3$ can each independently be hydrogen, F, Cl, CN, CF$_3$, C$_{1-3}$ alkyl, or C$_{1-3}$ alkoxy; $R^4$ can be hydrogen or methyl; $R^5$ can be C$_{3-6}$ alkyl; X can be F, Cl, Br, I, or OTs; and PG can be an amino protecting group.

The compound having the Formula PG-NHC(=NH)NH$_2$ can be in any suitable form.

In some embodiments, the compound having the Formula PG-NHC(=NH)NH$_2$ can be in a neutral form. In some embodiments, the compound having the Formula PG-NHC(=NH)NH$_2$ can be in a salt form. In some embodiments, the compound having the Formula PG-NHC(=NH)NH$_2$ can be a hemisulfate, a sulfate, a chloride, a bromide, a carbonate, a nitrate, or an acetate salt thereof. In some embodiments, the compound having the Formula PG-NHC(=NH)NH$_2$ can be of Formula IX:

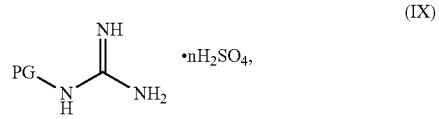

(IX)

wherein n can be from 0 to 1. In some embodiments, the compound of Formula IX can be a hemisulfate salt wherein n can be ½, a sulfate salt wherein n can be 1, or a combination thereof. In some embodiments, the compound of Formula IX can be a hemisulfate salt wherein n can be ½.

In some embodiments, PG can be an amino protecting group. Suitable amino protecting groups include, but are not limited to, a carbobenzyloxy (Cbz) group, a p-methoxybenzyl carbonyl (Moz or MeOZ) group, a tert-Butyloxycarbonyl (BOC) group, a 2-trimethylsilylethyoxymethyl (SEM) group, a 9-fluorenylmethyloxycarbonyl (Fmoc) group, an acetyl (Ac) group, a benzoyl (Bz) group, a benzyl (Bn) group, a carbamate group, a p-methoxybenzyl (PMB) group, a 2,4-dimethoxybenzyl group (DMB), a 1-(2,4-dimethoxyphenyl)ethyl, a 3,4-dimethoxybenzyl (DMPB) group, a p-methoxyphenyl (PMP) group, a tosyl (Ts) group, a Troc (trichloroethyl chloroformate) group, and other sulfonamides (Nosyl & Nps) groups. In some embodiments, PG can be 2,4-dimethoxybenzyl.

In some embodiments, the compound of Formula IX can be of Formula IXa:

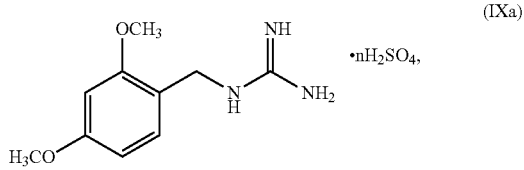 [SMILES: COc1ccc(CNC(=N)N)c(OC)c1]

(IXa)

wherein n can be from 0 to 1. In some embodiments, the compound of Formula IXa can be a hemisulfate salt wherein n can be ½, a sulfate salt wherein n can be 1, or a combination thereof. In some embodiments, the compound of Formula IXa can be a hemisulfate salt having Formula IXb:

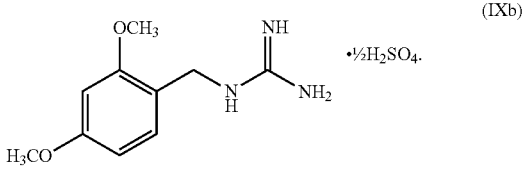 [SMILES: COc1ccc(CNC(=N)N)c(OC)c1]

(IXb)

In some embodiments, X can be Br. In some embodiments, the compound of Formula V can be the compound of Formula Vb.

In some embodiments, the first transition-metal catalyst can be a compound that includes one or more transition metals or transition metal cations. Suitable transition metals include, but are not limited to, Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Suitable transition metal cations include, but are not limited to, $Cd^{2+}$, $C^{2+}$, $Co^+$, $Cr^{2+}$, $Cr^+$, $Cu^+$ (i.e., Cu(I)), $Cu^{2+}$ (i.e., Cu(II)), $Fe^{2+}$, $Fe^+$, $Mn^{2+}$, $Mn^+$, $Ni^{2+}$, $Ni^+$, $Pd^{2+}$ (i.e., Pd(II)), and $Zn^{2+}$. In some embodiments, the first transition-metal catalyst includes a copper metal, a copper oxide, a copper (I) salt, a copper (II) salt, or combinations thereof. In some embodiments, the first transition-metal catalyst includes a copper (I) salt. In some embodiments, the first transition-metal catalyst can be a copper (I) salt. In some embodiments, the first transition-metal catalyst includes a copper (II) salt. In some embodiments, the first transition-metal catalyst can be a copper (II) salt. In some embodiments, the first transition-metal catalyst can be Cu(I) iodide, Cu(I) bromide, Cu(I) chloride, Cu(I) acetate, Cu(I) carbonate, Cu(I) nitrate, Cu(I) sulfate, Cu(I) phosphate, Cu(I) 3-methylsalicylate, Cu(I) thiophene-2-carboxylate, Cu(I) oxide, Cu(II) iodide, Cu(II) bromide, Cu(II) chloride, Cu(II) acetate, Cu(II) carbonate, Cu(II) nitrate, Cu(II) sulfate, Cu(II) pyrophosphate, Cu(II) phosphate, Cu(II) tartrate, Cu(II) oxide, or combinations thereof. In some embodiments, the first transition-metal catalyst can be Cu(II) iodide, Cu(II) bromide, Cu(II) chloride, Cu(II) acetate, Cu(II) carbonate, Cu(II) nitrate, Cu(II) sulfate, Cu(II) pyrophosphate, Cu(II) phosphate, Cu(II) tartrate, Cu(II) oxide, or combinations thereof. In some embodiments, the first transition-metal catalyst includes Cu(I) iodide. In some embodiments, the first transition-metal catalyst can be Cu(I) iodide.

The first base can be an alkali carbonate, an alkali bicarbonate, an alkali phosphate tribasic, a carboxylate, an amidine-based compound, or combinations thereof. Suitable alkali carbonates include lithium carbonate, sodium carbonate, potassium carbonate, and cesium carbonate. Suitable alkali bicarbonates include lithium bicarbonate, sodium bicarbonate, and potassium bicarbonate. Suitable alkali phosphates tribasic include sodium phosphate tribasic and potassium phosphate tribasic. Suitable carboxylates include, but are not limited to, lithium acetate, sodium acetate, potassium acetate, cesium acetate, potassium trimethylacetate, and tetrabutylphosphonium malonate. Suitable amidine-based compounds include, but are not limited to, 1,8-diazabicyclo[5.4.0]undec-7-ene (DBU) and 1,5-diazabicyclo[4.3.0]non-5-en (DBN). In some embodiments, the first base can be lithium carbonate, sodium carbonate, potassium carbonate, cesium carbonate, lithium bicarbonate, sodium bicarbonate, potassium bicarbonate, sodium phosphate tribasic, potassium phosphate tribasic, potassium acetate, potassium trimethylacetate, tetrabutylphosphonium malonate, 1,8-diazabicyclo[5.4.0]undec-7-ene, 1,5-diazabicyclo[4.3.0]non-5-en, or combinations thereof. In some embodiments, the first base includes potassium phosphate tribasic. In some embodiments, the first base can be potassium phosphate tribasic.

The first solvent can be any suitable polar or non-polar, protic or aprotic solvent. In some embodiments, the first solvent can be acetonitrile, propionitrile, N,N-dimethylacetamide, N-methyl-2-pyrrolidinone, dimethylsulfoxide, tetrahydrofuran, 2-methyltetrahydrofuran, 1,4-dioxane, cyclopentyl methyl ether, isopropanol, 2-methylbutan-2-ol, ethyl acetate, isopropyl acetate, methyl isobutyl ketone, toluene, trifluorotoluene, xylenes, or combinations thereof. In some embodiments, the first solvent includes acetonitrile. In some embodiments, the first solvent can be acetonitrile.

In some embodiments, the first reaction mixture further includes a first ligand. In some embodiments, the first ligand can be an amino acid, a polypyridyl ligand, or a tertiary amine. Suitable amino acids include naturally occurring and synthetic amino acids, as well as amino acid analogs that function in a manner similar to the naturally occurring amino acids. Suitable polypyridyl ligands include, but are not limited to, 2,2'-bipyridine, 1,10-phenanthroline, 4,4'-dimethyl-2,2'-bipyridine, 6,6'-dimethyl-2,2'-bipyridine, 4,4'-di-tert-butyl-2,2-bipyridine, 2,2'-bipyridine-4,4'-dicarboxylic acid and 2,2':6'2''-terpyridine. Suitable tertiary amines include, but are not limited to, triethylamine, tri-n-butylamine, N,N-diisopropylethylamine, N-methylpyrrolidine, N-methylmorpholine, 1,4-diazabicylo[2.2.2]-octane, and N,N,N',N'-tetramethylethylenediamine. In some embodiments, the first ligand can be arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, α-(methylamino)isobutyric acid, (4-methyl-1-piperazinyl)acetic acid, N-acetyl-cysteine, 2,2'-bipyridine, 1,10-phenanthroline, 4,4'-dimethyl-2,2'-bipyridine, 6,6'-dimethyl-2,2'-bipyridine, 4,4'-di-tert-butyl-2,2-bipyridine, 2,2'-bipyridine-4,4'-dicarboxylic acid, N,N,N',N'-tetramethylethylenediamine, or combinations thereof. In some embodiments, the first ligand includes 2,2'-bipyridine, 1,10-phenanthroline, 4,4'-dimethyl-2,2'-bipyridine, 6,6'-dimethyl-2,2'-bipyridine, 4,4'-di-tert-butyl-2,2-bipyridine, 2,2'-bipyridine-4,4'-dicarboxylic acid and 2,2':6'2''-terpyridine. In some embodiments, the first ligand includes 2,2'-bipyridine. In some embodiments, the first ligand can be 2,2'-bipyridine.

In some embodiments, the first reaction mixture further includes a dehydrating agent or additive. In some embodiments, the dehydrating agent or additive can be a 3 Å sieve, a 4 Å sieve, a 5 Å sieve, or a silica gel. In some embodiments, the dehydrating agent or additive can be a 3 Å sieve.

In general, the first reaction (i.e., step a)) can be performed at an ambient to an elevated temperature. For example, the first reaction mixture can be at a temperature of from 30° C. to 110° C. or heated to reflux. In some embodiments, the first reaction mixture can be at a temperature of from 40° C. to 100° C., from 50° C. to 100° C., from 50° C. to 90° C., from 60° C. to 90° C., from 70° C. to 90° C., or about 80° C. In some embodiments, the first reaction mixture can be at a temperature of from 50° C. to a reflux temperature. In some embodiments, the first reaction mixture can be heated to reflux.

Once the first reaction is complete, the first transition metal catalyst can be removed from the reaction mixture by a second ligand, for example, ethylenediaminetetraacetic acid (EDTA) or EDTA disodium salt. In some embodiments, upon completion of the first reaction, the first transition metal catalyst can be removed from the first reaction mixture using a second ligand. In some embodiments, the second ligand includes ethylenediaminetetraacetic acid or a salt thereof. In some embodiments, upon completion of the first reaction, the first transition metal catalyst can be removed from the first reaction mixture using ethylenediaminetetraacetic acid or a salt thereof. In some embodiments, upon completion of the first reaction, Cu(I) can be removed from the first reaction mixture using ethylenediaminetetraacetic acid disodium salt.

The compound of Formula II can be deprotected by various methods known in the art to provide the compound of Formula I or a salt thereof. When PG is 2,4-dimethoxybenzyl, the compound of Formula II can be deprotected by various methods, for example, under acidic, reductive (hydrogenolysis), or oxidative conditions to provide the compound of Formula I or the salt thereof, as described in Section-1 under Section-A.

C. Method of Preparing Compounds of Formula I from Formula III Via Unprotected Guanidine In some embodiments, the present disclosure provides a method for preparing a compound of Formula I:

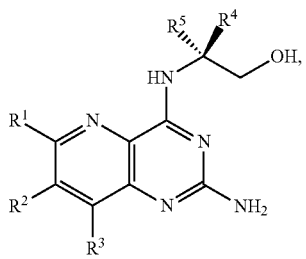

(I)

or a salt thereof, comprising:
a) forming a first reaction mixture comprising a compound of Formula III:

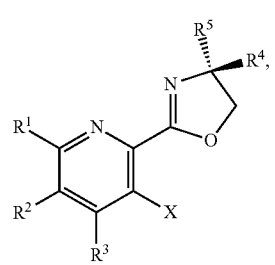

(III)

a compound having the Formula $H_2NC(=NH)NH_2$ or a salt thereof, a first base, and a first solvent to form the compound of Formula I or the salt thereof, wherein $R^1$, $R^2$, and $R^3$ can each independently be hydrogen, F, Cl, CN, $CF_3$, $C_{1-3}$ alkyl, or $C_{1-3}$ alkoxy; $R^4$ can be hydrogen or methyl; $R^5$ can be $C_{3-6}$ alkyl; and X can be F, Cl, Br, I, or OTs.

In some embodiments, X can be F.

The compound having the Formula $H_2NC(=NH)NH_2$ can be in any suitable form. In some embodiments, the compound having the Formula $H_2NC(=NH)NH_2$ can be in a neutral form. In some embodiments, the compound having the Formula $H_2NC(=NH)NH_2$ can be in a salt form. In some embodiments, the compound having the Formula $H_2NC(=NH)NH_2$ can be a hemisulfate, a sulfate, a chloride, a bromide, a carbonate, a nitrate, or an acetate salt thereof. In some embodiments, the compound having the Formula $H_2NC(=NH)NH_2$ can be of Formula XIV:

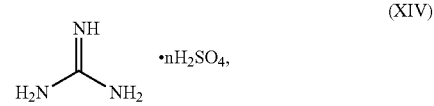

(XIV)

wherein n can be from 0 to 1. In some embodiments, the compound of Formula XIV can be a hemisulfate salt wherein n can be ½, a sulfate salt wherein n can be 1, or a combination thereof. In some embodiments, the compound of Formula XIV can be a hemisulfate salt wherein n can be ½.

In some embodiments, the first base can be absent or present. The first base, when present, can be a carbonate (e.g., cesium carbonate, sodium carbonate, potassium carbonate, rubidium carbonate, magnesium carbonate, calcium carbonate, strontium carbonate, barium carbonate, or ammonium carbonate), a metal oxide (e.g., magnesium oxide), a hydroxide (e.g., potassium hydroxide, sodium hydroxide, lithium hydroxide, cesium hydroxide, barium hydroxide, ammonium hydroxide, or tetra-n-butylammonium hydroxide), lithium phenoxide, a silanolate (e.g, potassium trimethylsilanolate, sodium trimethylsilanolate, lithium silanolate, or sodium dimethylphenylsilanolate), a phosphate (e.g., potassium phosphate tribasic, calcium phosphate tribasic, magnesium phosphate tribasic, sodium phosphate tribasic, sodium phosphate dibasic, or potassium phosphate dibasic), a hydride (e.g., sodium hydride or potassium hydride), an amine (e.g., 1,4-diazabicyclo[2.2.2]octane, 1-azabicyclo[2.2.2]octane, 1,8-diaza[5.4.0] undec-7-ene and 1,5-diazabicyclo[4.3.0]non-5-ene pyridine, 1,1,3,3-tetramethylguanidine, 4-methylmorpholine, 2-tert-buty-1,1,3,3-tetramethylguanidine, 1,3,4,6,7,8-hexahydro-1-methyl-2H-pyrimido[1,2-a]pyrimidine, 1,8-bis(dimethylamino) naphthalene, or N,N,N'N'-tetramethyl-1,8-napthalenediamine), an amide (e.g., lithium bis(trimethylsilyl)amide, sodium bis(trimethylsilyl)amide, potassium bis(trimethylsilyl)amide, lithium diisopropyl amide, sodium diisopropyl amide, or lithium dicyclohexylamide), an alkylmetal (e.g., n-butyllithium, tert-butyllithium, methyllithium, phenyllithium, lithium naphthalenide, or sodium naphthalenide), an alkoxide (e.g., magnesium tert-butoxide, potassium tert-butoxide, sodium tert-butoxide, sodium tert-pentoxide, or potassium tert-pentoxide), a phosphorane (e.g., tert-butylimino-tri(pyrrolidino) phosphorene, 2-tert-butylimino-tri(pyrrolidino)phosphorene, or 2-tert-butylimino-2-diethylamino-1,3- dimethylperhydro-1,3,2-diazaphorene), or combinations thereof. In some embodiments, the first base can be lithium carbonate, sodium carbonate, potassium carbonate, cesium carbonate, lithium bicarbonate, sodium bicarbonate, potassium bicarbonate, sodium phosphate tribasic, potassium phosphate tribasic, potassium acetate, potassium trimethylacetate, tetrabutylphosphonium malonate, 1,8-diazabicyclo[5.4.0]undec-7-ene, 1,5-diazabicyclo[4.3.0]non-5-en, or combinations thereof. In some embodiments, the first base is present and includes cesium carbonate. In some embodiments, the first base can be cesium carbonate.

The first solvent can be any suitable polar or non-polar, protic or aprotic solvent. The first solvent can be a polar aprotic solvent (e.g., N,N'-dimethylformamide, N,N'-dimethylacetamide, N-methylpyrrolidinone, dimethylsulfoxide, sulfolane, acetonitrile, propionitrile, butyronitrile, nitromethane, or nitroethane), an ether (tetrahydrofuran, 2-methyltetrahydrofuran, 1,4-dioxane, dibutyl ether, methyl tert-butyl ether, or cyclopentyl methyl ether), an alcohol (e.g., methanol, ethanol, n-butanol, 2-butanol, tert-butanol, 2-methylbutan-2-ol, 2,2,2-trifluoroethanol, or hexafluoro-2-propanol), a ketone (e.g, methyl isobutyl ketone, or methyl ethyl ketone), an ester (e.g., isopropyl acetate, or n-butylacetate), a chlorinate solvent (e.g., 1,2-dichloroethane, chlorobenzene, or trifluorotoluene), an aromatic solvent (e.g., toluene, xylenes, or anisole), water, or combinations thereof. In some embodiments, the first solvent can be acetonitrile, propionitrile, N,N-dimethylacetamide, N-methyl-2-pyrrolidinone, dimethylsulfoxide, tetrahydrofuran, 2-methyltetrahydrofuran, 1,4-dioxane, cyclopentyl methyl ether, isopropanol, 2-methylbutan-2-ol, ethyl acetate, isopropyl acetate, methyl isobutyl ketone, toluene, trifluorotoluene, xylenes, or combinations thereof. In some embodiments, the first solvent includes N,N'-dimethylacetamide. In some embodiments, the first solvent can be N,N'-dimethylacetamide.

In some embodiments, the first reaction mixture further includes an additive. The additive can be 4-dimethylaminopyridine, 4-piperidinopyridine, 4-pyrolidinopyridine, imidazole, N-methylimidazole, or 9-azajulolidine. In some embodiments, the additive is absent.

In general, the first reaction (i.e., step a)) can be performed at an ambient to an elevated temperature. For example, the first reaction mixture can be at a temperature of from 20° C. to 150° C. In some embodiments, the first reaction mixture can be at a temperature of from 30° C. to 100° C., from 40° C. to 100° C., from 50° C. to 90° C., from 50° C. to 80° C., from 60° C. to 80° C., or about 80° C. In some embodiments, the first reaction mixture can be at a temperature of from 60° C. to 80° C. In some embodiments, the first reaction mixture can be at a temperature of about 80° C.

The compound of Formula III can be prepared according to any one of the methods as described herein. Embodiments of Formula I, III, IV, V, VII, and VIII are as described according to Section-9 under Section-A.

In some embodiments, the present disclosure provides a method for preparing a compound of Formula Ib:

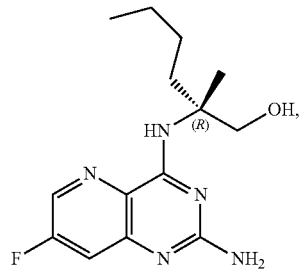

or a salt thereof, the method including:

a) forming a first reaction mixture including the compound of Formula IIIb-1:

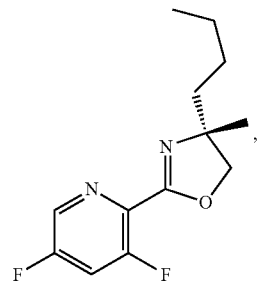

or a salt thereof, a compound of Formula XIVa:

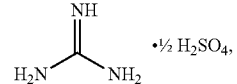

cesium carbonate, and N,N'-dimethylacetamide to form the compound of Formula Ib or the salt thereof.

D. Method of Preparing Compounds of Formula I Via Guanidine Salt

In some embodiments, the present disclosure provides a method for preparing a compound of Formula XVIII:

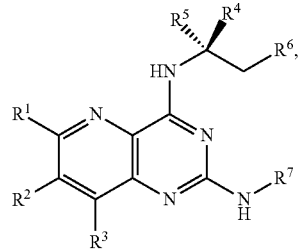

or a salt thereof, comprising:

a) forming a first reaction mixture comprising a compound of Formula XV:

a compound of Formula XVI-1:

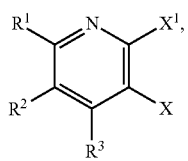

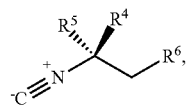

or a salt thereof, a compound having the Formula R$^7$—NHC(=NH)NH$_2$ or a salt thereof, a first transition-metal catalyst, a first base, and a first solvent, to form the compound of Formula XVIII or the salt thereof, wherein
R$^1$, R$^2$, and R$^3$ are each independently hydrogen, F, Cl, CN, CF$_3$, C$_{1-3}$ alkyl, or C$_{1-3}$ alkoxy;
R$^4$ is hydrogen or methyl;
R$^5$ is C$_{1-6}$ alkyl;
R$^6$ is hydrogen, OH, or O-PG$^1$;
R$^7$ is hydrogen or PG;
X and X$^1$ are each independently F, Cl, Br, I, or OTs;
PG is an amino protecting group; and
PG1 is a hydroxy protecting group.

In some embodiments, R$^6$ can be hydrogen. In some embodiments, R$^6$ can be OH.

In some embodiments, the compound of Formula XVIII can be of Formula I:

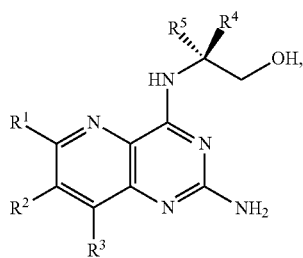

or a salt thereof, wherein R$^5$ is C$_{3-6}$ alkyl.

In some embodiments, the compound of Formula XVI is of Formula XVIa:

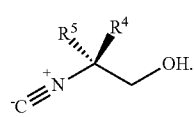

In some embodiments, PG$^1$ can be a hydroxy protecting group. Suitable hydroxy protecting groups include, but are not limited to, a silyl group (e.g., trimethylsilyl, triethylsilyl, triisopropylsilyl, tert-butyldimethylsilyl, phenyl dimethylsilyl, di-tert-butylsilyl, [2-(trimethylsilyl)ethoxy]methyl, or 2-trimethylsilyl)ethoxycarbonyl), an acyl group (e.g., acetyl, propionyl, isobutyryl, trimetylacetyl, or trifluoroacetyl), an aryl group (e.g., phenyl, 4-methoxyphenyl, or 4-bromophenyl), an alkyl or heterocycloalkyl group (e.g., allyl, tert-butyl, or tertahydropyranyl), an arylalkyl group (e.g., benzyl, para-methoxybenzyl, or 2,4-dimethoxybenzyl). In some embodiments, PG$^1$ can be 2,4-dimethoxybenzyl.

In some embodiments, R$^7$ can be hydrogen. In some embodiments, the Formula R$^7$—NHC(=NH)NH$_2$ can be the Formula H$_2$NC(=NH)NH$_2$. The compound having the Formula H$_2$NC(=NH)NH$_2$ can be in any suitable form. In some embodiments, the compound having the Formula H$_2$NC(=NH)NH$_2$ can be in a neutral form. In some embodiments, the compound having the Formula H$_2$NC(=NH)NH$_2$ can be in a salt form. In some embodiments, the compound having the Formula H$_2$NC(=NH)NH$_2$ can be a hemisulfate, a sulfate, a chloride, a bromide, a carbonate, a nitrate, or an acetate salt thereof. In some embodiments, the compound having the Formula H$_2$NC(=NH)NH$_2$ can be of Formula XIV:

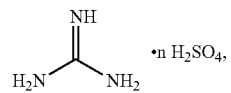

wherein n can be from 0 to 1. In some embodiments, the compound of Formula XIV can be a hemisulfate salt wherein n can be ½, a sulfate salt wherein n can be 1, or a combination thereof.

In some embodiments, the compound of Formula XIV can be a hemisulfate salt wherein n can be ½.

In some embodiments, R$^7$ can be PG. In some embodiments, the Formula R$^7$—NHC(=NH)NH$_2$ can be the Formula PG-NHC(=NH)NH$_2$. The compound having the Formula PG-NHC(=NH)NH$_2$ can be in any suitable form. In some embodiments, the compound having the Formula PG-NHC(=NH)NH$_2$ can be in a neutral form. In some embodiments, the compound having the Formula PG-NHC(=NH)NH$_2$ can be in a salt form. In some embodiments, the compound having the Formula PG-NHC(=NH)NH$_2$ can be a hemisulfate, a sulfate, a chloride, a bromide, a carbonate, a nitrate, or an acetate salt thereof. In some embodiments, the compound having the Formula PG-NHC(=NH)NH$_2$ can be of Formula IX:

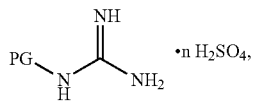

wherein n can be from 0 to 1. In some embodiments, the compound of Formula IX can be a hemisulfate salt wherein n can be ½, a sulfate salt wherein n can be 1, or a combination thereof. In some embodiments, the compound of Formula IX can be a hemisulfate salt wherein n can be ½.

In some embodiments, PG can be an amino protecting group. Suitable amino protecting groups include, but are not limited to, tert-butyloxycarbonyl, 9-fluorenylmethoxycarbonyl, benzyloxylcarbonyl, allyloxycarbonyl, acetyl, trifluoroacetyl, 2,2,5,7,8-Pentamethyl-chromane-6-sulfonyl chloride, para-toluenesulfonyl, 4-methoxy-2,3,6- trimethylbenzenesulfonyl, 4-methoxybenzyl, 2-chlorobenzyl, or 2,4-dimethoxybenzyl. In some embodiments, PG can be 2,4-dimethoxybenzyl.

In some embodiments, the compound of Formula IX can be of Formula IXa:

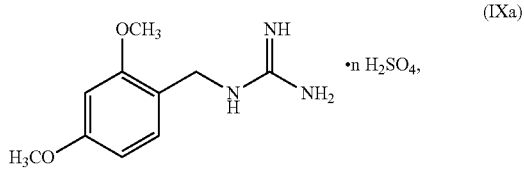 [SMILES: COc1ccc(CNC(=N)N)c(OC)c1]

(IXa)

wherein n can be from 0 to 1. In some embodiments, the compound of Formula IXa can be a hemisulfate salt wherein n can be ½, a sulfate salt wherein n can be 1, or a combination thereof. In some embodiments, the compound of Formula IXa can be a hemisulfate salt having Formula IXb:

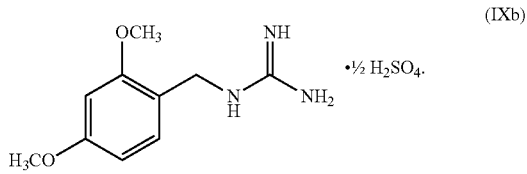 [SMILES: COc1ccc(CNC(=N)N)c(OC)c1]

(IXb)

The first transition-metal catalyst can be a compound that includes one or more transition metals or transition metal cations. Suitable transition metals include, but are not limited to, Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Suitable transition metal cations include, but are not limited to, $Cd^{2+}$, $Co^{2+}$, $Co^+$, $Cr^{2+}$, $Cr^+$, $Cu^+$ (i.e., Cu(I)), $Cu^{2+}$ (i.e., Cu(II)), $Fe^{2+}$, Fe, $Mn^{2+}$, Mn, $Ni^{2+}$, $Ni^+$, $Pd^{2+}$ (i.e., Pd(II)), and $Zn^{2+}$. In some embodiments, the first transition-metal catalyst includes a Pd catalyst. In some embodiments, the first transition-metal catalyst can be a Pd catalyst. In some embodiments, the first transition-metal catalyst includes a Pd(II) catalyst. In some embodiments, the first transition-metal catalyst can be a Pd(II) catalyst. In some embodiments, the Pd(II) catalyst can be palladium(II) acetate, palladium (II) pivolate, palladium (II) propionate, palladium (II) trifloroacetate, palladium (II) bromide, palladium (II) chloride, tris(dibenzylideneacetone)dipalladium (0); bis(acetonitrile)palladium(II) dichloride, (2-Dicyclohexylphosphino-1,1'-biphenyl)[2-(2'-amino-1,1'-biphenyl)]palladium(II) methanesulfonate, (2-dicyclohexylphosphino-2',4',6'-triisopropyl-1,1'-biphenyl)[2-(2'-amino-1,1'-biphenyl)]palladium(II) methanesulfonate, [(2-di-tert-butylphosphino-3,6-dimethoxy-2',4',6'-triisopropyl-1,1'-biphenyl)-2-(2'-amino-1,1'-biphenyl)]palladium(II) methanesulfonate, (2-dicyclohexylphosphino-2',6'-dimethoxybiphenyl) [2-(2'-amino-1,1'-biphenyl)]palladium(II) methanesulfonate, [(di(1-adamantyl)-butylphosphine)-2-(2'-amino-1,1'-biphenyl)]palladium(II) methanesulfonate, [(2-di-cyclohexylphosphino-3,6-dimethoxy-2',4',6'-triisopropyl-1,1'-biphenyl)-2-(2'-amino-1,1'-biphenyl)]palladium(II) methanesulfonate, [(2-di-tert-butylphosphino-2',4',6'-triisopropyl-1,1'-biphenyl)-2-(2'-amino-1,1'-biphenyl)] palladium(II) methanesulfonate, [(1,3,5,7-tetramethyl-6-phenyl-2,4,6-trioxa-6-phosphaadamantane)-2-(2'-amino-1,1'-biphenyl)palladium(II) methanesulfonate, [(2-{bis[3,5-bis (trifluoromethyl)phenyl]phosphine}-3,6-dimethoxy-2',4',6'-triisopropyl-1,1'-biphenyl)-2-(2'-amino-1,1'-biphenyl)]palladium(II) methanesulfonate, (2-dicyclohexylphosphino-2',6'-diisopropoxy-1,1'-biphenyl)[2-(2'-amino-1,1'-biphenyl)]palladium(II) methanesulfonate, [(2-di-tert-butylphosphino-3-methoxy-6-methyl-2',4',6'-triisopropyl-1,1'-biphenyl)-2-(2-aminobiphenyl)]palladium(II) methanesulfonate, [2-(di-1-adamantylphosphino)-2',4',6'-triisopropyl-3,6-dimethoxybiphenyl][2-(2'-amino-1,1'-biphenyl)]palladium(II) methanesulfonate, [(di-tert-butylneopentylphosphine)-2-(2-aminobiphenyl)]palladium(II) methanesulfonate, mesyl(2-(di-tert-butylphosphino)-1,1'-binaphthyl)[2-(2'-amino-1,1'-biphenyl)]palladium(II), methanesulfonato (di-tert-butyl) methylphosphino (2'-amino-1,1'-biphenyl-2-yl) palladium(II), methanesulfonato 2-dicyclohexylphosphino-2-(N,N-dimethylamino)biphenyl (2'-amino-1,1'-biphenyl-2-yl) palladium(II), or combinations thereof. In some embodiments, the first transition-metal catalyst includes palladium(II) acetate. In some embodiments, the first transition-metal catalyst can be palladium(II) acetate.

In some embodiments, the first base can be any suitable inorganic or organic base. In some embodiments, the first base can be a carbonate (e.g., cesium carbonate, lithium carbonate, sodium carbonate, potassium carbonate, calcium carbonate, strontium carbonate, barium carbonate, or ammonium carbonate), a hydroxide (e.g., potassium hydroxide, sodium hydroxide, lithium hydroxide, cesium hydroxide, barium hydroxide, ammonium hydroxide, or tetra-n-butylammonium hydroxide), a silanolate (e.g., potassium trimethylsilanolate, sodium trimethylsilanolate, lithium silanolate, or sodium dimethylphenylsilanolate), a phosphate (e.g., potassium phosphate tribasic, calcium phosphate tribasic, magnesium phosphate tribasic, sodium phosphate tribasic, sodium phosphate dibasic, or potassium phosphate dibasic), a carboxylate (e.g., sodium acetate, potassium acetate, potassium trimethyl acetate, or potassium propionate), an alkoxide (e.g., sodium tert-butoxide, potassium tert-butoxide, or sodium tert-pentoxide), an amine (e.g., N,N-diisopropylethyl amine, triethylamine, N,N,N',N'-tetramethylethylenediamine, 1,4-diazabicyclo[2.2.2]octane, 1-azabicyclo [2.2.2]octane, 1,8-diaza[5.4.0] undec-7-ene and 1,5-diazabicyclo[4.3.0]non-5-ene pyridine, 1,1,3,3-tetramethylguanidine, 4-methylmorpholine, 2-tert-buty-1,1,3,3-tetramethylguanidine, 1,3,4,6,7,8-hexahydro-1-methyl-2H-pyrimido[1,2-a]pyrimidine, 1,8-bis(dimethylamino) naphthalene, or N,N,N'N'-tetramethyl-1,8-napthalenediamine), an amide (e.g., lithium bis (trimethylsilyl)amide, sodium bis(trimethylsilyl)amide, potassium bis(trimethylsilyl)amide, lithium diisopropyl amide, sodium diisopropyl amide, lithium dicyclohexylamide), or combinations thereof. In some embodiments, the first base can be cesium carbonate, lithium carbonate, sodium carbonate, potassium carbonate, calcium carbonate, strontium carbonate, barium carbonate, or ammonium carbonate, or combinations thereof. In some embodiments, the first base can be lithium carbonate, sodium carbonate, potassium carbonate, cesium carbonate, or combinations thereof. In some embodiments, the first base includes cesium carbonate. In some embodiments, the first base can be cesium carbonate.

In some embodiments, the first solvent can be any suitable polar or non-polar, protic or aprotic solvent. In some embodiments, the first solvent can be a polar aprotic solvent (e.g., N,N'-dimethylformamide, N,N'-dimethylacetamide, N-methylpyrrolidinone, dimethylsulfoxide, sulfolane, acetonitrile, propionitrile, butyronitrile, nitromethane, or nitroethane), an ether (e.g., tetrahydrofuran, 2-methyltetrahydrofuran, 1,4-dioxane, dibutyl ether, methyl tert-butyl ether, or cyclopentyl methyl ether), an alcohol (e.g., 2-propanol, 2-butanol, tert-butanol, 2-methylbutan-2-ol, 2,2,2-trifluoroethanol, or hexafluoro-2-propanol), a ketone (e.g., methyl isobutyl ketone, or methyl ethyl ketone), an ester (e.g. isopropyl acetate, or n-butylacetate), a chlorinate solvent (1,2-dichloroethane, chlorobenzene, or trifluorotoluene), an aromatic solvent (toluene, xylenes, or anisole), or combinations thereof. In some embodiments, the first solvent can be toluene, trifluorotoluene, chlorobenzene, xylenes, anisole, or combinations thereof. In some embodiments, the first solvent includes toluene. In some embodiments, the first solvent can be toluene.

In some embodiments, the first reaction mixture further includes a first ligand. In some embodiments, the first ligand can be 1,3-bis(dicyclohexylphosphino)propane, 1,2-bis(dimethylphosphino)ethane, bis(diphenylphosphino)methane, di(1-adamantyl)-n-butylphosphine, 2-(dicyclohexylphosphino)biphenyl, triphenylphosphine, tri-ortho-tolylphosphine, tri-tert-butylphosphine, di-tert-butyl-(methyl)phosphine, di-tert-butyl(phenyl)phosphine, tricyclohexylphosphine, tri-isopropylphosphine, n-butyldiadamantylphosphine, 2,2'-bis(diphenylphosphino)-1,1'-binaphthyl, 4,5-bis(diphenylphosphino)-9,9-dimethylxanthene, bis[(2-diphenylphosphino)phenyl] ether, 1,1'-bis(diphenlphosphino)ferrocene, (2R)-1-[(1R)-1-[bis(1,1-dimethylethyl)phosphino]ethyl]-2-(dicyclohexylphosphino) ferrocene, 1,3-bis(diphenylphosphino)propane, 5-(di-tert-butylphosphino)-1', 3', 5'-triphenyl-1'H-[1,4']bipyrazole, di(1-adamantyl)-2-morpholinophenylphosphine, N,N'-(2,6-diisopropylphenyl)dihydroimidazolium chloride, (2-biphenyl)di-tert-butylphosphine, (2-biphenylyl)di-tert-butylphosphine, 2-(di-tert-butylphosphino)biphenyl, (2-biphenyl) dicyclohexylphosphine, 2-dicyclohexylphosphino-2'-(N,N-dimethylamino)biphenyl, 2-dicyclohexylphosphino-2',6'-diisopropoxybiphenyl, 2-dicyclohexylphosphino-2',6'-dimethoxybiphenyl, 2-dicyclohexylphosphino-2',4',6'-triisopropylbiphenyl, 2-(dicyclohexylphosphino)3,6-dimethoxy-2',4',6'-triisopropyl-1,1'-biphenyl, 2-di-tert-butylphosphino-2',4',6'-triisopropylbiphenyl, 2-(di-tert-butylphosphino)-2',4',6'-triisopropyl-3,6-dimethoxy-1,1'-biphenyl, 2-di-tert-butylphosphino-3,4,5,6-tetramethyl-2',4',6'-triisopropyl-1,1'-biphenyl, or a tetrafluoroborate salt thereof. In some embodiments, the first ligand includes 1,3-bis(dicyclohexylphosphino)propane. In some embodiments, the first ligand can be 1,3-bis(dicyclohexylphosphino)propane.

In general, the first reaction (i.e., step a)) can be performed at an ambient to an elevated temperature. For example, the first reaction mixture can be at a temperature of from 50° C. to 120° C. In some embodiments, the first reaction mixture can be at a temperature of from 40° C. to 120° C., from 50° C. to 120° C., from 60° C. to 120° C., from 60° C. to 110° C., from 70° C. to 110° C., or about 90° C. In some embodiments, the first reaction mixture can be at a temperature of from 70° C. to 110° C. In some embodiments, the first reaction mixture can be at about 90° C.

In some embodiments, once the first reaction is complete, the first transition metal catalyst can be removed from the reaction mixture by filtration through a silica gel.

In some embodiments, the compound of Formula I can be of Formula Ia:

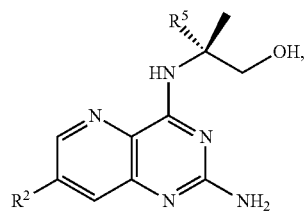

(Ia)

or a salt thereof, wherein $R^2$ and $R^5$ are defined and described herein.

In some embodiments, the compound of Formula I can be of Formula Ib:

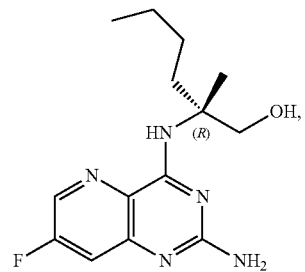

(Ib)

or a salt thereof.

In some embodiments, the compound of Formula XV can be of Formula XVa:

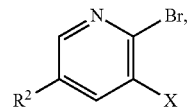

(XVa)

or a salt thereof, wherein $R^2$ and X are defined and described herein.

In some embodiments, the compound of Formula XV can be of Formula XVb:

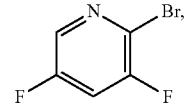

(XVb)

or a salt thereof.

In some embodiments, the compound of Formula XVI-1 or XVI-2 can be of Formula XVIa

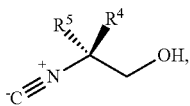

(XVIa)

or a salt thereof, wherein $R^4$ and $R^5$ are defined and described herein.

In some embodiments, the compound of Formula XVI-1 or XVI-2 can be of Formula XVIb

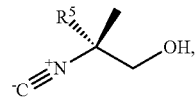
(XVIb)

or a salt thereof, wherein $R^5$ is defined and described herein.

In some embodiments, the compound of Formula XVI-1 or XVI-2 can be of Formula XVIc

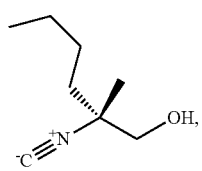
(XVIc)

or a salt thereof.

In some embodiments, the present disclosure provides a method for preparing a compound of Formula Ib:

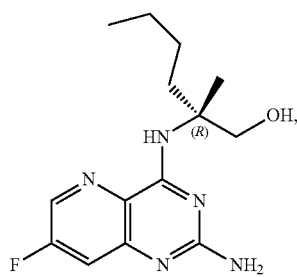
(Ib)

or a salt thereof, comprising:
a) forming a first reaction mixture comprising a compound of Formula XVb:

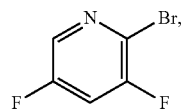
(XVb)

or a salt thereof, a compound of Formula XVIc:

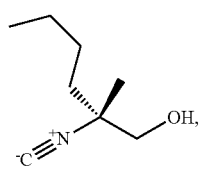
(XVIc)

or a salt thereof, a compound a compound of Formula XIVa:

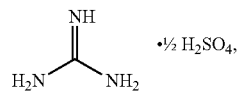
(XIVa)

palladium(II) acetate, cesium carbonate, 1,3-bis(dicyclohexylphosphino)propane, and toluene to form the compound of Formula Ib or the salt thereof.

E. Method of Preparing Compounds of Formula I from Formula XI

In another embodiment, the present disclosure provides a method for preparing a compound of Formula I:

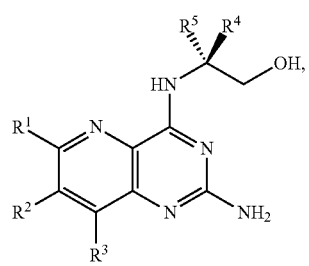
(I)

or a salt thereof, the method including:
a) forming a first reaction mixture including a compound of Formula XI:

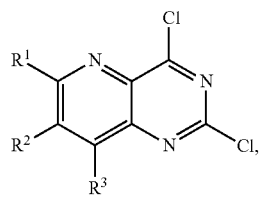
(XI)

or a salt thereof, a compound of Formula VI:

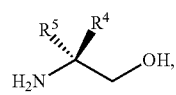
(VI)

or a salt thereof, a first base, and a first solvent to form a compound of Formula

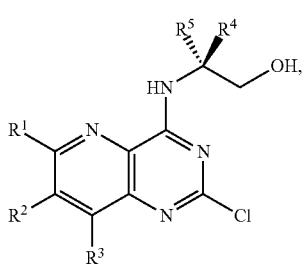
(X)

or a salt thereof, b) forming a second reaction mixture including the compound of Formula X or the salt thereof, a compound of PG-NH$_2$ or a salt thereof, a second base, and a second solvent to form a compound of Formula II:

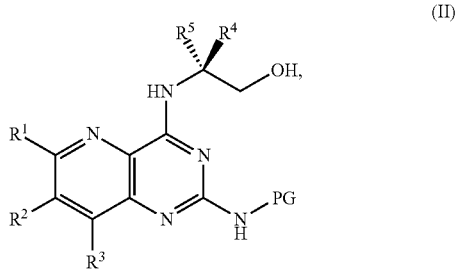

(II)

or a salt thereof, and c) forming a third reaction mixture including the compound of Formula II or the salt thereof, a deprotecting agent, and a third solvent to provide the compound of Formula I or the salt thereof, wherein R$^1$, R$^2$, and R$^3$ can each independently be hydrogen, F, Cl, CN, CF$_3$, C$_{1-3}$ alkyl, or C$_{1-3}$ alkoxy; R$^4$ can be hydrogen or methyl; R$^5$ can be C$_{3-6}$ alkyl; and PG can be an amino protecting group.

The compound of Formula VI can be in any suitable form. In some embodiments, the compound of Formula VI can be in a neutral form. In some embodiments, the compound of Formula VI can be in a salt form. In some embodiments, the compound of Formula VI can be a tosylate salt thereof.

The first base can be a tertiary amine, an aromatic amine base, an amidine-based compound, an alkali carbonate, an alkali bicarbonate, an alkali phosphate tribasic, an alkali phosphate dibasic, or combinations thereof. Suitable tertiary amines include, but are not limited to, triethylamine, tri-n-butylamine, N,N-diisopropylethylamine, N,N,N',N'-tetramethylethylenediamine, N-methylmorpholine, N-methylpiperidine, quinuclidine, and 1,4-diazabicylo[2.2.2]-octane. Suitable aromatic amine bases include, but are not limited to, pyridine, lutidines (e.g., 2,6-lutidine, 3,5-lutidine, and 2,3-lutidine), collidines (e.g., 2,3,4-collidine, 2,3,5-collidine, 2,3,6-collidine, 2,4,5-collidine, 2,4,6-collidine, and 3,4,5-collidine), 4-dimethylaminopyridine, imidazole, and 1,8-bis(dimethylamino)naphthalene. Suitable amidine-based compounds include, but are not limited to, 1,8-diazabicyclo[5.4.0]undec-7-ene (DBU) and 1,5-diazabicyclo-4.3.0]non-5-ene (DBN). Suitable alkali carbonates include lithium carbonate, sodium carbonate, potassium carbonate, and cesium carbonate. Suitable alkali bicarbonates include lithium bicarbonate, sodium bicarbonate, and potassium bicarbonate. Suitable alkali phosphates tribasic include sodium phosphate tribasic and potassium phosphate tribasic. Suitable alkali phosphates dibasic include sodium phosphate dibasic and potassium phosphate dibasic. In some embodiments, the first base can be triethylamine, tri-n-butylamine, N,N-diisopropylethylamine, N,N,N',N'-tetramethylethylenediamine, N-methylmorpholine, N-methylpiperidine, 1,4-diazabicylo[2.2.2]-octane, 1,8-diazabicyclo[5.4.0]undec-7-ene, 1,5-diazabicyclo-4.3.0]non-5-ene, pyridine, 2,6-lutidine, 2,4,6-collidine, 4-dimethylaminopyridine, imidazole, 1,8-bis(dimethylamino)naphthalene, sodium bicarbonate, sodium carbonate, sodium phosphate tribasic, sodium phosphate dibasic, potassium bicarbonate, potassium carbonate, potassium phosphate tribasic, potassium phosphate dibasic, cesium carbonate, or combinations thereof. In some embodiments, the first base includes N,N-diisopropylethylamine. In some embodiments, the first base can be N,N-diisopropylethylamine.

The first solvent can be any suitable polar aprotic solvent and/or non-polar solvent. In some embodiments, the first solvent can be ethyl acetate, isopropyl acetate, butyl acetate, isobutyl acetate, diethyl ether, methyl tert-butyl ether, tetrahydrofuran, 2-methyltetrahydrofuran, 1,4-dioxane, toluene, benzene, xylenes, trifluorotoluene, N,N-dimethylformamide, N,N-dimethylacetamide, N-methyl-2-pyrrolidone, dimethylsulfoxide, acetonitrile, propionitrile, butyronitrile, dichloromethane, 1,2-dichloroethane, chlorobenzene, or combination thereof. In some embodiments, the first solvent includes isopropyl acetate and 2-methyltetrahydrofuran. In some embodiments, the first solvent can be isopropyl acetate and 2-methyltetrahydrofuran.

The compound of PG-NH$_2$ can be in any suitable form. In some embodiments, the compound of PG-NH$_2$ can be in a neutral form. In some embodiments, the compound of PG-NH$_2$ can be in a salt form. In some embodiments, the compound of PG-NH$_2$ can be a hemisulfate, a sulfate, a chloride, a bromide, a carbonate, a nitrate, or an acetate salt thereof.

PG can be an amino protecting group. Suitable amino protecting groups include, but are not limited to, a carbobenzyloxy (Cbz) group, a p-methoxybenzyl carbonyl (Moz or MeOZ) group, a tert-Butyloxycarbonyl (BOC) group, a 2-trimethylsilylethyoxymethyl (SEM) group, a 9-fluorenylmethyloxycarbonyl (Fmoc) group, an acetyl (Ac) group, a benzoyl (Bz) group, a benzyl (Bn) group, a carbamate group, a p-methoxybenzyl (PMB) group, a 2,4-dimethoxybenzyl group (DMB), a 1-(2,4-dimethoxyphenyl)ethyl, a 3,4-dimethoxybenzyl (DMPB) group, a p-methoxyphenyl (PMP) group, a tosyl (Ts) group, a Troc (trichloroethyl chloroformate) group, and other sulfonamides (Nosyl & Nps) groups. In some embodiments, PG can be 2,4-dimethoxybenzyl.

In some embodiments, the compound of PG-NH$_2$ can be 2,4-dimethoxybenzylamine.

The second base can be a tertiary amine, an aromatic amine base, an amidine-based compound, an alkali carbonate, an alkali bicarbonate, an alkali phosphate tribasic, an alkali phosphate dibasic, or combinations thereof. Suitable tertiary amines include, but are not limited to, triethylamine, tri-n-butylamine, N,N-diisopropylethylamine, N,N,N',N'-tetramethylethylenediamine, N-methylmorpholine, N-methylpiperidine, quinuclidine, and 1,4-diazabicylo[2.2.2]-octane. Suitable aromatic amine bases include, but are not limited to, pyridine, lutidines (e.g., 2,6-lutidine, 3,5-lutidine, and 2,3-lutidine), collidines (e.g., 2,3,4-collidine, 2,3,5-collidine, 2,3,6-collidine, 2,4,5-collidine, 2,4,6-collidine, and 3,4,5-collidine), 4-dimethylaminopyridine, imidazole, and 1,8-bis(dimethylamino)naphthalene. Suitable amidine-based compounds include, but are not limited to, 1,8-diazabicyclo[5.4.0]undec-7-ene (DBU) and 1,5-diazabicyclo-4.3.0]non-5-ene (DBN). Suitable alkali carbonates include lithium carbonate, sodium carbonate, potassium carbonate, and cesium carbonate. Suitable alkali bicarbonates include lithium bicarbonate, sodium bicarbonate, and potassium bicarbonate. Suitable alkali phosphates tribasic include sodium phosphate tribasic and potassium phosphate tribasic.

Suitable alkali phosphates dibasic include sodium phosphate dibasic and potassium phosphate dibasic. In some embodiments, the second base can be triethylamine, tri-n-butylamine, N,N-diisopropylethylamine, N,N,N',N'-tetramethylethylenediamine, N-methylmorpholine, N-methylpiperidine, 1,4-diazabicylo[2.2.2]-octane, 1,8-diazabicyclo

[5.4.0]undec-7-ene, 1,5-diazabicyclo-4.3.0]non-5-ene, pyridine, 2,6-lutidine, 2,4,6-collidine, 4-dimethylaminopyridine, imidazole, 1,8-bis(dimethylamino)naphthalene, sodium bicarbonate, sodium carbonate, sodium phosphate tribasic, sodium phosphate dibasic, potassium bicarbonate, potassium carbonate, potassium phosphate tribasic, potassium phosphate dibasic, cesium carbonate, or combinations thereof. In some embodiments, the second base includes potassium carbonate. In some embodiments, the second base can be potassium carbonate.

The second solvent can be any suitable polar aprotic solvent and/or non-polar solvent. In some embodiments, the second solvent can be ethyl acetate, isopropyl acetate, butyl acetate, isobutyl acetate, diethyl ether, methyl tert-butyl ether, tetrahydrofuran, 2-methyltetrahydrofuran, 1,4-dioxane, toluene, benzene, xylenes, trifluorotoluene, N,N-dimethylformamide, N,N-dimethylacetamide, N-methyl-2-pyrrolidone, dimethylsulfoxide, acetonitrile, propionitrile, butyronitrile, dichloromethane, 1,2-dichloroethane, chlorobenzene, or combinations thereof. In some embodiments, the second solvent includes isopropyl acetate and 2-methyltetrahydrofuran. In some embodiments, the second solvent can be isopropyl acetate and 2-methyltetrahydrofuran.

In general, the first reaction (i.e., step a)) can be performed at an ambient temperature to an elevated temperature. For example, the first reaction mixture can be at a temperature of from 20° C. to 100° C. or heated to reflux. In some embodiments, the first reaction mixture can be at a temperature of from 30° C. to 100° C., from 40° C. to 100° C., from 50° C. to 100° C., from 60° C. to 90° C., from 70° C. to 90° C., or about 80° C. In some embodiments, the first reaction mixture can be at a temperature of from 50° C. to a reflux temperature. In some embodiments, the first reaction mixture can be at a temperature of about 80° C. In some embodiments, the first reaction mixture can be heated to reflux.

In general, the second reaction (i.e., step b)) can be performed at an ambient temperature to an elevated temperature. For example, the second reaction mixture can be at a temperature of from 20° C. to 100° C. or heated to reflux. In some embodiments, the second reaction mixture can be at a temperature of from 30° C. to 100° C., from 40° C. to 100° C., from 50° C. to 100° C., from 60° C. to 90° C., from 60° C. to 80° C., or about 70° C. In some embodiments, the second reaction mixture can be at a temperature of from 50° C. to a reflux temperature. In some embodiments, the second reaction mixture can be at a temperature of about 70° C. In some embodiments, the second reaction mixture can be heated to reflux.

The compound of Formula II or the salt thereof can be deprotected by various methods known in the art to provide the compound of Formula I or the salt thereof. When PG is 2,4-dimethoxybenzyl, the compound of Formula II can be deprotected by various methods, for example, under acidic, reductive (hydrogenolysis), or oxidative conditions to provide the compound of Formula I or the salt thereof.

In some embodiments, the deprotecting agent can be an acid. In some embodiments, the acid can be trifluoroacetic acid, trichloroacetic acid, acetic acid, formic acid, hydrochloric acid, sulfuric acid, phosphoric acid, or combinations thereof. In some embodiments, the acid includes trifluoroacetic acid. In some embodiments, the acid can be trifluoroacetic acid.

In some embodiments, the deprotecting agent can be a hydrogen source and the third reaction mixture further includes a transition-metal catalyst. In some embodiments, the hydrogen source can be ammonium formate, formic acid, hydrogen gas, or combinations thereof. In some embodiments, the hydrogen source includes hydrogen gas. In some embodiments, the hydrogen source includes ammonium formate. In some embodiments, the hydrogen source includes formic acid. In some embodiments, the transition-metal catalyst can be palladium hydroxide on carbon, palladium on carbon, or platinum oxide. In some embodiments, the transition-metal catalyst includes palladium hydroxide on carbon. In some embodiments, the transition-metal catalyst includes palladium on carbon. In some embodiments, the transition-metal catalyst includes platinum oxide. In some embodiments, the deprotecting agent can be hydrogen gas and the third reaction mixture further includes palladium hydroxide on carbon, palladium on carbon, or platinum oxide. In some embodiments, the deprotecting agent includes ammonium formate and the third reaction mixture further includes palladium hydroxide on carbon, palladium on carbon, or platinum oxide. In some embodiments, the deprotecting agent includes formic acid and the third reaction mixture further includes palladium hydroxide on carbon, palladium on carbon, or platinum oxide.

In some embodiments, the hydrogen source can be ammonium formate. In some embodiments, the hydrogen source can be formic acid. In some embodiments, the transition-metal catalyst can be palladium hydroxide on carbon. In some embodiments, the transition-metal catalyst can be palladium on carbon. In some embodiments, the transition-metal catalyst can be platinum oxide. In some embodiments, the deprotecting agent can be ammonium formate and the third reaction mixture further includes palladium hydroxide on carbon, palladium on carbon, or platinum oxide. In some embodiments, the deprotecting agent can be formic acid and the third reaction mixture further includes palladium hydroxide on carbon, palladium on carbon, or platinum oxide.

In some embodiments, the deprotecting agent can be boron tribromide, 2,3-dichloro-5,6-dicyano-1,4-benzoquinone, ceric ammonium nitrate, or a combination of trifluoromethanesulfonic acid and 1,3-dimethoxybenzene.

The third solvent can be any suitable polar or non-polar, protic or aprotic solvent. In some embodiments, the third solvent can be ethyl acetate, isopropyl acetate, butyl acetate, isobutyl acetate, tetrahydrofuran, 2-methyltetrahydrofuran, 1,4-dioxane, toluene, benzene, xylenes, trifluorotoluene, anisole, dimethylsulfoxide, propionitrile, butyronitrile, dichloromethane, 1,2-dichloroethane, chlorobenzene, methanol, ethanol, isopropanol, water, formic acid, acetic acid, trichloroacetic acid, or combinations thereof. In some embodiments, the third solvent includes formic acid. In some embodiments, the deprotecting agent can be formic acid, and the third solvent can be formic acid. In some embodiments, the third solvent includes dichloromethane. In some embodiments, the third solvent can be dichloromethane.

In general, the third reaction (i.e., step c)) can be performed at any suitable temperature, for example, at a temperature of from –10° C. to 80° C. In some embodiments, the third reaction mixture can be at a temperature of from –10° C. to 80° C., from 0° C. to 50° C., from 10° C. to 50° C., from 20° C. to 50° C., or from 20° C. to 40° C. In some embodiments, the third reaction mixture can be at a temperature of from 20° C. to 40° C. In some embodiments, the third reaction mixture can be at a temperature of about 30° C. In some embodiments, the third reaction mixture can be at a temperature of about 40° C. In some embodiments, the third solvent can be dichloromethane, and the third reaction mixture can be heated to reflux.

In some embodiments, the method further includes d) forming a fourth reaction mixture including the salt of the compound of Formula I, a third base, and a fourth solvent to provide the compound of Formula I in a neutral form.

The third base can be an alkali carbonate or alkali hydroxide. Suitable alkali carbonates include sodium carbonate and potassium carbonate. Suitable alkali hydroxides includes sodium hydroxide and potassium hydroxide. In some embodiments, the third base can be sodium hydroxide or potassium hydroxide. In some embodiments, the third base includes sodium hydroxide. In some embodiments, the third base can be in an aqueous solution. In some embodiments, the third base includes an aqueous solution of sodium hydroxide. In some embodiments, the third base can be an aqueous solution of sodium hydroxide.

The fourth solvent can be any suitable alcohol solvent, ester solvent, and/or water. In some embodiments, the fourth solvent can be methanol, ethanol, isopropanol, ethyl acetate, isopropyl acetate, water, or combinations thereof. In some embodiments, the fourth solvent includes i) ethanol and water, or ii) ethyl acetate and water. In some embodiments, the fourth solvent includes ethanol and water. In some embodiments, the fourth solvent includes ethyl acetate and water. In some embodiments, the fourth solvent can be i) ethanol and water, or ii) ethyl acetate and water. In some embodiments, the fourth solvent can be ethanol and water. In some embodiments, the fourth solvent can be ethyl acetate and water.

When the fourth solvent includes an ester solvent (e.g., ethyl acetate or isopropyl acetate), upon completion of the reaction, the reaction mixture after partition can be further treated with an aqueous solution of sodium bicarbonate.

In general, the fourth reaction (i.e., step d)) can be performed at any suitable temperature. For example, the fourth reaction mixture can be at a temperature of from 0° C. to 60° C. In some embodiments, the fourth reaction mixture can be at a temperature of from 0° C. to 60° C., from 10° C. to 60° C., from 10° C. to 50° C., or from 20° C. to 40° C. In some embodiments, the fourth reaction mixture can be at a temperature of from 20° C. to 40° C. In some embodiments, the fourth reaction mixture can be at a temperature of about 20° C. In some embodiments, the fourth reaction mixture can be at a temperature of about 40° C.

In some embodiments of any one of formulae I, II, X, and XI, $R^2$ can be Cl, F, CN, $CF_3$, $C_{1-3}$ alkyl, or $C_{1-3}$ alkoxy; and $R^1$ and $R^3$ can each independently be hydrogen, F, Cl, CN, $CF_3$, $C_{1-3}$ alkyl, or $C_{1-3}$ alkoxy. The $C_{1-3}$ alkyl can be methyl, ethyl, n-propyl, or isopropyl. The $C_{1-3}$ alkoxy can be methoxy, ethoxy, n-propoxy, or isopropoxy. In some embodiments of any one of formulae I, II, X, and XI, $R^2$ can be Cl, F, CN, $CF_3$, methyl, ethyl, n-propyl, isopropyl, methoxy, ethoxy, n-propoxy, or isopropoxy; and $R^1$ and $R^3$ can each independently be hydrogen, F, Cl, CN, $CF_3$, methyl, ethyl, n-propyl, isopropyl, methoxy, ethoxy, n-propoxy, or isopropoxy. In some embodiments of any one of formulae I, II, X, and XI, $R^2$ can be Cl, F, CN, $CF_3$, methyl, ethyl, n-propyl, isopropyl, methoxy, ethoxy, n-propoxy, or isopropoxy; and $R^1$ and $R^3$ can each be hydrogen. In some embodiments of any one of formulae I, II, X, and XI, $R^2$ can be F, and $R^1$ and $R^3$ can each be hydrogen.

In some embodiments of any one of formulae I, II, VI, and X, $R^4$ can be hydrogen. In some embodiments of any one of formulae I, II, VI, and X, $R^4$ can be methyl.

In some embodiments of any one of formulae I, II, VI, and X, $R^5$ can be $C_{3-6}$ alkyl. In some embodiments, $R^5$ can be n-propyl, isopropyl, n-butyl, isobutyl, sec-butyl, tert-butyl, n-pentyl, isopentyl, or hexyl. In some embodiments of any one of formulae I, II, VI, and X, $R^5$ can be n-butyl.

In some embodiments of any one of formulae I, II, VI, and X, $R^4$ can be methyl; and $R^5$ can be $C_{3-6}$ alkyl. In some embodiments of any one of formulae I, II, VI, and X, $R^4$ can be methyl; and $R^5$ can be n-propyl, isopropyl, n-butyl, isobutyl, sec-butyl, tert-butyl, n-pentyl, isopentyl, or hexyl. In some embodiments of any one of formulae I, II, VI, and X, $R^4$ can be methyl; and $R^5$ can be n-butyl.

In some embodiments, the compound of Formula I can be of Formula Ia:

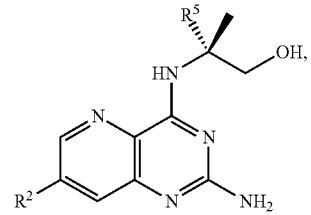

or a salt thereof, wherein $R^2$ and $R^5$ are defined and described herein.

In some embodiments, the compound of Formula I can be of Formula Ib:

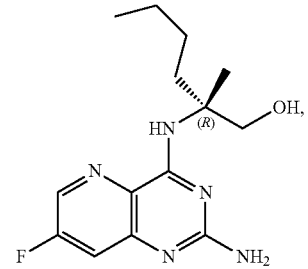

or a salt thereof.

In some embodiments, the compound of Formula XI can be of Formula XIa:

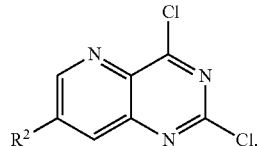

or a salt thereof, wherein $R^2$ is defined and described herein.

In some embodiments, the compound of Formula XI can be of Formula Xb:

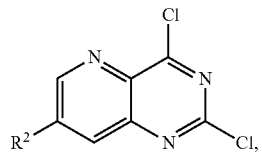

or a salt thereof.

In some embodiments, the compound of Formula VI can be of Formula VIa:

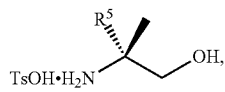
(VIa)

wherein $R^5$ is defined and described herein.

In some embodiments, the compound of Formula VI can be of Formula VIb:

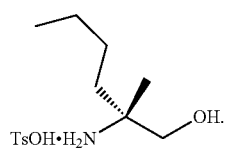
(VIb)

In some embodiments, the compound of Formula X can be of Formula IXa:

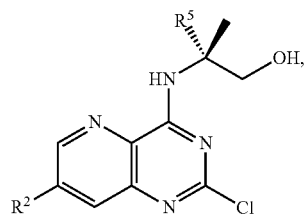
(Xa)

or a salt thereof, wherein $R^2$ and $R^5$ are defined and described herein.

In some embodiments, the compound of Formula X can be of Formula IXb:

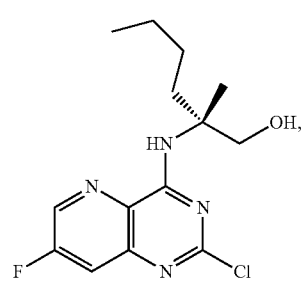
(Xb)

or a salt thereof.

In some embodiments, the present disclosure provides a method for preparing a compound of Formula Ib:

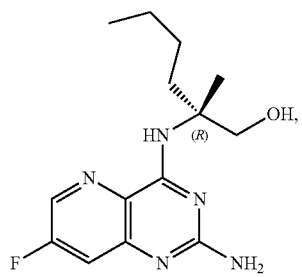
(Ib)

or a salt thereof, the method including:

a) forming a first reaction mixture including a compound of Formula XIb:

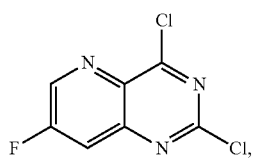
(XIb)

or the salt thereof, a compound of Formula VIb:

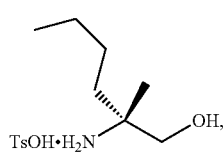
(VIb)

N,N-diisopropylethylamine, 2-methyltetrahydrofuran, and isopropyl acetate to form a compound of Formula Xb:

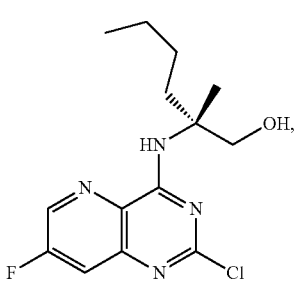
(Xb)

or a salt thereof, b) forming a second reaction mixture including the compound of Formula Xb or the salt thereof, 2,4-dimethoxybenzylamine, potassium carbonate, 2-methyltetrahydrofuran, and isopropyl acetate to form a compound of Formula IIb:

(IIb)

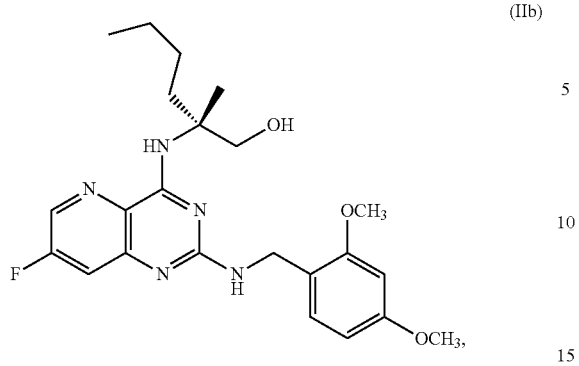

or a salt thereof, and c) forming a third reaction mixture including the compound of Formula Ib or the salt thereof, trifluoroacetic acid, and dichloromethane to prepare a trifluoroacetic acid salt of the compound of Formula Ib:

(Ib)

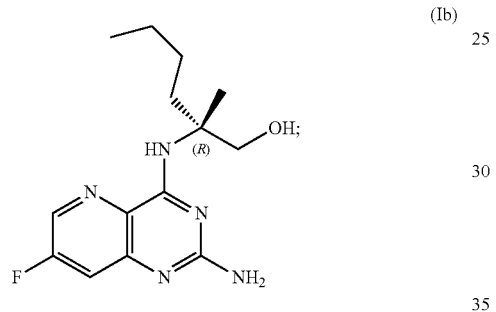

and d) forming a fourth reaction mixture including the trifluoroacetic acid salt of the compound of Formula Ib, sodium hydroxide, ethanol, and water to provide the compound of Formula Ib in a salt-free form.

In some embodiments, the compound of Formula Xb or the salt thereof can be isolated in a solution including 2-methyltetrahydrofuran and isopropyl acetate and used in the following step b) without purification and/or removal of the 2-methyltetrahydrofuran and isopropyl acetate. In some embodiments, the compound of Formula Xb or the salt thereof can be isolated in a solution including 2-methyltetrahydrofuran and isopropyl acetate and used in the following step b) without removal of the 2-methyltetrahydrofuran and isopropyl acetate. In some embodiments, the compound of Formula Xb or the salt thereof can be isolated in a solid by precipitation upon addition of n-heptane to a solution including 2-methyltetrahydrofuran and isopropyl acetate. In some embodiments, the compound of Formula Xb or the salt thereof can be isolated in a solid by precipitation upon addition of n-heptane to a solution including 2-methyltetrahydrofuran and isopropyl acetate and used in the following step b) without purification.

F. Methods of Preparing Intermediates

The intermediates used in the methods of the present disclosure can be prepared by a variety of methods.

1. Preparation of a Salt of (R)-2-Amino-2-methylhexan-1-ol, Route 1

In some embodiments, the present disclosure provides a method for preparing a salt of (R)-2-amino-2-methylhexan-1-ol:

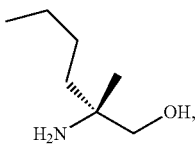

the method including:

1) forming a first reaction mixture including $C_{1-4}$ alkyl alaninate having the formula:

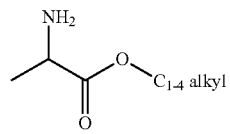

or a salt thereof, an aldehyde, a first base, a desiccant, and a first solvent to form an imine of $C_{1-4}$ alkyl alaninate having the formula:

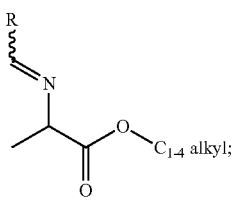

2a) forming a second mixture including the imine of $C_{1-4}$ alkyl alaninate, an electorophile, a second base, and a second solvent to form an imine of $C_{1-4}$ alkyl 2-amino-2-methylhexanoate having the formula:

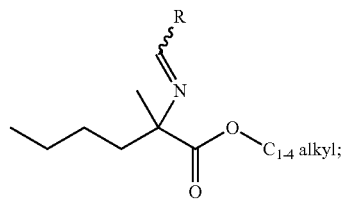

2b) forming a third reaction mixture including the imine of $C_{1-4}$ alkyl 2-amino-2-methylhexanoate, a first acid and a third solvent to form a first salt of $C_{1-4}$ alkyl 2-amino-2-methylhexanoate:

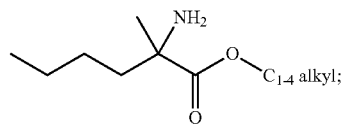

2c) forming a fourth reaction mixture including the first salt of $C_{1-4}$ alkyl 2-amino-2-methylhexanoate, a third base, a fourth solvent, and water to form $C_{1-4}$ alkyl 2-amino-2-methylhexanoate in a neutral form;

3) forming a fifth reaction mixture including $C_{1-4}$ alkyl 2-amino-2-methylhexanoate, a second acid, and a fifth solvent to form a second salt of $C_{1-4}$ alkyl 2-amino-2-methylhexanoate;

4) forming a sixth reaction mixture including the second salt of $C_{1-4}$ alkyl 2-amino-2-methylhexanoate, an enzyme, a fourth base, and a sixth solvent to provide $C_{1-4}$ alkyl (R)-2-amino-2-methylhexanoate:

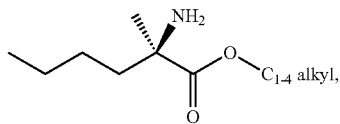

or a salt thereof, 5) forming a seventh reaction mixture including $C_{1-4}$ alkyl (R)-2-amino-2-methylhexanoate or the salt thereof, a BOC protecting reagent, and a seventh solvent to form $C_{1-4}$ alkyl (R)-2-((tert-butoxycarbonyl)amino)-2-methylhexanoate:

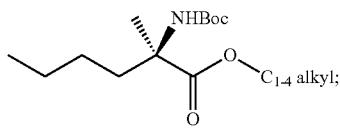

6) forming an eighth reaction mixture including $C_{1-4}$ alkyl (R)-2-((tert-butoxycarbonyl)amino)-2-methylhexanoate, a reductant, a promoter, and an eighth solvent to form tert-butyl (R)-(1-hydroxy-2-methylhexan-2-yl)carbamate:

and 7) forming a ninth reaction mixture including tert-butyl (R)-(1-hydroxy-2-methylhexan-2-yl)carbamate, a third acid, and a ninth solvent to provide the salt of (R)-2-amino-2-methylhexan-1-ol, wherein R can be unsubstituted or substituted aryl or unsubstituted or substituted aryl-CH=CH—.

Figure 3A:
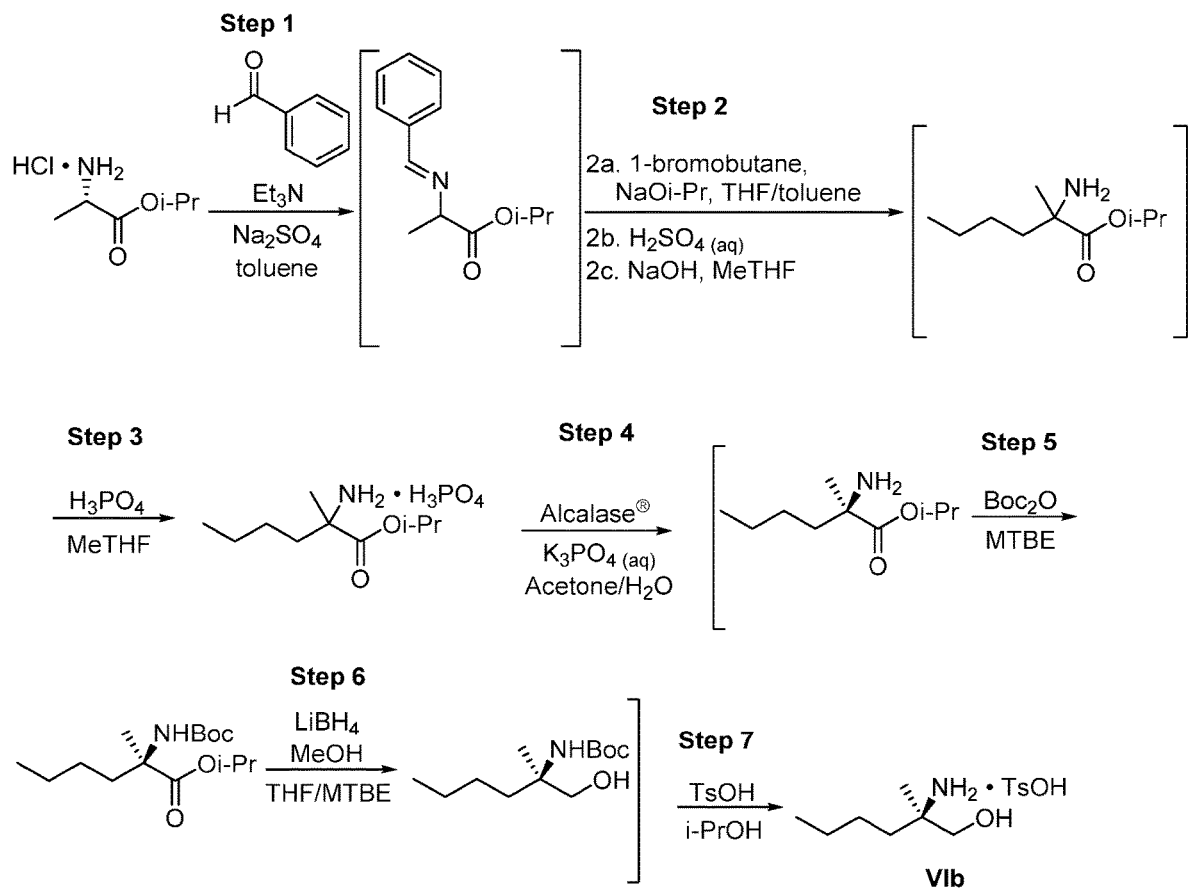
FIG. 3A shows the preparation of the compound of Formula VIb via steps of condensation, alkylation/hydrolysis, salt formation, enzymatic resolution, BOC protection, reduction, and deprotection/TsOH salt formation.

In some embodiments, the salt of (R)-2-amino-2-methylhexan-1-ol can be prepared according to steps 1-7 as shown in the scheme of FIG. 3A.

In some embodiments, $C_{1-4}$ alkyl in any one of formulae or compounds in steps 1, 2a, 2b, 2c, and 3-6 can be methyl, ethyl, n-propyl, isopropyl, n-butyl, sec-butyl, or tert-butyl. In some embodiments, $C_{1-4}$ alkyl in any one of formulae or compounds in steps 1, 2a, 2b, 2c, and 3-6 can be isopropyl.

With respect to step 1, $C_{1-4}$ alkyl alaninate or the salt thereof, the aldehyde, the first base, the desiccant, the first solvent, the imine of $C_{1-4}$ alkyl alaninate, and reaction temperature are described herein.

In some embodiments, $C_{1-4}$ alkyl alaninate can be $C_{1-4}$ alkyl L-alaninate, $C_{1-4}$ alkyl D-alaninate, or a mixture thereof. In some embodiments, $C_{1-4}$ alkyl alaninate can be methyl alaninate, ethyl alaninate, n-propyl alaninate, isopropyl alaninate, n-butyl alaninate, sec-butyl alaninate, or tert-butyl alaninate. In some embodiments, $C_{1-4}$ alkyl alaninate can be isopropyl alaninate. In some embodiments, $C_{1-4}$ alkyl alaninate can be isopropyl L-alaninate. Isopropyl L-alaninate can be in any suitable form, for example, in a neutral form or a salt form. In some embodiments, isopropyl L-alaninate can be a HCl salt thereof.

The aldehyde can be any suitable aldehyde capable of forming an imine with an amine.

For example, the aldehyde can be benzaldehyde, 2-chlorobenzaldehyde, 4-chlorobenzaldehyde, 3-hydroxybenzaldehyde, 4-hydroxybenzaldehyde, 3-phenylprop-2-enal, 3-(4-methylphenyl)prop-2-enal, 3-(4-hydroxy-3-methyoxyphenyl)prop-2-enal, 2-methylbenzaldehyde, 4-methylbenzaldehyde, or 4-methoxybenzaldehyde. In some embodiments, the aldehyde can be benzaldehyde.

The first base can be a tertiary amine (e.g., trimethylamine, triethylamine, N,N-diisopropylethylamine, N-methylpiperidine, or tri-n-butylamine), a carboxylate (e.g., sodium acetate or potassium acetate), or an inorganic base (e.g., sodium carbonate, potassium carbonate; cesium carbonate, sodium bicarbonate, potassium bicarbonate, sodium phosphate tribasic, or potassium phosphate tribasic). In some embodiments, the first base includes trimethylamine. In some embodiments, the first base can be trimethylamine.

The desiccant can be any suitable agent or method capable of removing water formed from the condensation. For example, the desiccant can be sodium sulfate, magnesium sulfate, a trialkyl orthoformate (e.g., trimethyl orthoformate), molecular sieves, or an azeotropic removal of water (e.g., using a Dean-Stark trap). In some embodiments, the desiccant includes sodium sulfate. In some embodiments, the desiccant can be sodium sulfate.

The first solvent can be an aromatic solvent (e.g., toluene, xylenes, chlorobenzene, fluorobenzene, or trifluorotoluene), an ether (e.g., diethyl ether, methyl tert-butyl ether, tetrahydrofuran, 2-methyltetrahydrofuran, or 1,4-dioxane), a chlorinated solvent (e.g., dichloromethane or 1,2-dichloroethane), an ester (e.g., ethyl acetate, butyl acetate, or isobutyl acetate), an alcohol (e.g., methanol, ethanol, or isopropanol), or combinations thereof. In some embodiments, the first solvent includes toluene. In some embodiments, the first solvent can be toluene.

In some embodiments, the imine of $C_{1-4}$ alkyl alaninate has the formula:

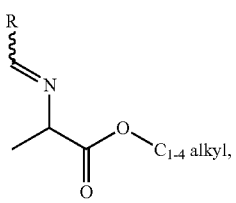

wherein R can be phenyl, 2-chlorophenyl, 4-chlorophenyl, 3-hydroxyphenyl, 4-hydroxyphenyl, 2-phenylvinyl, 2-(4-methylphenyl)vinyl, 2-(4-hydroxy-3-methyoxyphenyl)vinyl, 2-methylphenyl, 4-methylphenyl, or 4-methoxyphenyl. In some embodiments, R can be phenyl. In some embodiments, the imine of $C_{1-4}$ alkyl alaninate can be an imine of isopropyl alaninate having the formula:

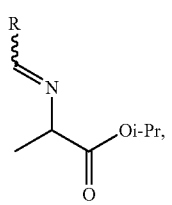

wherein R can be phenyl, 2-chlorophenyl, 4-chlorophenyl, 3-hydroxyphenyl, 4-hydroxyphenyl, 2-phenylvinyl, 2-(4-methylphenyl)vinyl, 2-(4-hydroxy-3-methyoxyphenyl)vinyl, 2-methylphenyl, 4-methylphenyl, or 4-methoxyphenyl. In some embodiments, R can be phenyl.

In some embodiments, the imine of isopropyl alaninate can be isopropyl 2-(benzylideneamino)propanoate:

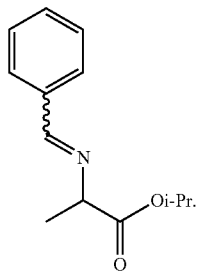

The imine of isopropyl alaninate can be isolated in a solution of the first solvent that can be used in the condensation reaction. In some embodiments, isopropyl 2-(benzylideneamino)propanoate can be isolated as a solution in toluene and used directly in the following step without purification and/or removal of the solvent.

In general, the condensation reaction (i.e., step 1) can be performed at any suitable temperature. For example, the condensation reaction mixture can be at a temperature of from 0° C. to 80° C. In some embodiments, the condensation reaction mixture can be at a temperature of from 20° C. to 30° C.

Step 2 includes three steps as described in steps 2a, 2b, and 2c.

With respect to step 2a, the imine of $C_{1-4}$ alkyl alaninate, the electorophile, the second base, the second solvent, the imine of $C_{1-4}$ alkyl 2-amino-2-methylhexanoate, and reaction temperature are described herein.

In some embodiments, the imine of $C_{1-4}$ alkyl alaninate can be an imine of isopropyl alaninate. In some embodiments, the imine of isopropyl alaninate can be isopropyl 2-(benzylideneamino)propanoate. In some embodiments, the imine of isopropyl alaninate can be a solution of isopropyl 2-(benzylideneamino)propanoate in toluene.

In some embodiments, the electorophile can be n-butyl bromide, n-butyl iodide, n-butyl methanesulphonate, n-butyl 4-methylbenzenesulfonate, or n-butyl sulfate. In some embodiments, the electorophile can be n-butyl bromide.

The second base can be an alkali alkoxide (e.g., sodium isopropoxide, sodium methoxide, sodium tert-butoxide, potassium tert-butoxide, or potassium isopropoxide), an alkali hydroxide in the presence of a phase transfer catalyst (e.g., sodium hydroxide or potassium hydroxide in combination with tetra-n-butylammonium bromide or tetra-n-butylammonium hydroxide), an alkali amide (e.g., lithium diisopropylamide, lithium bis(trimethylsilyl)amide, potassium bis(trimethylsilyl)-amide, or lithium 2,2,6,6-tetramethylpiperidide), an alkali carbonate (e.g., sodium carbonate, potassium carbonate, or cesium carbonate), or sodium hydride. In some embodiments, the second base includes sodium isopropoxide. In some embodiments, the second base can be sodium isopropoxide.

The second solvent can be an aromatic solvent (e.g., toluene, xylenes, chlorobenzene, or fluorobenzene), an ether (e.g., diethyl ether, methyl tert-butyl ether, tetrahydrofuran, 2-methyltetrahydrofuran, or 1,4-dioxane), a polar aprotic solvent (e.g., dimethylsulfoxide, N-methyl-2-pyrrolidone, or sulfolane), an alcohol (e.g., isopropanol, tert-butanol, or 2-methylbutan-2-ol), a chlorinated solvent (e.g., dichloromethane, or chlorobenzene), or combinations thereof. In some embodiments, the second solvent includes tetrahydrofuran and toluene. In some embodiments, the second solvent can be tetrahydrofuran and toluene.

In some embodiments, the imine of $C_{1-4}$ alkyl 2-amino-2-methylhexanoate has the formula:

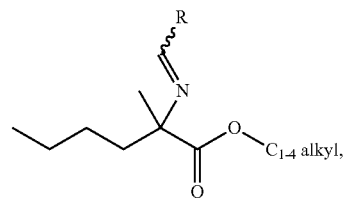

wherein R can be phenyl, 2-chlorophenyl, 4-chlorophenyl, 3-hydroxyphenyl, 4-hydroxyphenyl, 2-phenylvinyl, 2-(4-methylphenyl)vinyl, 2-(4-hydroxy-3-methyoxyphenyl)vinyl, 2-methylphenyl, 4-methylphenyl, or 4-methoxyphenyl. In some embodiments, R can be phenyl. In some embodiments, the imine of $C_{1-4}$ alkyl 2-amino-2-methylhexanoate can be an imine of isopropyl 2-amino-2-methylhexanoate having the formula:

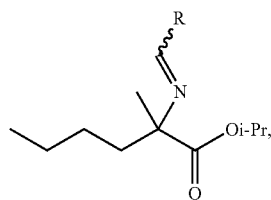

wherein R can be phenyl, 2-chlorophenyl, 4-chlorophenyl, 3-hydroxyphenyl, 4-hydroxyphenyl, 2-phenylvinyl, 2-(4-methylphenyl)vinyl, 2-(4-hydroxy-3-methyoxyphenyl)vinyl, 2-methylphenyl, 4-methylphenyl, or 4-methoxyphenyl. In some embodiments, R can be phenyl. In some embodiments, the imine of isopropyl 2-amino-2-methylhexanoate can be isopropyl 2-(benzylideneamino)-2-methylhexanoate:

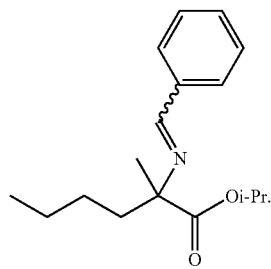

The second reaction mixture upon completion can be directly used in the following step without removal of the second solvent. In some embodiments, upon completion of the alkylation reaction, the second reaction mixture including isopropyl 2-(benzylideneamino)-2-methylhexanoate, tetrahydrofuran, and toluene can be directly used in the following step without removal of the solvent.

In general, the alkylation reaction (i.e., step 2a) can be performed at any suitable temperature, for example, at a temperature of from 0° C. to 80° C. In some embodiments, the reaction mixture of the alkylation reaction can be at a temperature of from 40° C. to 50° C.

With respect to step 2b, the imine of $C_{1-4}$ alkyl 2-amino-2-methylhexanoate, the first acid, the third solvent, the first salt of $C_{1-4}$ alkyl 2-amino-2-methylhexanoate, and reaction temperature are described herein.

In some embodiments, the imine can be an imine of isopropyl 2-amino-2-methylhexanoate. In some embodiments, the imine can be isopropyl 2-(benzylideneamino)-2-methylhexanoate. In some embodiments, the imine can be the reaction mixture from step 2a including isopropyl 2-(benzylideneamino)-2-methylhexanoate, tetrahydrofuran, and toluene.

The first acid can be a mineral acid (e.g., sulfuric acid, hydrochloric acid or phosphoric acid) or an organic acid (e.g., methanesulfonic acid, fumaric acid, acetic acid, formic acid, or ascorbic acid). In some embodiments, the first acid includes sulfuric acid. In some embodiments, the first acid can be in an aqueous solution. In some embodiments, the first acid includes an aqueous solution of sulfuric acid. In some embodiments, the first acid can be an aqueous solution of sulfuric acid.

In some embodiments, the first salt of $C_{1-4}$ alkyl 2-amino-2-methylhexanoate can be a first salt of isopropyl 2-amino-2-methylhexanoate. In some embodiments, the first salt of isopropyl 2-amino-2-methylhexanoate can be a sulfuric acid salt thereof.

The third solvent can be an aromatic solvent (e.g., toluene, xylenes, chlorobenzene, or fluorobenzene), an ether (e.g., diethyl ether, methyl tert-butyl ether, tetrahydrofuran, 2-methyltetrahydrofuran, or 1,4-dioxane), a polar aprotic solvent (e.g., dimethylsulfoxide, N-methyl-2-pyrrolidone, or sulfolane), an alcohol (e.g., isopropanol, tert-butanol, or 2-methylbutan-2-ol), a chlorinated solvent (e.g., dichloromethane, or chlorobenzene), water, or combinations thereof. In some embodiments, the third solvent includes tetrahydrofuran, toluene, and water. In those embodiments, the third reaction mixture can be a biphasic reaction mixture. In some embodiments, the third solvent can be tetrahydrofuran, toluene, and water.

In some embodiments, the first salt of isopropyl 2-amino-2-methylhexanoate can be isolated in an aqueous solution and used directly in the following step without purification and/or removal of water. In some embodiments, the sulfuric acid salt of isopropyl 2-amino-2-methylhexanoate can be isolated in an aqueous solution and used directly in the following step without purification and removal of water.

In general, the hydrolysis reaction (i.e., step 2b) can be performed at any suitable temperature, for example, at a temperature of from 0° C. to 80° C. In some embodiments, the reaction mixture of the hydrolysis reaction can be at a temperature of from 20° C. to 30° C.

Steps 2a and 2b can be performed in an one-pot reaction, in which the second reaction mixture upon completion can be directly treated with an aqueous solution of the first acid to form the third reaction mixture.

With respect to step 2c, the first salt of $C_{1-4}$ alkyl 2-amino-2-methylhexanoate, the third base, the fourth solvent, $C_{1-4}$ alkyl 2-amino-2-methylhexanoate, and reaction temperature are described herein.

In some embodiments, the first salt of $C_{1-4}$ alkyl 2-amino-2-methylhexanoate can be a first salt of isopropyl 2-amino-2-methylhexanoate. In some embodiments, the first salt of isopropyl 2-amino-2-methylhexanoate can be the sulfuric acid salt thereof. In some embodiments, the first salt of isopropyl 2-amino-2-methylhexanoate can be the aqueous solution of the sulfuric acid salt thereof.

The third base can be an inorganic base (e.g., lithium hydroxide, sodium hydroxide, potassium hydroxide, sodium carbonate, potassium carbonate, sodium bicarbonate, potassium bicarbonate, sodium phosphate tribasic, or potassium phosphate tribasic) or an organic base (e.g., sodium acetate, potassium acetate, sodium methoxide, sodium tert-butoxide, or potassium tert-butoxide). In some embodiments, the third base can be in an aqueous solution. In some embodiments, the third base includes an aqueous solution of sodium hydroxide. In some embodiments, the third base can be an aqueous solution of sodium hydroxide.

The fourth solvent can be an aromatic solvent (e.g., toluene, xylenes, or trifluorotoluene); an ether (e.g., diethyl ether, methyl tert-butyl ether, tetrahydrofuran, 2-methyltetrahydrofuran, or 1,4-dioxane), a chlorinated solvent (e.g., dichloromethane or 1,2-dichloroethane), or combinations thereof. In some embodiments, the fourth solvent includes 2-methyltetrahydrofuran. In some embodiments, the neutralization reaction (i.e., step 2c) can be performed by extraction. In some embodiments, the fourth solvent can be 2-methyltetrahydrofuran.

In some embodiments, $C_{1-4}$ alkyl 2-amino-2-methylhexanoate can be isopropyl 2-amino-2-methylhexanoate. In some embodiments, isopropyl 2-amino-2-methylhexanoate can be isolated as a solution in the fourth solvent. In some embodiments, isopropyl 2-amino-2-methylhexanoate can be isolated as a solution in 2-methyltetrahydrofuran and used directly in the following step without purification and/or removal of the solvent.

In general, the neutralization reaction (i.e., step 2c) can be performed at any suitable temperature, for example, at a temperature of from 0° C. to 40° C. In some embodiments, the reaction mixture of the neutralization reaction can be at a temperature of from 20° C. to 30° C.

With respect to step 3, $C_{1-4}$ alkyl 2-amino-2-methylhexanoate, the second acid, the fifth solvent, the second salt of $C_{1-4}$ alkyl 2-amino-2-methylhexanoate, and reaction temperature are described herein.

In some embodiments, $C_{1-4}$ alkyl 2-amino-2-methylhexanoate can be isopropyl 2-amino-2-methylhexanoate. In some embodiments, the isopropyl 2-amino-2-methylhexanoate can be the solution thereof in 2-methyltetrahydrofuran.

The second acid can be phosphoric acid, sulfuric acid, 4-nitrobenzoic acid, fumaric acid, succinic acid, or tartaric acid. In some embodiments, the second acid includes phosphoric acid. In some embodiments, the second acid can be in an aqueous solution. In some embodiments, the second acid includes an aqueous solution of phosphoric acid. In some embodiments, the second acid can be an aqueous solution of phosphoric acid.

The fifth solvent can be an ether (e.g., diethyl ether, methyl tert-butyl ether, tetrahydrofuran, 2-methyltetrahydrofuran, or 1,4-dioxane), a ketone (e.g., acetone or methyl isobutyl ketone), an alcohol (e.g., ethanol or isopropanol), an ester (e.g., ethyl acetate, butyl acetate, or isobutyl acetate), a hydrocarbon (e.g., n-heptane, hexanes, cyclohexane, methylcyclohexane), water, or combinations thereof. In some embodiments, the fifth solvent includes 2-methyltetrahydrofuran and water. In some embodiments, the fifth solvent can be 2-methyltetrahydrofuran and water.

In some embodiments, the second salt of $C_{1-4}$ alkyl 2-amino-2-methylhexanoate can be a second salt of isopropyl 2-amino-2-methylhexanoate. In some embodiments, the second salt of isopropyl 2-amino-2-methylhexanoate can be a phosphate salt thereof. In some embodiments, the phosphate salt of isopropyl 2-amino-2-methylhexanoate can be used directly without purification.

In general, the salt formation reaction (i.e., step 3) can be performed at any suitable temperature, for example, at a temperature of from 0° C. to 40° C. In some embodiments, the reaction mixture of the salt formation can be at a temperature of from 20° C. to 30° C.

With respect to step 4, the second salt of $C_{1-4}$ alkyl 2-amino-2-methylhexanoate, the enzyme, the fourth base, the sixth solvent, $C_{1-4}$ alkyl (R)-2-amino-2-methylhexanoate or the salt thereof, and reaction temperature are described herein.

In some embodiments, the second salt of $C_{1-4}$ alkyl 2-amino-2-methylhexanoate can be a second salt of isopropyl 2-amino-2-methylhexanoate. In some embodiments, the second salt of isopropyl 2-amino-2-methylhexanoate can be the phosphate salt thereof.

The enzyme of step 4) can be a serine endopeptidase subtilisin A (e.g., Alcalase® or other formulations thereof), or other proteases and hydrolases (e.g., protease from *Aspergillus oryzae*, amano lipase A from *Aspergillus niger*, or lipase from *Candida lipolytica*). In some embodiments, the enzyme includes a serine endopeptidase subtilisin A. In some embodiments, the enzyme includes Alcalase®. In some embodiments, the enzyme can be a serine endopeptidase subtilisin A. In some embodiments, the enzyme can be Alcalase®.

The fourth base can be an inorganic base (e.g., sodium phosphate tribasic, potassium phosphate tribasic, sodium phosphate dibasic, potassium phosphate dibasic, sodium carbonate, potassium carbonate, sodium bicarbonate, or potassium bicarbonate) or an organic base (e.g., sodium acetate or potassium acetate). In some embodiments, the fourth base includes potassium phosphate tribasic. In some embodiments, the fourth base can be in an aqueous solution. In some embodiments, the fourth base includes an aqueous solution of potassium phosphate tribasic. In some embodiments, the fourth base can be an aqueous solution of potassium phosphate tribasic.

The sixth solvent can be a mixture of water and a water-miscible organic co-solvent (e.g., acetone, dimethylsulfoxide, acetonitrile, or tert-butanol), a mixture of water and a water-immiscible organic co-solvent (e.g., methyl tert-butyl ether, ethyl acetate, or methyl isobutyl ketone). In some embodiments, the sixth solvent includes acetone and water. In some embodiments, the sixth solvent can be acetone and water.

In some embodiments, $C_{1-4}$ alkyl (R)-2-amino-2-methylhexanoate can be isopropyl (R)-2-amino-2-methylhexanoate. Isopropyl (R)-2-amino-2-methylhexanoate can be isolated in a solution of the water-immiscible organic co-solvent that can be used in the sixth reaction mixture. In some embodiments, isopropyl (R)-2-amino-2-methylhexanoate can be isolated as a solution in methyl tert-butyl ether and used directly in the following step without purification and/or removal of the solvent.

In general, the enzymatic resolution reaction (i.e., step 4) can be performed at any suitable temperature, for example, at a temperature of from 0° C. to 50° C. In some embodiments, the reaction mixture of the enzymatic resolution reaction can be at a temperature of from 30° C. to 40° C.

With respect to step 5, $C_{1-4}$alkyl (R)-2-amino-2-methylhexanoate or the salt thereof, the BOC protecting reagent, the seventh solvent, $C_{1-4}$ alkyl (R)-2-((tert-butoxycarbonyl)amino)-2-methylhexanoate, and reaction temperature are described herein.

In some embodiments, $C_{1-4}$ alkyl (R)-2-amino-2-methylhexanoate can be isopropyl (R)-2-amino-2-methylhexanoate. In some embodiments, isopropyl (R)-2-amino-2-methylhexanoate can be the solution thereof in methyl tert-butyl ether.

In some embodiments, the BOC protecting reagent can be di-tert-butyl dicarbonate, di-tert-butyl-iminodicarboxylate, or tert-butyl chloroformate. In some embodiments, the BOC protecting reagent includes di-tert-butyl dicarbonate. In some embodiments, the BOC protecting reagent can be di-tert-butyl dicarbonate.

The seventh solvent can be an ether (e.g., diethyl ether, methyl tert-butyl ether, tetrahydrofuran, 2-methyltetrahydrofuran, or 1,4-dioxane), a ketone (e.g., acetone or methyl isobutyl ketone, etc.), an ester (e.g., ethyl acetate, butyl acetate, or isobutyl acetate), an aromatic solvent (e.g., toluene or xylenes), a chlorinated solvent (e.g., dichloromethane or 1,2-dichloroethane), water, or combinations thereof. In some embodiments, the seventh solvent includes methyl tert-butyl ether. In some embodiments, the seventh solvent can be methyl tert-butyl ether.

In some embodiments, $C_{1-4}$ alkyl (R)-2-((tert-butoxycarbonyl)amino)-2-methylhexanoate can be isopropyl (R)-2-((tert-butoxycarbonyl)amino)-2-methylhexanoate. Isopropyl (R)-2-((tert-butoxycarbonyl)amino)-2-methylhexanoate can be isolated in the seventh solvent. In some embodiments, isopropyl (R)-2-((tert-butoxycarbonyl)amino)-2-methylhexanoate can be isolated as a solution in methyl tert-butyl ether and used directly in the following step without purification and/or removal of methyl tert-butyl ether.

In general, the BOC-protecting reaction (i.e., step 5) can be performed at any suitable temperature, for example, at a temperature of from 0° C. to 100° C. In some embodiments, the reaction mixture of the BOC-protecting reaction can be at a temperature of from 20° C. to 30° C.

With respect to step 6, $C_{1-4}$alkyl (R)-2-((tert-butoxycarbonyl)amino)-2-methylhexanoate, the reductant, the promoter, the eighth solvent, isolation of tert-butyl (R)-(1-hydroxy-2-methylhexan-2-yl)carbamate, and reaction temperature are described herein.

In some embodiments, $C_{1-4}$ alkyl (R)-2-((tert-butoxycarbonyl)amino)-2-methylhexanoate can be isopropyl (R)-2-((tert-butoxycarbonyl)amino)-2-methylhexanoate. In some embodiments, isopropyl (R)-2-((tert-butoxycarbonyl)amino)-2-methylhexanoate can be the solution thereof in methyl tert-butyl ether.

The reductant can be any suitable reducing agent capable of reducing an ester group (e.g., isopropyl ester) to the corresponding —$CH_2OH$. For example, the reductant can be a borohydride reagent (e.g., lithium borohydride, potassium borohydride, lithium triethylborohydride, or sodium borohydride/iodine), an aluminum hydride reagent (e.g., lithium aluminum hydride or diisobutylaluminum hydride). In some embodiments, the reductant includes lithium borohydride. In some embodiments, the reductant includes a solution of lithium borohydride in tetrahydrofuran. In some embodiments, the reductant can be lithium borohydride. In some embodiments, the reductant can be a solution of lithium borohydride in tetrahydrofuran.

The promoter can be an alcohol (e.g., methanol, ethanol, n-propanol, isopropanol, or tert-butanol). In some embodiments, the promoter includes methanol. In some embodiments, the promoter can be methanol.

The eighth solvent can be an ether (diethyl ether, methyl tert-butyl ether, tetrahydrofuran, 2-methyltetrahydrofuran, 1,4-dioxane, or 1,2-dimethoxyethane, etc.), an aromatic solvent (e.g., toluene or xylenes), or combinations thereof. In some embodiments, the eighth solvent includes methyl tert-butyl ether and tetrahydrofuran. In some embodiments, the eighth solvent can be methyl tert-butyl ether and tetrahydrofuran.

tert-Butyl (R)-(1-hydroxy-2-methylhexan-2-yl)carbamate can be isolated in the eighth solvent. In some embodiments, tert-butyl (R)-(1-hydroxy-2-methylhexan-2-yl)carbamate can be isolated as a solution in methyl tert-butyl ether and used directly in the following step without purification and/or removal of methyl tert-butyl ether.

In general, the reduction reaction (i.e., step 6) can be performed at any suitable temperature, for example, at a temperature of from 0° C. to 60° C. In some embodiments, the reaction mixture of the reduction reaction can be at a temperature of from 20° C. to 30° C.

With respect to step 7, the tert-butyl (R)-(1-hydroxy-2-methylhexan-2-yl)carbamate, the third acid, the ninth solvent, the salt of (R)-2-amino-2-methylhexan-1-ol, and reaction temperature are described herein.

In some embodiments, the tert-butyl (R)-(1-hydroxy-2-methylhexan-2-yl)carbamate can be the solution thereof in methyl tert-butyl ether.

The third acid can be a sulfonic acid (e.g., p-toluenesulfonic acid, methanesulfonic acid, or benzenesulfonic acid), a mineral acid (e.g., hydrochloric acid or sulfuric acid), or an organic acid (e.g., trifluoroacetic acid). In some embodiments, the third acid includes p-toluenesulfonic acid. In some embodiments, the third acid can be p-toluenesulfonic acid.

The ninth solvent can be an alcohol (e.g., methanol, ethanol, n-propanol, isopropanol, or n-butanol), an ether (e.g., diethyl ether, methyl tert-butyl ether, tetrahydrofuran, 2-methyltetrahydrofuran, 1,4-dioxane, or 1,2 dimethoxyethane), an aromatic solvent (e.g., toluene or xylenes), a chlorinated solvent (e.g., dichloromethane or 1,2-dichloroethane), a ketone solvent (e.g., acetone or methyl isobutyl ketone), an ester (e.g., ethyl acetate, butyl acetate, or isobutyl acetate), or combinations thereof. In some embodiments, the ninth solvent includes isopropanol. In some embodiments, the ninth solvent can be isopropanol.

In some embodiments, the salt of (R)-2-amino-2-methylhexan-1-ol can be a compound of Formula VIb:

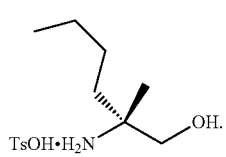

(VIb)

In general, the BOC-deprotecting reaction (i.e., step 7) can be performed at any suitable temperature, for example, at a temperature of from 0° C. to 100° C. In some embodiments, the reaction mixture of the BOC-deprotecting reaction can be at a temperature of from 40° C. to 60° C.

2. Preparation of a Salt of (R)-2-Amino-2-Methylhexan-1-Ol, Route 2

Figure 3B:
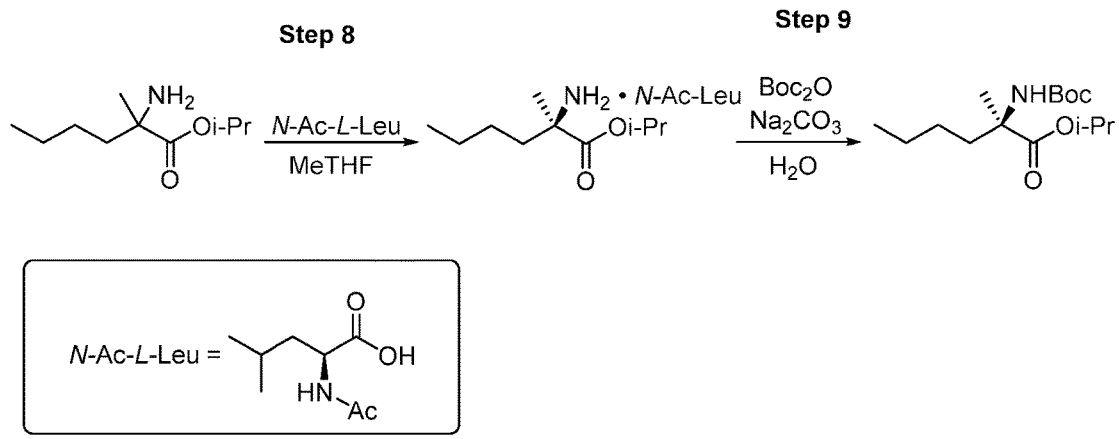
FIG. 3B shows an alternative method for preparing isopropyl (R)-2-((tert-butoxycarbonyl)amino)-2-methylhexanoate.

In some embodiments, the above steps 3, 4, and 5 can be replaced with steps 8 and 9 as shown in the scheme of FIG. 3B to provide the Boc-protected isopropyl (R)-2-amino-2-methylhexanoate.

In some embodiments, the present disclosure provides a method for preparing a salt of (R)-2-amino-2-methylhexan-1-ol:

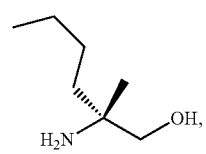

the method including:
1) forming a first reaction mixture including $C_{1-4}$ alkyl alaninate:

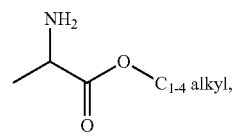

or a salt thereof, an aldehyde, a first base, a desiccant, and a first solvent to form an imine of $C_{1-4}$ alkyl alaninate having the formula:

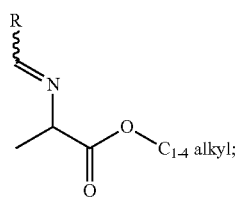

2a) forming a second mixture including the imine of $C_{1-4}$ alkyl alaninate, an electrophile, a second base, and a second solvent to form an imine of $C_{1-4}$ alkyl 2-amino-2-methylhexanoate having the formula:

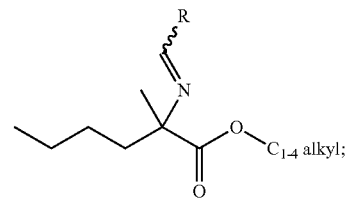

2b) forming a third reaction mixture including the imine of $C_{1-4}$ alkyl 2-amino-2-methylhexanoate, a first acid and a third solvent to form a salt of $C_{1-4}$ alkyl 2-amino-2-methylhexanoate:

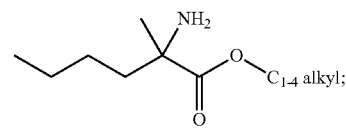

2c) forming a fourth reaction mixture including the salt of $C_{1-4}$ alkyl 2-amino-2-methylhexanoate, a third base, a fourth solvent, and water to form $C_{1-4}$ alkyl 2-amino-2-methylhexanoate in a neutral form;

8) forming a fifth reaction mixture including $C_{1-4}$ alkyl 2-amino-2-methylhexanoate, a second acid, and a fifth solvent to form a first salt of $C_{1-4}$ alkyl (R)-2-amino-2-methylhexanoate:

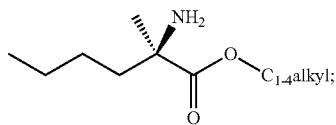

9) forming a sixth reaction mixture including the first salt of $C_{1-4}$ alkyl (R)-2-amino-2-methylhexanoate, a BOC-protecting reagent, a fourth base, and a sixth solvent to form $C_{1-4}$ alkyl (R)-2-((tert-butoxycarbonyl)amino)-2-methylhexanoate:

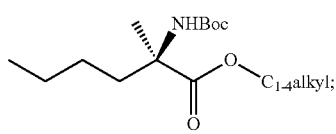

6) forming an eighth reaction mixture including $C_{1-4}$ alkyl (R)-2-((tert-butoxycarbonyl)amino)-2-methylhexanoate, a reductant, a promoter, and an eighth solvent to form tert-butyl (R)-(1-hydroxy-2-methylhexan-2-yl) carbamate:

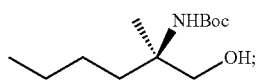

and 7) forming a ninth reaction mixture including tert-butyl (R)-(1-hydroxy-2-methylhexan-2-yl)carbamate, a third acid, and a ninth solvent to provide the salt of (R)-2-amino-2-methylhexan-1-ol, wherein R can be unsubstituted or substituted aryl or unsubstituted or substituted aryl-CH=CH—.

In some embodiments, $C_{1-4}$ alkyl in any one of formulae or compounds in steps 1, 2a, 2b, 2c, 8-9, and 6 can be methyl, ethyl, n-propyl, isopropyl, n-butyl, sec-butyl, or tert-butyl. In some embodiments, $C_{1-4}$ alkyl in any one of formulae or compounds in steps 1, 2a, 2b, 2c, 8-9, and 6 can be isopropyl.

Steps 1, 2a, 2b, 3c, 6, and 7 are described above in the preparation of the salt of (R)-2-amino-2-methylhexan-1-ol, Route 1.

With respect to step 8, $C_{1-4}$ alkyl 2-amino-2-methylhexanoate, the second acid, the fifth solvent, the first salt of $C_{1-4}$ alkyl (R)-2-amino-2-methylhexanoate, and reaction temperature are described herein.

In some embodiments, $C_{1-4}$ alkyl 2-amino-2-methylhexanoate can be isopropyl 2-amino-2-methylhexanoate. In some embodiments, isopropyl 2-amino-2-methylhexanoate can be the solution thereof in 2-methyltetrahydrofuran.

The second acid can be an amino acid (e.g., N-acetyl-L-leucine, N-acetyl-L-aspartic acid, or N-acetyl-L-phenylalanine), a tartaric acid or a derivative thereof (e.g., dibenzoyl-D-tartaric acid, di-p-toluoyl-D-tartaric acid, L-mandelic acid, or O-acetyl-D-mandelic acid). In some embodiments, the second acid includes N-acetyl-L-leucine. In some embodiments, the second acid can be N-acetyl-L-leucine.

The fifth solvent can be an ether (e.g., diethyl ether, methyl tert-butyl ether, tetrahydrofuran, 2-methyltetrahydrofuran, 1,4-dioxane, or 1,2 dimethoxyethane), a ketone (e.g., acetone or methyl isobutyl ketone), an alcohol (e.g., methanol, ethanol, n-propanol, or isopropanol), an ester (e.g., ethyl acetate, butyl acetate, or isobutyl acetate), a hydrocarbon solvent (e.g., hexanes, n-heptane, cyclohexane, or methylcyclohexane), or combinations thereof.

In some embodiments, the fifth solvent includes 2-methyltetrahydrofuran. In some embodiments, the fifth solvent can be 2-methyltetrahydrofuran.

In some embodiments, the first salt of $C_{1-4}$ alkyl (R)-2-amino-2-methylhexanoate can be a first salt of isopropyl (R)-2-amino-2-methylhexanoate. In some embodiments, the first salt of $C_{1-4}$ alkyl (R)-2-amino-2-methylhexanoate can be a N-acetyl-L-leucine salt of the formula:

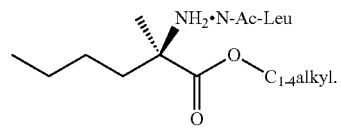

In some embodiments, the first salt of $C_{1-4}$ alkyl (R)-2-amino-2-methylhexanoate can be a N-acetyl-L-leucine salt of the formula:

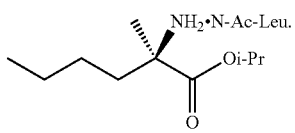

The first salt of isopropyl (R)-2-amino-2-methylhexanoate can be used directly in the following step 9 without purification. In some embodiments, the N-acetyl-L-leucine salt of isopropyl (R)-2-amino-2-methylhexanoate can be used directly in the following step 9 without purification.

In general, the salt formation and resolution reaction (i.e., step 8) can be performed at any suitable temperature, for example, at a temperature of from 0° C. to 80° C. In some embodiments, the reaction mixture of the salt formation and resolution reaction can be at a temperature of from 20° C. to 50° C.

With respect to step 9, the first salt of $C_{1-4}$ alkyl (R)-2-amino-2-methylhexanoate, the BOC-protecting reagent, the fourth base, the sixth solvent, $C_{1-4}$ alkyl (R)-2-((tert-butoxycarbonyl)amino)-2-methylhexanoate, and reaction temperature are described herein.

In some embodiments, the first salt of $C_{1-4}$ alkyl (R)-2-amino-2-methylhexanoate can be a first salt of isopropyl (R)-2-amino-2-methylhexanoate. In some embodiments, the first salt of isopropyl (R)-2-amino-2-methylhexanoate can be the N-acetyl-L-leucine salt.

In some embodiments, the BOC protecting reagent can be di-tert-butyl dicarbonate, di-tert-butyl-iminodicarboxylate, or tert-butyl chloroformate. In some embodiments, the BOC protecting reagent includes di-tert-butyl dicarbonate. In some embodiments, the BOC protecting reagent can be di-tert-butyl dicarbonate.

The sixth solvent can be an ether (e.g., diethyl ether, methyl tert-butyl ether, tetrahydrofuran, 2-methyltetrahydrofuran, 1,4-dioxane, or 1,2-dimethoxyethane), a ketone (e.g., acetone or methyl isobutyl ketone), an ester (e.g., ethyl acetate, butyl acetate, or isobutyl acetate), an aromatic solvent (e.g., toluene or xylenes), a chlorinated solvent (e.g., dichloromethane or 1,2-dichloroethane), an alcohol (e.g., ethanol, n-butanol, or 2 propanol), water, or combinations thereof. In some embodiments, the sixth solvent includes water. In some embodiments, the sixth solvent can be water.

In some embodiments, $C_{1-4}$ alkyl (R)-2-((tert-butoxycarbonyl)amino)-2-methylhexanoate can be isopropyl (R)-2-((tert-butoxycarbonyl)amino)-2-methylhexanoate. In some embodiments, isopropyl (R)-2-((tert-butoxycarbonyl)amino)-2-methylhexanoate can be isolated in the fifth solvent. In some embodiments, isopropyl (R)-2-((tert-butoxycarbonyl)amino)-2-methylhexanoate can be isolated as a solution in methyl tert-butyl ether and used directly in the following step without purification and/or removal of methyl tert-butyl ether.

In general, the BOC-protection reaction (i.e., step 9) can be performed at any suitable temperature, for example, at a temperature of from 0° C. to 100° C. In some embodiments, the reaction mixture of the BOC-protecting reaction can be at a temperature of from 20° C. to 30° C.

3. Preparation of a Salt of (R)-2-Amino-2-methylhexan-1-ol, Route 3

In some embodiments, the present disclosure provides a method for preparing a salt of (R)-2-amino-2-methylhexan-1-ol:

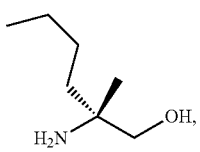

the method including:
10) forming a first reaction mixture including (R)-2-amino-2-phenylethan-1-ol or a salt thereof, a substrate, a dehydrating agent or additive, and a first solvent to form (R)-3-methyl-5-phenyl-5,6-dihydro-2H-1,4-oxazin-2-one:

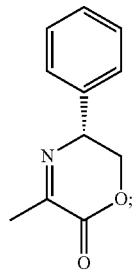

11) forming a second reaction mixture including (R)-3-methyl-5-phenyl-5,6-dihydro-2H-1,4-oxazin-2-one, a Lewis acid, a nucleophile, and a second solvent to form (3R,5R)-3-butyl-3-methyl-5-phenylmorpholin-2-one:

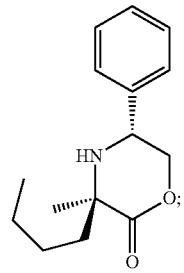 [SMILES: CCCC[C@@]1(C)N[C@H](c2ccccc2)COC1=O]

12) forming a third reaction mixture including (3R,5R)-3-butyl-3-methyl-5-phenylmorpholin-2-one, a reducing agent, and a third solvent to form (R)-2-(((R)-2-hydroxy-1-phenylethyl)amino)-2-methylhexan-1-ol:

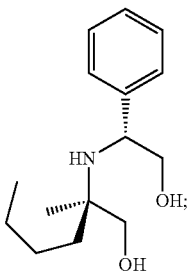 [SMILES: CCCC[C@](C)(CO)N[C@@H](CO)c1ccccc1]

and
13) forming a fourth reaction mixture including (R)-2-(((R)-2-hydroxy-1-phenylethyl)amino)-2-methylhexan-1-ol, a hydrogen source, a catalyst, an acid, and a fourth solvent to provide the salt of (R)-2-amino-2-methylhexan-1-ol.

Figure 4:
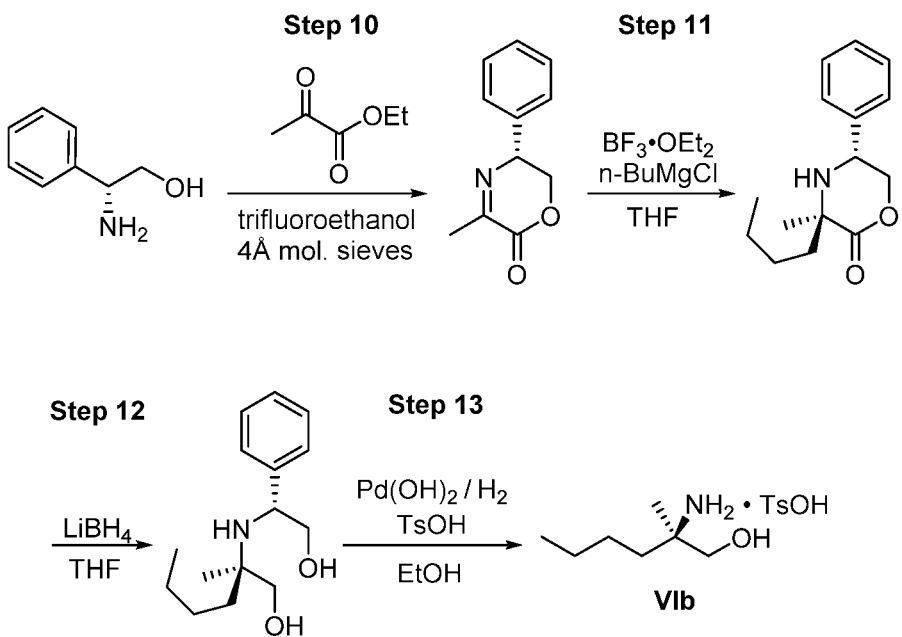
FIG. 4 shows the preparation of the compound of Formula VIb via steps of cyclocondensation, nucleophilic addition, reduction, and hydrogenolysis/TsOH salt formation.

In some embodiments, the salt of (R)-2-amino-2-methylhexan-1-ol can be prepared according to steps 10-13 as shown in the scheme of FIG. 4.

With respect to step 10, the substrate, the dehydrating agent or additive, the first solvent, and reaction temperature are described herein.

The substrate can be an alkyl pyruvate (e.g., methyl pyruvate or ethyl pyruvate), pyruvic acid, or 2,2-diethoxypropionic acid ethyl ester. In some embodiments, the substrate includes ethyl pyruvate. In some embodiments, the substrate can be ethyl pyruvate.

The dehydrating agent or additive can be an organic acid (e.g., para-toluenesulfonic acid, benzensulfonic acid, methanesulfonic acid, trifluoromethanesulfonic acid, trifluoroacetic acid, or trichloroacetic acid), a metal halide (lithium chloride, magnesium chloride, or zinc chloride), magnesium sulfate, sodium sulfate, an azeotropic removal of water (e.g., a Dean Stark trap), or 4 Å molecular sieves. In some embodiments, the dehydrating agent or additive includes 4 Å molecular sieves. In some embodiments, the dehydrating agent or additive can be 4 Å molecular sieves.

The first solvent can be an ether (e.g., tetrahydrofuran, 2-methyltetrahydrofuran, 1,4-dioxane, cyclopentyl methyl ether, or methyl tert-butyl ether), an aromatic solvent (e.g., toluene, trifluorotoluene, benzene, or xylenes), a hydrocarbon solvent (e.g., n-heptane, cyclohexane, or methylcyclohexane), an alcohol solvent (e.g, methanol, ethanol, 1-butanol, 2,2,2-trifluoroethanol, or hexafluoro-isopropanol), a chlorinated solvent (e.g., dichloromethane, 1,2-dichloroethane, or chloroform), or combinations thereof. In some embodiments, the first solvent includes 2,2,2-trifluoroethanol. In some embodiments, the first solvent can be 2,2,2-trifluoroethanol.

In general, the cyclocondensation reaction (i.e., step 10) can be performed at any suitable temperature, for example, at a temperature of from 20° C. to 110° C. In some embodiments, the reaction mixture of the cyclocondensation reaction can be at a temperature of from 20° C. to a reflux temperature. In some embodiments, the reaction mixture of the cyclocondensation reaction can be heated to reflux.

With respect to step 11, the Lewis acid, the nucleophile, the second solvent, and reaction temperature are described herein.

The Lewis acid can be boron trifluoride diethyl etherate, lithium chloride, zinc chloride, titanium tetrachloride, silicon tetrachloride, aluminum chloride, samarium(II) iodide, cerium(III) chloride, or lanthanum(III) chloride lithium chloride complex. In some embodiments, the Lewis acid includes boron trifluoride diethyl etherate. In some embodiments, the Lewis acid can be boron trifluoride diethyl etherate.

The nucleophile can be n-butylmagnesium chloride, n-butyl lithium, or n-butylzinc bromide. In some embodiments, the nucleophile includes n-butylmagnesium chloride. In some embodiments, the nucleophile can be n-butylmagnesium chloride.

The second solvent can be an ether (e.g., tetrahydrofuran, 2-methyltetrahydrofuran, 1,4-dioxane, cyclopentyl methyl ether, methyl tert-butyl ether, or diethyl ether), an aromatic solvent (e.g., toluene or trifluorotoluene), a hydrocarbon solvent (n-hexane, n-heptane, cyclohexane, or methylcyclohexane), a chlorinated solvent (e.g., dichloromethane or chlorobenzene), or combinations thereof. In some embodiments, the second solvent includes tetrahydrofuran. In some embodiments, the second solvent can be tetrahydrofuran.

In general, the nucleophilic addition reaction (i.e., step 11) can be performed at any suitable temperature, for example, at a temperature of from −78° C. to −40° C.

With respect to step 12, the reducing agent, the third solvent, and reaction temperature are described herein.

The reducing agent can be lithium borohydride, lithium aluminum hydride, aluminum hydride, sodium bis(2-methoxyethoxy)aluminum hydride, borane complexes of tetrahydrofuran and dimethyl sulfide, lithium triethylborohydride, sodium borohydride aluminum chloride complex, lithium 9-boratabicyclo[3.3.1]nonane, diisobutylaluminum hydride, lithium tri-tert-butoxyaluminum hydride, or potassium borohydride. In some embodiments, the reducing agent includes lithium borohydride. In some embodiments, the reducing agent can be lithium borohydride.

The third solvent can be an ether (e.g., tetrahydrofuran, 2-methyltetrahydrofuran, 1,4-dioxane, cyclopentyl methyl ether, methyl tert-butyl ether, or diethyl ether), an aromatic solvent (e.g., toluene, xylene, or trifluorotoluene), a hydrocarbon solvent (e.g., n-hexane, n-heptane, or cyclohexane), or combinations thereof. In some embodiments, the third solvent includes tetrahydrofuran. In some embodiments, the third solvent can be tetrahydrofuran.

The reduction reaction mixture (i.e., step 12) can further include an additive. The additive can be an alcohol (e.g., methanol, ethanol, n-butanol, isopropanol, or tert-butanol).

In general, the reduction reaction (i.e., step 12) can be performed at any suitable temperature, for example, at a temperature of from −40° C. to 50° C. In some embodiments, the reaction mixture of the reduction reaction can be at a temperature of from 0° C. to 20° C.

With respect to step 13, the hydrogen source, the catalyst, the acid, the fourth solvent, the salt of (R)-2-amino-2-methylhexan-1-ol, and reaction temperature are described herein.

The hydrogen source can be hydrogen gas, formic acid, ammonium formate, cyclohexene, hydrazine, or sodium hypophosphite. In some embodiments, the hydrogen source includes hydrogen gas. In some embodiments, the hydrogen source can be hydrogen gas.

The catalyst can be palladium hydroxide on carbon, palladium on carbon, or platinum oxide. In some embodiments, the catalyst includes palladium hydroxide on carbon. In some embodiments, the catalyst can be palladium hydroxide on carbon.

The acid can be a sulfonic acid (e.g., p-toluenesulfonic acid, methanesulfonic acid, or benzenesulfonic acid), a mineral acid (e.g., hydrochloric acid or sulfuric acid), or an organic acid (e.g., trifluoroacetic acid). In some embodiments, the acid includes p-toluenesulfonic acid. In some embodiments, the acid can be p-toluenesulfonic acid.

The fourth solvent can be an alcohol solvent (e.g., methanol, ethanol, or isopropanol), an organic acid solvent (e.g., acetic acid or formic acid), an ether (e.g., tetrahydrofuran, 2-methyltetrahydrofuran, 1,4-dioxane, cyclopentyl methyl ether, or tert-butyl methyl ether), a polar aprotic solvent (e.g., N-methyl-2-pyrrolidone, N,N-dimethylformamide, or N,N-dimethylacetamide), or combinations thereof. In some embodiments, the fourth solvent includes ethanol. In some embodiments, the fourth solvent can be ethanol.

In some embodiments, the salt of (R)-2-amino-2-methylhexan-1-ol can be a compound of Formula VIb:

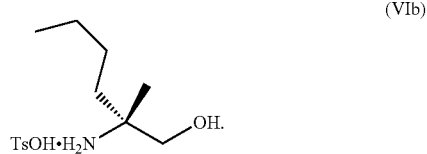

(VIb)

In general, the hydrogenation reaction (i.e., step 13) can be performed at any suitable temperature, for example, at a temperature of from 0° C. to 85° C. In some embodiments, the reaction mixture of the hydrogenation reaction can be at a temperature of from 20° C. to a reflux temperature. In some embodiments, the reaction mixture of the hydrogenation reaction can be heated to reflux.

4. Preparation of a Salt of (R)-2-Amino-2-methylhexan-1-ol, Route 4

In some embodiments, the present disclosure provides a method for preparing a salt of (R)-2-amino-2-methylhexan-1-ol:

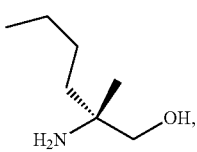

the method including:

1) forming a first reaction mixture including an imine of $C_{1-4}$ alkyl alaninate having the formula:

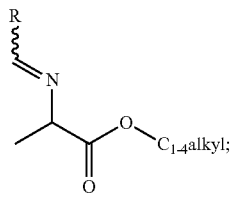

an electrophile, a first base, a first catalyst, and a first solvent to form an imine of $C_{1-4}$ alkyl (R)-2-amino-2-methylhexanoate having the formula:

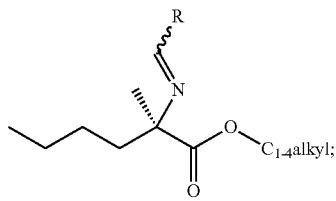

2a) forming a second reaction mixture including the imine of $C_{1-4}$ alkyl (R)-2-amino-2-methylhexanoate, a first acid and a second solvent to form a crude first salt of (R)-2-amino-2-methylhexanoate:

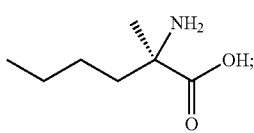

2b) triturating the crude first salt of (R)-2-amino-2-methylhexanoate in the second solvent to provide the first salt of (R)-2-amino-2-methylhexanoate;

3a) forming a third reaction mixture including the first salt of (R)-2-amino-2-methylhexanoate, benzyl chloride, a second base, a third solvent, and water to form a salt of (R)-2-benzamido-2-methylhexanoic acid having the formula:

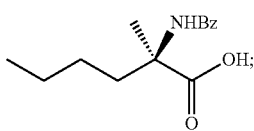

3b) forming a fourth reaction mixture including the salt of (R)-2-benzamido-2-methylhexanoic acid, a second acid, a fourth solvent, and water to form (R)-2-benzamido-2-methylhexanoic acid;

4a) forming a fifth reaction mixture including (R)-2-benzamido-2-methylhexanoic acid, a first reducing agent, and a fifth solvent to form (R)—N-(1-hydroxy-2-methylhexan-2-yl)benzamide having the formula:

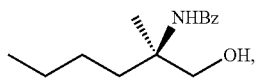

or a salt thereof, 4b) forming a sixth reaction mixture including (R)—N-(1-hydroxy-2-methylhexan-2-yl)benzamide or the salt thereof, a second reducing agent, a second catalyst, a third acid, and a sixth solvent to provide the salt of (R)-2-amino-2-methylhexan-1-ol, wherein R can be unsubstituted or substituted aryl or unsubstituted or substituted aryl-CH=CH—.

Figure 14:
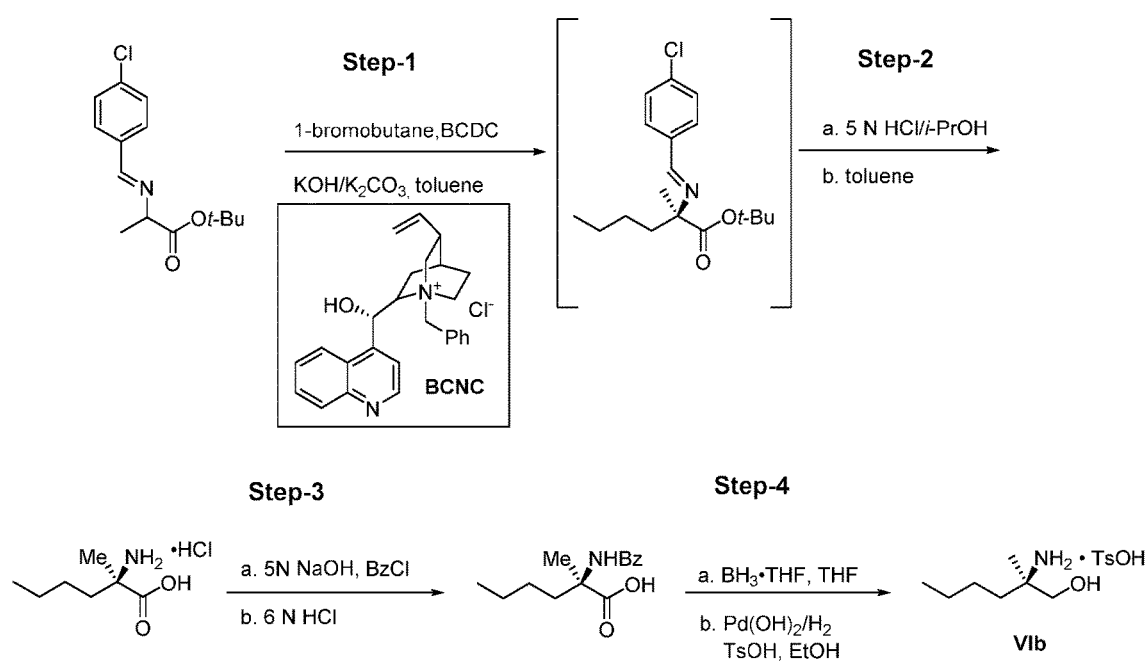
FIG. 14 shows the preparation of the compound of Formula VIb via steps of nucleophilic addition, Bz protection, reduction, and deprotection/TsOH salt formation.

In some embodiments, the salt of (R)-2-amino-2-methylhexan-1-ol can be prepared according to steps 1-4 as shown in the scheme of FIG. 14.

In some embodiments, $C_{1-4}$ alkyl in any one of formulae or compounds in step 1 can be methyl, ethyl, n-propyl, isopropyl, n-butyl, sec-butyl, or tert-butyl. In some embodiments, $C_{1-4}$ alkyl in any one of formulae or compounds in step 1 includes isopropyl. In some embodiments, $C_{1-4}$ alkyl in any one of formulae or compounds in step 1 can be isopropyl. In some embodiments, $C_{1-4}$ alkyl in any one of formulae or compounds in step 1 includes tert-butyl. In some embodiments, $C_{1-4}$ alkyl in any one of formulae or compounds in step 1 can be tert-butyl.

The imine of $C_{1-4}$ alkyl alaninate in Step 1 can be prepared according to the methods as described herein, for example in Section 1 under Section F, and in Example 8.

With respect to step 1, the imine of $C_{1-4}$ alkyl alaninate, the electrophile, the first base, the first catalyst, the first solvent, the imine of $C_{1-4}$ alkyl (R)-2-amino-2-methylhexanoate, and reaction temperature are described herein.

In some embodiments, the imine of $C_{1-4}$ alkyl alaninate has the formula:

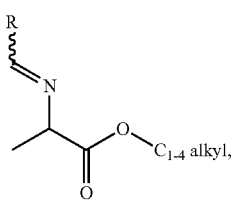

wherein R can be phenyl, 2-chlorophenyl, 4-chlorophenyl, 3-hydroxyphenyl, 4-hydroxyphenyl, 2-phenylvinyl, 2-(4-methylphenyl)vinyl, 2-(4-hydroxy-3-methyoxyphenyl)vinyl, 2-methylphenyl, 4-methylphenyl, or 4-methoxyphenyl. In some embodiments, R includes 4-chlorophenyl. In some embodiments, the imine of $C_{1-4}$ alkyl alaninate can be an imine of tert-butyl alaninate having the formula:

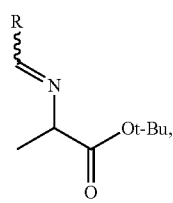

wherein R can be phenyl, 2-chlorophenyl, 4-chlorophenyl, 3-hydroxyphenyl, 4-hydroxyphenyl, 2-phenylvinyl, 2-(4-methylphenyl)vinyl, 2-(4-hydroxy-3-methyoxyphenyl)vinyl, 2-methylphenyl, 4-methylphenyl, or 4-methoxyphenyl. In some embodiments, R can be 4-chlorophenyl. In some embodiments, the imine of tert-butyl alaninate can be tert-butyl 2-((4-chlorobenzylidene)amino)propanoate:

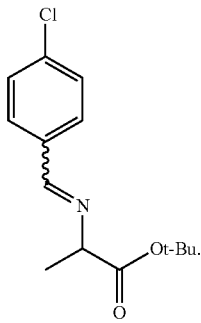 [SMILES: CC(N=Cc1ccc(Cl)cc1)C(=O)OC(C)(C)C]

In some embodiments, the imine of tert-butyl alaninate can be a solution of tert-butyl 2-((4-chlorobenzylidene)amino) propanoate in toluene.

In some embodiments, the electrophile can be n-butyl bromide, n-butyl iodide, n-butyl methanesulphonate, n-butyl 4-methylbenzenesulfonate, or n-butyl sulfate. In some embodiments, the electrophile includes n-butyl bromide. In some embodiments, the electrophile can be n-butyl bromide.

The first base can be a hydroxide (e.g., lithium hydroxide, sodium hydroxide, potassium hydroxide, cesium hydroxide, rubidium hydroxide, barium hydroxide, calcium hydroxide, or tetra-n-butylammonium hydroxide), an alkoxide (e.g., sodium methoxide, sodium tert-butoxide, potassium tert-butoxide, potassium isopropoxide, or sodium tert-pentoxide), a carbonate (e.g., sodium carbonate, potassium carbonate, rubidium carbonate, magnesium carbonate, calcium carbonate, strontium carbonate, barium carbonate, or ammonium carbonate), a hydride (e.g., sodium hydride or potassium hydride), or combinations thereof. In some embodiments, the first base includes potassium hydroxide and potassium carbonate. In some embodiments, the first base can be potassium hydroxide and potassium carbonate.

In some embodiments, the first catalyst can be a chiral auxiliary. In some embodiments, the first catalyst can be N-benzylcinchonidinium chloride, N-benzylcinchonidinium bromide, N-[4-(trifluoromethyl)benzyl]cinchoninium bromide, N-(9-anthracenylmethyl)cinchoninium chloride, (11bS)-(+)-4,4-Dibutyl-4,5-dihydro-2,6-bis(3,4,5-trifluorophenyl)-3H-dinaphth[2,1-c:1',2'-e]azepinium bromide, (11bS)-4,4-dibutyl-4,5-dihydro-2,6-bis[3,5-bis(trifluoromethyl)phenyl]-3H-dinaphtho[2,1-c:1',2'-e]phosphepinium bromide, or O-allyl-N-(9-anthracenylmethyl)cinchonidinium bromide. In some embodiments, the first catalyst includes N-benzylcinchonium chloride (BCNC). In some embodiments, the first catalyst can be N-benzylcinchonium chloride (BCNC).

In some embodiments, the first solvent can be an ether (e.g., tetrahydrofuran, 2-methyltetrahydrofuran, 1,4-dioxane, dibutyl ether, methyl tert-butyl ether, or cyclopentyl methyl ether), a chlorinate solvent (e.g., dichloronethane, 1,2-dichloroethane, or chlorobenzene), an aromatic solvent (e.g., toluene, xylenes, anisole, or trifluorotoluene), water, or combinations thereof. In some embodiments, the first solvent includes toluene. In some embodiments, the first solvent can be toluene.

In some embodiments, the imine of $C_{1-4}$ alkyl (R)-2-amino-2-methylhexanoate has the formula:

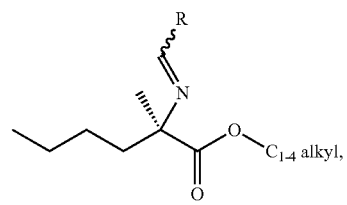

wherein R can be phenyl, 2-chlorophenyl, 4-chlorophenyl, 3-hydroxyphenyl, 4-hydroxyphenyl, 2-phenylvinyl, 2-(4-methylphenyl)vinyl, 2-(4-hydroxy-3-methyoxyphenyl)vinyl, 2-methylphenyl, 4-methylphenyl, or 4-methoxyphenyl. In some embodiments, R can be 4-chlorophenyl. In some embodiments, the imine of $C_{1-4}$ alkyl (R)-2-amino-2-methylhexanoate can be an imine of tert-butyl (R)-2-amino-2-methylhexanoate having the formula:

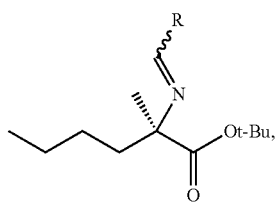

wherein R can be phenyl, 2-chlorophenyl, 4-chlorophenyl, 3-hydroxyphenyl, 4-hydroxyphenyl, 2-phenylvinyl, 2-(4-methylphenyl)vinyl, 2-(4-hydroxy-3-methyoxyphenyl)vinyl, 2-methylphenyl, 4-methylphenyl, or 4-methoxyphenyl. In some embodiments, R can be 4-chlorophenyl. In some embodiments, the imine of tert-butyl (R)-2-amino-2-methylhexanoate can be tert-butyl(R)-2-(chlorobenzylideneamino)-2-methylhexanoate:

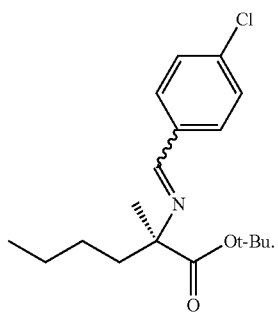 [SMILES: CCCC[C@@](C)(N=Cc1ccc(Cl)cc1)C(=O)OC(C)(C)C]

In some embodiments, the imine of $C_{1-4}$ alkyl (R)-2-amino-2-methylhexanoate can be directly used in the following step after removal of the first solvent. In some embodiments, upon completion of the alkylation reaction, tert-butyl (R)-2-(chlorobenzylideneamino)-2-methylhexanoate can be directly used in the following step after removal of the first solvent.

In some embodiments, the first reaction mixture upon completion can be directly used in the following step without removal of the first solvent. In some embodiments, upon completion of the alkylation reaction, the second reaction mixture including tert-butyl (R)-2-(chlorobenzylideneamino)-2-methylhexanoate and toluene can be directly used in the following step without removal of the solvent.

In general, the alkylation reaction (i.e., step 1) can be performed at any suitable temperature, for example, at a temperature of from −10° C. to 40° C. In some embodiments, the reaction mixture of the alkylation reaction can be at a temperature of from 0° C. to 30° C.

In some embodiments, step 2 includes two steps as described in steps 2a and 2b.

In some embodiments, with respect to steps 2a and 2b, the imine of $C_{1-4}$ alkyl (R)-2-amino-2-methylhexanoate, the first acid, the second solvent, the first salt of (R)-2-amino-2-methylhexanoate, and reaction temperature are described herein.

In some embodiments, the imine can be an imine of tert-butyl (R)-2-amino-2-methylhexanoate. In some embodiments, the imine can be tert-butyl (R)-2-(chlorobenzylideneamino)-2-methylhexanoate. In some embodiments, the imine can be the reaction mixture from step 1 including tert-butyl (R)-2-(chlorobenzylideneamino)-2-methylhexanoate and toluene.

In some embodiments, the first acid can be a mineral acid (e.g., hydrochloric acid, phosphoric acid, sulfuric acid, chlorosulfuric acid, or oleum), an organic acid (e.g., methanesulfonic acid, fumaric acid, acetic acid, formic acid, or ascorbic acid), or combinations thereof. In some embodiments, the first acid includes hydrochloric acid. In some embodiments, the first acid can be hydrochloric acid. In some embodiments, the first acid can be in an aqueous solution. In some embodiments, the first acid includes an aqueous solution of hydrochloric acid.

In some embodiments, the first acid can be an aqueous solution of hydrochloric acid.

In some embodiments, the first salt of (R)-2-amino-2-methylhexanoate can be a hydrochloric acid salt thereof.

In some embodiments, the second solvent can be an aromatic solvent (toluene, xylenes, or trifluorotoluene), an ether (e.g., diethyl ether, methyl tert-butyl ether, tetrahydrofuran, or 1,4-dioxane), a chlorinated solvent (e.g., dichloromethane or 1,2-dichloroethane), an alcohol (e.g., ethanol, 2-propanol, 1-butanol, tert-butanol, 2-methylbutan-2-ol, or trifluoroethanol), a hydrocarbon solvent (e.g., n-heptane, hexanes, cyclohexane, or methylcyclohexane), or combinations thereof. In some embodiments, the second solvent includes 2-propanol. In some embodiments, the second solvent can be 2-propanol. In some embodiments, the second solvent includes toluene and 2-propanol. In some embodiments, the second solvent can be toluene and 2-propanol.

In some embodiments, the crude first salt of (R)-2-amino-2-methylhexanoate can be triturated with the second solvent to provide the first salt of (R)-2-amino-2-methylhexanoate. In some embodiments, the crude first salt of (R)-2-amino-2-methylhexanoate can be triturated with toluene to provide the first salt of (R)-2-amino-2-methylhexanoate. In some embodiments, the crude hydrochloric acid salt of (R)-2-amino-2-methylhexanoate can be triturated with toluene to provide the hydrochloric acid salt of (R)-2-amino-2-methylhexanoate. In some embodiments, the first salt of (R)-2-amino-2-methylhexanoate can be used directly in the following step without purification. In some embodiments, the hydrochloric acid salt of (R)-2-amino-2-methylhexanoate can be used directly in the following step without purification.

In general, the hydrolysis reaction (i.e., step 2a) can be performed at any suitable temperature, for example, at a temperature of from 20° C. to 80° C. In some embodiments, the reaction mixture of the hydrolysis reaction can be at a temperature of from 50° C. to 70° C. In general, the trituration (i.e., step 2b) can be performed at any suitable temperature, for example, at a temperature of from 10° C. to 40° C. In some embodiments, the trituration can be at room temperature.

In some embodiments, step 3 includes two steps as described in steps 3a and 3b.

In some embodiments, with respect to step 3a, the first salt of (R)-2-amino-2-methylhexanoate, the second base, the third solvent, the salt of (R)-2-benzamido-2-methylhexanoic acid, and reaction temperature are described herein.

In some embodiments, the first salt of (R)-2-amino-2-methylhexanoate is the hydrochloric acid salt thereof.

In some embodiments, the second base can be a hydroxide (e.g., lithium hydroxide, sodium hydroxide, cesium hydroxide, or tetra-n-butylammonium hydroxide), an alkoxide (e.g., sodium methoxide, sodium tert-butoxide, potassium tert-butoxide, or sodium tert-pentoxide), a carbonate (e.g., sodium carbonate or potassium carbonate), a hydride (e.g., sodium hydride or potassium hydride), an amine (e.g., triethylamine, tri-n-butylamine, N,N'-diisopropylethylamine, N-methylpyrrolidine, N-methylmorpholine, pyridine, 2,6-lutidine, collidine, or 4-dimethylaminopyridine), or combinations thereof. In some embodiments, the second base can be in an aqueous solution. In some embodiments, the second base includes an aqueous solution of sodium hydroxide. In some embodiments, the second base can be an aqueous solution of sodium hydroxide.

In some embodiments, the third solvent can be an ether (e.g., tetrahydrofuran, 2-methyltetrahydrofuran, 1,4-dioxane, dibutyl ether, methyl tert-butyl ether, or cyclopentyl methyl ether), a chlorinate solvent (e.g., dichloronethane, 1,2-dichloroethane, or chlorobenzene), an aromatic solvent (e.g., toluene, xylenes, anisole, or trifluorotoluene), water, or combinations thereof. In some embodiments, the third solvent includes water. In some embodiments, the third solvent can be water.

In some embodiments, the salt of (R)-2-benzamido-2-methylhexanoic acid can be a sodium salt thereof. In some embodiments, the sodium salt of (R)-2-benzamido-2-methylhexanoic acid can be used directly without purification.

In general, the protection reaction (i.e., step 3a) can be performed at any suitable temperature, for example, at a temperature of from −10° C. to 50° C. In some embodiments, the reaction mixture of the protection reaction can be at a temperature of from 0° C. to 30° C.

In some embodiments, with respect to step 3b, the salt of (R)-2-benzamido-2-methylhexanoic acid, the second acid, the fourth solvent, and reaction temperature are described herein.

In some embodiments, the salt of (R)-2-benzamido-2-methylhexanoic acid is a sodium salt thereof.

In some embodiments, the second acid can be a mineral acid (hydrochloric acid, hydrobromic acid, phosphoric acid, or sulfuric acid), an organic acid (e.g., trichloroacetic acid or formic acid), or combinations thereof. In some embodiments, the second acid can be in an aqueous solution. In some embodiments, the second acid includes an aqueous solution of hydrochloric acid. In some embodiments, the second acid can be an aqueous solution of hydrochloric acid.

In some embodiments, the fourth solvent can be an ether (e.g., tetrahydrofuran, 2-methyltetrahydrofuran, 1,4-dioxane, dibutyl ether, methyl tert-butyl ether, or cyclopentyl methyl ether), a chlorinate solvent (e.g., dichloromethane, 1,2-dichloroethane, or chlorobenzene), an aromatic solvent (toluene, xylenes, anisole, or trifluorotoluene), an alcohol (e.g., 2-propanol, 2-butanol, tert-butanol, 2-methylbutan-2-ol, 2,2,2-trifluoroethanol, or hexafluoro-2-propanol), a ketone (methyl isobutyl ketone, or methyl ethyl ketone), an ester (e.g., isopropyl acetate, or n-butylacetate), water, or combinations thereof. In some embodiments, the fourth solvent includes water. In some embodiments, the fourth solvent can be water.

In general, the acidification reaction (i.e., step 3b) can be performed at any suitable temperature, for example, at a temperature of from −10° C. to 50° C. In some embodiments, the reaction mixture of the acidification reaction can be at a temperature of from 0° C. to 30° C.

In some embodiments, step 4 includes two steps as described in steps 4a and 4b.

In some embodiments, with respect to step 4a, the first reducing agent, the fifth solvent, and reaction temperature are described herein.

In some embodiments, the first reducing agent can be any suitable reducing agent capable of reducing an ester group (e.g., isopropyl ester) to the corresponding —CH$_2$OH. In some embodiments, the first reducing agent can be diborane, borane tetrahydrofuran complex, borane dimethyl sulfide complex, borane dodecyl methyl sulfide complex, borane dimethylamine complex, borane ammonia complex, borane pyridine complex, borane trimethylamine complex, borane N,N-diethylaniline complex, borane morpholine complex, borane methyl 6-morpholinohexyl sulfide complex, borane diphenylphosphine complex, sodium borohydride/boron trifluoride, lithium aluminum hydride, aluminum hydride, or diisobutylaluminum hydride. In some embodiments, the first reducing agent includes borane tetrahydrofuran complex. In some embodiments, the first reducing agent can be borane tetrahydrofuran complex.

In some embodiments, the fifth solvent can be an ether (e.g., tetrahydrofuran, 2-methyltetrahydrofuran, 1,4-dioxane, cyclopentyl methyl ether, methyl tert-butyl ether, or diethyl ether), an aromatic solvent (e.g., toluene, xylene, or trifluorotoluene), a hydrocarbon solvent (e.g., n-hexane, n-heptane, or cyclohexane), or combinations thereof. In some embodiments, the fifth solvent includes tetrahydrofuran. In some embodiments, the fifth solvent can be tetrahydrofuran.

In general, the reduction reaction (i.e., step 4a) can be performed at any suitable temperature, for example, at a temperature of from −40° C. to 80° C. In some embodiments, the reaction mixture of the reducing reaction can be at a temperature of from 25° C. to 65° C.

In some embodiments, with respect to step 4b, the second reducing agent, the second catalyst, the third acid, the sixth solvent, the salt of (R)-2-amino-2-methylhexan-1-ol, and reaction temperature are described herein.

In some embodiments, the second reducing agent can be a hydrogen gas, formic acid, ammonium formate, cyclohexene, hydrazine, sodium hypophosphite, or combinations thereof.

In some embodiments, the second reducing agent includes a hydrogen gas. In some embodiments, the second reducing agent can be a hydrogen gas.

In some embodiments, the second catalyst can be a palladium catalyst. In some embodiments, the second catalyst can be palladium hydroxide on carbon, palladium on carbon, platinum on carbon, or platinum oxide. In some embodiments, the second catalyst includes palladium hydroxide on carbon. In some embodiments, the second catalyst can be palladium hydroxide on carbon.

In some embodiments, the third acid can be a sulfonic acid (e.g., para-toluenesulfonic acid, methanesulfonic acid, or benzenesulfonic acid), a mineral acid (e.g., hydrochloric acid or sulfuric acid), an organic acid (e.g., trifluoroacetic acid). In some embodiments, the third acid includes para-toluenesulfonic acid. In some embodiments, the third acid can be para-toluenesulfonic acid.

In some embodiments, the sixth solvent can be an ether (e.g., tetrahydrofuran, 2-methyltetrahydrofuran, 1,4-dioxane, dibutyl ether, methyl tert-butyl ether, or cyclopentyl methyl ether), a chlorinate solvent (e.g., dichloromethane, 1,2-dichloroethane, or chlorobenzene), an aromatic solvent (toluene, xylenes, anisole, or trifluorotoluene), an alcohol (e.g., ethanol, 2-propanol, 2-butanol, tert-butanol, 2-methylbutan-2-ol, 2,2,2-trifluoroethanol, or hexafluoro-2-propanol), a ketone (e.g., methyl isobutyl ketone, or methyl ethyl ketone), an ester (e.g., isopropyl acetate or n-butylacetate), or combinations thereof. In some embodiments, the sixth solvent includes ethanol. In some embodiments, the sixth solvent can be ethanol.

In some embodiments, the salt of (R)-2-amino-2-methylhexan-1-ol can be a compound of Formula VIb:

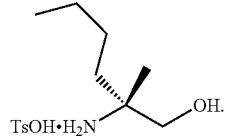

(VIb)

In general, the Bz-deprotection reaction (i.e., step 4b) can be performed at any suitable temperature, for example, at a temperature of from 0° C. to 85° C. In some embodiments, the reaction mixture of the Bz-deprotecting reaction can be at a temperature of from 20° C. to 80° C.

Alternatively, in some embodiments, the Bz-deprotection reaction of step 4b can be achieved with lead tetraacetate or sodium periodate with bromine.

5. Preparation of a Salt of (R)-2-Amino-2-methylhexan-1-ol, Route 5,

In some embodiments, the present disclosure provides a method for preparing a salt of (R)-2-amino-2-methylhexan-1-ol:

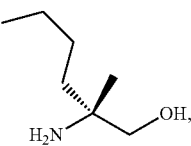

the method including:

1) forming a first reaction mixture including a first salt of (R)-2-amino-2-methylhexanoate:

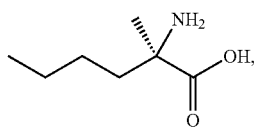

a reducing agent, and a first solvent to form (R)-2-amino-2-methylhexan-1-ol having the formula:

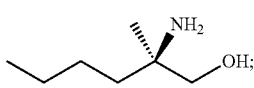

2) forming a second reaction mixture including (R)-2-amino-2-methylhexan-1-ol, an acid, and a second solvent to provide the salt of (R)-2-amino-2-methylhexan-1-ol.

Figure 15:
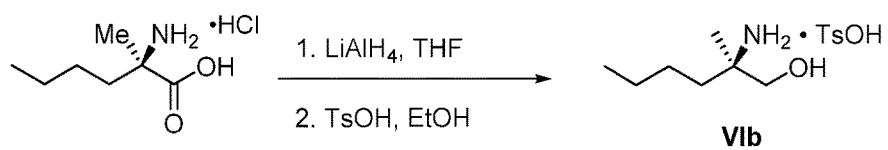
FIG. 15 shows the preparation of the compound of Formula VIb via steps of reduction of a salt of (R)-2-amino-2-methylhexanoic acid and TsOH salt formation.

In some embodiments, the salt of (R)-2-amino-2-methylhexan-1-ol can be prepared according to steps 1 and 2 as shown in the scheme of FIG. 15.

In some embodiments, the respect to step 1, the first salt of (R)-2-amino-2-methylhexanoate, the reducing agent, the first solvent, and reaction temperature are described herein.

In some embodiments, the first salt of (R)-2-amino-2-methylhexanoate is the hydrochloric acid salt thereof.

In some embodiments, the reducing agent can be any suitable reducing agent capable of reducing an ester group (e.g., isopropyl ester) to the corresponding —CH$_2$OH. In some embodiments, the reducing agent can be diborane, borane dimethyl sulfide complex, borane dodecyl methyl sulfide complex, borane dimethylamine complex, borane ammonia complex, borane pyridine complex, borane trimethyl amine complex, borane N,N-diethylaniline complex, borane morpholine complex, borane methyl 6-morpholino-hexyl sulfide complex, sodium borohydride/boron trifluoride, diisobutylaluminum hydride, or lithium aluminum hydride. In some embodiments, the reducing agent includes lithium aluminum hydride. In some embodiments, the reducing agent can be lithium aluminum hydride.

In some embodiments, the first solvent can be an ether (e.g., tetrahydrofuran, 2-methyltetrahydrofuran, 1,4-dioxane, cyclopentyl methyl ether, methyl tert-butyl ether, or diethyl ether), an aromatic solvent (e.g., toluene, xylene, or trifluorotoluene), a hydrocarbon solvent (e.g., n-hexane, n-heptane, or cyclohexane), or combinations thereof. In some embodiments, the first solvent includes tetrahydrofuran. In some embodiments, the first solvent can be tetrahydrofuran.

In general, the reduction reaction (i.e., step 1) can be performed at any suitable temperature, for example, at a temperature of from 0° C. to 40° C. In some embodiments, the reaction mixture of the reduction reaction can be at a temperature of from 10° C. to 20° C.

In some embodiments, with respect to step 2, the acid, the second solvent, the salt of (R)-2-amino-2-methylhexan-1-ol, and reaction temperature are described herein.

In some embodiments, the acid can be a sulfonic acid (e.g., para-toluenesulfonic acid, methanesulfonic acid, or benzenesulfonic acid), a mineral acid (e.g., hydrochloric acid or sulfuric acid), an organic acid (e.g., trifluoroacetic acid), or combinations thereof. In some embodiments, the acid includes para-toluenesulfonic acid. In some embodiments, the acid can be para-toluenesulfonic acid.

In some embodiments, the second solvent can be an alcohol (methanol, ethanol, n-propanol, or n-butanol), an ether (e.g., diethyl ether, methyl tert-butyl ether, tetrahydrofuran, 2-methyltetrahydrofuran, 1,4-dioxane, or 1,2-dimethoxyethane), an aromatic solvent (e.g., toluene, xylenes, fluorobenzene, or trifluorotoluene), a chlorinated solvent (e.g., dichloromethane or 1,2-dichloroethane), a ketone (e.g., acetone or methyl isobutyl ketone), an ester (e.g., ethyl acetate, butyl acetate, or isobutyl acetate), or combinations thereof. In some embodiments, the second solvent includes ethanol. In some embodiments, the second solvent can be ethanol.

In some embodiments, the salt of (R)-2-amino-2-methylhexan-1-ol can be a compound of Formula VIb:

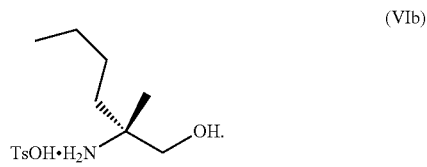

(VIb)

In general, the acidification reaction (i.e., step 2) can be performed at any suitable temperature, for example, at a temperature of from 0° C. to 100° C. In some embodiments, the reaction mixture of the acidification reaction can be at a temperature of from 15° C. to 30° C.

6. Preparation of a Salt of (R)-2-Amino-2-methylhexan-1-ol, Route 6

In some embodiments, the present disclosure provides a method for preparing a salt of (R)-2-amino-2-methylhexan-1-ol:

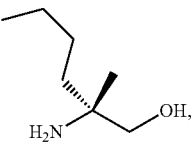

the method including:
1) forming a first reaction mixture including (2S,4R)-3-benzoyl-4-methyl-2-phenyloxazolidin-5-one having the formula:

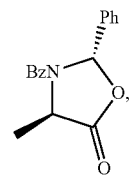

or a salt thereof, an electrophile, a base, and a first solvent to form (2S,4R)-3-benzoyl-4-butyl-4-methyl-2-phenyloxazolidin-5-one having the formula:

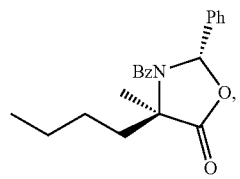

or a salt thereof, and
2) forming a second reaction mixture including (2S,4R)-3-benzoyl-4-butyl-4-methyl-2-phenyloxazolidin-5-one or the salt thereof, an acid, and optional a second solvent to form the salt of (R)-2-amino-2-methylhexan-1-ol.

Figure 16:
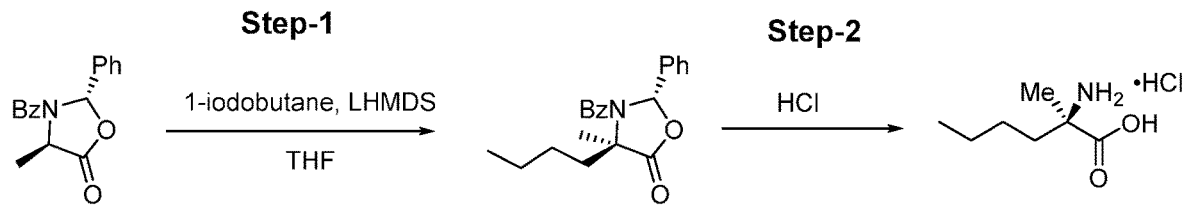
FIG. 16 shows the preparation of (R)-2-amino-2-methylhexanoic acid hydrochloride from (2S,4R)-3-benzoyl-4-methyl-2-phenyloxazolidin-5-one via steps of alkylation and hydrolysis.

In some embodiments, the salt of (R)-2-amino-2-methyl-hexan-1-ol can be prepared according to steps 1 and 2 as shown in the scheme of FIG. 16.

In some embodiments, with respect to step 1, the electrophile, the base, the first solvent, and reaction temperature are described herein.

In some embodiments, the electrophile can be n-butyl bromide, n-butyl iodide, n-butyl methanesulphonate, n-butyl 4-methylbenzenesulfonate, or n-butyl sulfate. In some embodiments, the electrophile includes n-butyl iodide. In some embodiments, the electrophile can be n-butyl iodide.

In some embodiments, the base can be lithium diisopropylamide, lithium diethylamide, lithium dicyclohexylamide, lithium dimethylamide, lithium 2,2,6,6,-tetramethylpiperidide, lithium bis(trimethylsilyl)amide, sodium bis(trimethylsilyl)amide, potassium bis(trimethylsilyl)amide), or sodium hydride. In some embodiments, the base includes lithium bis(trimethylsilyl)amide. In some embodiments, the base can be lithium bis(trimethylsilyl)amide.

In some embodiments, the first solvent can be an aromatic solvent (e.g., toluene, xylenes, chlorobenzene, fluorobenzene, or trifluorotoluene), an ether (e.g., diethyl ether, methyl tert-butyl ether, tetrahydrofuran, 2-methyltetrahydrofuran, or 1,4-dioxane), a chlorinated solvent (e.g., dichloromethane, or chlorobenzene), or combinations thereof. In some embodiments, the first solvent includes tetrahydrofuran. In some embodiments, the first solvent can be tetrahydrofuran.

In general, the alkylation reaction (i.e., step 1) can be performed at any suitable temperature, for example, at a temperature of from −100° C. to 0° C. In some embodiments, the reaction mixture of the alkylation reaction can be at a temperature of from −78° C. to −50° C.

In some embodiments, the alkylation reaction of step 1 can also include an additive. Suitable additives include, but are not limited to, hexamethylphosphoramide, 1,3-dimethyl-3,4,5,6-tetrahydro-2(1H)-pyrimidinone, and 1,3-dimethyl-2-imidazolidinone.

In some embodiments, with respect to step 2, the acid, the second solvent, the salt of (R)-2-amino-2-methylhexan-1-ol, and reaction temperature are described herein.

In some embodiments, the acid can be a mineral acid (e.g., hydrochloric acid, hydrobromic acid, sulfuric acid, or phosphoric acid), a sulfonic acid (e.g., para-toluenesulfonic acid, methanesulfonic acid, or benzenesulfonic acid), an organic acid (e.g., trifluoroacetic acid). In some embodiments, the acid includes hydrochloric acid. In some embodiments, the acid includes an aqueous solution of hydrochloric acid. In some embodiments, the acid can be hydrochloric acid. In some embodiments, the acid can be an aqueous solution of hydrochloric acid.

In some embodiments, the second solvent is absent. In some embodiments, the second solvent, when present, can be an alcohol (e.g., methanol, ethanol, or 2-propanol), an ether (e.g., diethyl ether, methyl tert-butyl ether, tetrahydrofuran, 2-methyltetrahydrofuran, 1,4-dioxane, or 1,2-dimethoxyethane), an aromatic solvent (toluene, xylenes, fluorobenzene, or trifluorotoluene), a chlorinated solvent (e.g., dichloromethane or 1,2-dichloroethane), an ester (e.g., ethyl acetate, butyl acetate, or isobutyl acetate), water, or combinations thereof. In some embodiments, the second solvent includes water. In some embodiments, the second solvent can be water.

In some embodiments, the salt of (R)-2-amino-2-methylhexan-1-ol can be a compound of Formula VIb:

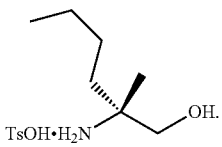

(VIb)

In some embodiments, the salt of (R)-2-amino-2-methylhexan-1-ol can be a compound of the Formula:

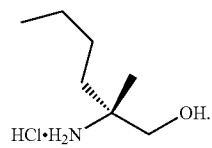

In general, the hydrolysis reaction (i.e., step 2) can be performed at any suitable temperature, for example, at a temperature of from 0° C. to 120° C. In some embodiments, the reaction mixture of the hydrolysis reaction can be at a temperature of from 60° C. to 100° C.

7. Preparation of Compound of Formula VIIIb, Route 1

In some embodiments, the present disclosure provides a method for preparing the compound of Formula VIIIb:

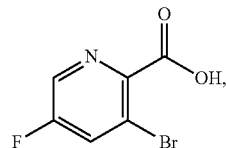

(VIIIb)

or a salt thereof, the method including:
14) forming a first reaction mixture including 2,3-dibromo-5-fluoropyridine or a salt thereof, a first iodination reagent, an additive, and a first solvent to form 3-bromo-5-fluoro-2-iodopyridine:

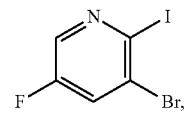

or a salt thereof, or
17) forming a second reaction mixture including 2,3-dibromo-5-fluoropyridine or a salt thereof, a second iodination reagent, a catalyst, a first ligand, and a second solvent to form 3-bromo-5-fluoro-2-iodopyridine or a salt thereof,
15) forming a third reaction mixture including 3-bromo-5-fluoro-2-iodopyridine or the salt thereof, a cyanation reagent, a second ligand, and a third solvent to form 3-bromo-5-fluoropicolinonitrile:

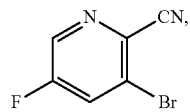

or a salt thereof, and 16) forming a fourth reaction mixture including 3-bromo-5-fluoropicolinonitrile or the salt thereof, an acid, and a fourth solvent to provide the compound of Formula VIIIb or the salt thereof, or forming a fifth reaction mixture including 3-bromo-5-fluoropicolinonitrile or the salt thereof, an enzyme, and a fifth solvent to provide the compound of Formula VIIIb or the salt thereof.

Figure 5A:
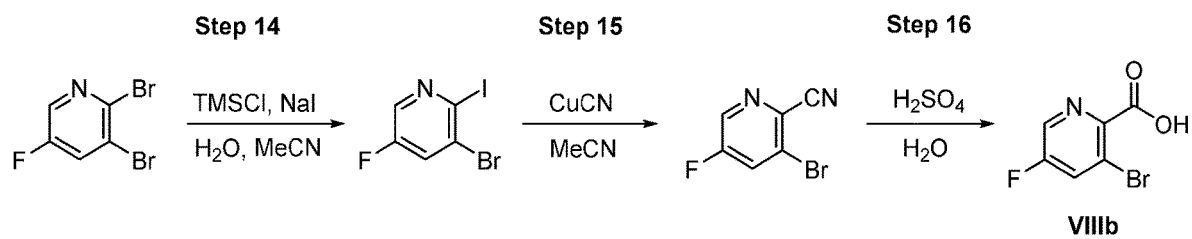
FIG. 5A shows the preparation of the compound of Formula VIIIb via steps of halogen exchange, cyanation, and hydrolysis.
Figure 5B:
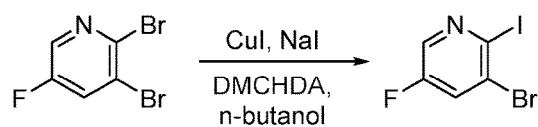
FIG. 5B shows an alternative method for preparing 3-bromo-5-fluoro-2-iodopyridine.
Figure 5B:
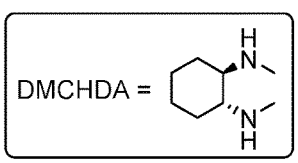

In some embodiments, the compound of Formula VIIIb can be prepared according to steps 14-16 as shown in the scheme of FIG. 5A. In some embodiments, the compound of Formula VIIIb can be prepared according to steps 17 as shown in the scheme of FIG. 5B and steps 15-16 as shown in the scheme of FIG. 5A.

With respect to step 14, the first iodination reagent, the additive, the first solvent, and reaction temperature are described herein.

The first iodination reagent can be sodium iodide, lithium iodide, potassium iodide, cesium iodide, zinc iodide, magnesium iodide, copper(I) iodide, hydroiodic acid, trimethylsilyl iodide, or iodine. In some embodiments, the first iodination reagent includes sodium iodide. In some embodiments, the first iodination reagent can be sodium iodide.

The additive can be water, trimethylsilyl chloride, an ammonium salt (e.g., tetra-n-butylammonium iodide), 2,6-di-tert-butylpyridine, 2,6-di-tert-butyl-4-methylphenol, trimethylsilyl trifluoromethanesulfonate, an organic acid (e.g., acetic acid, formic acid, trichloroacetic acid, trifluoroacetic acid, trifluoromethanesulfonic acid, or methanesulfonic acid), a mineral acid (e.g., hydrochloric acid or sulfuric acid), a dehydrating agent (e.g., bis(trimethylsilyl) acetamide, acetyl chloride, or triethyl orthoformate), or combinations thereof. In some embodiments, the additive includes trimethylsilyl chloride and water. In some embodiments, the additive can be trimethylsilyl chloride and water.

The first solvent can be an ester (e.g., ethyl acetate, butyl acetate, isopropyl acetate, or isobutyl acetate), an ether (e.g., tetrahydrofuran, 2 methyltetrahydrofuran, 1,4-dioxane, cyclopentyl methyl ether, or methyl tert-butyl ether), a polar aprotic solvent (e.g., acetonitrile, propionitrile, benzonitrile, N,N dimethylformamide, N,N-dimethylacetamide, dimethylsulfoxide, N-methyl-2-pyrrolidone, or sulfolane), an aromatic solvent (e.g., toluene, trifluorotoluene, benzene, or xylenes), an organic acid solvent (e.g., acetic acid or formic acid), or combinations thereof. In some embodiments, the first solvent includes acetonitrile. In some embodiments, the first solvent can be acetonitrile.

In general, the halogen exchange reaction (i.e., step 14) can be performed at any suitable temperature, for example, at a temperature of from 20° C. to 110° C. In some embodiments, the reaction mixture of the halogen exchange reaction can be at a temperature of from 20° C. to a reflux temperature. In some embodiments, the reaction mixture of the halogen exchange reaction can be heated to reflux.

In some embodiments, the halogen exchange reaction of step 14 can be replaced with the halogen exchange reaction of step 17. With respect to step 17, the second iodination reagent, the catalyst, the first ligand, the second solvent, and reaction temperature are described herein.

The second iodination reagent can be sodium iodide, lithium iodide, potassium iodide, cesium iodide, zinc iodide, or magnesium iodide. In some embodiments, the second iodination reagent includes sodium iodide. In some embodiments, the second iodination reagent can be sodium iodide.

The catalyst can be copper(I) iodide, copper(II) iodide, copper(I)bromide, or copper(II)bromide. In some embodiments, the catalyst includes copper(I) iodide. In some embodiments, the catalyst can be copper(I) iodide.

The first ligand can be trans-N,N'-dimethylcycloheane-1,2-diamine (DMCHDA), N,N,N',N'-tetramethylethylenediamine, or N,N'-dimethylethylenediamine. In some embodiments, the first ligand includes trans-N,N'-dimethylcycloheane-1,2-diamine. In some embodiments, the first ligand can be trans-N,N'-dimethylcycloheane-1,2-diamine.

The second solvent can be an ether (e.g., 1,4-dioxane or cyclopentyl methyl ether), an alcohol solvent (e.g., n-butanol, 1-hexanol, 2-methylbutan-2-ol, or isopropanol), a polar aprotic solvent (e.g, benzonitrile, N,N-dimethylformamide, N,N-dimethylacetamide, dimethylsulfoxide, N-methyl-2-pyrrolidone, or sulfolane), an aromatic solvent (e.g., toluene, trifluorotoluene, benzene, or xylenes), or combinations thereof. In some embodiments, the second solvent includes n-butanol. In some embodiments, the second solvent can be n-butanol.

In general, the halogen exchange reaction (i.e., step 17) can be performed at any suitable temperature, for example, at a temperature of from 50° C. to 150° C. In some embodiments, the reaction mixture of the hydrolysis reaction can be at a temperature of from 80° C. to a reflux temperature.

With respect to step 15, the cyanation reagent, the second ligand, the third solvent, and reaction temperature are described herein.

The cyanation reagent can be copper (I) cyanide, sodium cyanide, potassium cyanide, or trimethylsilyl cyanide. In some embodiments, the cyanation reagent includes copper (I) cyanide. In some embodiments, the cyanation reagent can be copper (I) cyanide.

The second ligand can be absent or present. When the second ligand is present, the second ligand can be 1,10-phenanthroline, 3,4,7,8-tetramethyl-1,10-phenanthroline, 4,7-dichloro-1,10-phenanthroline, 4,7-dimethoxy-1,10-phenanthroline, trans-1,2-diaminocyclohexane, N,N'-dimethyl-1,2-cyclohexanediamine, 4-dimethylaminopyridine, 8-hydroxyquinoline, tetramethylethylenediamine, L-proline, 1-butylimidazole, or 2-isobutylcyclohexanone. In some embodiments, the second ligand can be absent.

The third solvent can be an ester (e.g., butyl acetate, isopropyl acetate, or isobutyl acetate) an ether (e.g., tetrahydrofuran, 2-methyltetrahydrofuran, 1,4-dioxane, or cyclopentyl methyl ether), an alcohol solvent (e.g., n-butanol, 2-methylbutan-2-ol, or isopropanol), a polar aprotic solvent (e.g., acetonitrile, propionitrile, benzonitrile, N,N-dimethylformamide, N,N-dimethylacetamide, dimethylsulfoxide, N-methyl-2-pyrrolidone, or sulfolane), an aromatic solvent (e.g., toluene, benzene, xylenes, or trifluorotoluene), a chlorinated solvent (dichloromethane, 1,2-dichloroethane, chlorobenzene, or chloroform), or combinations thereof. In some embodiments, the third solvent includes acetonitrile. In some embodiments, the third solvent can be acetonitrile.

In general, the cyanation reaction (i.e., step 15) can be performed at any suitable temperature, for example, at a temperature of from 20° C. to 120° C. In some embodiments, the reaction mixture of the cyanation reaction can be at a temperature of from 20° C. to a reflux temperature. In some embodiments, the reaction mixture of the cyanation reaction can be heated to reflux.

With respect to step 16, the acid, the fourth solvent, the enzyme, and fifth solvent, and reaction temperature are described herein.

The acid can be sulfuric acid, phosphoric acid, hydrochloric acid, hydrobromic acid, chloric acid, perchloric acid, nitric acid, trifluoroacetic acid, trifluoromethanesulfonic acid, methanesulfonic acid, or phthalic acid. In some embodiments, the acid includes sulfuric acid. In some embodiments, the acid can be sulfuric acid.

The fourth solvent can be water, an alcohol (e.g., methanol, ethanol, n-propanol, or isopropanol), or combinations thereof. In some embodiments, the fourth solvent includes water. In some embodiments, the fourth solvent can be water.

The hydrolysis reaction by the acid in step 16 can be replaced with an enzymatic hydrolysis reaction. In some embodiments, the enzymatic includes a nitrilase enzyme. The enzymatic hydrolysis reaction can be performed in an aqueous buffer solution with and without the addition of an organic co-solvent. In some embodiments, the fifth solvent includes aqueous buffer solution. In some embodiments, the fifth solvent includes aqueous buffer solution and an organic co-solvent. The organic co-solvent can be an alcohol (e.g., methanol, ethanol, n-propanol, or isopropanol).

In some embodiments, the enzymatic can be a nitrilase enzyme. In some embodiments, the fifth solvent can be an aqueous buffer solution. In some embodiments, the fifth solvent can be an aqueous buffer solution and an organic co-solvent. The organic co-solvent can be an alcohol (e.g., methanol, ethanol, n-propanol, or isopropanol).

In general, the hydrolysis reaction (i.e., step 16) can be performed at any suitable temperature, for example, at a temperature of from 20° C. to 120° C. In some embodiments, the reaction mixture of the hydrolysis reaction can be at a temperature of from 20° C. to 100° C.

8. Preparation of Compound of Formula VIIIb, Route 2

In some embodiments, the present disclosure provides a method for preparing the compound of Formula VIIIb:

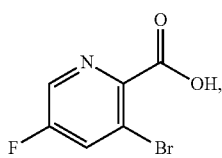

(VIIIb)

or a salt thereof, the method including:
18a) forming a first reaction mixture including 5-fluoropicolinic acid or a salt thereof, an activating agent, a promoter, and a first solvent to activate the —C(O)OH group of 5-fluoropicolinic acid, thereby forming an activated form of 5-fluoropicolinic acid or a salt thereof;
18b) forming a second reaction mixture including the activated form of 5-fluoropicolinic acid or the salt thereof, an amine of $R^6R^7NH$, a first base, and a second solvent to form a compound of Formula XIII:

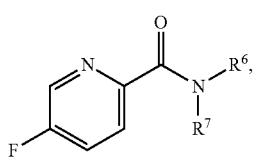

(XIII)

or a salt thereof;
19) forming a third reaction mixture including the compound of Formula XIII or the salt thereof, a brominating agent, a second base, an additive, and a third solvent to form a compound of Formula XIIb:

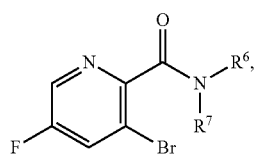

(XIIb)

or a salt thereof, and
20) forming a fourth reaction mixture including the compound of Formula XIIb or the salt thereof, an acid, and a fourth solvent to provide the compound of Formula VIIIb or the salt thereof,
wherein $R^6$ and $R^7$ are each independently hydrogen, $C_{1-4}$ alkyl, or $C_{3-6}$ cycloalkyl, or $R^6$ and $R^7$ are combined to form a 3-6 membered N-linked heterocycloalkyl, optionally having an additional 1-2 heteroatoms selected from O and S.

Figure 6:
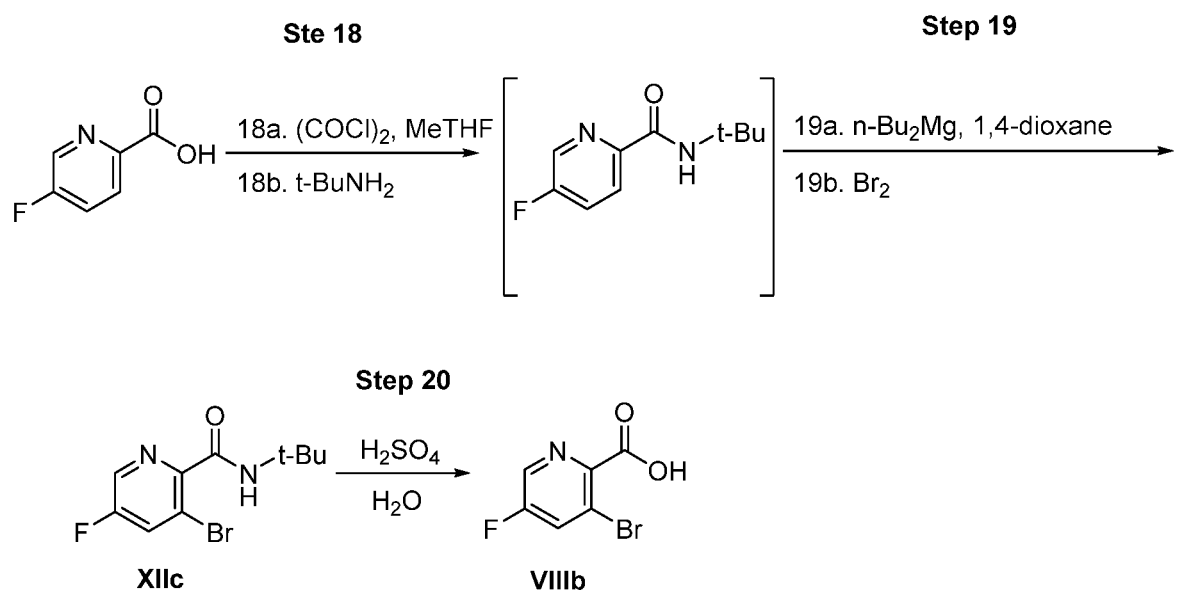
FIG. 6 shows the preparation of the compound of Formula VIIIb via steps of amidation, bromination, and hydrolysis.

In some embodiments, the compound of Formula VIIIb or the salt thereof can be prepared according to steps 18-20 as shown in the scheme of FIG. 6.

Step 18 includes steps 18a and 18b.

With respect to step 18a, the activating agent, the promoter, the first solvent, the activated form of 5-fluoropicolinic acid, and reaction temperature are described herein. With respect to step 18b, the amine of $R^6R^7NH$, the first base, the second solvent, the compound of Formula XIII, and reaction temperature are described herein.

The activating agent can be a chlorinating agent. In some embodiments, the chlorinating agent can be oxalyl chloride, thionyl chloride, phosphorus(V) oxychloride, phosphorus (V) pentachloride, or (chloromethylene)dimethyliminium chloride. In some embodiments, the activating (or chlorinating) agent includes oxalyl chloride. In some embodiments, the activated form of 5-fluoropicolinic acid can be 5-fluoropicolinoyl chloride.

The activating agent can be any peptide coupling reagent capable of activating an acid group (e.g., the acid group of 5-fluoropicolinic acid), thereby reacting with an amine (e.g., the amine in step 18b) to form an amide bond (e.g., the amide group of Formula XIII). In some embodiments, the activating agent can be 1,1'-carbonyldiimidazole or isobutyl chloroformate. In some embodiments, the activated form of 5-fluoropicolinic acid can be (5-fluoropyridin-2-yl)(1H-imidazol-1-yl)methanone or 5-fluoropicolinic (isobutyl carbonic) anhydride.

The promoter can be N,N-dimethylformamide, N,N-dimethylacetamide, or dichloromethylene-dimethyliminium chloride. In some embodiments, the promoter includes N,N-dimethylformamide. In some embodiments, the promoter can be N,N-dimethylformamide.

The amine of $R^6R^7NH$ can be a primary amine (e.g., ethyl amine, isopropylamine, tert-butylamine, or cyclohexylamine) or a secondary amine (e.g., diethyl amine or morpholine). In some embodiments, the amine of $R^6R^7NH$ can be tert-butylamine.

The first base can be absent or present. When the base is present, the base can be a tertiary amine (e.g., triethylamine, N,N-diisopropylethylamine, N-methylpyrrolidine, or N-methylmorpholine), an aromatic amine base (e.g., pyridine), or an inorganic base (e.g., sodium hydroxide, sodium carbonate, sodium bicarbonate, potassium hydroxide, potassium carbonate, cesium carbonate, or potassium phosphate tribasic). In some embodiments, the first base can be absent.

The first and second solvents can be an ether (e.g., tetrahydrofuran, 2-methyltetrahydrofuran, methyl tert-butyl ether, or 1,4-dioxane), a chlorinated solvent (e.g., dichloromethane, chloroform, or 1,2-dichloroethane, etc.), an aromatic solvent (e.g., benzene, toluene, or xylenes), or combinations thereof. In some embodiments, the first solvent includes 2-methyltetrahydrofuran. In some embodiments, the second solvent includes 2-methyltetrahydrofuran. The second reaction mixture (i.e., step 18b) can further include water to have a biphasic reaction. In some embodiments, the first solvent can be 2-methyltetrahydrofuran. In some embodiments, the second solvent can be 2-methyltetrahydrofuran. The second reaction mixture (i.e., step 18b) can further include water to have a biphasic reaction.

With respect to the amine of $R^6R^7NH$ or the compound of Formula XIII, $R^6$ and $R^7$ are as defined and described herein.

In some embodiments, $R^6$ can be hydrogen or $C_{1-4}$ alkyl. The $C_{1-4}$ alkyl can be methyl, ethyl, n-propyl, isopropyl, n-butyl, sec-butyl, or tert-butyl. In some embodiments, $R^6$ can be hydrogen or ethyl. In some embodiments, $R^6$ can be hydrogen. In some embodiments, $R^6$ can be ethyl.

In some embodiments, $R^7$ can be $C_{1-4}$ alkyl or $C_{3-6}$ cycloalkyl. The $C_{1-4}$ alkyl can be methyl, ethyl, n-propyl, isopropyl, n-butyl, sec-butyl, or tert-butyl. The $C_{3-6}$ cycloalkyl can be cyclopropyl, cyclobutyl, cyclopentyl, or cyclohexyl. In some embodiments, $R^7$ can be ethyl, n-propyl, isopropyl, n-butyl, sec-butyl, tert-butyl, or cyclohexyl. In some embodiments, $R^7$ can be ethyl, isopropyl, tert-butyl, or cyclohexyl. In some embodiments, $R^7$ can be tert-butyl.

In some embodiments, $R^6$ can be hydrogen; and $R^7$ can be $C_{1-4}$ alkyl, or $C_{3-6}$ cycloalkyl. In some embodiments, $R^6$ can be hydrogen; and $R^7$ can be ethyl, n-propyl, isopropyl, n-butyl, sec-butyl, tert-butyl, or cyclohexyl. In some embodiments, $R^6$ can be hydrogen; and $R^7$ can be ethyl, isopropyl, tert-butyl, or cyclohexyl. In some embodiments, $R^6$ can be hydrogen and $R^7$ can be tert-butyl. In some embodiments, $R^6$ can be ethyl; and $R^7$ can be $C_{1-4}$ alkyl. In some embodiments, $R^6$ and $R^7$ can each be ethyl.

In some embodiments, $R^6$ and $R^7$ can be combined to form N-linked morpholinyl.

In some embodiments, the compound of Formula XIII can be N-(tert-butyl)-5-fluoropicolinamide having the formula:

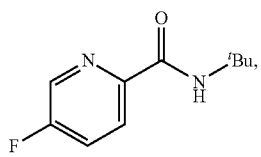 [SMILES: CC(C)(C)NC(=O)c1ccc(F)cn1]

or a salt thereof.

In some embodiments, N-(tert-butyl)-5-fluoropicolinamide can be isolated as a solution in methylcyclohexane and used directly in the following step without purification and/or removal of methylcyclohexane. In some embodiments, N-(tert-butyl)-5-fluoropicolinamide can be isolated as a solution in 1,4-dioxane and used directly in the following step without purification and/or removal of 1,4-dioxane. In some embodiments, N-(tert-butyl)-5-fluoropicolinamide can be isolated as a solution in methyl cyclopentyl ether and used directly in the following step without purification and/or removal of methyl cyclopentyl ether.

In general, the reactions of step 18a and step 18b can be performed at any suitable temperature, for example, at a temperature of from 5° C. to 60° C. In some embodiments, the reaction mixtures of both step 18a and step 18b can be at a temperature of from 15° C. to 30° C.

Step 19 includes steps 19a and 19b. Step 19a includes a metalation step and step 19b includes a bromination step.

With respect to step 19, the brominating agent, the second base, the additive, the third solvent, the compound of Formula XIIb, and reaction temperature are described herein.

In some embodiments, the compound of Formula XIII can be N-(tert-butyl)-5-fluoropicolinamide or a salt thereof. In some embodiments, N-(tert-butyl)-5-fluoropicolinamide or the salt thereof can be the solution thereof in methylcyclohexane. In some embodiments, N-(tert-butyl)-5-fluoropicolinamide or the salt thereof can be the solution thereof in 1,4-dioxane. In some embodiments, N-(tert-butyl)-5-fluoropicolinamide or the salt thereof can be the solution thereof in methylcyclopentyl ether.

The brominating agent can be bromine, N-bromosuccinimide, triphenylphosphine dibromide, tetrabutylammonium tribromide, trimethylphenylammonium tribromide, N-bromoacetamide, pyridinium tribromide, dibromodimethylhydantoin, tribromoisocyanuric acid, N-bromosaccharin, or 1,2-dibromo-1,1,2,2-tetrachloroethane. In some embodiments, the brominating agent includes bromine. In some embodiments, the brominating agent can be bromine.

The second base can be a metal amide base (e.g., lithium diisopropylamide, 2,2,6,6-tetramethylpiperidinylmagnesium chloride, lithium 2,2,6,6-tetramethylpiperidide, bis(2,2,6,6-tetramethylpiperidinyl)magnesium, or di-n-butyllithium(2,2,6,6-tetramethylpiperidinyl)magnesate), an alkyl- and alkenylmetal (n-butyllithium, isopropylmagnesium chloride, tri-n-butyllithium magnesate, di-n-butylmagnesium, ethyl n-butylmagnesium, or di-sec-butylmagnesium). In some embodiments, the base includes di-n-butylmagnesium. In some embodiments, the base can be di-n-butylmagnesium.

The additive can be absent or present. When the additive is present, the additive can be lithium chloride, lanthanum (III) chloride, N,N'-dimethylpropyleneurea, N,N,N',N'-tetramethylethylenediamine, or hexamethylphosphoramide. In some embodiments, the additive can be absent.

The third solvent can be an ether (tetrahydrofuran, 2-methyltetrahydrofuran, methyl tert-butyl ether, methyl cyclopentyl ether, or 1,4-dioxane), a nonpolar solvent (e.g., cyclohexane, methylcyclohexane, or n-heptane), an aromatic solvent (e.g., benzene, toluene, or xylenes), a chlorinated solvent (e.g, dichloromethane, 1,2-dichloroethane, or chlorobenzene), or combinations thereof. In some embodiments, the third solvent includes methylcyclohexane. In some embodiments, the third solvent can be methylcyclohexane.

With respect to the compound of Formula XIIb, $R^6$ and $R^7$ are defined and described herein (also see Section IV, compounds of Formula XII). In some embodiments, $R^6$ can be hydrogen; and $R^7$ can be ethyl, isopropyl, tert-butyl, or cyclohexyl. In some embodiments, $R^6$ can be hydrogen and $R^7$ can be tert-butyl. In some embodiments, $R^6$ can be ethyl; and $R^7$ can be $C_1$ alkyl. In some embodiments, $R^6$ and $R^7$ can each be ethyl. In some embodiments, $R^6$ and $R^7$ can be combined to form N-linked morpholinyl.

In some embodiments, the compound of Formula XIIb can be of Formula XIIc:

(XIIc)

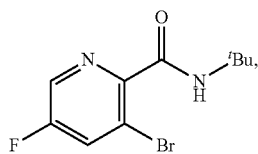

or a salt thereof.

In general, the metalation step (i.e., step 19a) in the bromination reaction (i.e., step 19) can be performed at any suitable temperature, for example, at a temperature of from room temperature to a reflux temperature. In some embodiments, the reaction mixture of the metalation step in the bromination reaction can be at a temperature of from 30° C. to 80° C. In general, the bromination step (i.e., step 19b) in the bromination reaction (i.e., step 19) can be performed at any suitable temperature, for example, at a temperature of from −40° C. to 0° C. In some embodiments, the reaction mixture of the bromination step in the bromination reaction can be at a temperature of from −40° C. to −15° C.

With respect to step 20, the acid, the fourth solvent, and reaction temperature are described herein.

The acid can be sulfuric acid, phosphoric acid, hydrochloric acid, hydrobromic acid, chloric acid, perchloric acid, nitric acid, trifluoroacetic acid, trifluoromethanesulfonic acid, methanesulfonic acid, or phthalic acid. In some embodiments, the acid includes sulfuric acid. In some embodiments, the acid can be sulfuric acid.

The fourth solvent can be water. In some embodiments, the solvent includes water.

In general, the hydrolysis reaction (i.e., step 20) can be performed at any suitable temperature, for example, at a temperature of from 20° C. to 100° C. In some embodiments, the reaction mixture of the hydrolysis reaction can be at a temperature of from 50° C. to 100° C.

9. Preparation of Compound of Formula XIb, Route 1

In some embodiments, the present disclosure provides a method for preparing a compound of Formula XIb:

(XIb)

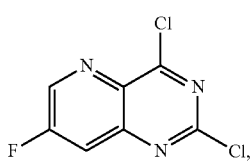

or a salt thereof, the method including:
21) forming a first reaction mixture including 2-bromo-5-fluoropyridin-3-amine or a salt thereof, a cyanide source, a catalyst, and a first solvent to form 3-amino-5-fluoropicolinonitrile:

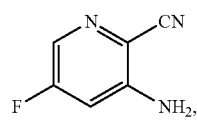

or a salt thereof,
22) forming a second reaction mixture including 3-amino-5-fluoropicolinonitrile or the salt thereof, carbon dioxide, a first base, and a second solvent to form 7-fluoropyrido[3,2-d]pyrimidine-2,4-diol

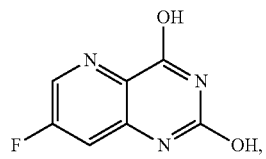

or a salt thereof, and
23) forming a third reaction mixture including 7-fluoropyrido[3,2-d]pyrimidine-2,4-diol, a chlorinating agent, a second base, and a third solvent to form the compound of Formula XIb or the salt thereof.

Figure 7A:
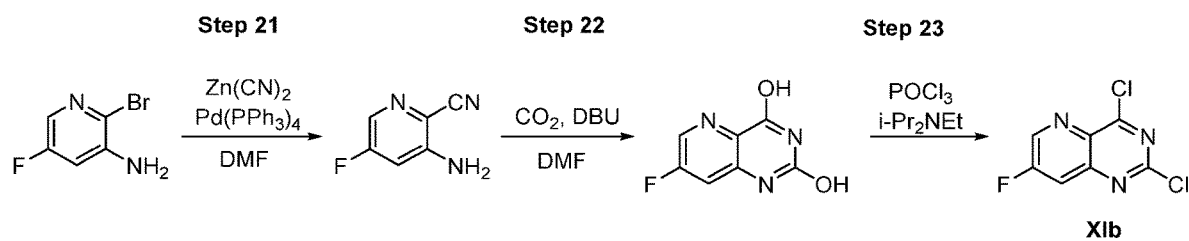
FIG. 7A shows the preparation of the compound of Formula XIb via steps of cyanation, cyclization with carbon dioxide, and chlorination.

In some embodiments, the compound of Formula XIb can be prepared according to steps 21-23, as shown in the scheme of FIG. 7A.

With respect to step 21, the cyanide source, the catalyst, the first solvent, and reaction temperature are described herein.

The cyanide source can be zinc cyanide, potassium ferricyanide, copper(I) cyanide, potassium cyanide, sodium cyanide, trimethylsilyl cyanide, acetone cyanohydrin, hexamethylenetetramine, or ethyl cyanoacetate. In some embodiments, the cyanide source includes zinc cyanide. In some embodiments, the cyanide source can be zinc cyanide.

The catalyst can be a palladium catalyst with or without a tertiary phosphine ligand (e.g., tetrakis(triphenylphosphine)palladium (0), tris(dibenzylideneacetone)dipalladium (0), palladium(II) acetate, palladium(II) chloride, bis(triphenylphosphine)palladium(II) dichloride; bis(acetonitrile) palladium(II) dichloride, (1,1'-bis(diphenylphosphino) ferrocene)palladium(II) dichloride, palladium(π-cinnamyl) chloride dimer, or (2-dicyclohexylphosphino-2',4',6'-triisopropyl-1,1'-biphenyl)[2-(2'-amino-1,1'-biphenyl)]palladium (II) methanesulfonate), a copper(I) catalyst with or without a diamine or amino acid ligand (e.g., copper(I) cyanide, copper(I) iodide, copper(I) bromide, or copper(I) chloride), or a nickel(II) catalyst (e.g., (N,N,N'N'-tetramethylethylenediamine)NiCl(o-tolyl) or trans-chloro-(2-napthyl)-bis(triphenylphosphine)nickel(II)). In some embodiments, the catalyst includes tetrakis(triphenylphosphine)palladium (0). In some embodiments, the catalyst can be tetrakis(triphenylphosphine)palladium (0).

The first solvent can be a polar aprotic solvent (e.g., N,N-dimethylformamide, N-methyl-2-pyrrolidone, or N,N-dimethylacetamide), an ether (e.g., 1,4-dioxane, tetrahydrofuran, 2-methyltetrahydrofuran, or 1,2-dimethoxyethane), an alcohol (e.g, methanol, ethanol, 1-butanol, or 2 propanol), an aromatic solvent (e.g., toluene, xylenes, or anisole), or combinations thereof. The first solvent can further include water. In some embodiments, the first solvent includes N,N-dimethylformamide. In some embodiments, the first solvent can be N,N-dimethylformamide.

In general, the cyanation reaction (i.e., step 21) can be performed at any suitable temperature, for example, at a temperature of from 40° C. to 140° C. In some embodiments, the reaction mixture of the cyanation reaction can be at a temperature of from 80° C. to 110° C.

With respect to step 22, the first base, the second solvent, and reaction temperature are described herein.

The first base can be 1,8-diazabicyclo[5.4.0]undec-7-ene (DBU), 1,5-diazabicyclo[4.3.0]non-5-ene (DBN), tetramethylguanidine, 1,5,7-triazabicyclo[4.4.0]dec-5-ene (TBD), 7-methyl-1,5,7-triazabicyclo[4.4.0]dec-5-ene (MTBD), or tert-butylimino-tri(pyrrolidino)phosphorene. In some embodiments, the first base includes 1,8-diazabicyclo[5.4.0]undec-7-ene. In some embodiments, the first base can be 1,8-diazabicyclo[5.4.0]undec-7-ene.

The second solvent can be a polar aprotic solvent (e.g., N,N-dimethylformamide, N-methyl-2-pyrrolidone, N,N-dimethylacetamide, dimethylsulfoxide, or sulfolane), an aromatic amine base (e.g., pyridine, 2,6-lutidine, or collidines), an ether (e.g., 1,4-dioxane or cyclopentyl methyl ether), a chlorinated solvent (e.g., 1,2-dichloroethane or chlorobenzene), an aromatic solvent (e.g., toluene, xylenes, or trifluorotoluene, etc.), or combinations thereof. In some embodiments, the second solvent includes N,N-dimethylformamide. In some embodiments, the second solvent can be N,N-dimethylformamide.

In general, the cyclization reaction (i.e., step 22) can be performed at any suitable temperature, for example, at a temperature of from 40° C. to 150° C. In some embodiments, the reaction mixture of the cyclization reaction can be at a temperature of from 40° C. to 60° C.

With respect to step 23, the chlorinating agent, the second base, the third solvent, and reaction temperature are described herein.

The chlorinating agent can be phosphorus oxychloride, phosphorus(V) chloride, or triphenylphosphine dichloride. In some embodiments, the chlorinating agent includes phosphorus oxychloride. In some embodiments, the chlorinating agent can be phosphorus oxychloride.

The second base can be present or absent. When the second base is present, the second base can be a tertiary amine (e.g., triethylamine, tri-n-butylamine, N,N-diisopropylethylamine, dimethylaniline, or diethylaniline), or an aromatic amine base (e.g., pyridine, 2,6-lutidine, or collidines). In some embodiments, the second base includes N,N-diisopropylethylamine. In some embodiments, the second base can be N,N-diisopropylethylamine.

The third solvent can be absent and the chlorination reaction can be performed in neat phosphorus oxychloride. When the third solvent is present, the third solvent can be an aromatic solvent (e.g., toluene or xylenes), an aromatic amine solvent (e.g., diethylaniline), a chlorinated solvent (e.g, chlorobenzene), or combinations thereof. In some embodiments, the third solvent includes toluene. In some embodiments, the third solvent can be toluene.

In general, the chlorination reaction (i.e., step 23) can be performed at any suitable temperature, for example, at a temperature of from 50° C. to 140° C. In some embodiments, the reaction mixture of the chlorination reaction can be at a temperature of from 80° C. to 120° C.

10. Preparation of Compound of Formula XIb, Route 2

Figure 7B:
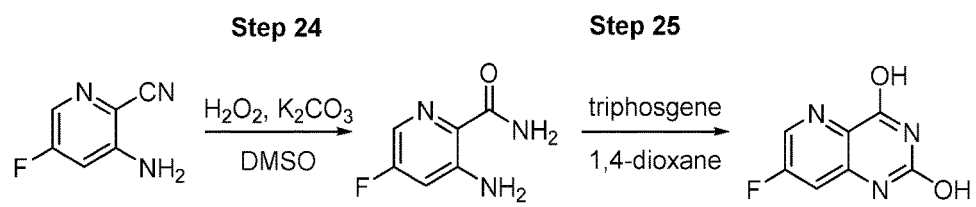
FIG. 7B shows an alternative method for preparing 7-fluoropyrido[3,2-d]pyrimidine-2,4-diol via steps of oxidation and cyclization with triphosgene.
Figure 8:
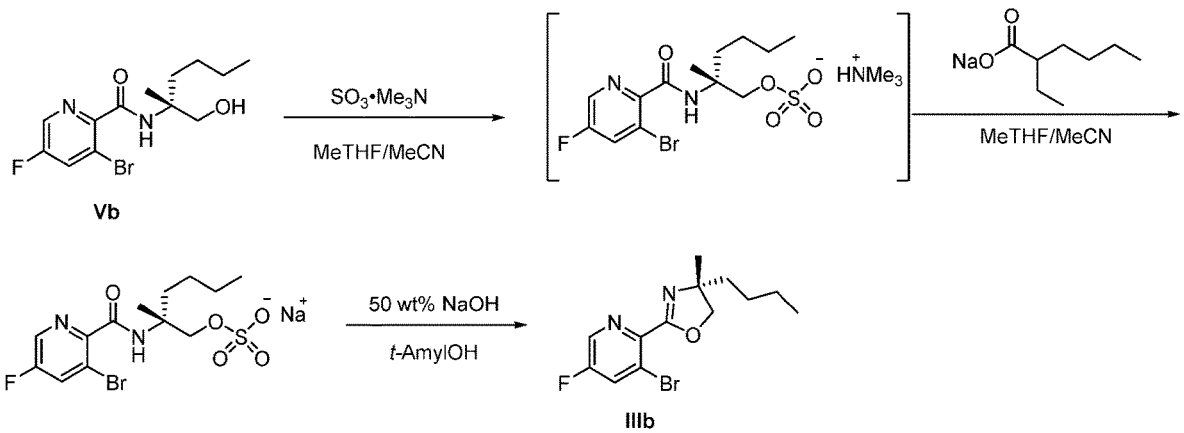
FIG. 8 shows the preparation of the compound of IIIb from the compound of Formula IIb via steps of sulfonation, ion-exchange, and cyclization.
Figure 9:
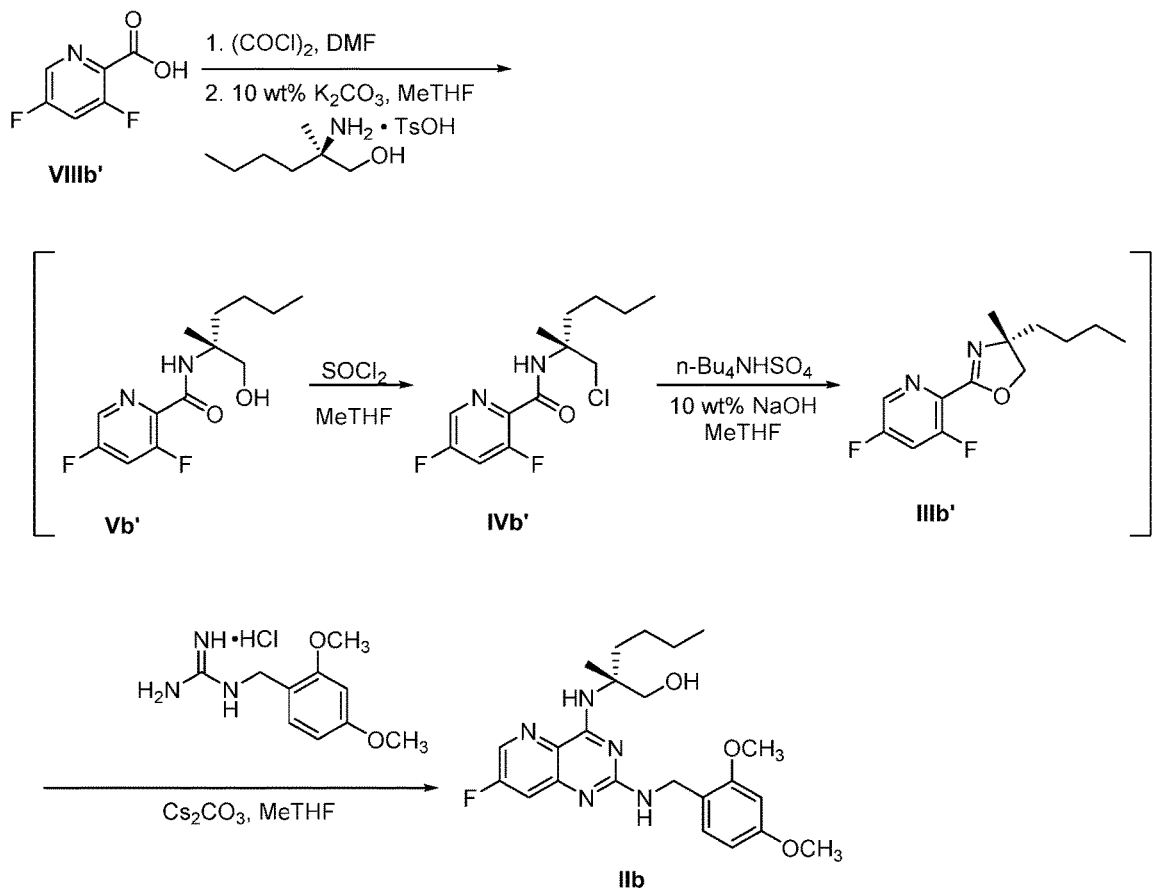
FIG. 9 shows the preparation of the compound of Formula IIb from 3,5-difluoropicolinic acid (VIIIb-1) via a coupling reaction of (R)-2-(3-fluoro-5-fluoropyridin-2-yl)-4-butyl-4-methyl-4,5-dihydrooxazole (IIb-1) with a protected guanidine compound.
Figure 10:
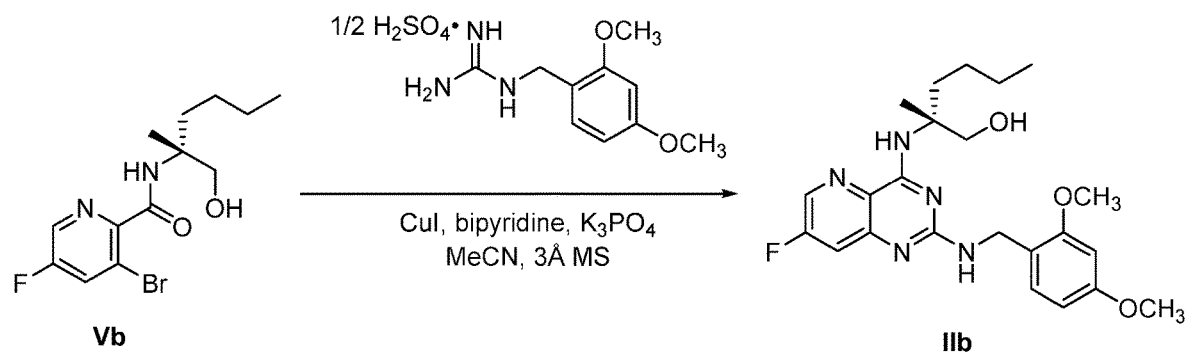
FIG. 10 shows the preparation of the compound of Formula IIb via a transition-metal mediated coupling reaction of (R)-3-bromo-5-fluoro-N-(1-hydroxy-2-methylhexan-2-yl)picolinamide (Vb) with a protected guanidine compound.
Figure 11:
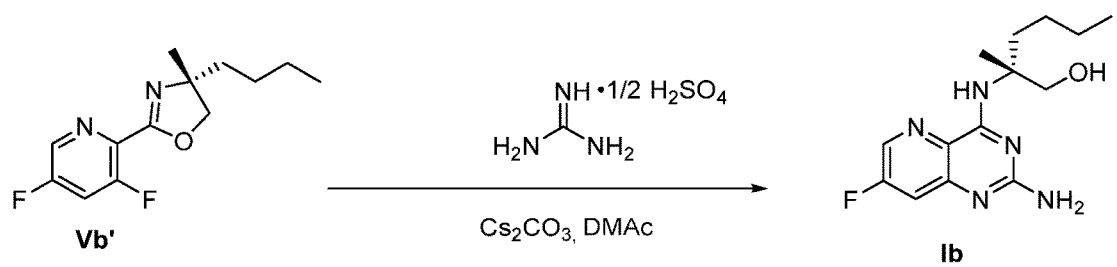
FIG. 11 shows the preparation the compound of Formula Ib via a direct coupling reaction of (R)-2-(3-fluoro-5-fluoropyridin-2-yl)-4-butyl-4-methyl-4,5-dihydrooxazole (IIb-1) with a guanidine salt.
Figure 12:
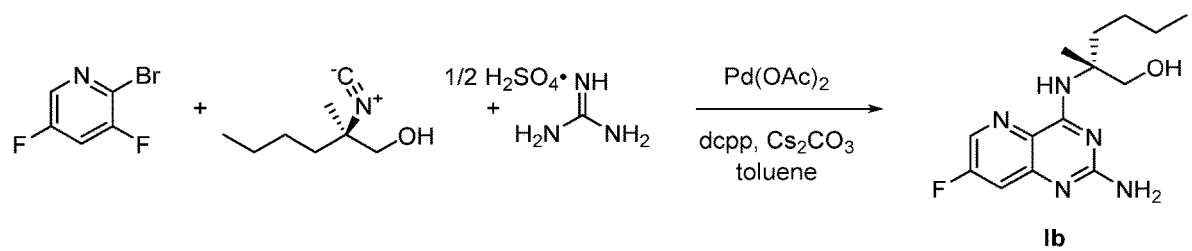
FIG. 12 shows the preparation the compound of Formula Ib via a condensation reaction of 2-bromo-3,5-difluoropyridine, (R)-2-isocyano-2-methylhexan-1-ol, and a guanidine salt.

In some embodiments, the above step 22 can be replaced with steps 24 and 25, as shown in the scheme of FIG. 7B.

In some embodiments, the present disclosure provides a method for preparing a compound of Formula XIb:

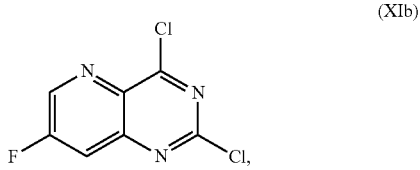 [SMILES: Fc1cnc2c(Cl)nc(Cl)nc2c1]

(XIb)

or a salt thereof, the method including:
21) forming a first reaction mixture including 2-bromo-5-fluoropyridin-3-amine or a salt thereof, a cyanide source, a catalyst, and a first solvent to form 3-amino-5-fluoropicolinonitrile:

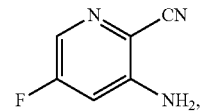

or a salt thereof,
24) forming a second reaction mixture including 3-amino-5-fluoropicolinonitrile or the salt thereof, an oxidant, a first base, and a second solvent to form 3-amino-5-fluoropicolinamide:

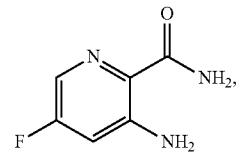

or a salt thereof,
25) forming a third reaction mixture including 3-amino-5-fluoropicolinamide or the salt thereof, a cyclization reagent, and a third solvent to form 7-fluoropyrido[3,2-d]pyrimidine-2,4-diol:

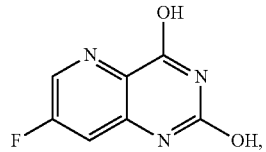

or a salt thereof, and
23) forming a fourth reaction mixture including 7-fluoropyrido[3,2-d]pyrimidine-2,4-diol or the salt thereof, a chlorinating agent, a second base, and a fourth solvent to form the compound of Formula XIb or the salt thereof.

Steps 21 and 23 are described above in the preparation of the compound of Formula XIb, Route 1.

With respect to step 24, the oxidant, the first base, the second solvent, and reaction temperature are described herein.

The oxidant can be hydrogen peroxide, hydrogen peroxide urea adduct, lithium peroxide, benzoyl peroxide, or tert-butyl peroxide. In some embodiments, the oxidant includes hydrogen peroxide. In some embodiments, the oxidant can be in an aqueous solution. In some embodiments, the oxidant can be an aqueous solution of hydrogen peroxide. In some embodiments, the oxidant can be hydrogen peroxide.

The first base can be an alkali carbonate (e.g., sodium carbonate, potassium carbonate, or cesium carbonate); or an alkali hydroxide (e.g., sodium hydroxide, potassium hydroxide, or ammonium hydroxide). In some embodiments, the first base includes potassium carbonate. In some embodiments, the first base can be potassium carbonate.

The second solvent can be a polar aprotic solvent (e.g., N-methyl-2-pyrrolidone, N,N-dimethylacetamide, or dimethylsulfoxide), an alcohol (e.g., methanol, ethanol, or tert-butanol), 1,4-dioxane, water, or combinations thereof. In some embodiments, the second solvent includes dimethylsulfoxide. In some embodiments, the second solvent can be dimethylsulfoxide.

In general, the oxidation reaction (i.e., step 24) can be performed at any suitable temperature, for example, at a temperature of from 20° C. to 120° C. In some embodiments, the reaction mixture of the oxidation reaction can be at a temperature of from 20° C. to 40° C.

The oxidation reaction of step 24 can be replaced with a hydrolysis reaction using a mineral acid. In some embodiments, 3-amino-5-fluoropicolinonitrile or the salt thereof can be subjected to hydrolysis by a mineral acid, for example, sulfuric acid, to form 3-amino-5-fluoropicolinamide or the salt thereof.

With respect to step 25, the cyclization reagent, the third solvent, and reaction temperature are described herein.

The cyclization reagent can be triphosgene, 1,1'-carbonyldiimidazole, phosgene, diphosgene, diphenylcarbonate, or sodium cyanate. In some embodiments, the cyclization reagent includes triphosgene. In some embodiments, the cyclization reagent can be triphosgene.

The third solvent can be an ether (e.g., tetrahydrofuran, 2-methyltetrahydrofuran, or 1,4-dioxane); an aromatic solvent (e.g., toluene or xylenes), a polar aprotic solvent (e.g., acetonitrile, propionitrile, or n-butylnitrile), an organic acid (e.g., acetic acid or chloroacetic acid), or combinations of thereof. In some embodiments, the third solvent includes 1,4-dioxane. In some embodiments, the third solvent can be 1,4-dioxane.

In general, the cyclization reaction of step 25 can be performed at any suitable temperature, for example, at a temperature of from 20° C. to 150° C. In some embodiments, the reaction mixture of the cyclization reaction can be at a temperature of from 90° C. to 110° C.

11. Preparation of Formula IXa

In some embodiments, the present disclosure provides a method for preparing a compound of Formula IXa:

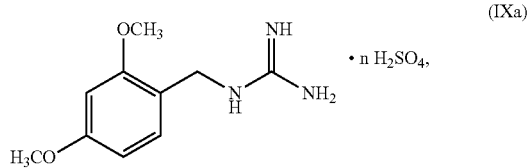 [SMILES: COc1ccc(CNC(=N)N)c(OC)c1]

the method including forming a guanylation reaction mixture including a guanylation reagent, (2,4-dimethoxyphenyl)methanamine, a base, an additive, and a solvent to form the compound of Formula IXb, wherein n can be from 0 to 1.

The guanylation reagent can be thiourea, 1H-pyrazole-1-carboxamidine hydrochloride, cyanamide, N,N-di-tert-butyloxycarbonyl-1H-pyrazole-1-carboxamidine, N,N-di-tert-butyloxycarbonyl-thiourea, S—C$_{1-6}$ alkyl isothiourea (e.g., S-methylisothiourea, S-ethylisothiourea, S-butylisothiourea, S-tert-butyl-isothiourea, or S-hexylisothiourea), or a salt thereof. In some embodiments, the guanylation reagent includes S—C$_{1-6}$ alkyl isothiourea. In some embodiments, the guanylation reagent includes S-methylisothiourea. In some embodiments, the guanylation reagent includes S-methylisothiourea hemisulfate. In some embodiments, the guanylation reagent can be S—C$_{1-6}$ alkyl isothiourea. In some embodiments, the guanylation reagent can be S-methylisothiourea. In some embodiments, the guanylation reagent can be S-methylisothiourea hemisulfate.

The base can be absent or present. When the base is present, the base can be a tertiary amine (e.g., triethylamine, tri-n-butylamine, or N,N-diisopropylethylamine). In some embodiments, the base can be absent.

The additive can be absent or present. When the additive is present, the additive can be a Lewis acid (e.g., tris-dimethylamino-aluminum dimer or scandium triflate). In some embodiments, the additive can be absent.

The solvent can be an ether (e.g., tetrahydrofuran, 2-methyltetrahydrofuran, 1,4-dioxane, or cyclopentyl methyl ether, etc.), an alcohol (e.g., methanol, ethanol, n-butanol, 2-methylbutan-2-ol, or isopropanol), water, a polar aprotic solvent (N-methyl-2-pyrrolidone, N,N-dimethylformamide, N,N-dimethylacetamide, dimethylsulfoxide, or sulfolane), a chlorinated solvent (e.g., dichloromethane, 1,2-dichloroethane, chlorobenzene, or chloroform) or combinations thereof. In some embodiments, the solvent includes N-methyl-2-pyrrolidone. In some embodiments, the solvent can be N-methyl-2-pyrrolidone.

In some embodiments, the compound of Formula IXa can be of Formula IXb:

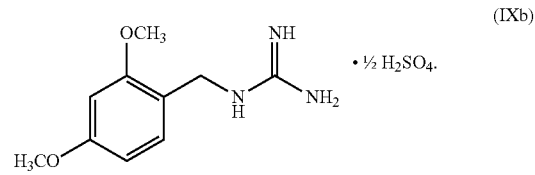 [SMILES: COc1ccc(CNC(=N)N)c(OC)c1]

In some embodiments, the present disclosure provides a method for preparing a compound of Formula IXb:

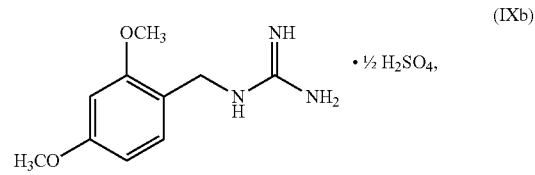 [SMILES: COc1ccc(CNC(=N)N)c(OC)c1]

the method including forming a guanylation reaction mixture including S-methylisothiourea hemisulfate, (2,4-dimethoxyphenyl)methanamine, and N-methyl-2-pyrrolidone to form the compound of Formula IXb.

In general, the guanylation reaction can be performed at any suitable temperature, for example, at a temperature of from 20° C. to 130° C. In some embodiments, the reaction mixture of the guanylation reaction can be at a temperature of from 50° C. to 110° C.

12. Preparation of C$_{1-4}$ alkyl 2-amino-2-methylhexanoate via 2-amino-2-methylhexanenitrile In some embodiments, the present disclosure provides a method for preparing C$_{1-4}$ alkyl 2-amino-2-methylhexanoate:

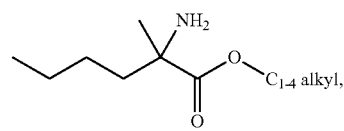

or a salt thereof, the method including:
1) forming a first reaction mixture including hexan-2-one having the formula:

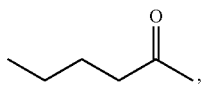

a cyanide, optionally a first acid, a desiccant, optionally an additive, and a first solvent to form 2-amino-2-methylhexanenitrile having the formula:

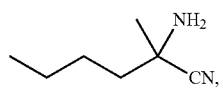

or a salt thereof,
2a) forming a second reaction mixture including 2-amino-2-methylhexanenitrile or the salt thereof, a $C_{1-4}$ alkyl alcohol, a second acid, and water to form a salt of $C_{1-4}$ alkyl 2-amino-2-methylhexanoate; and
2b) forming a third reaction mixture including the salt of $C_{1-4}$ alkyl 2-amino-2-methylhexanoate, a base, and a second solvent to form $C_{1-4}$ alkyl 2-amino-2-methylhexanoate in a neutral form.

In some embodiments, $C_{1-4}$ alkyl 2-amino-2-methylhexanoate can be isopropyl 2-amino-2-methylhexanoate having the formula:

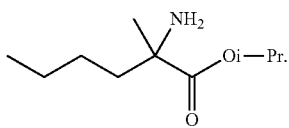

Figure 13:
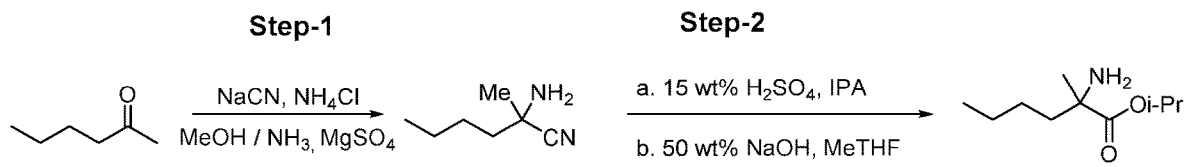
FIG. 13 shows the preparation of isopropyl 2-amino-2-methylhexanoate from hexan-2-one via 2-amino-2-methylhexanenitrile.

In some embodiments, isopropyl 2-amino-2-methylhexanoate can be prepared according to steps as shown in the scheme of FIG. 13.

In some embodiments, the $C_{1-4}$ alkyl in $C_{1-4}$ alkyl 2-amino-2-methylhexanoate or the salt thereof can be methyl, ethyl, n-propyl, isopropyl, n-butyl, sec-butyl, or tert-butyl. In some embodiments, the $C_{1-4}$ alkyl in $C_{1-4}$ alkyl 2-amino-2-methylhexanoate or the salt thereof can be isopropyl.

In some embodiments, with respect to step 1, the cyanide, the first acid, the desiccant, the additive, the first solvent, and reaction temperature are described herein.

In some embodiments, the cyanide can be hydrogen cyanide, sodium cyanide, potassium cyanide, ammonium cyanide, trimethylsilyl cyanide, tert-butyldimethylsilyl cyanide, potassium hexacyanoferrate(III), potassium hexacyanoferrate(II), sodium ferrocyanide, acetone cyanohydrin, triphenyl acetonitrile, ethyl cyanoformate, diethyl cyanophosphate, acetyl cyanide, or combinations thereof. In some embodiments, the cyanide includes sodium cyanide. In some embodiments, the cyanide can be sodium cyanide.

In some embodiments, the first acid is absent. In some embodiments, the first reaction mixture further comprises a first acid. The first acid can be ammonium chloride, para-toluenesulfonic acid, oxalic acid, formic acid, acetic acid, guanidine hydrochloric acid, cyanuric acid, hydrochloric acid, sulfuric acid, phosphoric acid, or combinations thereof.

In some embodiments, the acid includes ammonium chloride. In some embodiments, the acid can be ammonium chloride.

In some embodiments, the desiccant can be magnesium sulfate, sodium sulfate, a trialkyl orthoformate (e.g., trimethyl orthoformate), an azeotropic removal of water (e.g., a Dean Stark trap), or molecular sieves. In some embodiments, the desiccant includes magnesium sulfate.

In some embodiments, the additive is absent. In some embodiments, the first reaction mixture further comprises an additive. In some embodiments, the additive can be a Lewis acid including scandium(III)triflate, boron trifluoride etherate, zinc iodide, lithium chlorite, trimethylsilyl trifluoromethanesulfonate, bismuth chloride, magnesium bromide, ruthenium(III) chloride, or combinations thereof.

In some embodiments, the first solvent can be an alcohol (e.g., methanol, ethanol, 2-propanol, 1-butanol, tert-butanol, 2-methylbutan-2-ol, or trifluoroethanol), a hydrocarbon solvent (e.g., n-heptane, hexanes, cyclohexane, or methylcyclohexane), a polar aprotic solvent (e.g., acetonitrile, propionitrile, or butyronitrile), an organic acid (e.g., acetic acid, formic acid, or trifluoroacetic acid), a chlorinated solvent (e.g., dichloromethane or chlorobenzene), an aromatic solvent (e.g., toluene, xylene, nitrobenzene, trifluorotoluene, or fluorobenzene), water, or combinations thereof. In some embodiments, the first solvent includes methanol. In some embodiments, the first solvent can be methanol.

In general, the first reaction (i.e., step 1) can be performed at any suitable temperature. For example, the first reaction mixture can be at a temperature of from 0° C. to 70° C. In some embodiments, the first reaction mixture can be at a temperature of from 0° C. to 40° C.

In some embodiments, step 2 includes two steps as described in steps 2a and 2b.

In some embodiments, with respect to step 2a, the $C_{1-4}$ alkyl alcohol, the second acid, the salt of $C_{1-4}$ alkyl 2-amino-2-methylhexanoate, and reaction temperature are described herein.

In some embodiments, the $C_{1-4}$ alkyl alcohol can be methanol, ethanol, n-propanol, isopropanol, n-butanol, sec-butanol, or tert-butanol. In some embodiments, the $C_{1-4}$ alkyl alcohol includes methanol. In some embodiments, the $C_{1-4}$ alkyl alcohol can be methanol.

In some embodiments, the second acid can be a mineral acid (e.g., sulfuric acid, hydrochloric acid, phosphoric acid, chlorosulfuric acid, oleum, fluorosulfuric acid, or fluoroantimonic acid), an organic acid (e.g., methanesulfonic acid or triflic acid), or combinations thereof. In some embodiments, the second acid includes sulfuric acid. In some embodiments, the second acid can be sulfuric acid In some embodiments, the salt of $C_{1-4}$ alkyl 2-amino-2-methylhexanoate can be a sulfuric acid salt, hydrochloric acid salt, phosphoric acid salt, chlorosulfuric acid salt, oleum salt, fluorosulfuric acid salt, fluoroantimonic acid salt, methanesulfonic acid salt, or triflic acid salt. In some embodiments, the salt of $C_{1-4}$ alkyl 2-amino-2-methylhexanoate can be a sulfate.

In some embodiments, the salt of $C_{1-4}$ alkyl 2-amino-2-methylhexanoate can be isopropyl 2-amino-2-methylhexanoate sulfate.

In general, the second reaction (i.e., step 2a) can be performed at any suitable temperature. For example, the second reaction mixture can be at a temperature of from 50° C. to 150° C. In some embodiments, the second reaction mixture can be at a temperature of from 70° C. to 100° C.

In some embodiments, with respect to step 2b, the base, the second solvent, and reaction temperature are described herein.

In some embodiments, the base can be an inorganic base (e.g., lithium hydroxide, sodium hydroxide, potassium hydroxide, sodium carbonate, potassium carbonate, sodium bicarbonate, potassium bicarbonate, sodium phosphate tribasic, or potassium phosphate tribasic), an organic base (e.g., sodium acetate, potassium acetate, sodium methoxide, sodium tert-butoxide, or potassium tert-butoxide), or combinations thereof. In some embodiments, the base includes sodium hydroxide. In some embodiments, the base can be sodium hydroxide. In some embodiments, the base can be in an aqueous solution. In some embodiments, the base includes an aqueous solution of sodium hydroxide. In some embodiments, the base can be an aqueous solution of sodium hydroxide.

In some embodiments, the second solvent can be an aromatic solvent (e.g., toluene, xylenes, or trifluorotoluene), an ether (e.g., diethyl ether, methyl tert-butyl ether, tetrahydrofuran, 2-methyltetrahydrofuran, or 1,4-dioxane), a chlorinated solvent (e.g., dichloromethane, or 1,2-dichloroethane), or combinations thereof. In some embodiments, the second solvent includes 2-methyltetrahydrofuran. In some embodiments, the second solvent can be 2-methyltetrahydrofuran.

In general, the third reaction (i.e., step 2b) can be performed at any suitable temperature. For example, the third reaction mixture can be at a temperature of from 0° C. to 40° C. In some embodiments, the third reaction mixture can be at a temperature of from 20° C. to 30° C.

IV. Compounds

In another embodiment, the present disclosure provides a compound of Formula III:

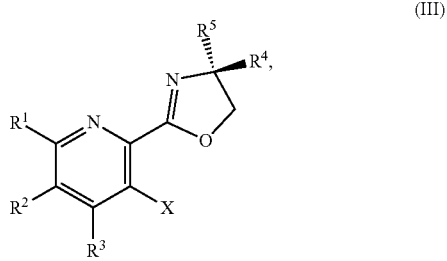

(III)

or a salt thereof, wherein $R^1$, $R^2$, and $R^3$ can each independently be hydrogen, F, Cl, CN, $CF_3$, $C_{1-3}$ alkyl, or $C_{1-3}$ alkoxy; $R^4$ can be hydrogen or methyl; $R^5$ can be $C_{3-6}$ alkyl; and X can be F, Cl, Br, I, or OTs.

In another embodiment, the present disclosure provides a compound of Formula III:

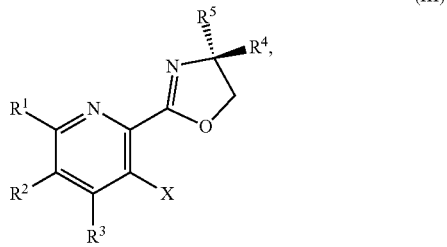

(III)

or a salt thereof, wherein $R^1$, $R^2$, and $R^3$ can each independently be hydrogen, F, Cl, CN, $CF_3$, $C_{1-3}$ alkyl, or $C_{1-3}$ alkoxy; $R^4$ can be hydrogen or methyl; $R^5$ can be $C_{3-6}$ alkyl; and X can be Cl, Br, I, or OTs.

In some embodiments, $R^2$ can be Cl, F, CN, $CF_3$, $C_{1-3}$ alkyl, or $C_{1-3}$ alkoxy; and $R^1$ and $R^3$ can each independently be hydrogen, F, Cl, CN, $CF_3$, $C_{1-3}$ alkyl, or $C_{1-3}$ alkoxy. The $C_{1-3}$ alkyl can be methyl, ethyl, propyl, or isopropyl. The $C_{1-3}$ alkoxy can be methoxy, ethoxy, n-propoxy, or isopropoxy. In some embodiments, $R^2$ can be Cl, F, CN, $CF_3$, methyl, ethyl, n-propyl, isopropyl, methoxy, ethoxy, n-propoxy, or isopropoxy; and $R^1$ and $R^3$ can each independently be hydrogen, F, Cl, CN, $CF_3$, methyl, ethyl, n-propyl, isopropyl, methoxy, ethoxy, n-propoxy, or isopropoxy. In some embodiments, $R^2$ can be Cl, F, CN, $CF_3$, methyl, ethyl, n-propyl, isopropyl, methoxy, ethoxy, n-propoxy, or isopropoxy; and $R^1$ and $R^3$ can each be hydrogen. In some embodiments, $R^2$ can be F, and $R^1$ and $R^3$ can each be hydrogen.

In some embodiments, $R^4$ can be hydrogen. In some embodiments, $R^4$ can be methyl.

In some embodiments, $R^5$ can be $C_{3-6}$ alkyl. In some embodiments, $R^5$ can be n-propyl, isopropyl, n-butyl, isobutyl, sec-butyl, tert-butyl, n-pentyl, isopentyl, or hexyl. In some embodiments, $R^5$ can be n-butyl.

In some embodiments, $R^4$ can be methyl; and $R^5$ can be $C_{3-6}$ alkyl. In some embodiments, $R^4$ can be methyl; and $R^5$ can be n-propyl, isopropyl, n-butyl, isobutyl, sec-butyl, tert-butyl, n-pentyl, isopentyl, or hexyl. In some embodiments, $R^4$ can be methyl; and $R^5$ can be n-butyl.

In some embodiments, X can be F, Br, I, or OTs. In some embodiments, X can be Br, I, or OTs. In some embodiments, X can be Br. In some embodiments, X can be F.

In some embodiments, the compound of Formula III can be of Formula IIIa:

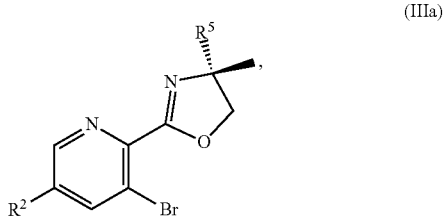

(IIIa)

or a salt thereof, wherein $R^2$ and $R^5$ are defined and described herein.

In some embodiments, the compound of Formula III can be of Formula IIIa-1:

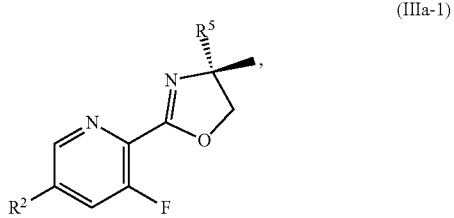

(IIIa-1)

or a salt thereof, wherein $R^2$ and $R^5$ are defined and described herein.

In some embodiments, the compound of Formula III can be of Formula IIIb:

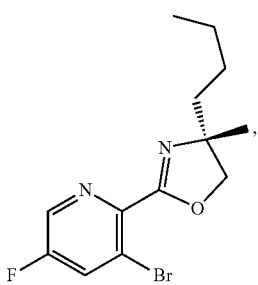

(IIIb)

or a salt thereof.

In some embodiments, the compound of Formula III can be of Formula IIIb-1:

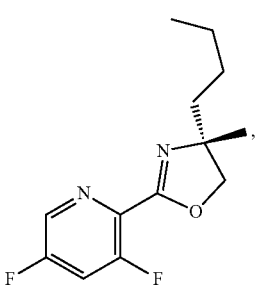

(IIIb-1)

or a salt thereof.

In another embodiment, the present disclosure provides a compound of Formula IV:

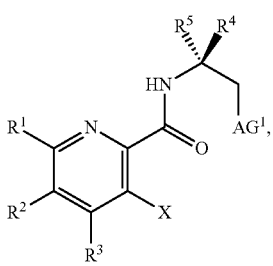

(IV)

or a salt thereof, wherein $R^1$, $R^2$, and $R^3$ can each independently be hydrogen, F, Cl, CN, $CF_3$, $C_{1-3}$ alkyl, or $C_{1-3}$ alkoxy; $R^4$ can be hydrogen or methyl; $R^5$ can be $C_{3-6}$ alkyl; X can be F, Cl, Br, I, or OTs; and $AG^1$ can be Cl, Br, $OSO_3H$, $OSO_3^-$, OMs, OTs, or OTf.

In another embodiment, the present disclosure provides a compound of Formula IV:

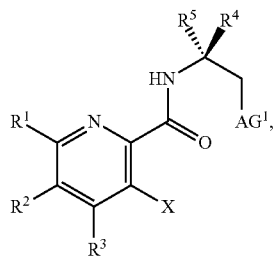

(IV)

or a salt thereof, wherein $R^1$, $R^2$, and R can each independently be hydrogen, F, Cl, CN, $CF_3$, $C_{1-3}$ alkyl, or $C_{1-3}$ alkoxy; $R^4$ can be hydrogen or methyl; $R^5$ can be $C_{3-6}$ alkyl; X can be Cl, Br, I, or OTs; and $AG^1$ can be Cl, Br, OMs, OTs, or OTf.

In some embodiments, $R^2$ can be Cl, F, CN, $CF_3$, $C_{1-3}$ alkyl, or $C_{1-3}$ alkoxy; and $R^1$ and $R^3$ can each independently be hydrogen, F, Cl, CN, $CF_3$, $C_{1-3}$ alkyl, or $C_{1-3}$ alkoxy. The $C_{1-3}$ alkyl can be methyl, ethyl, n-propyl, or isopropyl. The $C_{1-3}$ alkoxy can be methoxy, ethoxy, n-propoxy, or isopropoxy. In some embodiments, $R^2$ can be Cl, F, CN, $CF_3$, methyl, ethyl, n-propyl, isopropyl, methoxy, ethoxy, n-propoxy, or isopropoxy; and $R^1$ and $R^3$ can each independently be hydrogen, F, Cl, CN, $CF_3$, methyl, ethyl, n-propyl, isopropyl, methoxy, ethoxy, n-propoxy, or isopropoxy. In some embodiments, $R^2$ can be Cl, F, CN, $CF_3$, methyl, ethyl, n-propyl, isopropyl, methoxy, ethoxy, n-propoxy, or isopropoxy; and $R^1$ and $R^3$ can each be hydrogen. In some embodiments, $R^2$ can be F, and $R^1$ and $R^3$ can each be hydrogen.

In some embodiments, $R^4$ can be hydrogen. In some embodiments, $R^4$ can be methyl.

In some embodiments, $R^5$ can be $C_{3-6}$ alkyl. In some embodiments, $R^5$ can be n-propyl, isopropyl, n-butyl, isobutyl, sec-butyl, tert-butyl, n-pentyl, isopentyl, or hexyl. In some embodiments, $R^5$ can be n-butyl.

In some embodiments, $R^4$ can be methyl; and $R^5$ can be $C_{3-6}$ alkyl. In some embodiments, $R^4$ can be methyl; and $R^5$ can be n-propyl, isopropyl, n-butyl, isobutyl, sec-butyl, tert-butyl, n-pentyl, isopentyl, or hexyl. In some embodiments, $R^4$ can be methyl; and $R^5$ can be n-butyl.

In some embodiments, X can be F, Br, I, or OTs. In some embodiments, X can be Br, I, or OTs. In some embodiments, X can be Br. In some embodiments, X can be F.

In some embodiments, $AG^1$ can be Cl. In some embodiments, $AG^1$ can be Br. In some embodiments, $AG^1$ can be OMs, OTs, or OTf. In some embodiments, $AG^1$ can be $OSO_3H$ or $OSO_3^-$.

In some embodiments, the compound of Formula IV can be of Formula IV-1:

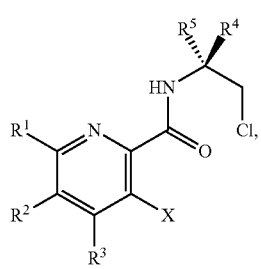

(IV-1)

or a salt thereof, wherein $R^1$, $R^2$, $R^3$, $R^4$, $R^5$, and X are defined and described herein.

In some embodiments, the compound of formula IV-1 can be of Formula IVa-1:

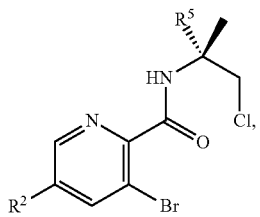

(IVa-1)

or a salt thereof, wherein $R^2$ and $R^5$ are defined and described herein.

In some embodiments, the compound of formula IV-1 can be of Formula IVa-2:

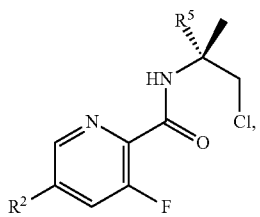

(IVa-2)

or a salt thereof, wherein $R^2$ and $R^5$ are defined and described herein.

In some embodiments, the compound of Formula IV-1 can be of Formula IVb-1:

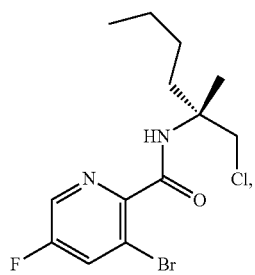

(IVb-1)

or a salt thereof.

In some embodiments, the compound of Formula IV-1 can be of Formula IVb-2:

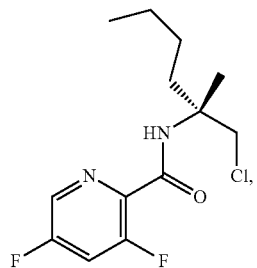

(IVb-2)

or a salt thereof.

In another embodiment, the present disclosure provides a compound of Formula V:

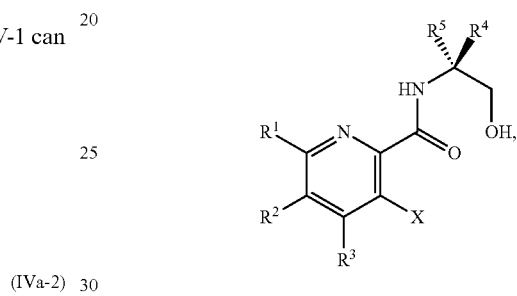

(V)

or a salt thereof, wherein $R^1$, $R^2$, and $R^3$ can each independently be hydrogen, F, Cl, CN, $CF_3$, $C_{1-3}$ alkyl, or $C_{1-3}$ alkoxy; $R^4$ can be hydrogen or methyl; $R^5$ can be $C_{3-6}$ alkyl; and X can be F, Cl, Br, I, or OTs.

In another embodiment, the present disclosure provides a compound of Formula V:

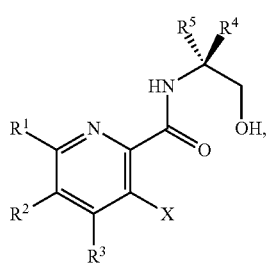

(V)

or a salt thereof, wherein $R^1$, $R^2$, and $R^3$ can each independently be hydrogen, F, Cl, CN, $CF_3$, $C_{1-3}$ alkyl, or $C_{1-3}$ alkoxy; $R^4$ can be hydrogen or methyl; $R^5$ can be $C_{3-6}$ alkyl; and X can be Cl, Br, I, or OTs.

In some embodiments, $R^2$ can be Cl, F, CN, $CF_3$, $C_{1-3}$ alkyl, or $C_{1-3}$ alkoxy; and $R^1$ and $R^3$ can each independently be hydrogen, F, Cl, CN, $CF_3$, $C_{1-3}$ alkyl, or $C_{1-3}$ alkoxy. The $C_{1-3}$ alkyl can be methyl, ethyl, n-propyl, or isopropyl. The $C_{1-3}$ alkoxy can be methoxy, ethoxy, n-propoxy, or isopropoxy. In some embodiments, $R^2$ can be Cl, F, CN, $CF_3$, methyl, ethyl, n-propyl, isopropyl, methoxy, ethoxy, n-propoxy, or isopropoxy; and $R^1$ and $R^3$ can each independently be hydrogen, F, Cl, CN, $CF_3$, methyl, ethyl, n-propyl, isopropyl, methoxy, ethoxy, n-propoxy, or isopropoxy. In some embodiments, $R^2$ can be Cl, F, CN, $CF_3$, methyl, ethyl, n-propyl, isopropyl, methoxy, ethoxy, n-propoxy, or isopropoxy; and $R^1$ and $R^3$ can each be hydrogen. In some embodiments, $R^2$ can be F, and $R^1$ and $R^3$ can each be hydrogen.

In some embodiments, $R^4$ can be hydrogen. In some embodiments, $R^4$ can be methyl.

In some embodiments, $R^5$ can be $C_{3-6}$ alkyl. In some embodiments, $R^5$ can be n-propyl, isopropyl, n-butyl, isobutyl, sec-butyl, tert-butyl, n-pentyl, isopentyl, or hexyl. In some embodiments, $R^5$ can be n-butyl.

In some embodiments, $R^4$ can be methyl; and $R^5$ can be $C_{3-6}$ alkyl. In some embodiments, $R^4$ can be methyl; and $R^5$ can be n-propyl, isopropyl, n-butyl, isobutyl, sec-butyl, tert-butyl, n-pentyl, isopentyl, or hexyl. In some embodiments, $R^4$ can be methyl; and $R^5$ can be n-butyl.

In some embodiments, X can be F, Br, I, or OTs. In some embodiments, X can be Br, I, or OTs. In some embodiments, X can be Br. In some embodiments, X can be F.

In some embodiments, the compound of Formula V is not 3-bromo-N-(1-hydroxy-3-methylbutan-2-yl)picolinamide,
3-bromo-N-(1-hydroxy-3,3-dimethylbutan-2-yl)picolinamide,
3-bromo-N-(1-hydroxy-4-methylpentan-2-yl)picolinamide,
3-bromo-N-(1-hydroxy-4-methylpentan-2-yl)picolinamide,
3,6-dichloro-N-(1-hydroxy-3-methylbutan-2-yl)picolinamide,
3,6-dichloro-N-(1-hydroxy-4-methylpentan-2-yl)picolinamide,
3,4,5-trichloro-N-(1-hydroxy-3-methylbutan-2-yl)picolinamide,
3,6-dichloro-N-(1-hydroxy-4,4-dimethylpentan-2-yl)picolinamide, or
3,4,5-trichloro-N-(1-hydroxy-4-methylpentan-2-yl)picolinamide.

In some embodiments, the compound of Formula V can be of Formula Va:

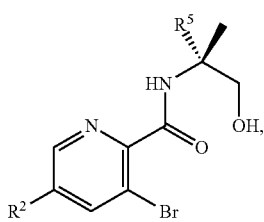

(Va)

or a salt thereof, wherein $R^2$ and $R^5$ are defined and described herein.

In some embodiments, the compound of Formula V can be of Formula Va-1:

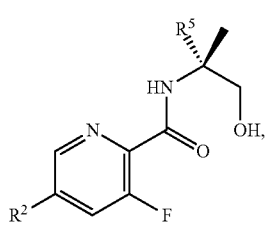

(Va-1)

or a salt thereof, wherein $R^2$ and $R^5$ are defined and described herein.

In some embodiments, the compound of Formula V can be of Formula Vb:

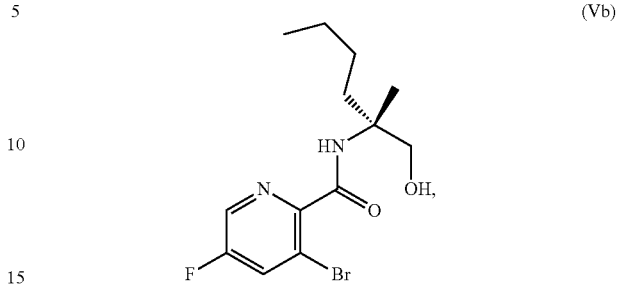

(Vb)

or a salt thereof.

In some embodiments, the compound of Formula V can be of Formula Vb-1:

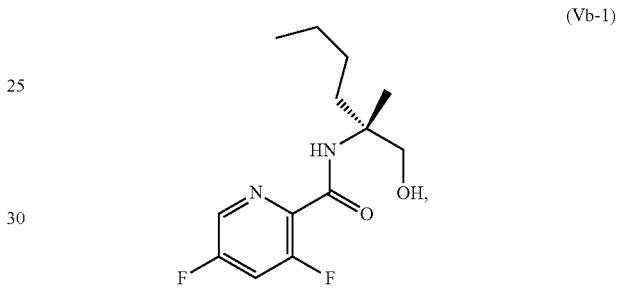

(Vb-1)

or a salt thereof.

In another embodiment, the present disclosure provides a compound of Formula XII:

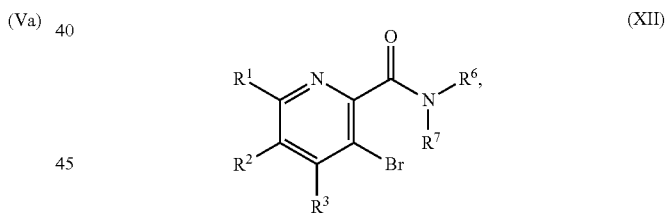

(XII)

or a salt thereof, wherein
$R^1$, $R^2$, and $R^3$ are each independently hydrogen, F, Cl, CN, $CF_3$, $C_{1-3}$ alkyl, or $C_{1-3}$ alkoxy; and
$R^6$ and $R^7$ are each independently hydrogen, $C_{1-4}$ alkyl, or $C_{3-6}$ cycloalkyl, or
$R^6$ and $R^7$ are combined to form a 3-6 membered N-linked heterocycloalkyl, optionally having an additional 1-2 heteroatoms selected from O and S,
provided that at least one of $R^1$, $R^2$, and $R^3$ can be F, Cl, CN, $CF_3$, $C_{1-3}$ alkyl, or $C_{1-3}$ alkoxy.

In some embodiments, $R^2$ can be Cl, F, CN, $CF_3$, $C_{1-3}$ alkyl, or $C_{1-3}$ alkoxy; and $R^1$ and $R^3$ can each independently be hydrogen, F, Cl, CN, $CF_3$, $C_{1-3}$ alkyl, or $C_{1-3}$ alkoxy. The $C_{1-3}$ alkyl can be methyl, ethyl, n-propyl, or isopropyl. The $C_{1-3}$ alkoxy can be methoxy, ethoxy, n-propoxy, or isopropoxy. In some embodiments, $R^2$ can be Cl, F, CN, $CF_3$, methyl, ethyl, n-propyl, isopropyl, methoxy, ethoxy, n-propoxy, or isopropoxy; and $R^1$ and $R^3$ can each independently be hydrogen, F, Cl, CN, $CF_3$, methyl, ethyl, n-propyl, isopropyl, methoxy, ethoxy, n-propoxy, or isopropoxy. In some embodiments, $R^2$ can be Cl, F, CN, $CF_3$, methyl, ethyl, n-propyl, isopropyl, methoxy, ethoxy, n-propoxy, or isopropoxy; and $R^1$ and $R^3$ can each be hydrogen. In some embodiments, $R^1$ and $R^3$ can each be hydrogen and $R^2$ can be F.

In some embodiments, $R^6$ can be hydrogen or $C_{1-4}$ alkyl. The $C_{1-4}$ alkyl can be methyl, ethyl, n-propyl, isopropyl, n-butyl, sec-butyl, or tert-butyl. In some embodiments, $R^6$ can be hydrogen or ethyl. In some embodiments, $R^6$ can be hydrogen. In some embodiments, $R^6$ can be ethyl.

In some embodiments, $R^7$ can be $C_{1-4}$ alkyl or $C_{3-6}$ cycloalkyl. The $C_{1-4}$ alkyl can be methyl, ethyl, n-propyl, isopropyl, n-butyl, sec-butyl, or tert-butyl. The $C_{3-6}$ cycloalkyl can be cyclopropyl, cyclobutyl, cyclopentyl, or cyclohexyl. In some embodiments, $R^7$ can be ethyl, n-propyl, isopropyl, n-butyl, sec-butyl, tert-butyl, or cyclohexyl. In some embodiments, $R^7$ can be ethyl, isopropyl, tert-butyl, or cyclohexyl. In some embodiments, $R^7$ can be tert-butyl.

In some embodiments, $R^6$ can be hydrogen; and $R^7$ can be $C_{1-4}$ alkyl, or $C_{3-6}$ cycloalkyl. In some embodiments, $R^6$ can be hydrogen; and $R^7$ can be ethyl, n-propyl, isopropyl, n-butyl, sec-butyl, tert-butyl, or cyclohexyl. In some embodiments, $R^6$ can be hydrogen; and $R^7$ can be ethyl, isopropyl, tert-butyl, or cyclohexyl. In some embodiments, $R^6$ can be hydrogen and $R^7$ can be tert-butyl. In some embodiments, $R^6$ can be ethyl; and $R^7$ can be $C_{1-4}$ alkyl. In some embodiments, $R^6$ and $R^7$ can each be ethyl.

In some embodiments, $R^6$ and $R^7$ can be combined to form N-linked morpholinyl.

In some embodiments, $R^1$ and $R^3$ can each be hydrogen; $R^2$ can be F; $R^6$ can be hydrogen; and $R^7$ can be tert-butyl.

In some embodiments, the compound of Formula XII can be of Formula XIIa:

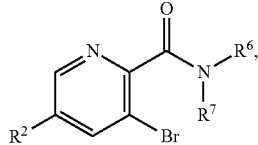

(XIIa)

or a salt thereof, wherein $R^2$, $R^6$, and $R^7$ are defined and described herein.

In some embodiments, the compound of Formula XII can be of Formula XIIb:

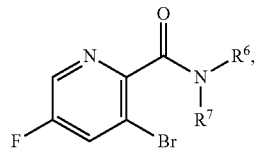

(XIIb)

or a salt thereof, wherein $R^6$ and $R^7$ are defined and described herein.

In some embodiments, the compound of Formula XII can be of Formula XIIc:

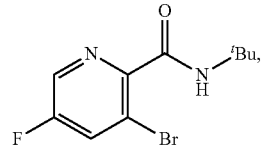

(XIIc)

or a salt thereof.

In some embodiments, the compound of Formula XII is not 3-bromo-N-(tert-butyl)picolinamide or 3,5-dibromo-N-(tert-butyl)picolinamide.

In some embodiments, the compound of Formula XVIII can be of the Formula:

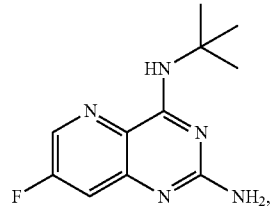

or a salt thereof.

In some embodiments, the compound of Formula XVIII can be of the Formula:

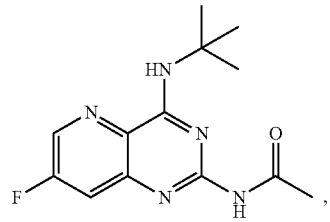 [SMILES: CC(=O)Nc1nc(NC(C)(C)C)c2ncc(F)cc2n1]

or a salt thereof.

V. EXAMPLES

Example 1: Preparation of (R)-3-bromo-5-fluoro-N-(1-hydroxy-2-methylhexan-2-yl)picolinamide (Compound of Formula Vb)

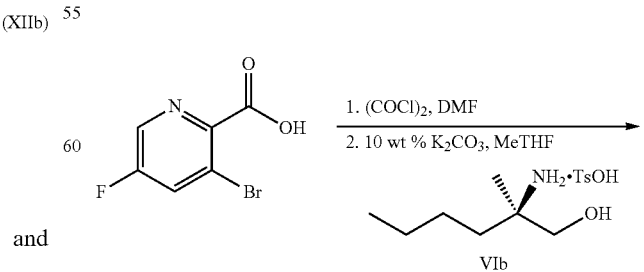

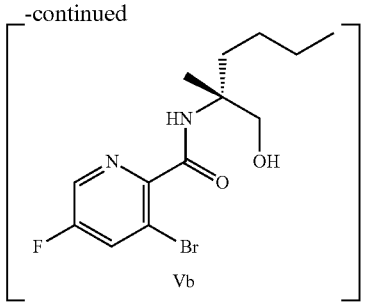

Oxalyl chloride (1.1 equiv) was charged over about 15 minutes to a reaction vessel containing 3-bromo-5-fluoropicolinic acid (scaling factor, 1.00 equiv) and N,N-dimethylformamide (0.1 equiv) in 2-methyltetrahydrofuran (10 volumes). The mixture was aged at about 20° C. The acid chloride mixture was transferred to a second reactor containing (R)-2-amino-2-methylhexan-1-ol 4-methylbenzenesulfonate salt (1.0 equiv) and potassium carbonate (3.0 equiv) in water (10 volumes) over approximately 30 minutes. The reaction mixture was aged at about 20° C. Agitation was stopped and the phases were allowed to separate. The aqueous layer was discharged, and the organics were washed with water (5 volumes). The final organic layer was azeotropically dried, and the volume was adjusted to about 10 volumes by the addition of 2-methyltetrahydrofuran. The compound of Formula Vb was then isolated. $^1$H NMR (400 MHz, DMSO-d$_6$): δ 8.61 (d, J 2.5 Hz, 1H), 8.27 (dd, J 8.5, 2.5 Hz, 1H), 7.86 (br s, 1H), 4.82 (t, J 5.6 Hz, 1H), 3.53 (dd, J 10.7, 5.7 Hz, 1H), 3.46 (dd, J 10.7, 5.6 Hz, 1H), 1.77 (m, 1H), 1.67 (m, 1H), 1.32-1.22 (m, 4H), 1.27 (s, 3H), 0.88 (m, 3H).

Example 2: Preparation of (R)-2-(3-bromo-5-fluoropyridin-2-yl)-4-butyl-4-methyl-4,5-dihydrooxazole (Compound of Formula Ib)

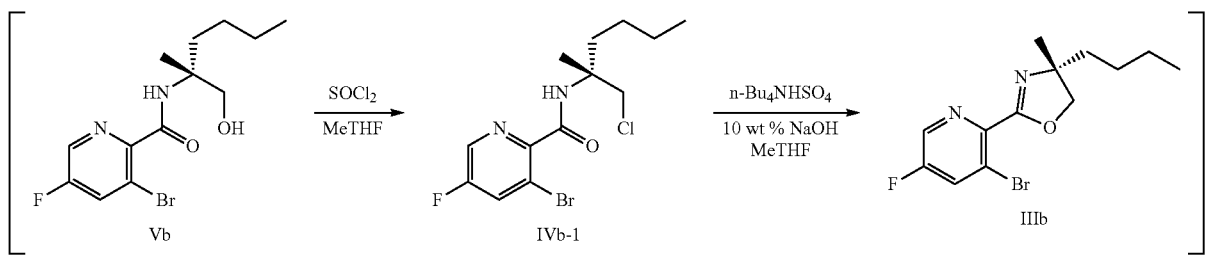

Thionyl chloride (1.2 equiv) was charged over approximately 15 min to a reaction vessel containing the solution of the compound of Formula Vb (1.0 equiv, prepared from Example 1) in 2-methyltetrahydrofuran (10 volumes). The mixture was aged at about 50° C. The contents were adjusted to about 10° C., and the reaction mixture was washed with 10 wt % aqueous sodium hydroxide and water. To the organic solution of the compound of formula IVb-1 was charged n-Bu$_4$HSO$_4$ (0.1 equiv.), followed by a 10 wt % sodium hydroxide solution in water (3.5 volumes). The contents were adjusted to about 35° C., and aged at this temperature. The contents were adjusted to about 20° C., and agitation was stopped and the layers were allowed to separate. The aqueous layer was discharged, and the organic layer was washed with water. Following azeotropic drying, the compound of Formula IIIb was isolated. $^1$H NMR (500 MHz, CDCl$_3$): δ 8.50 (d, J 2.0 Hz, 1H), 7.76 (dd, J 7.5, 2.5 Hz, 1H), 4.27 (d, J=8.0 Hz, 1H), 4.12 (d, J=8.5 Hz, 1H), 1.69-1.43 (m, 3H), 1.42 (s, 3H), 1.36-1.34 (m, 3H), 0.92 (t, J=7.0 Hz, 3H).

Example 3: Preparation of (R)-2-((2-((2,4-dimethoxybenzyl)amino)-7-fluoropyrido[3,2-d]pyrimidin-4-yl)amino)-2-methylhexan-1-ol (Compound of Formula IIb)

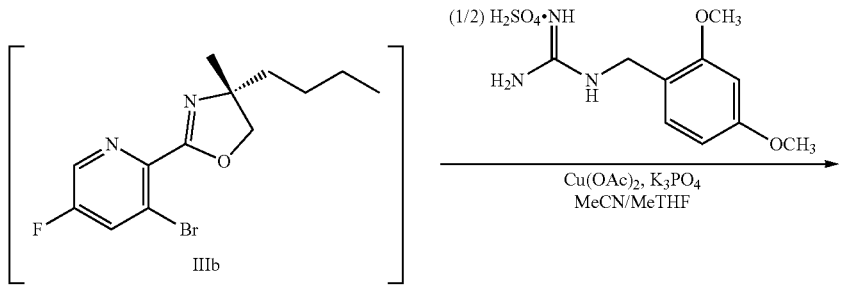

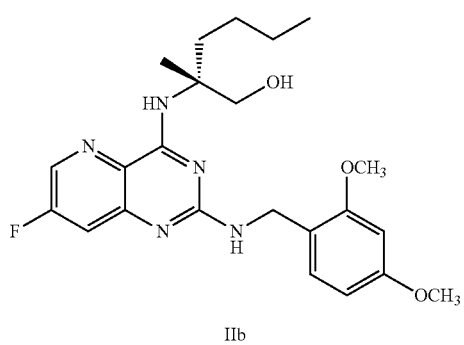

A reaction vessel was charged with DMB-NHC(=NH)NH$_2$·½ H$_2$SO$_4$ (1.2 equiv), copper(II) acetate (0.15 equiv), potassium phosphate tribasic (4 equiv), and acetonitrile (6.6 volumes) and was agitated at about 20° C. A solution of the compound of Formula IIIb (1.0 equiv, scaling factor) in 2-methyltetrahydrofuran (3.3 volumes) was charged to the reactor. The reaction mixture was heated to reflux for approximately 4 hours. The contents were cooled to about 20° C., charged with 2-methyltetrahydrofuran (5 volumes) and an aqueous solution of 5 wt % ethylenediaminetetraacetic acid disodium salt dihydrate (10 volumes), and the mixture was agitated for approximately 30 minutes. The phases were allowed to separate and the aqueous phase was partitioned. The organics were further washed with aqueous 5 wt % ethylenediaminetetraacetic acid disodium salt dihydrate, 10 wt % potassium carbonate, and water. The solvent was exchanged to acetonitrile and the contents were heated to reflux. The mixture was cooled to about 45° C. over approximately 3 hours, then cooled to about 0° C. over approximately 5 hours and held at about 0° C. for approximately 7 hours. The resulting slurry was filtered, and the cake was washed with acetonitrile (2.5 volumes) and dried to provide the compound of Formula IIb. $^1$H NMR (400 MHz, CDCl$_3$): δ 8.12 (d, J=2.5 Hz, 1H), 7.32-7.29 (m, 2H), 7.10 (br s, 1H), 6.47 (d, J 2.53 Hz, 1H), 6.43 (dd, J 8.2, 2.4 Hz, 1H), 4.55 (s, 2H), 3.85 (s, 3H), 3.80 (s, 3H), 3.79-3.72 (m, 2H), 2.01-1.91 (m, 1H), 1.75 (dt, J 13.3, 6.8 Hz, 1H), 1.47-1.29 (m, 7H), 0.92 (t, J=7.0 Hz, 3H).

Example 4: Preparation of (R)-2-((2-amino-7-fluoropyrido[3,2-d]pyrimidin-4-yl)amino)-2-methylhexan-1-ol (Compound of Formula Ib)

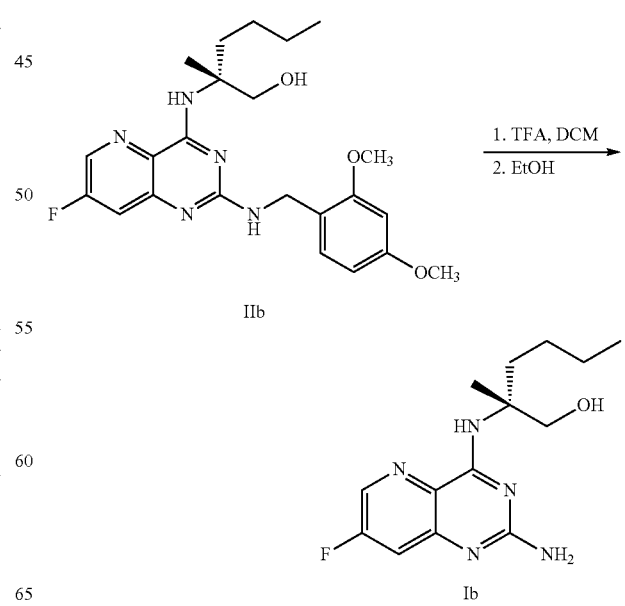

A reaction vessel was charged with the compound of Formula IIb (1.0 equiv, scaling factor) and dichloromethane (2 volumes) and the contents were agitated. Trifluoroacetic acid (7.8 equiv) was charged to the vessel at a rate to maintain the internal temperature at about 30° C. The reaction mixture was heated to about 30° C. and aged for approximately 8 hours. The contents were cooled to 20° C. Ethanol (3.2 volumes) was charged and the contents were aged for approximately 14 hours. The slurry was filtered and the residue was washed with ethanol. The filtrate was charged to a reaction vessel and concentrated to approximately 3 volumes. The contents were cooled to about 20° C. and ethanol (1.3 volumes) and water (1.0 volume) were charged to the reaction vessel. The pH was adjusted to about 12 with the addition of a solution of aqueous 50 wt % sodium hydroxide. The contents were cooled to about 20° C. and water (3 volumes) was charged over about 30 minutes. The contents are further cooled to about 0° C. over approximately 2 hours and aged at this temperature for about 2 hours. The slurry was filtered and the wet-cake was washed with a mixture of ethanol and water and dried to provide the compound of Formula Ib. $^1$H NMR (500 MHz, Methanol-$d_4$) δ 8.23 (d, J 2.5 Hz, 1H), 7.25 (dd, J=10.0, 2.5 Hz, 1H), 3.92 (d, J=11.5 Hz, 1H), 3.74 (d, J=11.5 Hz, 1H), 2.08-1.81 (m, 2H), 1.46 (s, 3H), 1.35-1.29 (m, 4H), 0.91 (t, J 7.0 Hz, 3H).

Example 5: Preparation of (R)-2-((2-chloro-7-fluoropyrido[3,2-d]pyrimidin-4-yl)amino)-2-methylhexan-1-ol (Compound of Formula IXb)

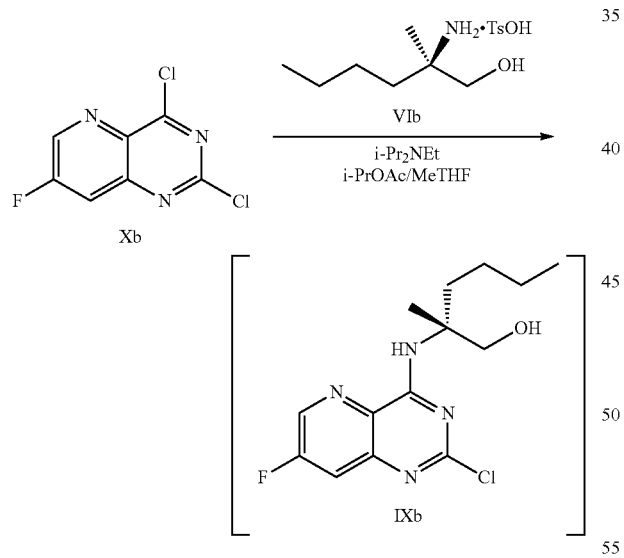

A reaction vessel was charged with the compound of Formula Xb (scaling factor, 1.0 equiv), the compound of Formula VIb (1.0 equiv), 2-methyltetrahydrofuran (3 volumes), isopropyl acetate (7 volumes), and N,N-diisopropylethylamine (2.2 equiv). The reaction mixture was agitated and heated to about 80° C. for approximately 6 hours. The reaction mixture was cooled to about 40° C., then washed with 10 wt % aqueous potassium carbonate (12 volumes) and water (10 volumes). The compound of Formula IXb was isolated. $^1$H NMR (400 MHz, DMSO-$d_6$) δ 8.82 (d, J=2.6 Hz, 1H), 7.97 (dd, J=9.6 Hz, 2.6 Hz, 1H), 7.79 (s, 1H), 5.06 (br s, 1H), 3.72 (d, J=10.9 Hz, 1H), 3.50 (d, J=10.9 Hz, 1H), 1.97-1.84 (m, 2H), 1.42 (s, 3H), 1.31-1.16 (m, 4H), 0.89-0.78 (m, 3H).

Example 6: Preparation of (R)-2-((2-((2,4-dimethoxybenzyl)amino)-7-fluoropyrido[3,2-d]pyrimidin-4-yl)amino)-2-methylhexan-1-ol (Compound of Formula IIb)

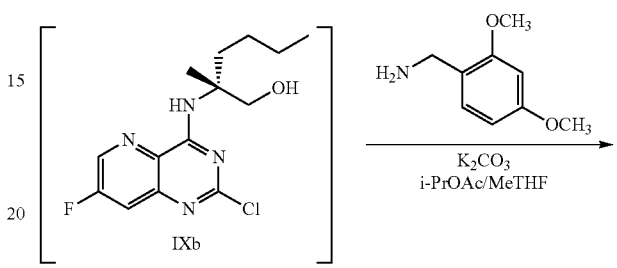

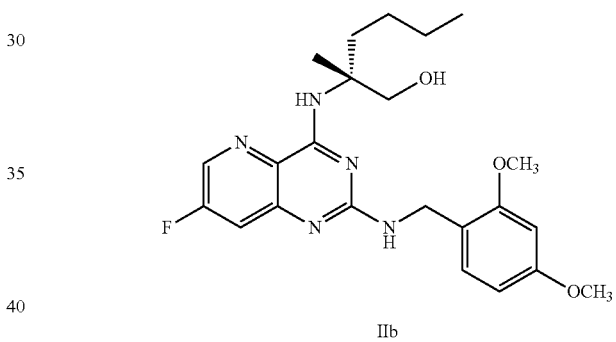

A reaction vessel was charged with the compound of Formula IXb (1.0 equiv, prepared from Example 5) as a solution in 2-methyltetrahydrofuran and isopropyl acetate. Potassium carbonate (1.4 equiv) and 2,4-dimethoxybenzylamine (2.0 equiv) were charged to the reaction vessel. The reaction mixture was heated to about 70° C. for approximately 16 hours. The reaction mixture was cooled to about 35° C. and washed with water (10 volumes), 5 wt % aqueous acetic acid (10 volumes), 10 wt % aqueous potassium carbonate (10 volumes), and water (10 volumes). The organic layer was concentrated to about 7 volumes, crude compound of Formula IIb (0.5 wt %) was charged, and the mixture was agitated for approximately 1 hour. n-Heptane (17 volumes) was charged over approximately 2 hours, then the slurry was cooled to about 20° C. over approximately 1 hour and agitated for approximately 1 hour. The slurry was filtered, and the cake was washed with a mixture of n-heptane (2.1 volumes) and isopropyl acetate (0.85 volumes), and dried to provide the compound of Formula IIb. $^1$H NMR (500 MHz, DMSO-$d_6$) δ 8.08 (s, 1H), 7.30-7.26 (m, 2H), 7.05 (s, 1H), 6.44 (s, 1H), 6.41 (d, J=8.0 Hz, 1H), 4.54 (s, 2H), 3.82 (s, 3H), 3.78 (s, 3H), 3.76 (m, 2H), 1.95-1.72 (m, 2H), 1.41-1.27 (m, 7H), 0.90 (t, J=7.0 Hz, 3H).

Example 7: Preparation of (R)-2-((2-amino-7-fluoropyrido[3,2-d]pyrimidin-4-yl)amino)-2-methylhexan-1-ol (Compound of Formula Ib)

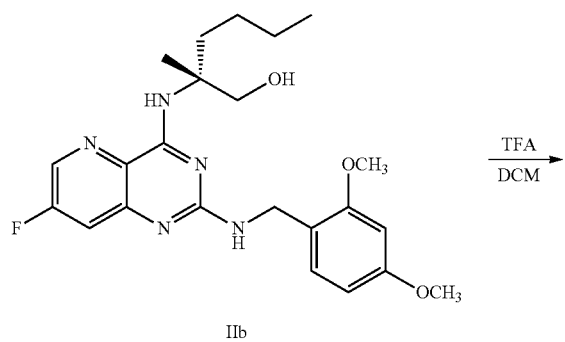

A reaction vessel was charged with the compound of Formula IIb (1.0 equiv, scaling factor) and dichloromethane (13 volumes) and the contents were agitated. Trifluoroacetic acid (9.7 equiv) was charged to the vessel at a rate to maintain the internal temperature at about 40° C. The reaction mixture was heated to about 40° C. and aged for approximately 3 hours. The contents were cooled to 25° C. Ethanol (4.0 volumes) was charged and the contents were aged for approximately 24 hours. The slurry was filtered and the cake was washed with dichloromethane. The filtrate was charged to a reaction vessel and water (6.8 volumes), ethyl acetate (13.5 volumes) and 30 wt % aqueous sodium hydroxide (3.2 volumes) were charged and the contents were heated to about 40° C. with agitation. The aqueous layer was partitioned and the organic layer was washed with 4.5 wt % aqueous sodium bicarbonate (5.0 volumes) and water (5.0 volumes). Following azeotropic drying from ethyl acetate, the contents were heated to about 80° C. and aged for approximately 30 minutes. The contents were cooled to about 20° C. over approximately 1 hour. The slurry was filtered and the wet-cake was washed with ethyl acetate (5 volumes) to provide the compound of Formula Ib. $^1$H NMR (500 MHz, Methanol-$d_4$) δ 8.23 (d, J 2.5 Hz, 1H), 7.25 (dd, J=10.0, 2.5 Hz, 1H), 3.92 (d, J=11.5 Hz, 1H), 3.74 (d, J=11.5 Hz, 1H), 2.08-1.81 (m, 2H), 1.46 (s, 3H), 1.35-1.29 (m, 4H), 0.91 (t, J 7.0 Hz, 3H).

Example 8: Preparation of (R)-2-Amino-2-methylhexan-1-ol p-Toluenesulfonic Acid Salt (Compound of Formula VIb) According to FIG. 3A

Step-1: Preparation of Isopropyl (E)-2-(benzylideneamino)propanoate

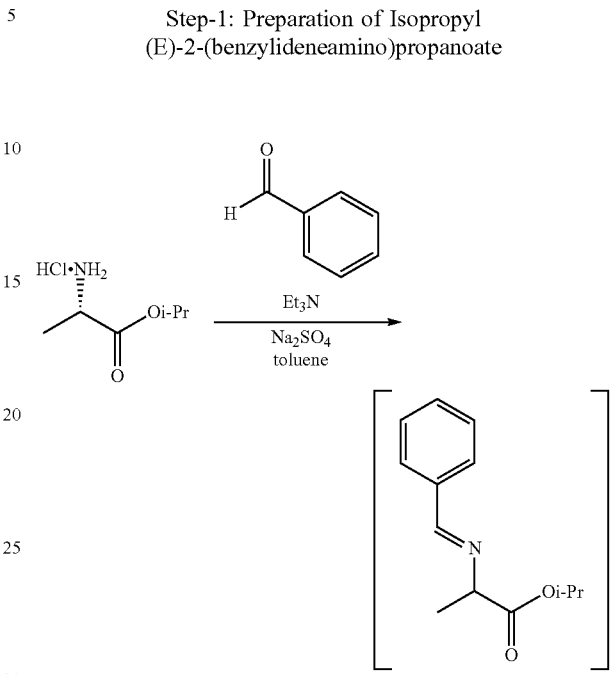

A reaction vessel was charged with the HCl salt of isopropyl L-alaninate (1.0 equiv, scaling factor) and toluene (5 volumes) and the contents were agitated at about 20° C. Triethylamine (1.5 equiv), sodium sulfate (0.6 equiv) and benzaldehyde (1.01 equiv) were charged to the reaction vessel. The slurry was agitated at about 20° C. for approximately 20 hours. The slurry was filtered and the cake was washed with toluene (2 volumes). Isopropyl (E)-2-(benzylideneamino)propanoate was then isolated. $^1$H NMR (400 MHz, DMSO-$d_6$) δ 8.38 (s, 1H), 7.81-7.73 (m, 2H), 7.53-7.39 (m, 3H), 4.93 (hept, J=6.2 Hz, 1H), 4.14 (q, J=6.7 Hz, 1H), 1.38 (d, J=6.7 Hz, 3H), 1.17 (dd, J=12.3, 6.2 Hz, 6H).

Step 2: Preparation of Isopropyl 2-amino-2-methylhexanoate

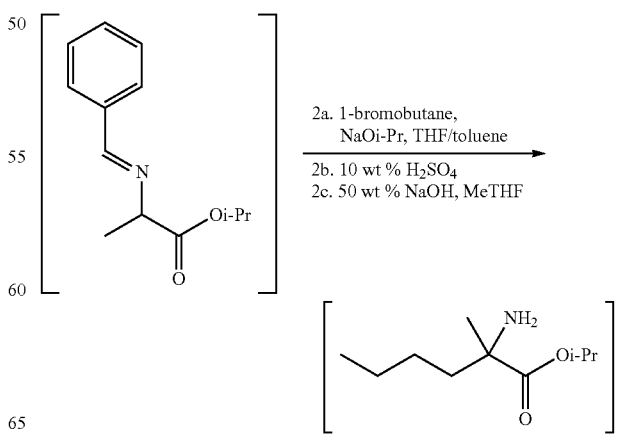

A reaction vessel was charged with isopropyl (E)-2-(benzylideneamino)propanoate (1.0 equiv, prepared from Example 8) in toluene (7 volumes). 1-Bromobutane (1.2 equiv) was charged to the reaction vessel, and the contents were heated to about 40° C. Sodium isopropoxide (1.2 equiv, 20% wt/wt in tetrahydrofuran) was charged to the reaction vessel, and the reaction mixture was agitated for approximately 4 hours. The reaction mixture was cooled to about 15° C. and 10 wt % aqueous sulfuric acid (1.2 equiv) was charged to the reaction vessel. The mixture was agitated at about 20° C. for approximately 1 hour. The phases were allowed to separate, and the aqueous layer was partitioned. The organic layer was washed with water (2 volumes). The combined aqueous layers were charged to a separate reaction vessel and extracted with 2-methyltetrahydrofuran (5 volumes) and aqueous 50 wt % sodium hydroxide (2.5 equiv). Isopropyl 2-amino-2-methylhexanoate was isolated. $^1$H NMR (400 MHz, DMSO-$d_6$) δ 4.86 (hept, J=6.3 Hz, 1H), 1.68 (br s, 2H), 1.59-1.48 (m, 1H), 1.47-1.35 (m, 1H), 1.24-1.19 (m, 4H), 1.16 (d, J=6.3 Hz, 6H), 1.14 (s, 3H), 0.83 (t, J=7.1 Hz, 3H).

Step-3: Preparation of Isopropyl 2-amino-2-methylhexanoate Phosphate Salt

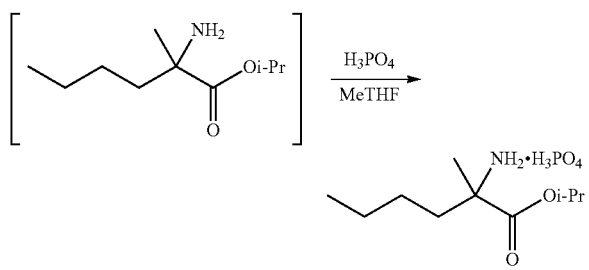

To a reaction vessel containing isopropyl 2-amino-2-methylhexanoate (1.0 equiv, scaling factor) in 2-methyltetrahydrofuran (8 volumes) was charged a mixture of aqueous 85 wt % phosphoric acid (1.05 equiv) and 2-methyltetrahydrofuran (2 volumes). The resulting slurry was agitated at about 20° C. for approximately 15 hours. The slurry was filtered and then the cake was washed with 2-methyltetrahydrofuran and dried. $^1$H NMR (400 MHz, DMSO-$d_6$) δ 7.02 (br s, 5H), 4.88 (hept, J=6.2 Hz, 1H), 1.65-1.57 (m, 2H), 1.28 (s, 3H), 1.34-1.08 (m, 3H), 1.16 (d, J=6.3 Hz, 6H), 1.08-0.95 (m, 1H), 0.80 (t, J=7.2 Hz, 3H).

Step-4: Preparation of Isopropyl (R)-2-amino-2-methylhexanoate

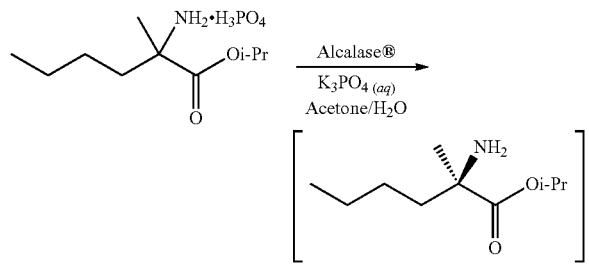

A reaction vessel was charged with the phosphate salt of isopropyl 2-amino-2-methylhexanoate (1.0 equiv, scaling factor), a solution of potassium phosphate tribasic (1.37 equiv) in water (24 volumes), and acetone (6 volumes). The mixture was agitated and heated to about 30° C. Alcalase© (2 volumes) was charged to the reaction vessel and the mixture was agitated at about 30° C. for approximately 20 hours. The reaction mixture was cooled to about 20° C., charged with methyl tert-butyl ether (20 volumes) and aqueous 45 wt % potassium hydroxide (2.0 equiv), and agitated for approximately 30 minutes. The phases were allowed to separate, and the aqueous layer was partitioned. Isopropyl (R)-2-amino-2-methylhexanoate was isolated. $^1$H NMR (400 MHz, DMSO-$d_6$) δ 4.86 (hept, J=6.3 Hz, 1H), 1.68 (br s, 2H), 1.59-1.48 (m, 1H), 1.47-1.35 (m, 1H), 1.24-1.19 (m, 4H), 1.16 (d, J=6.3 Hz, 6H), 1.14 (s, 3H), 0.83 (t, J=7.1 Hz, 3H).

Step-5: Preparation of Isopropyl (R)-2-((tert-butoxycarbonyl)amino)-2-methylhexanoate

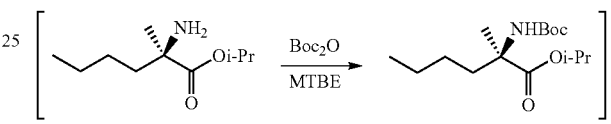

A reaction vessel was charged with isopropyl (R)-2-amino-2-methylhexanoate (1.0 equiv, scaling factor) as a solution in methyl tert-butyl ether (10 volumes). Di-tert-butyl dicarbonate (1.2 equiv) was charged to the reaction vessel and the mixture was agitated at about 20° C. for approximately 24 hours. Isopropyl (R)-2-((tert-butoxycarbonyl)amino)-2-methylhexanoate was isolated. $^1$H NMR (400 MHz, DMSO-$d_6$) δ 7.00 (br s, 1H), 4.86 (hept, J=6.3 Hz, 1H), 1.69 (ddd, J=16.1, 11.7, 4.9 Hz, 1H), 1.57 (ddd, J=13.3, 10.8, 5.3 Hz, 1H), 1.36 (s, 9H), 1.26 (s, 3H), 1.30-1.06 (m, 4H), 1.14 (d, J=6.3 Hz, 6H), 0.84 (t, J=7.1 Hz, 3H).

Step-6: Preparation of tert-Butyl (R)-(1-hydroxy-2-methylhexan-2-yl)carbamate

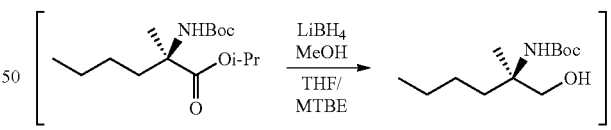

A reaction vessel was charged with a solution of isopropyl (R)-2-((tert-butoxycarbonyl)amino)-2-methylhexanoate (1.0 equiv, scaling factor) in methyl tert-butyl ether (10 volumes). Lithium borohydride solution (2.2 equiv, 5% wt/wt in tetrahydrofuran) was slowly charged to the vessel, and the reaction mixture was agitated at about 20° C. Methanol (2.2 equiv) as a solution in methyl tert-butyl ether (1.5 volumes) was charged to the reaction vessel. The reaction mixture was agitated for approximately 1 hour at about 20° C. A separate vessel was charged with citric acid monohydrate (2.5 equiv) and water (10 volumes). The contents of the reaction vessel were transferred to the vessel containing citric acid in water, and then the mixture was agitated for approximately 15 minutes. The phases were allowed to separate, and the aqueous layer was partitioned. The organic layer was washed with water and tert-butyl (R)-(1-hydroxy-2-methylhexan-2-yl)carbamate was isolated. ¹H NMR (400 MHz, DMSO-d₆) δ 6.02 (br s, 1H), 4.62 (t, J=5.8 Hz, 1H), 3.35 (dd, J=10.6, 5.8 Hz, 1H), 3.27 (dd, J=10.6, 5.8 Hz, 1H), 1.60 (dt, J=15.2, 8.1 Hz, 1H), 1.54-1.39 (m, 1H), 1.36 (s, 9H), 1.30-1.11 (m, 4H), 1.08 (s, 3H), 0.85 (t, J=7.1 Hz, 3H).

Step-7: Preparation of (R)-2-Amino-2-methylhexan-1-ol P-Toluenesulfonic Acid Salt (Compound of Formula VIb)

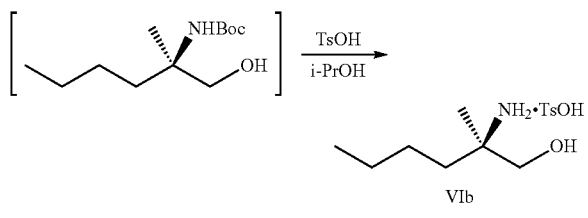

VIb

A reaction vessel was charged with a solution of tert-butyl (R)-(1-hydroxy-2-methylhexan-2-yl)carbamate (1.0 equiv, scaling factor) in methyl tert-butyl ether, and the solvent was exchanged for isopropanol to give a solution at about 6 volumes. The temperature was adjusted to about 50° C. and a solution of p-toluenesulfonic acid (2 equiv) in isopropanol (4 volumes) was charged to the reaction vessel. The contents were agitated for approximately 15 hours at about 50° C. The solvent was exchanged for methyl tert-butyl ether to give a mixture at about 15 volumes at about 40° C. Crude (R)-2-amino-2-methylhexan-1-ol p-toluenesulfonic acid salt (about 0.01 wt %) was charged to the reaction vessel. Methyl tert-butyl ether (5 volumes) was charged to the reaction vessel, and the resulting slurry was agitated for approximately 2 hours at about 40° C. The slurry was cooled to about 5° C. and agitated for approximately 12 hours. The slurry was filtered, and then the cake was washed with a solution of isopropanol in methyl tert-butyl ether (1% wt/wt isopropanol in methyl tert-butyl ether), and dried to provide a compound of Formula VIb. ¹H NMR (400 MHz, DMSO-d₆) δ 7.66 (br s, 3H), 7.49 (d, J=8.1 Hz, 2H), 7.12 (d, J=7.4 Hz, 2H), 5.43 (t, J=4.9 Hz, 1H), 3.38 (dd, J=11.2, 4.6 Hz, 1H), 3.33 (dd, J=11.2, 4.8 Hz, 1H), 2.29 (s, 3H), 1.57-1.40 (m, 2H), 1.28-1.19 (m, 4H), 1.10 (s, 3H), 0.87 (t, J=6.8 Hz, 3H).

Example 9: Preparation of Isopropyl (R)-2-((tert-butoxycarbonyl)amino)-2-methylhexanoate According to the Scheme of FIG. 3B (Alternative Method)

Step-8: Preparation of Isopropyl (R)-2-amino-2-methylhexanoate N—Ac-Leu Salt

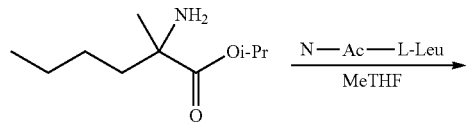

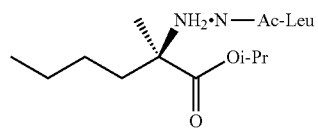

A reaction vessel was charged with N-acetyl-L-leucine (0.8 equiv) and 2-methyltetrahydrofuran (10 volumes), and the reaction mixture was agitated at about 50° C. The reaction vessel was charged with isopropyl 2-amino-2-methylhexanoate (1.0 equiv, scaling factor) as a solution in 2-methyltetrahydrofuran (10 volumes), and the total volume of the reaction mixture was adjusted to about 25 volumes with additional 2-methyltetrahyduran. The reaction mixture was agitated at about 50° C. for approximately 5 hours, and the resulting slurry was cooled to about 20° C. over approximately 3 hours and agitated at about 20° C. for approximately 12 hours. The slurry was filtered, and then the cake was washed with a mixture of methyl tert-butyl ether and 2-methyltetrahydrofuran, and dried. ¹H NMR (400 MHz, DMSO-d₆) δ 7.95 (d, J=8.1 Hz, 1H), 4.89 (hept, J=6.2 Hz, 1H), 4.16 (td, J=8.2, 6.2 Hz, 1H), 1.82 (s, 3H), 1.67-1.40 (m, 5H), 1.31-1.21 (m, 3H), 1.21 (s, 3H), 1.19 (d, J=6.3 Hz, 6H), 1.15-0.99 (m, 1H), 0.93-0.80 (m, 9H).

Step-9: Preparation of Isopropyl (R)-2-((tert-butoxycarbonyl)amino)-2-methylhexanoate

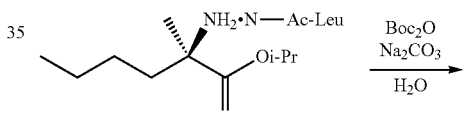

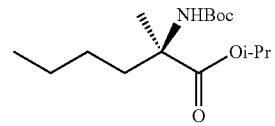

A reaction vessel was charged with the N—Ac-Leu salt of isopropyl (R)-2-amino-2-methylhexanoate (1.0 equiv, scaling factor), sodium carbonate (1.1 equiv) as a solution in water (5 volumes), and di-tert-butyl dicarbonate (1.05 equiv). The reaction mixture was agitated at about 20° C. for approximately 15 hours. Methyl tert-butyl ether (10 volumes) was charged, and the mixture was agitated for approximately 15 minutes. The phases were allowed to separate, and the aqueous layer was partitioned. Isopropyl (R)-2-((tert-butoxycarbonyl)amino)-2-methylhexanoate was isolated as a solution in methyl tert-butyl ether.

Example 10: Preparation of (R)-2-Amino-2-methylhexan-1-ol p-Toluenesulfonic Acid Salt (Compound of Formula VIb) According to the Scheme in FIG. 4

Step-10: Preparation of (R)-3-Methyl-5-phenyl-5,6-dihydro-2H-1,4-oxazin-2-one

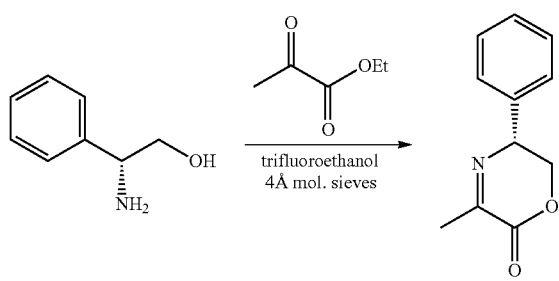

A reaction vessel was charged with (R)-2-amino-2-phenylethan-1-ol (scaling factor, 1.0 equiv), molecular sieves (1.5 wt/wt) and 2,2,2-trifluoroethanol (10 volumes), followed by ethyl pyruvate (1.05 equiv). The mixture was agitated and heated to about 80° C. for approximately 9 hours. The contents were cooled to about 25° C. and filtered through diatomaceous earth. The cake was washed with isopropyl acetate (3 volumes). The filtrate is concentrated to about 9 volumes and the solvent is exchanged for isopropanol, targeting approximately 9 volumes. The contents were heated to about 40° C., then isopropanol (3 volumes) and n-heptane (2 volumes) were charged. The contents were then cooled to about 0° C. over approximately 1.5 hours and aged at this temperature for approximately 16 hours. The residue was collected, washed with n-heptane (1 volume) and dried to provide (R)-3-methyl-5-phenyl-5,6-dihydro-2H-1,4-oxazin-2-one. $^1$H NMR (400 MHz, CDCl$_3$): δ 7.43-7.33 (m, 5H), 4.88-4.83 (m, 1H), 4.57 (dd, J=11.6, 4.5 Hz, 1H), 4.31 (t, J=11.6 Hz, 1H), 2.41 (s, 3H).

Step-11: Preparation of (3R,5R)-3-Butyl-3-methyl-5-phenylmorpholin-2-one

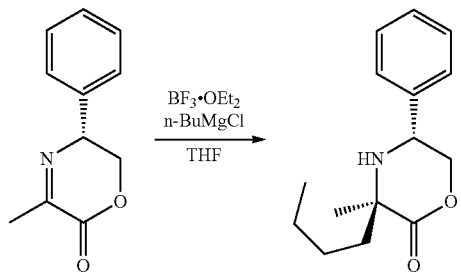 [SMILES: CC1=N[C@H](c2ccccc2)COC1=O ; "BF3·OEt2n-BuMgCl" ; CCCC[C@@]1(C)N[C@H](c2ccccc2)COC1=O ; "THF"]

A reaction vessel was charged with (R)-3-methyl-5-phenyl-5,6-dihydro-2H-1,4-oxazin-2-one (scaling factor, 1.0 equiv) and tetrahydrofuran (5 volumes), and the contents were cooled to about −78° C. Boron trifluoride diethyl etherate (2.3 equiv) was charged over approximately 2 hours, and the contents were agitated under these conditions for approximately 1 hour. n-Butylmagnesium chloride (2.3 equiv) was charged to the reaction mixture over approximately 4 hours. The reaction mixture was aged for approximately 1 hour, then warmed to about −55° C. and aged for approximately 1 hour. Water (10 volumes) was charged to the reaction vessel, and the mixture was warmed to about 10° C. The reaction vessel was charged with 10 wt % aqueous sodium carbonate (10 volumes) and methyl tert-butyl ether (10 volumes). The mixture was agitated, and then the aqueous layer was partitioned. The organic layer was washed with water (5 volumes) and 20 wt % aqueous sodium chloride (5 volumes). The solvent was exchanged for n-heptane targeting approximately 7 volumes. The contents were then aged for approximately 5 hours at about 10° C. The mixture was cooled to about 0° C. over approximately 2 hours, and the slurry was aged at this temperature for approximately 2 hours. The slurry was filtered; and then the cake was washed with n-heptane (2 volumes) and dried to provide (3R,5R)-3-butyl-3-methyl-5-phenylmorpholin-2-one. $^1$H NMR (400 MHz, DMSO-d$_6$): δ 7.46-7.28 (m, 5H), 4.42 (dd, J=9.9, 3.4 Hz, 1H), 4.36-4.30 (m, 1H), 4.26-4.20 (m, 1H), 2.88 (d, J=7.2 Hz, 1H), 1.91-1.83 (m, 1H), 1.65-1.59 (m, 1H), 1.32-1.27 (m, 7H), 1.32 (t, J=6.9 Hz, 3H).

Step-12: Preparation of (R)-2-(((R)-2-hydroxy-1-phenylethyl)amino)-2-methylhexan-1-ol

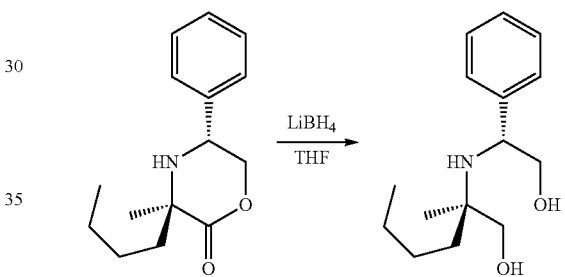

A reaction vessel was charged with (3R,5R)-3-butyl-3-methyl-5-phenylmorpholin-2-one (scaling factor, 1.0 equiv) and tetrahydrofuran (16 volumes), and the contents were cooled to about 0° C. A solution of lithium borohydride in tetrahydrofuran (2.2 equiv, 2.0 M in tetrahydrofuran) was charged over approximately 3 hours, and the reaction mixture was aged for approximately 30 minutes. The reaction mixture was then warmed to about 25° C. and aged for approximately 9 hours. The mixture was cooled to about 0° C. and 15 wt % aqueous sodium hydroxide (6 volumes) was charged over approximately 4 hours. The mixture was warmed to 25° C. and aged at this temperature for approximately 2 hours. Methyl tert-butyl ether (6.6 volumes) was charged to the reaction vessel, the mixture was agitated, and the aqueous layer was partitioned. The organic layer was washed with water (6.6 volumes) and 20 wt % aqueous sodium chloride (6.6 volumes). The solvent was exchanged for n-heptane targeting approximately 3 volumes. The slurry was aged at about 15° C. for approximately 1 hour. The slurry was filtered and the cake was washed with n-heptane (1 volume) and dried to provide (R)-2-(((R)-2-hydroxy-1-phenylethyl)amino)-2-methylhexan-1-ol. $^1$H NMR (400 MHz, DMSO-d$_6$): δ 7.37-7.35 (m, 2H), 7.25 (t, J=7.4 Hz, 2H), 7.18-7.14 (m, 1H), 5.05-5.03 (m, 1H), 4.36-4.33 (m, 1H), 3.77 (dd, J=9.2, 4.4 Hz, 1H), 3.34-3.33 (m, 1H), 3.22-3.15 (m, 2H), 2.99 (dd, J=10.6, 6.3 Hz, 1H), 1.96 (s, 1H), 1.18-1.12 (m, 3H) 1.08-1.02 (m, 2H), 0.93-0.90 (m, 1H), 0.73-0.70 (m, 6H).

Step-13: Preparation of (R)-2-Amino-2-methyl-hexan-1-ol P-Toluenesulfonic Acid Salt (Compound of Formula VIb)

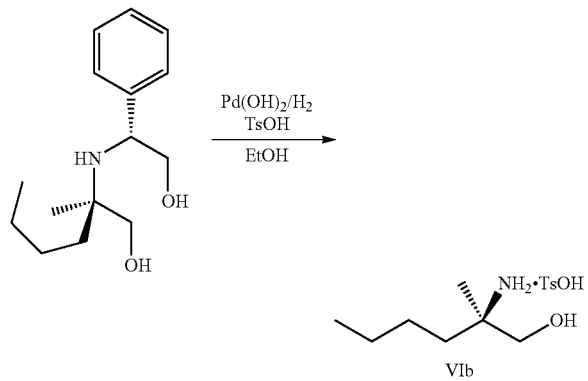

A reaction vessel was charged with (R)-2-(((R)-2-hydroxy-1-phenylethyl)amino)-2-methylhexan-1-ol (scaling factor, 1.0 equiv), ethanol (10 volumes) and p-toluenesulfonic acid (1.50 equiv), and the mixture was agitated. Palladium hydroxide (20% w/w on carbon, 0.7% w/w relative to (R)-2-(((R)-2-hydroxy-1-phenylethyl)amino)-2-methylhexan-1-ol was charged. The reaction vessel was purged with nitrogen and charged with hydrogen. The reaction mixture was heated to about 75° C. and aged for approximately 48 hours. The reaction mixture was filtered, and the filter cake was washed with ethanol. The filtrate was concentrated to about 1 volume. Methyl tert-butyl ether (15 volumes) was charged and the contents were heated to about 60° C. for approximately 2 hours, then cooled to about 0° C. over approximately 3 hours. The slurry was filtered and the cake was washed with methyl tert-butyl ether (6 volumes) and dried to provide the compound of Formula VIb. $^1$H NMR (400 MHz, DMSO-$d_6$) δ 7.66 (br s, 3H), 7.49 (d, J=8.1 Hz, 2H), 7.12 (d, J=7.4 Hz, 2H), 5.43 (t, J=4.9 Hz, 1H), 3.38 (dd, J=11.2, 4.6 Hz, 1H), 3.33 (dd, J=11.2, 4.8 Hz, 1H), 2.29 (s, 3H), 1.57-1.40 (m, 2H), 1.28-1.19 (m, 4H), 1.10 (s, 3H), 0.87 (t, J=6.8 Hz, 3H).

Example 11: Preparation of 3-Bromo-5-fluoropicolinic acid (Compound of Formula VIIb) According to the Schemes in FIG. 5A and FIG. 5B

Step-14: Preparation of 3-Bromo-5-fluoro-2-iodopyridine

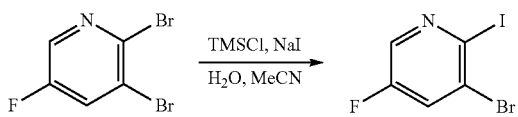

Sodium iodide (4.4 equiv) and acetonitrile (15 volumes) were charged to a reaction vessel and the contents were agitated. The mixture was azeotropically dried using acetonitrile. The contents were cooled to about 20° C., and 2,3-dibromo-5-fluoropyridine (1.0 equiv, scaling factor), water (0.3 equiv) and trimethylsilyl chloride (1.5 equiv) were charged to the reaction vessel. The contents were agitated at ambient temperature. The reaction vessel was charged with an aqueous solution of 5 wt % sodium hydroxide (5 volumes) and methyl tert-butyl ether (10 volumes), the mixture was agitated, and the aqueous layer was partitioned. The organic solution was washed with 15% aqueous sodium sulfite, 5 wt % sodium chloride, and water. The organic stream was concentrated to approximately 3 volumes. The contents were heated to about 60° C. and water (5 volumes) was charged over approximately 30 minutes. The mixture was aged at about 60° C. for approximately 1 hour and cooled to about 20° C. over approximately 1 hour. The resulting slurry was filtered, washed with a mixture of water and acetonitrile and the cake was dried to provide 3-bromo-5-fluoro-2-iodopyridine. $^1$H NMR (400 MHz, CDCl$_3$) δ 8.23 (d, J=2.8 Hz, 1H), 7.59 (dd, J=7.6, 2.8 Hz, 1H).

Step-15: Preparation of 3-Bromo-5-fluoropicolinonitrile

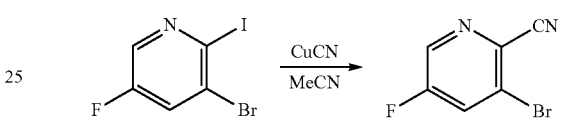

Copper(I) cyanide (1.2 equiv), 3-bromo-5-fluoro-2-iodopyridine (1.0 equiv, scaling factor) and acetonitrile (10 volumes) were charged to a reaction vessel. The contents were agitated and heated to reflux for approximately 12 hours. The contents were cooled to ambient temperature and an aqueous solution of sodium thiosulfate (10 volumes) was charged. The contents were aged for approximately 2 hours and then filtered through diatomaceous earth and rinsed with methyl tert-butyl ether. The combined filtrates were charged to a reaction vessel and the aqueous layer was partitioned and extracted with methyl tert-butyl ether (5 volumes). The organic layer was washed with 5 wt % aqueous sodium chloride. The solvent was exchanged for isopropanol and concentrated to approximately 3 volumes. The contents were heated to about 60° C. and water (7 volumes) is charged over approximately 1 hour. The mixture was aged at about 60° C. for approximately 30 minutes and cooled to about 20° C. over approximately 1 hour. The resulting slurry was filtered, and the cake was washed with a mixture of isopropanol and water and dried to provide 3-bromo-5-fluoropicolinonitrile. $^1$H NMR (400 MHz, CDCl$_3$) δ 8.50 (d, J=2.5 Hz, 1H), 7.78 (dd, J=7.2, 2.5 Hz, 1H).

Step-16: Preparation of 3-Bromo-5-fluoropicolinic acid (Compound of Formula VIIb)

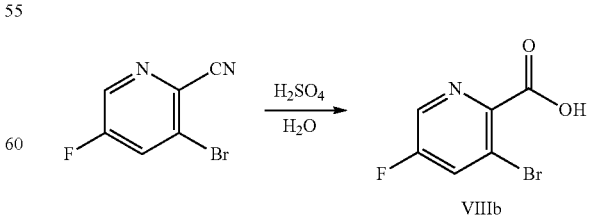

3-Bromo-5-fluoropicolinonitrile (1.0 equiv, scaling factor) and concentrated sulfuric acid (16.2 equiv, approximately 4 volumes) were charged to a reaction vessel. The contents were heated to about 50° C. for approximately 2 hours. Water (12.2 equiv, approximately 1 volume) was charged to the reaction vessel and the contents were heated to about 90° C. and aged under these conditions for approximately 12 hours. The contents were cooled to ambient temperature. To a separate reaction vessel was charged water (20 volumes), and the reaction mixture was transferred to this vessel over approximately 30 minutes. The resulting mixture was charged with a solution of 45 wt % aqueous potassium hydroxide (17 equiv) over approximately 30 minutes at about 40° C. Methyl tert-butyl ether (10 volumes) was charged to the reaction vessel, and the contents were heated to about 40° C. The aqueous layer was extracted with methyl tert-butyl ether. The organic layer was washed with water and distilled to 3 volumes. Additional methyl tert-butyl ether was charged and distilled as necessary to azeotropically dry the reaction stream. The contents were heated to about 50° C. and n-heptane (12 volumes) was charged over approximately 1 hour. The contents were aged under these conditions for approximately 1 hour and cooled to about −20° C. over approximately 3 hours and held at under these conditions for approximately 18 hours. The resulting slurry was filtered, and the cake was washed with n-heptane and dried to provide 3-bromo-5-fluoropicolinic acid. $^1$H NMR (500 MHz, CDCl$_3$) δ 10.34 (br, s, 1H), 8.55 (d, J=2.5 Hz, 1H), 7.93 (dd, J=7.5, 2.5 Hz, 1H).

Step-17: Preparation of
3-Bromo-5-fluoro-2-iodopyridine (Alternative Method)

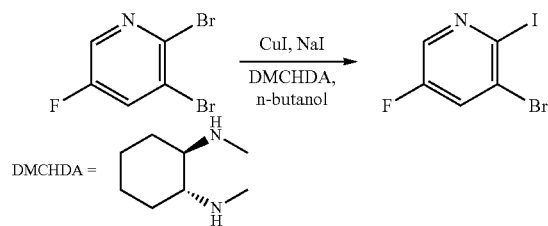

2,3-Dibromo-5-fluoropyridine (1.0 equiv, scaling factor), sodium iodide (2.0 equiv), copper(I) iodide (0.05 equiv), trans-N,N'-dimethylcycloheane-1,2-diamine (0.01 equiv) and 1-butanol (15 volumes) were charged to a reaction vessel and the contents were agitated. The contents were agitated at about 115° C. for approximately 20 hours. The contents were cooled to ambient temperature and the organics were washed with an aqueous solution of 15% aqueous sodium sulfite, 5 wt % sodium chloride, and water. The organic layer was filtered through diatomaceous earth and rinsed with acetonitrile. The combined filtrates were charged to a reaction vessel and the solvent was exchanged for acetonitrile with a target volume of approximately 3 volumes. The contents were heated to about 60° C. and water (5 volumes) was charged over approximately 30 minutes. The mixture was aged at about 60° C. for approximately 1 hour and cooled to about 20° C. over approximately 1 hour. The resulting slurry was filtered, washed with a mixture of water and acetonitrile and the cake was dried to provide 3-bromo-5-fluoro-2-iodopyridine.

Example 12: Preparation of
3-Bromo-5-fluoropicolinic Acid (Compound of Formula VIIIb) According to the Scheme in FIG. 6

Step-18: Preparation of
N-(tert-Butyl)-5-fluoropicolinamide

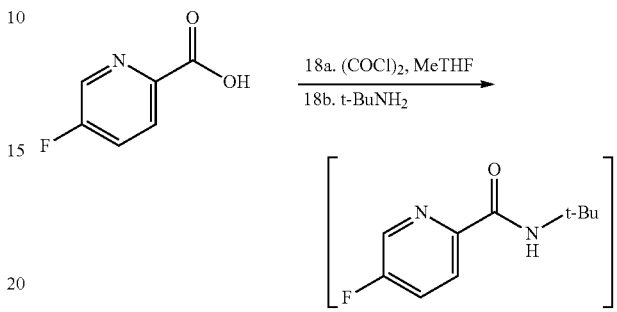

Oxalyl chloride (1.1 equiv) was charged over approximately 15 minutes to a reaction vessel containing 5-fluoropicolinic acid (1.0 equiv, scaling factor) and N,N-dimethylformamide (0.1 equiv) in 2-methyltetrahydrofuran (15 volumes) at about 10° C. The mixture was aged at about 20° C. The temperature was adjusted to about 10° C. and tert-butylamine (3.5 equiv) was then charged over approximately 30 minutes. The mixture was aged at about 20° C. for 2 hours. An aqueous solution of HCl (1 M, 7 volumes) was charged and the mixture was agitated for approximately 15 minutes. The aqueous layer was removed, and the organics were washed with 1N hydrochloric acid, phosphate buffer solution (1 M, pH=7), and water. The organics were exchanged into methylcyclohexane or 1,4-dioxane. The solution was filtered to afford N-(tert-butyl)-5-fluoropicolinamide. $^1$H NMR (400 MHz, CDCl$_3$): δ 8.34 (d, J 2.8 Hz, 1H), 8.20 (ddd, J 8.7, 4.7, 0.6 Hz, 1H), 7.81 (br s, 1H), 7.50 (ddd, J 8.7, 8.1, 2.8 Hz, 1H), 1.48 (s, 9H).

Step-19: Preparation of
3-Bromo-N-(tert-butyl)-5-fluoropicolinamide

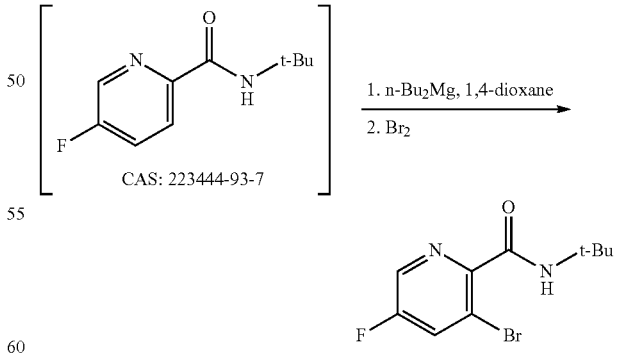

A solution of N-(tert-butyl)-5-fluoropicolinamide (1.0 equiv, scaling factor) in 1,4-dioxane (15 volumes) was charged to a reaction vessel. Di-n-butylmagnesium (1M in heptane, 1.3 equiv) was charged over approximately 30 minutes. The contents were warmed to about 60° C. and aged at this temperature for about 30 minutes. The contents were cooled to ambient temperature. A separate reaction vessel was charged with methylcyclohexane (10 volumes) and the contents were cooled to about −20° C. To this solution was charged bromine (2.8 equiv). Then the solution of metalated N-(tert-butyl)-5-fluoropicolinamide was charged to the bromine solution in methylcyclohexane over approximately 1 hour and aged for approximately 1 hour at about 20° C. The reaction mixture was cooled to about 5° C. and an aqueous solution of 20% aqueous sodium sulfite (5 volumes) was charged and the contents were aged for approximately 30 minutes. The reaction mixture was warmed to about 20° C. Methyl tert-butyl ether (5 volumes) and 1N sodium bisulfate (10 volumes) were charged to the reaction vessel, and the contents were agitated. The aqueous layer was partitioned, and the organics were washed with water. 3-Bromo-N-(tert-butyl)-5-fluoropicolinamide was then isolated. $^1$H NMR (400 MHz, CDCl$_3$): δ 8.34 (d, J 2.5 Hz, 1H), 8.34 (dd, J 7.7, 2.5 Hz, 1H), 7.52 (br s, 1H), 1.47 (s, 9H).

The above step-19 reaction can also be performed in methylcyclohexane (19 volumes).

Step-20: Preparation of 3-Bromo-5-fluoropicolinic acid (Compound of Formula VIIb)

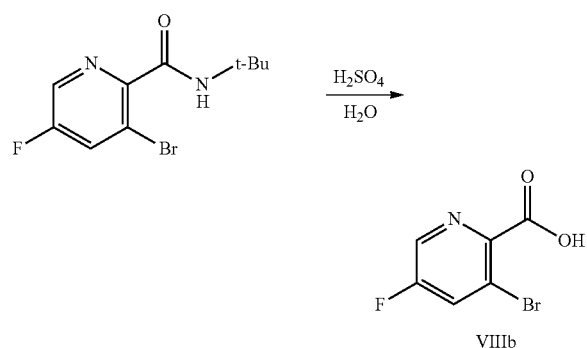

VIIIb

3-Bromo-N-(tert-butyl)-5-fluoropicolinamide (1.0 equiv, scaling factor), sulfuric acid (4 volumes) and water (2 volumes) were charged to a reaction vessel. The contents were heated to about 90° C. The contents were cooled to about 20° C. and transferred to a second vessel containing water (20 volumes). The resulting mixture was charged with a solution of 45 wt % aqueous potassium hydroxide (17 equiv) over approximately 30 minutes at about 40° C. Methyl tert-butyl ether (10 volumes) was charged to the reaction vessel, and the contents were heated to about 40° C. The aqueous layer was extracted with methyl tert-butyl ether. The organic layer was washed with water and distilled to 3 volumes. Additional methyl tert-butyl ether was charged and distilled as necessary to azeotropically dry the reaction stream. The contents were heated to about 50° C. and n-heptane (12 volumes) was charged over approximately 1 hour. The contents were aged under these conditions for approximately 1 hour and cooled to about −20° C. over approximately 3 hours and held at under these conditions for approximately 18 hours. The resulting slurry was filtered, and the cake was washed with n-heptane and dried to provide 3-bromo-5-fluoropicolinic acid.

Example 13: Preparation of 2,4-Dichloro-7-fluoro-pyrido[3,2-d]pyrimidine (Compound of Formula Xb) According to the Scheme of FIG. 7A Step-21: 3-Amino-5-fluoropicolinonitrile

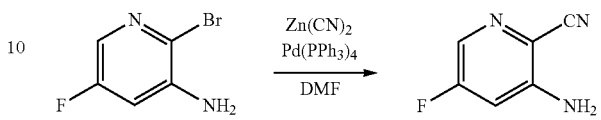

A reaction vessel was charged with 2-bromo-5-fluoropyridin-3-amine (scaling factor, 1.0 equiv), tetrakis(triphenylphosphine)palladium(0) (0.015 equiv), N,N-dimethylformamide (5 volumes) and zinc cyanide (0.80 equiv). The contents were heated to about 100° C. for approximately 3 hours. The mixture was cooled to about 25° C. and filtered through diatomaceous earth. The cake was rinsed with N,N-dimethylformamide (1.3 volumes) and then the filtrate was charged to a vessel containing a solution of ethylenediaminetetraacetic acid tetrasodium salt (1.5 equiv) and water (10 volumes) over approximately 30 minutes. The mixture was heated to about 40° C. and agitated for approximately 1.5 hours and then cooled to about 20° C. and aged for approximately 2 hours. The slurry was filtered and the cake was washed with water (1.7 volumes). The cake was suspended in THF (10 volumes) and filtered. The filtrate was concentrated to about 1 volume, and toluene (5 volumes) and DCM (1 volume) were charged. The contents were aged for approximately 30 minutes. The contents were filtered, and then the cake was washed with toluene (2 volumes), and dried to provide 3-amino-5-fluoropicolinonitrile. $^1$H NMR (400 MHz, DMSO-d$_6$): δ 7.85 (d, J=2.5 Hz, 1H), 7.01 (dd, J=11.0, 2.5 Hz, 1H), 6.59 (br s, 2H).

Step-22: 7-Fluoropyrido[3,2-d]pyrimidine-2,4-diol

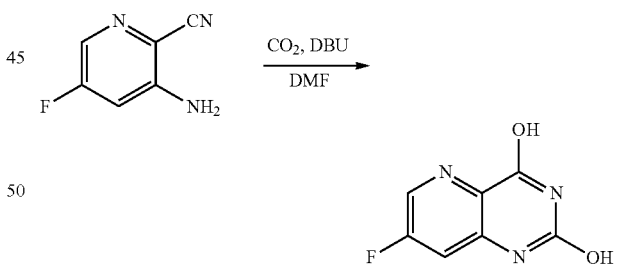

A reaction vessel was charged with 3-amino-5-fluoropicolinonitrile (scaling factor, 1.0 equiv), N,N-dimethylformamide (10 volumes) and 1,8-diazabicyclo[5.4.0]undec-7-ene (2.2 equiv). The reaction vessel was purged with a carbon dioxide atmosphere and the contents were heated to about 50° C. for approximately 24 hours. The mixture was cooled to about 40° C. and then charged to a vessel containing 2 N hydrochloride acid (10 volumes) over approximately 1 hour. The mixture was cooled to about 20° C. and aged for approximately 1 hour. The mixture was filtered and the cake was washed with water (5 volumes), isopropanol (5 volumes) and toluene (5 volumes) successively. The cake was dried to give 7-fluoropyrido[3,2-d]pyrimidine-2,4-diol.

¹H NMR (400 MHz, DMSO-d$_6$): δ 11.54 (s, 1H), 11.32 (s, 1H), 8.45 (d, J=2.5 Hz, 1H), 7.34 (dd, J=9.3, 2.5 Hz, 1H).

Step-23: 2,4-Dichloro-7-fluoropyrido[3,2-d]pyrimidine (Compound of Formula Xb)

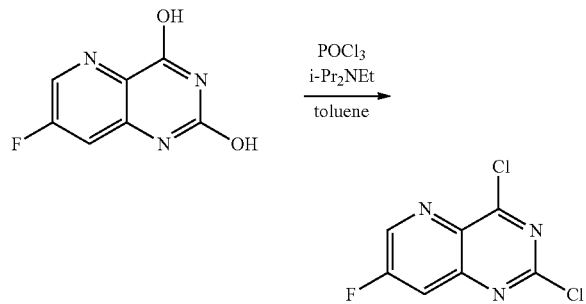

A reaction vessel was charged with 7-fluoropyrido[3,2-d]pyrimidine-2,4-diol (scaling factor, 1.0 equiv), toluene (10 volumes), and N,N-diisopropylethylamine (2.2 equiv). Phosphorus oxychloride (2.5 equiv) was charged to the reaction mixture while maintaining the contents below about 35° C. The reaction mixture was heated to about 110° C. over approximately 2 hours and then held at this temperature for approximately 18 hours. The reaction mixture was cooled to about 20° C. and charged with dichloromethane (3 volumes). The mixture was charged to a vessel containing a 20 wt % solution of aqueous potassium phosphate dibasic (10 volumes) while maintaining the contents below about 35° C. The pH of the contents were maintained between 4 to 7 by co-dosing a solution of 45 wt % potassium hydroxide. The mixture was agitated at about 20° C. for approximately 30 minutes, and then the aqueous phase was partitioned. The organic layer was filtered through diatomaceous earth and the filter cake was rinsed with toluene (2 volumes). The aqueous layer was partitioned, the organic layer was filtered through silica gel, and the cake washed with toluene (10 volumes). The organic layer was concentrated and the solvent was exchanged for n-heptane targeting a final volume of about 5 volumes. n-Heptane (4 volumes) and isopropyl acetate (0.74 volumes) were charged and the contents were heated to about 85° C. and then cooled to about 70° C. The crude compound of Formula Xb (0.02 wt %) was charged and then the mixture was aged for approximately 45 minutes. The mixture was cooled to about 20° C. over approximately 5 hours and aged for approximately 18 hours. The mixture was filtered, washed with n-heptane (5 volumes), and dried to give the compound of Formula Xb. ¹H NMR (400 MHz, CDCl$_3$) δ 9.01 (d, J=2.6 Hz, 1H), 7.94 (dd, J=7.8 Hz, 2.4 Hz, 1H).

Example 14: Preparation of 7-Fluoropyrido[3,2-d]pyrimidine-2,4-diol According to the Scheme of FIG. 7B (Alternative Method)

Step-24: 3-Amino-5-fluoropicolinamide

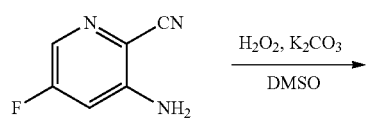

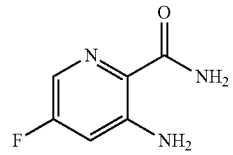

A reaction vessel was charged with 3-amino-5-fluoropicolinonitrile (scaling factor, 1.0 equiv), potassium carbonate (0.2 equiv) and dimethylsulfoxide (4 volumes). The mixture was charged with 30 wt % aqueous hydrogen peroxide (1.2 equiv) while maintaining the internal temperature below about 40° C., and the contents were agitated for approximately 1 hour at about 20° C. Water (4 volumes) was charged while maintaining the internal temperature below about 40° C. The mixture was cooled to about 20° C. and agitated for approximately 1 hour. The slurry was filtered, the cake was washed with water (2 volumes), and dried to give 3-amino-5-fluoropicolinamide. ¹H NMR (400 MHz, DMSO-d$_6$): δ 7.83 (s, 1H), 7.71 (d, J=2.5 Hz, 1H), 7.45-7.28 (m, 1H), 6.95 (dd, J=11.3, 2.5 Hz, 1H).

Step-25: 7-Fluoropyrido[3,2-d]pyrimidine-2,4-diol

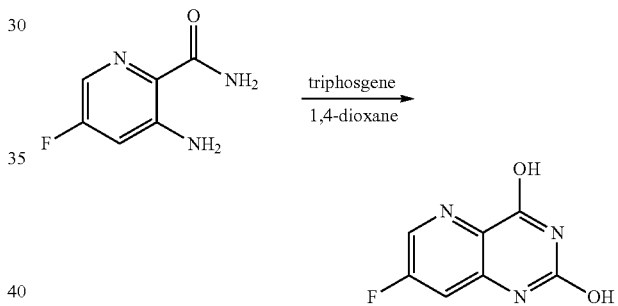

A reaction vessel was charged with 3-amino-5-fluoropicolinamide (scaling factor, 1.0 equiv) and 1,4-dioxane (5 volumes), and the contents were heated to about 100° C. The mixture was charged with a solution of triphosgene (1 equiv) in 1,4-dioxane (5 volumes) over approximately 1 hour. The mixture was aged at about 100° C. for approximately 3 hours. The mixture was cooled to about 20° C. The mixture was charged with water (15 volumes) while maintaining the contents below about 35° C. The mixture was aged at about 20° C. for approximately 1 hour and filtered, and then the cake was washed with water (1 volume) and dried to give 7-fluoropyrido[3,2-d]pyrimidine-2,4-diol. ¹H NMR (400 MHz, DMSO-d$_6$): δ 11.54 (s, 1H), 11.32 (s, 1H), 8.45 (d, J=2.5 Hz, 1H), 7.34 (dd, J=9.3, 2.5 Hz, 1H).

Example 15: 1-(2,4-Dimethoxybenzyl)guanidine Hemisulfate Salt

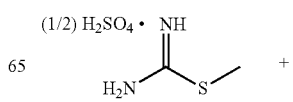

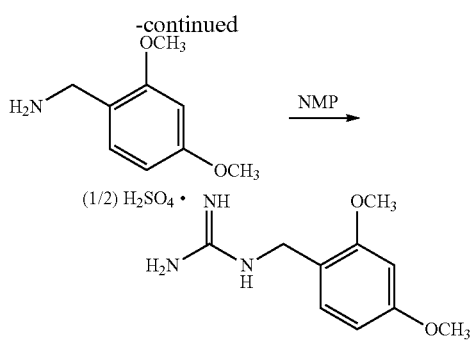

Methyl carbamimidothioate hemisulfate salt (1.0 equiv) and N-methyl-2-pyrrolidone (4.4 volumes) was charged to a reaction vessel. The contents were agitated and (2,4-dimethoxyphenyl)methanamine (1.0 equiv, scaling factor) was charged to the reaction vessel. The reaction mixture was heated to about 90° C. and agitated at this temperature for approximately 16 hours. The mixture was cooled to about 0° C. over approximately 5 hours and aged under these conditions for approximately 2 hours. The slurry was filtered and the cake was washed with water (3 volumes). The wet cake was combined with ethanol (1.5 volumes) and water (1.5 volumes) and this mixture was aged for approximately 2 hours at about 20° C. The slurry was filtered and the cake was washed with a mixture of ethanol and water and dried to provide 1-(2,4-Dimethoxybenzyl)guanidine hemisulfate salt. $^1$H NMR (500 MHz, Acetonitrile-d$_3$) δ 7.61 (t, J=5.0 Hz, 1H), 7.20 (d, J=8.5 Hz, 1H), 6.54 (dd, J=8.5, 2.5 Hz, 1H), 6.62 (d, J=2.5 Hz, 1H), 3.84 (s, 3H), 3.78 (s, 3H), 4.25 (m, 2H).

Example 16: Preparation of (R)-2-(3-bromo-5-fluoropyridin-2-yl)-4-butyl-4-methyl-4,5-dihydrooxazole Step-1: Sodium (R)-2-(3-bromo-5-fluoropicolinamido)-2-methylhexyl sulfate

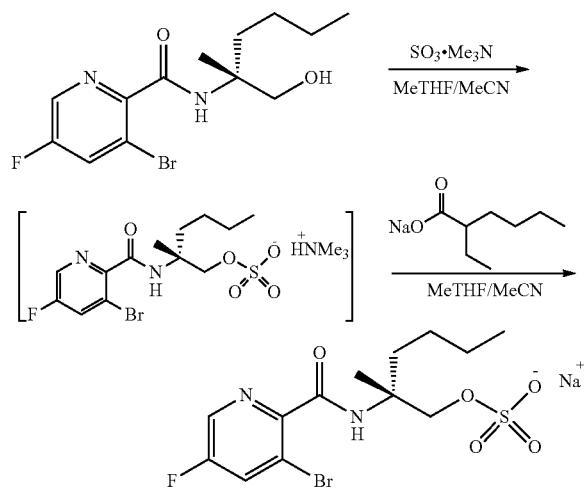

To a reaction vessel containing a solution of (R)-3-bromo-5-fluoro-N-(1-hydroxy-2-methylhexan-2-yl)picolinamide (1.0 equiv, scaling factor) in 2-methyltetrahydrofuran (10 volumes) was charged acetonitrile (5 volumes) and sulfur trioxide trimethylamine complex (2.0 equiv). The contents were heated to about 70° C. The contents were aged at this temperature for about 15 hours. Once the reaction is deemed complete, the reaction contents were cooled to about 20° C. The resulting mixture was filtered, and the filtrate was transferred to another reaction vessel. The solution was seeded with the sodium (R)-2-(3-bromo-5-fluoropicolinamido)-2-methylhexyl sulfate and a solution of sodium ethylhexanoate (1.0 equiv) in a 2:1 mixture of 2-methyltetrahydrofuran/acetonitrile (4 volumes) was charged over about 30 minutes. The mixture was aged for about 2.5 hours after the addition at about 20° C. The contents were filtered, and the resulting solids were washed with a 2:1 mixture of 2-methyltetrahydrofuran/acetonitrile (5 volumes) and dried at about 50° C. to afford sodium (R)-2-(3-bromo-5-fluoropicolinamido)-2-methylhexyl sulfate. $^1$H NMR (400 MHz, DMSO-d$_6$): δ 8.60 (d, J 2.5 Hz, 1H), 8.26 (dd, J 8.5, 2.5 Hz, 1H), 8.05 (br s, 1H), 3.90 (d, J=10.0 Hz, 1H), 3.82 (d, J=10.0 Hz, 1H), 1.83-1.70 (m, 2H), 1.32-1.21 (m, 4H), 1.32 (s, 3H), 0.88 (t, J=7.0 Hz, 3H).

Step-2: (R)-2-(3-bromo-5-fluoropyridin-2-yl)-4-butyl-4-methyl-4,5-dihydrooxazole

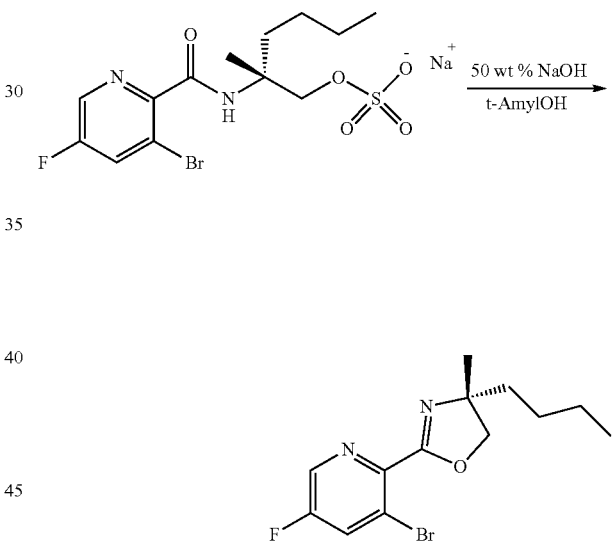

To a reaction vessel was charged sodium (R)-2-(3-bromo-5-fluoropicolinamido)-2-methylhexyl sulfate (1.0 equiv, scaling factor), 2-methyl-2-butanol (15 volumes). The temperature was adjusted to about 20° C. and then 50 wt % aqueous sodium hydroxide (1.5 equiv) was charged to the reaction vessel and the contents were aged for about 18 hours at about 20° C. Once the reaction is deemed complete, the contents were diluted in 2-methyltetrahydrofuran (10 volumes) and then washed with water (10 volumes) followed by 5 wt % aqueous sodium chloride (10 volumes). The contents were concentrated to about 5 volumes and polish filtered to provide (R)-2-(3-bromo-5-fluoropyridin-2-yl)-4-butyl-4-methyl-4,5-dihydrooxazole as a solution in a mixture of 2-methyl-2-butanol/2-methyltetrahydrofuran. $^1$H NMR (500 MHz, CDCl$_3$): δ 8.50 (d, J 2.0 Hz, 1H), 7.76 (dd, J 7.5, 2.5 Hz, 1H), 4.27 (d, J=8.0 Hz, 1H), 4.12 (d, J=8.5 Hz, 1H), 1.69-1.43 (m, 3H), 1.42 (s, 3H), 1.36-1.34 (m, 3H), 0.92 (t, J=7.0 Hz, 3H).

Example 17: Preparation of (R)-2-(3-Bromo-5-fluoropyridin-2-yl)-4-butyl-4-methyl-4,5-dihydrooxazole

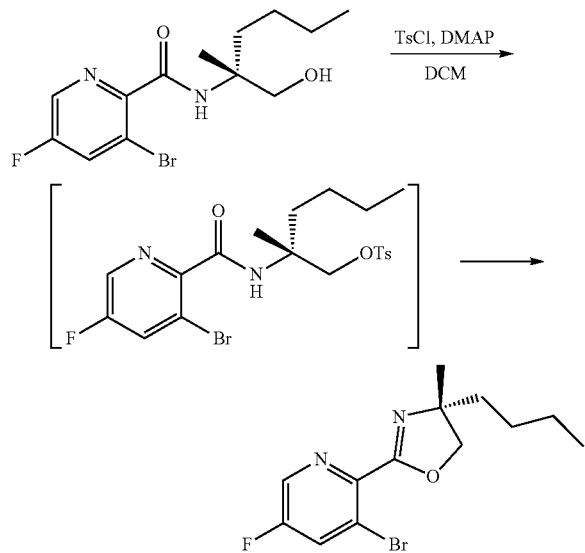

To a reaction vessel was charged (R)-3-bromo-5-fluoro-N-(1-hydroxy-2-methylhexan-2-yl)picolinamide (1.0 equiv, scaling factor), followed by dichloromethane (2.6 volumes) and 4-dimethylaminopyridine (1.2 equiv). The contents were cooled to about 0° C. and then para-toluenesulfonyl chloride (1.05 equiv) was added as a slurry in dichloromethane (3.5 volumes) over about 5 minutes. After the addition, the contents were heated to about 25° C. over about 1 hour. The contents were aged at this temperature for about 5 hours. Then 4-dimethylaminopyridine (1.0 equiv) was charged to the reaction vessel and the contents were aged at about 25° C. for about 17 hours. The contents were washed twice with a 10 wt % aqueous solution of sodium hydroxide (5 volumes). Then the contents were washed twice with a 20 wt % aqueous solution of ammonium chloride (5 volumes) and finally washed with water (5 volumes). The solvent was switched from dichloromethane to 2-methyltetrahydrofuran via distillation. (R)-2-(3-Bromo-5-fluoropyridin-2-yl)-4-butyl-4-methyl-4,5-dihydrooxazole was isolated as a solution in 2-methyltetrahydrofuran. $^1$H NMR (400 MHz, CDCl$_3$): δ 8.50 (d, J 2.0 Hz, 1H), 7.76 (dd, J 7.5, 2.5 Hz, 1H), 4.27 (d, J=8.0 Hz, 1H), 4.12 (d, J=8.5 Hz, 1H), 1.69-1.43 (m, 3H), 1.42 (s, 3H), 1.36-1.34 (m, 3H), 0.92 (t, J=7.0 Hz, 3H).

Example 18: Preparation of (R)-2-(3-Bromo-5-fluoropyridin-2-yl)-4-butyl-4-methyl-4,5-dihydrooxazole

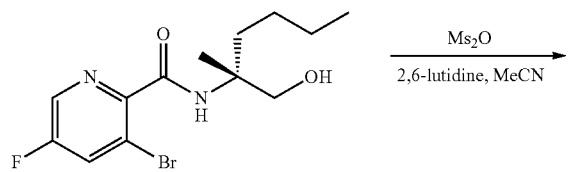

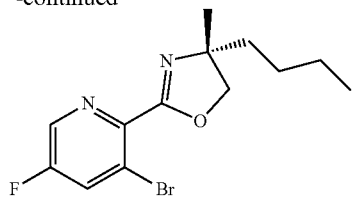

To a reaction vessel containing a solution of (R)-3-bromo-5-fluoro-N-(1-hydroxy-2-methylhexan-2-yl)picolinamide (1.0 equiv, scaling factor) in acetonitrile (10 volumes) was charged 2,6-lutidine (2.6 equiv). The contents were agitated at about 20° C. To a separate vessel was charged methanesulfonic anhydride (1.3 equiv) as a solution in acetonitrile (5 volumes). The solution of mathansulfonic anhydride was charged to the solution of (R)-3-bromo-5-fluoro-N-(1-hydroxy-2-methylhexan-2-yl)picolinamide and 2,6-lutidine over about 30 minutes. After the addition, the contents were aged for about 15 minutes. The contents were heated to about 50° C. and aged for about 4 hours. When the reaction was deemed complete the solvent was exchanged to 2-methyltetrahydrofuran (targeting about 10 volumes). The contents were cooled to about 20° C. and the organic solution was washed twice with 20 wt % aqueous ammonium chloride (10 volumes) followed by water (10 volumes). The contents were concentrated to about 5 volumes and polish filtered to provide (R)-2-(3-bromo-5-fluoropyridin-2-yl)-4-butyl-4-methyl-4,5-dihydrooxazole as a solution in 2-methyltetrahydrofuran. $^1$H NMR (500 MHz, CDCl$_3$): δ 8.50 (d, J 2.0 Hz, 1H), 7.76 (dd, J 7.5, 2.5 Hz, 1H), 4.27 (d, J=8.0 Hz, 1H), 4.12 (d, J=8.5 Hz, 1H), 1.69-1.43 (m, 3H), 1.42 (s, 3H), 1.36-1.34 (m, 3H), 0.92 (t, J=7.0 Hz, 3H).

Example 19: Preparation of (R)-2-((2-((2,4-dimethoxybenzyl)amino)-7-fluoropyrido[3,2-d]pyrimidin-4-yl)amino)-2-methylhexan-1-ol

Step-1 and 2: (R)-3,5-Difluoro-N-(1-hydroxy-2-methylhexan-2-yl)picolinamide

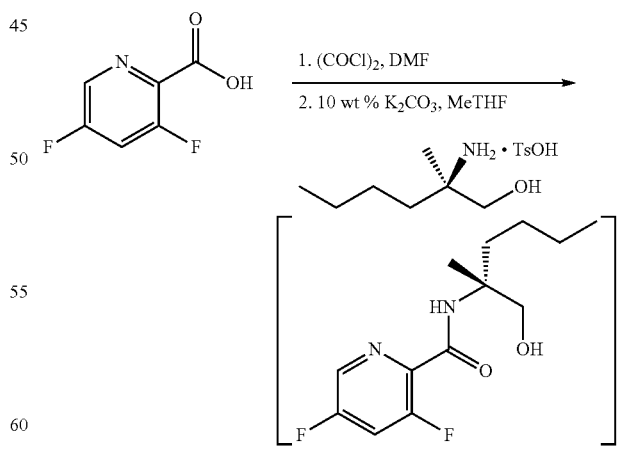

Oxalyl chloride (1.1 equiv) was charged over about 30 minutes to a reaction vessel containing 3,5-difluoropicolinic acid (scaling factor, 1.00 equiv) and N,N-dimethylformamide (0.1 equiv) in 2-methyltetrahydrofuran (10 volumes). The mixture was aged at about 20° C.

Once the reaction was deemed complete, the acid chloride mixture was transferred to a second reactor containing (R)-2-amino-2-methylhexan-1-ol 4-methylbenzenesulfonate salt (1.0 equiv) and potassium carbonate (3.0 equiv) in water (10 volumes) over about 30 minutes. The biphasic reaction mixture was aged at about 20° C. Once the reaction was deemed complete, the layers were separated, and the organic layer was washed with water (5 volumes). The organic layer was solvent exchanged to 2-methyltetrahydrofuran via distillation and the volume was adjusted to about 10 volumes. (R)-3,5-Difluoro-N-(1-hydroxy-2-methylhexan-2-yl)picolinamide was then isolated as a solution in 2-methyltetrahydrofuran. $^1$H NMR (400 MHz, CDCl$_3$): δ 8.31-8.26 (m, 1H), 7.79 (s, 1H), 7.38-7.29 (m, 1H), 3.79 (d, J 11.8 Hz, 1H), 3.73 (d, J 11.8 Hz, 1H), 1.91-1.79 (m, 1H), 1.75-1.63 (m, 1H), 1.47-1.21 (m, 7H), 0.99-0.84 (m, 3H).

Step-3 and 4: (R)-4-Butyl-2-(3,5-difluoropyridin-2-yl)-4-methyl-4,5-dihydrooxazole

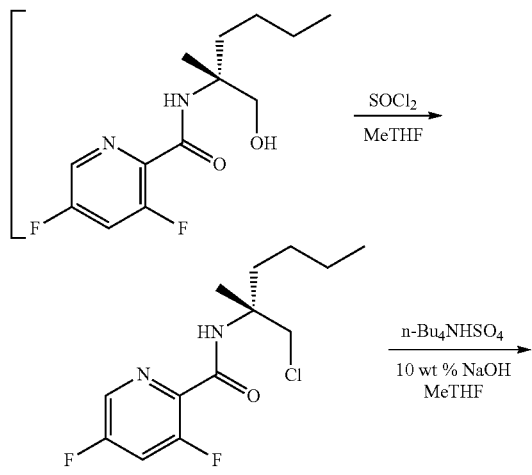

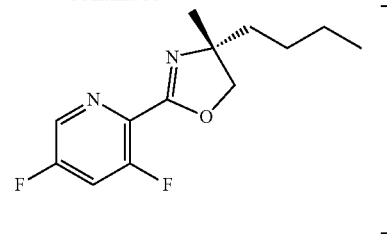

Thionyl chloride (1.2 equiv) was charged over about 1 hour to a reaction vessel containing a solution of (R)-3,5-difluoro-N-(1-hydroxy-2-methylhexan-2-yl)picolinamide (1.0 equiv, scaling factor) in 2-methyltetrahydrofuran (10 volumes). The mixture was aged at about 60° C. until the reaction was deemed complete. The contents were adjusted to about 0° C., and the reaction mixture was washed sequentially with 10 wt % aqueous sodium hydroxide (5 volumes) and water (5 volumes). To the organic solution of (R)—N-(1-chloro-2-methylhexan-2-yl)-3,5-difluoropicolinamide was charged n-Bu$_4$HSO$_4$ (0.1 equiv.), followed by 10 wt % aqueous sodium hydroxide (2.5 volumes). The contents were adjusted to about 20° C. and aged at this temperature until the reaction was deemed complete. Following reaction completion, the layers were separated, and the organic layer was washed with water (5 volumes). (R)-4-Butyl-2-(3,5-difluoropyridin-2-yl)-4-methyl-4,5-dihydrooxazole was isolated as a solution in 2-methyltetrahydrofuran. $^1$H NMR (400 MHz, CDCl$_3$): δ 8.47-8.41 (m, 1H), 7.32 (ddd, J 9.7, 8.0, 2.4 Hz, 1H), 4.26 (d, J 8.3 Hz, 1H), 4.09 (d, J=8.3 Hz, 1H), 1.44-1.20 (m, 7H), 0.94-0.85 (m, 3H).

Step-5: (R)-2-((2-((2,4-Dimethoxybenzyl)amino)-7-fluoropyrido[3,2-d]pyrimidin-4-yl)amino)-2-methylhexan-1-ol

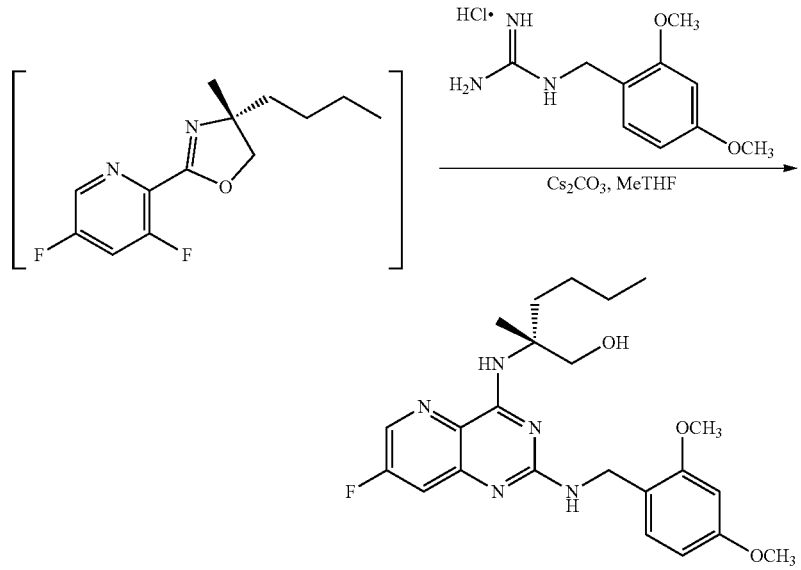

A reaction vessel was charged with 2,4-dimethyoxybenzyl guanidine hydrochloride (1.5 equiv) and cesium carbonate (4.0 equiv). A solution of (R)-4-butyl-2-(3,5-difluoropyridin-2-yl)-4-methyl-4,5-dihydrooxazole (1.0 equiv, scaling factor) in 2-methyltetrahydrofuran (7.5 volumes) was charged to the reactor. The reaction mixture was heated to about 80° C. Once the reaction was deemed complete the contents were cooled to about 35° C. and charged with water (10 volumes). The layers were separated, and the organics were washed sequentially with aqueous 5 wt % acetic acid (10 volumes) and water (10 volumes). The contents were concentrated to about 2 volumes. Isopropyl acetate (10 volumes) was charged and the contents were concentrated to about 5 volumes. The contents were adjusted to about 35° C. The resulting slurry was aged for about 1 hour at about 35° C., then cooled to about 20° C. over about 1.5 hours. The contents were aged at about 20° C. for about 1 hour. The contents were filtered and washed with a mixture of n-heptane and isopropyl acetate and dried to provide (R)-2-((2-((2,4-dimethoxybenzyl)amino)-7-fluoropyrido[3,2-d]pyrimidin-4-yl)amino)-2-methylhexan-1-ol. $^1$H NMR (400 MHz, CDCl$_3$): δ 8.12 (d, J=2.5 Hz, 1H), 7.32-7.29 (m, 2H), 7.10 (br s, 1H), 6.47 (d, J 2.53 Hz, 1H), 6.43 (dd, J 8.2, 2.4 Hz, 1H), 4.55 (s, 2H), 3.85 (s, 3H), 3.80 (s, 3H), 3.79-3.72 (m, 2H), 2.01-1.91 (m, 1H), 1.75 (dt, J 13.3, 6.8 Hz, 1H), 1.47-1.29 (m, 7H), 0.92 (t, J=7.0 Hz, 3H).

Example 20: Preparation of(R)-2-((2-(benzylamino)-7-fluoropyrido[3,2-d]pyrimidin-4-yl)amino)-2-methylhexan-1-ol

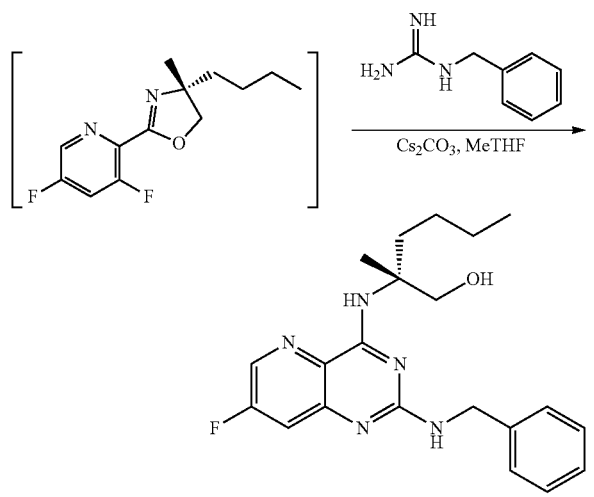

A reaction vessel was charged with 1-benzylguanidine (1.5 equiv) and cesium carbonate (2.0 equiv). A solution of 2,4-dimethyoxybenzyl guanidine hydrochloride (1.0 equiv, scaling factor) in 2-methyltetrahydrofuran (7.5 volumes) was charged to the reactor. The reaction mixture was heated to about 80° C. Once the reaction was deemed complete the contents were cooled to about 35° C., charged with water (10 volumes) and the contents were agitated. The phases were separated, and the organics were washed sequentially with aqueous 5 wt % acetic acid (10 volumes) and water (10 volumes). The contents were concentrated to about 2 volumes. Isopropyl acetate (10 volumes) was charged and the contents were concentrated to about 5 volumes. The contents were adjusted to about 35° C. The resulting slurry was aged for about 1 hour at about 35° C., then cooled to about 20° C. over about 1.5 hours. The contents were aged at about 20° C. for about 1 hour. The contents were filtered and washed with a mixture of n-heptane and isopropyl acetate and dried to provide (R)-2-((2-(benzylamino)-7-fluoropyrido[3,2-d]pyrimidin-4-yl)amino)-2-methylhexan-1-ol. $^1$H NMR (400 MHz, CDCl$_3$): δ 8.16 (d, J=2.5 Hz, 1H), 7.40-7.26 (m, 5H), 7.13 (br s, 1H), 4.70-4.60 (m, 2H), 3.80-3.72 (m, 2H), 1.98-1.86 (m, 1H), 1.78-1.66 (m, 1H), 1.48-1.19 (m, 7H), 0.91 (t, J 7.0 Hz, 3H).

Example 21: Preparation of(R)-2-((2-Amino-7-fluoropyrido[3,2-d]pyrimidin-4-yl)amino)-2-methylhexan-1-ol

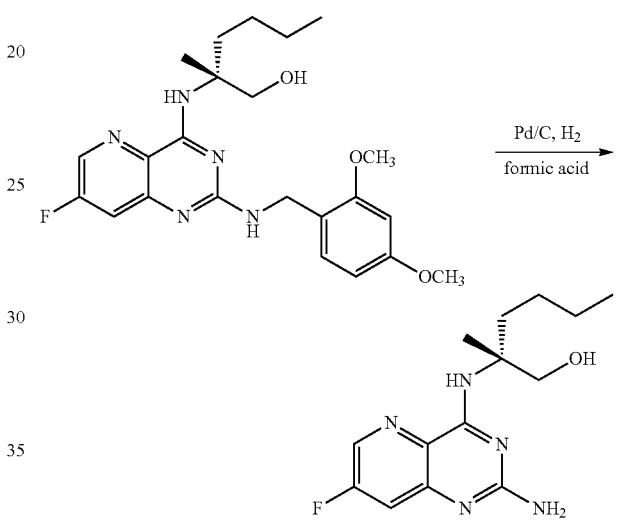

A pressure autoclave reaction vessel was charged with (R)-2-((2-((2,4-dimethoxybenzyl)amino)-7-fluoropyrido[3,2-d]pyrimidin-4-yl)amino)-2-methylhexan-1-ol (1.0 equiv, scaling factor), 10% dry palladium on carbon (0.125 g/g) and formic acid (5 volumes). The vessel was sealed and flushed with hydrogen three times. The hydrogen pressure was adjusted to about 85 psi and the contents were heated to about 85° C. and aged for about 18 hours. The contents were then cooled to about 20° C. and the vessel was vented and flushed three times with nitrogen. The reaction mixture was then filtered thought a pad of Celite (0.5 g/g) and the reaction vessel was rinsed with formic acid (1 volume). The filtrate was transferred to another reaction vessel. Water (5 volumes) and ethanol (2.5 volumes) were charged to the contents. The temperature was adjusted to about 20° C. and 50 wt % aqueous sodium hydroxide (14.5 volumes) was added slowly to maintain the internal temperature to about 35° C. The contents were aged for about 16 hours at about 20° C. The slurry was filtered, and the wet cake was washed with a mixture of ethanol and water and dried to provide (R)-2-(3-bromo-5-fluoropyridin-2-yl)-4-butyl-4-methyl-4,5-dihydrooxazole. $^1$H NMR (500 MHz, Methanol-d$_4$) δ 8.23 (d, J 2.5 Hz, 1H), 7.25 (dd, J=10.0, 2.5 Hz, 1H), 3.92 (d, J=11.5 Hz, 1H), 3.74 (d, J=11.5 Hz, 1H), 2.08-1.81 (m, 2H), 1.46 (s, 3H), 1.35-1.29 (m, 4H), 0.91 (t, J 7.0 Hz, 3H).

Example 22: Preparation of (R)-2-((2-((2,4-dimethoxybenzyl)amino)-7-fluoropyrido[3,2-d]pyrimidin-4-yl)amino)-2-methylhexan-1-ol

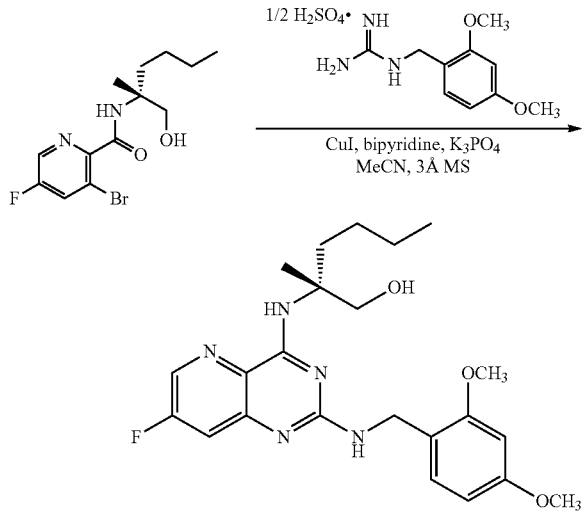

A reaction vessel was charged with (R)-3-bromo-5-fluoro-N-(1-hydroxy-2-methylhexan-2-yl)picolinamide (1.0 equiv, scaling factor), 3 Å molecular sieves (1 g/g) and acetonitrile (6.7 volumes). 1-(2,4-dimethoxybenzyl)guanidine hemisulfate salt (1.5 equiv), copper(I) iodide (0.10 equiv), 2,2'-bipyridine (0.20 equiv), potassium phosphate tribasic (3.5 equiv) and 3 Å molecular sieves (1 g/g) were then charged to the vessel. The mixture was heated to reflux for about 3 hours. The contents were cooled to about 20° C., charged with 2-methyltetrahydrofuran (5 volumes), followed by water (5 volumes). The phases were separated, the organics were concentrated, and the crude product was purified using silica gel chromatography to provide (R)-2-((2-((2,4-dimethoxybenzyl)amino)-7-fluoropyrido[3,2-d]pyrimidin-4-yl)amino)-2-methylhexan-1-ol. $^1$H NMR (400 MHz, CDCl$_3$): δ 8.12 (d, J=2.5 Hz, 1H), 7.32-7.29 (m, 2H), 7.10 (br s, 1H), 6.47 (d, J 2.53 Hz, 1H), 6.43 (dd, J 8.2, 2.4 Hz, 1H), 4.55 (s, 2H), 3.85 (s, 3H), 3.80 (s, 3H), 3.79-3.72 (m, 2H), 2.01-1.91 (m, 1H), 1.75 (dt, J 13.3, 6.8 Hz, 1H), 1.47-1.29 (m, 7H), 0.92 (t, J=7.0 Hz, 3H).

Example 23: Preparation of (R)-2-((2-amino-7-fluoropyrido[3,2-d]pyrimidin-4-yl)amino)-2-methylhexan-1-ol

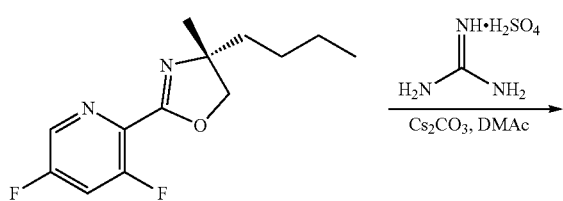

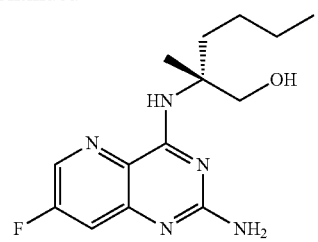

A reaction vessel was charged with guanidine sulfate (1.5 equiv), cesium carbonate (2.0 equiv). A solution of (R)-4-butyl-2-(3,5-difluoropyridin-2-yl)-4-methyl-4,5-dihydrooxazole (1.0 equiv, scaling factor) in dimethylacetamide (5 volumes) was charged to the reactor. The reaction mixture was heated to about 80° C. Once the reaction was deemed complete the contents were cooled to about 35° C., charged with water and 2-methyltetrahydrofruan. The phases were separated, the organics were concentrated, and the crude material was purified by silica gel chromatography to provide (R)-2-((2-amino-7-fluoropyrido[3,2-d]pyrimidin-4-yl)amino)-2-methylhexan-1-ol. $^1$H NMR (500 MHz, Methanol-d$_4$) δ 8.23 (d, J 2.5 Hz, 1H), 7.25 (dd, J=10.0, 2.5 Hz, 1H), 3.92 (d, J=11.5 Hz, 1H), 3.74 (d, J=11.5 Hz, 1H), 2.08-1.81 (m, 2H), 1.46 (s, 3H), 1.35-1.29 (m, 4H), 0.91 (t, J 7.0 Hz, 3H).

Example 24: Preparation of N-(4-(tert-butylamino)-7-fluoropyrido[3,2-d]pyrimidin-2-yl)acetamide

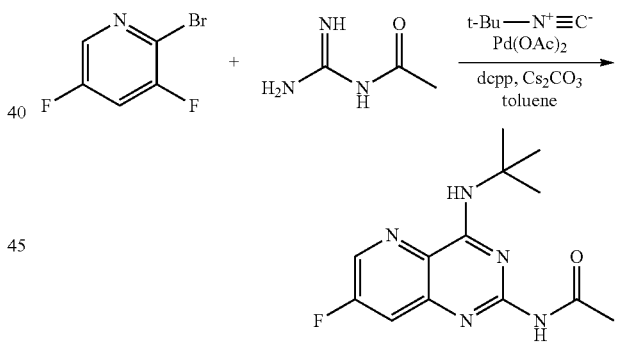

A reaction vessel was charged with palladium(II) acetate (0.10 equiv), followed by a solution of 1,3-bis(dicyclohexylphosphino)propane (0.2 equiv) in toluene (5 volumes). To the vessel was charged 2-bromo-3,5-difluoropyridine (1.0 equiv, scaling factor) and tert-butylisocyanide (1.1 equiv). Then N-acetyl guanidine (2.0 equiv) was charged to the reaction vessel, followed by cesium carbonate (2.6 equiv). The contents were heated to about 90° C. and aged for about 24 hours. The contents were cooled to about 20° C. and the contents were filtered through a plug of silica gel eluting with ethyl acetate. The crude product was concentrated and purified using silica gel chromatography to provide N-(4-(tert-butylamino)-7-fluoropyrido[3,2-d]pyrimidin-2-yl)acetamide. $^1$H NMR (400 MHz, CDCl$_3$): δ 8.32 (d, J=2.6, 1H), 7.92 (br s, 1H), 7.49 (dd, J=9.4, 2.6 Hz, 1H), 7.12 (br s, 1H), 2.58 (s, 3H), 1.53 (s, 9H).

Example 25: Preparation of (R)-2-((2-amino-7-fluoropyrido[3,2-d]pyrimidin-4-yl)amino)-2-methylhexan-1-ol

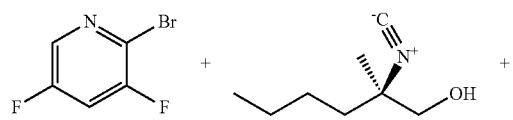

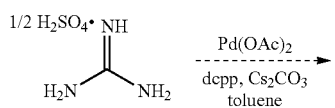

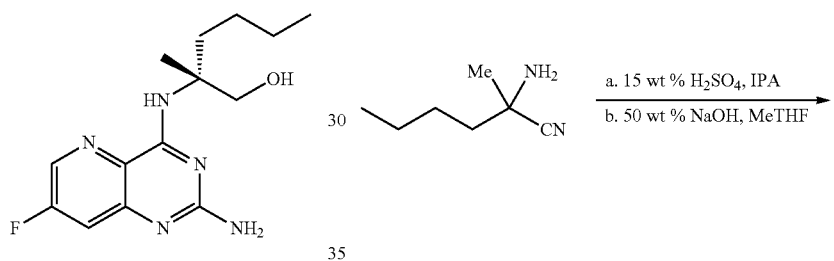

A reaction vessel is charged with palladium(II) acetate (0.10 equiv), followed by a solution of 1,3-bis(dicyclohexylphosphino)propane (0.2 equiv) in toluene (5 volumes). To the vessel is charged 2-bromo-3,5-difluoropyridine (1.0 equiv, scaling factor) and (R)-isocyano-2-methylhexan-1-ol (1.1 equiv). Then guanidine hemisulfate (2.0 equiv) is charged to the reaction vessel, followed by cesium carbonae (3.6 equiv). The contents are heated to about 90° C. and are agitated for about 24 hour. The contents are cooled to about 20° C. and the contents are filtered through a plug of silica gel eluting with ethyl acetate. The crude product is concentrated and purified using silica gel chromatography to provide (R)-2-((2-amino-7-fluoropyrido[3,2-d]pyrimidin-4-yl)amino)-2-methylhexan-1-ol.

Example 26: Preparation of Isopropyl 2-amino-2-methylhexanoate

Step 1: 2-Amino-2-methylhexanenitrile

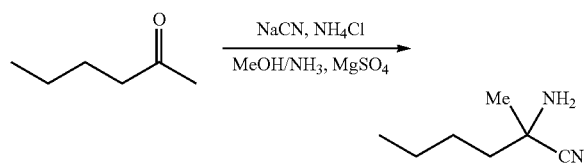

To a reaction vessel was charged sodium cyanide (1.0 equiv, scaling factor), magnesium sulfate (1.8 equiv), ammonium chloride (0.5 equiv) and ammonia in methanol (7 M, 3.0 equiv, 9 volumes). The contents were cooled to about 0° C. and 2-hexanone (1.1 equiv) was charged to the mixture. The contents were aged at this temperature for about 30 minutes. Then the contents were warmed to about 35° C. Once the internal temperature reached about 35° C., the contents were aged at this temperature for about 4 hours. The contents were then cooled to about 20° C., diluted with methyl tert-butyl ether (5 volumes) and the contents were concentrated. The residue was suspended in methyl tert-butyl ether (10 volumes) and concentrated once again. This process was repeated one more time. The contents were suspended in methyl tert-butyl ether (10 volumes) and filtered. The filter cake was washed with methyl tert-butyl ether (2 volumes) and the filtrate was concentrated to an oil. The oil was purified via vacuum distillation to afford 2-amino-2-methylhexanenitrile. $^1$H NMR (400 MHz, CDCl$_3$) δ 1.65-1.57 (m, 2H), 1.50-1.42 (m, 2H), 1.44 (s, 3H), 1.40-1.34 (m, 2H), 0.92 (t, J=7.2 Hz, 3H).

Step 2: Isopropyl 2-amino-2-methylhexanoate

To a reaction vessel was charged 2-amino-2-methylhexanenitrile (1.0 equiv, scaling factor) and 2-propanol (10 volumes). The contents were cooled to about 20° C. To this solution was charged 15 wt % aqueous sulfuric acid (10 equiv). The contents were heated to about 80° C. and aged at this temperature for about 36 hours. The contents were cooled to about 20° C. and 2-methyltetrahydrofuran (20 volumes) was charged. To the contents was charged 50 wt % aqueous sodium hydroxide (about 15 equiv) until the pH of the aqueous solution was basic. The aqueous layer was partitioned. The organic layer was washed twice with water (2 volumes) and the contents were distilled to provide isopropyl 2-amino-2-methylhexanoate as a solution in 2-methyltetrahydrofuran. $^1$H NMR (400 MHz, DMSO-d$_6$) δ 4.86 (hept, J=6.3 Hz, 1H), 1.68 (br s, 2H), 1.59-1.48 (m, 1H), 1.47-1.35 (m, 1H), 1.24-1.19 (m, 4H), 1.16 (d, J=6.3 Hz, 6H), 1.14 (s, 3H), 0.83 (t, J=7.1 Hz, 3H).

Example 27: Preparation of (R)-2-Amino-2-methylhexan-1-ol 4-methylbenzenesulfonate Step-1 and 2: (R)-2-Amino-2-methylhexanoic acid hydrochloride

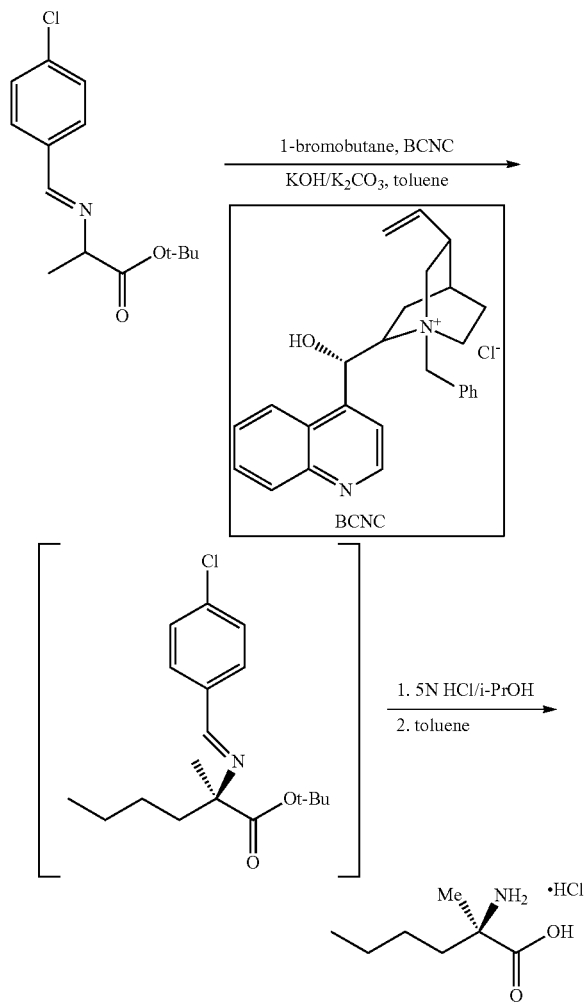

To reaction vessel was charged tert-butyl-2-(4-chlorobenzylidene)amino)propanoate (1.0 equiv, scaling factor) and toluene (10 volumes). To this solution was charged 1-bromobutane (1.33 equiv) and N-benzylcinchoninium chloride (0.10 equiv), followed by potassium hydroxide (2.4 equiv) and potassium carbonate (0.97 equiv). The mixture was aged at about 20° C. for about 17 hours. The organic solution was then washed twice with water (4 volumes×2) followed by saturated aqueous sodium chloride (4 volumes). The organic layer was concentrated. To this crude material was charged 2-propanol (12 volumes) and the contents were concentrated once again. To this mixture was charged 5 N hydrochloric acid in 2-propanol (3 volumes) and water (1.2 equiv). The contents were aged at about 60° C. for about 4 hours. The contents were concentrated to about 2 volumes. To this mixture was charged 2-propanol (1 volume) and methyl tert-butyl ether (1 volume) and the contents were slowly cooled to about 20° C. over about 4 hours. To this slurry was charged methyl tert-butyl ether (3 volumes) and the contents were aged at about 20° C. for about 18 hours. The slurry was filtered, and the wet cake was rinsed with a mixture of 2-propanol (1 volume) and methyl tert-butyl ether (2 volumes). The resulting solids were triturated with toluene (10 volumes). The slurry was filtered, and the wet cake was washed with toluene (10 volumes) and then dried to provide (R)-2-amino-2-methylhexanoic acid hydrochloride. $^1$H NMR (400 MHz, DMSO-d$_6$) δ 8.55 (br s, 3H), 2.50-1.74 (m, 2H), 1.43 (s, 3H), 1.41-1.14 (m, 5H), 0.83 (t, J=6.8 Hz, 3H).

Step-3: (R)-2-Amino-2-methylhexanoic acid hydrochloride

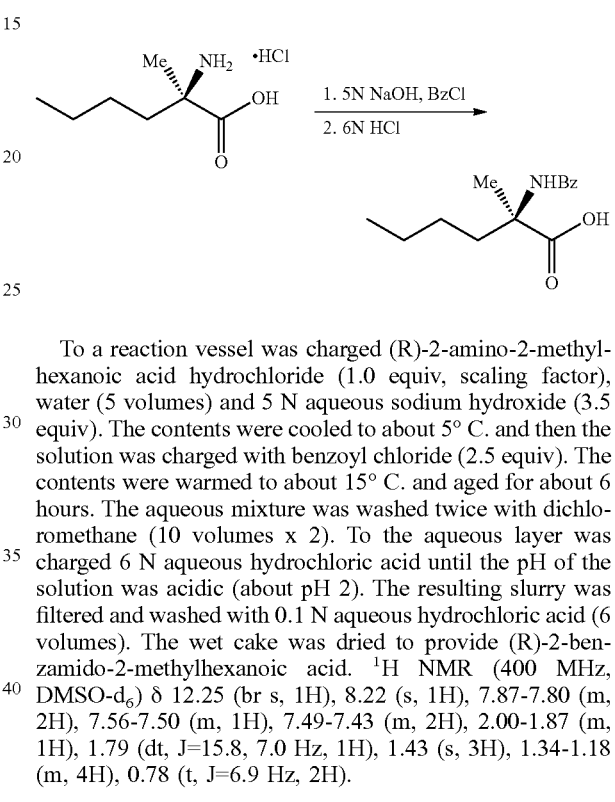

To a reaction vessel was charged (R)-2-amino-2-methylhexanoic acid hydrochloride (1.0 equiv, scaling factor), water (5 volumes) and 5 N aqueous sodium hydroxide (3.5 equiv). The contents were cooled to about 5° C. and then the solution was charged with benzoyl chloride (2.5 equiv). The contents were warmed to about 15° C. and aged for about 6 hours. The aqueous mixture was washed twice with dichloromethane (10 volumes x 2). To the aqueous layer was charged 6 N aqueous hydrochloric acid until the pH of the solution was acidic (about pH 2). The resulting slurry was filtered and washed with 0.1 N aqueous hydrochloric acid (6 volumes). The wet cake was dried to provide (R)-2-benzamido-2-methylhexanoic acid. $^1$H NMR (400 MHz, DMSO-d$_6$) δ 12.25 (br s, 1H), 8.22 (s, 1H), 7.87-7.80 (m, 2H), 7.56-7.50 (m, 1H), 7.49-7.43 (m, 2H), 2.00-1.87 (m, 1H), 1.79 (dt, J=15.8, 7.0 Hz, 1H), 1.43 (s, 3H), 1.34-1.18 (m, 4H), 0.78 (t, J=6.9 Hz, 2H).

Step-4: (R)-2-Amino-2-methylhexan-1-ol 4-methylbenzenesulfonate

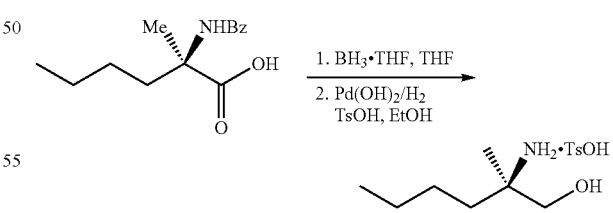

To a reaction vessel was charged (R)-2-benzamido-2-methylhexanoic acid (1.0 equiv, scaling factor) and tetrahydrofuran (5 volumes), and then the contents were cooled to about 0° C. Once at this temperature 1 M borane tetrahydrofuran complex in tetrahydrofuran (5 equiv) was charged over about 5 minutes. The contents were warmed to about 25° C. and aged at this temperature for 10 minutes. Then the contents were heated to about 50° C. and aged at this temperature for about 21 hours. The contents were cooled to about 20° C. and methanol (5 volumes) was charged. The contents were heated to about 100° C. and the contents were concentrated to about 8 volumes. This process of co-evaporation with methanol was repeated two more times. The contents were set to reflux and 1 M aqueous sodium hydroxide (12 volumes) was charged. The contents were refluxed for about 4 hours. Then the contents were cooled to about 20° C. and methyl tert-butyl ether (15 volumes) was charged. The layers were separated, and the organic layer was washed with 5 wt % aqueous sodium chloride (15 volumes). The layers were separated, and the organic layer was concentrated to provide the crude benzylamine intermediate, which was used in the next step without further purification.

To the crude benzylamine intermediate was charged ethanol (10 volumes) and 4-methylbenzenesulfonic acid (1.50 equiv), followed by palladium hydroxide (20% w/w on carbon, 0.7% w/w relative to (R)-2-benzamido-2-methylhexanoic acid). The reaction vessel was purged with nitrogen and charged with hydrogen. The reaction mixture was heated to about 75° C. and aged for about 48 hours. When the reaction was deemed complete, the reaction mixture was filtered, and the filter cake was washed with ethanol. The filtrate was concentrated to about 1 volume. Methyl tert-butyl ether (15 volumes) was charged and the contents were heated to about 60° C. for about 2 hours, then cooled to about 0° C. over about 3 hours. The slurry was filtered, and the solids were washed with methyl tert-butyl ether (6 volumes) and dried to provide (R)-2-amino-2-methylhexan-1-ol 4-methylbenzenesulfonate. $^1$H NMR (400 MHz, DMSO-$d_6$) δ 7.66 (br s, 3H), 7.49 (d, J=8.1 Hz, 2H), 7.12 (d, J=7.4 Hz, 2H), 5.43 (t, J=4.9 Hz, 1H), 3.38 (dd, J=11.2, 4.6 Hz, 1H), 3.33 (dd, J=11.2, 4.8 Hz, 1H), 2.29 (s, 3H), 1.57-1.40 (m, 2H), 1.28-1.19 (m, 4H), 1.10 (s, 3H), 0.87 (t, J=6.8 Hz, 3H).

Example 28: Preparation of (R)-2-Amino-2-methylhexan-1-ol 4-methylbenzenesulfonate

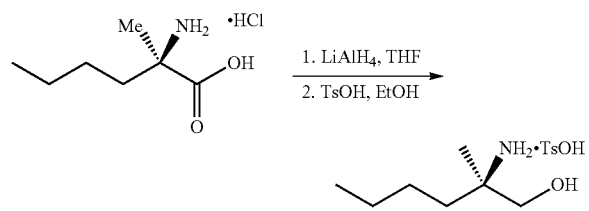

To a reaction vessel was charged (R)-2-amino-2-methylhexanoic acid hydrochloride (1.0 equiv, scaling factor) and tetrahydrofuran (7 volumes). The contents were cooled to about 0° C. and lithium aluminum hydride (4 equiv) was charged. The contents were heated to about 60° C. and aged at this temperature for about 3 hours. After this amount of time, the contents were cooled to about 0° C. and water (5 volumes) was charged. The contents were aged at this temperature for 30 minutes and warmed to about 20° C. To the contents was charged 15 wt % aqueous sodium hydroxide (3 volumes) and the contents were aged for an additional 30 minutes. The aqueous layer was extracted with dichloromethane (10 volumes). This was repeated three more times. The combined organic layers were concentrated to dryness. The crude (R)-2-amino-2-methylhexan-1-ol 4-methylbenzenesulfonate was diluted in ethanol (10 volumes) and filtered into another reaction vessel. To this filtrate was charged 4-methylbenzenesulfonic acid (1 equiv) and the contents were aged at about 25° C. for about 30 minutes. The contents were concentrated to dryness and co-evaporated with methyl tert-butyl ether (10 volumes). This process was repeated one more time. The resulting solids were filtered, and the solids were washed with methyl tert-butyl ether (2 volumes) and dried to provide (R)-2-amino-2-methylhexan-1-ol 4-methylbenzenesulfonate. $^1$H NMR (400 MHz, DMSO-$d_6$) δ 7.66 (br s, 3H), 7.49 (d, J=8.1 Hz, 2H), 7.12 (d, J=7.4 Hz, 2H), 5.43 (t, J=4.9 Hz, 1H), 3.38 (dd, J=11.2, 4.6 Hz, 1H), 3.33 (dd, J=11.2, 4.8 Hz, 1H), 2.29 (s, 3H), 1.57-1.40 (m, 2H), 1.28-1.19 (m, 4H), 1.10 (s, 3H), 0.87 (t, J=6.8 Hz, 3H).

Example 29: Preparation of (R)-2-amino-2-methylhexanoic acid hydrochloride

Step-1: (2S,4R)-3-Benzoyl-4-butyl-4-methyl-2-phenyloxazolidin-5-one

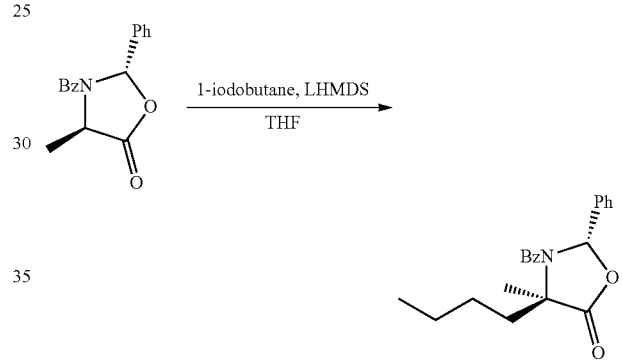

To a reaction vessel was charged (2S,4R)-3-benzoyl-4-methyl-2-phenyloxazolidin-5-one (1.0 equiv, scaling factor) and tetrahydrofuran (8 volumes), followed by hexamethylphosphoramide (4 volumes). The contents were then cooled to −78° C. To this solution was charged a 1 M solution of lithium bis(trimethylsilyl)amide in tetrahydrofuran (1.1 equiv) and the contents were aged at this temperature for about 15 minutes. Then 1-iodobutane (1.5 equiv) was charged as a solution in tetrahydrofuran (2 volumes). The contents were aged at about −78° C. for about 3 hours. The contents were then warmed to about 25° C. and aged at this temperature for about 21 hours. After this amount of time, the contents were quenched with saturated aqueous ammonium chloride (5 volumes). The contents were concentrated to remove tetrahydrofuran, dichloromethane (10 volumes) was charged, and the aqueous layer was extracted. This process was repeated two more times. The combined organic extracts were combined and concentrated to dryness. The crude product was purified by column chromatography using ethyl acetate and hexanes to provide (2S,4R)-3-benzoyl-4-butyl-4-methyl-2-phenyloxazolidin-5-one. $^1$H NMR (400 MHz, CDCl$_3$) δ 7.56-6.88 (m, 10H), 6.74 (s, 1H), 1.97-1.75 (m, 2H), 1.43 (s, 3H), 1.32-1.18 (m, 5H), 0.78 (t, J=6.8 Hz, 2H).

Step-2: (R)-2-amino-2-methylhexanoic acid hydrochloride

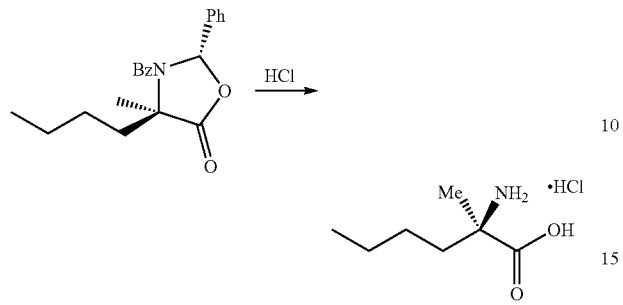

To a reaction vessel was charged (2S,4R)-3-benzoyl-4-butyl-4-methyl-2-phenyloxazolidin-5-one (1.0 equiv, scaling factor) followed by concentrated hydrochloric acid (7 volumes). The contents were heated to about 90° C. and aged at this temperature for about 4 hours. The contents were cooled to about 20° C. and diluted with water (10 volumes). The solvent was exchanged for toluene under vacuum (targeting approximately 1 volume). Then the contents were suspended using 2-propanol (1 volume) and methyl tert-butyl ether (2 volumes) and filtered. The resulting solids were triturated with toluene (10 volumes). The slurry was filtered, and the wet cake was washed with toluene (10 volumes) and dried to provide (R)-2-amino-2-methyl-hexanoic acid hydrochloride. $^1$H NMR (400 MHz, DMSO-$d_6$) δ 8.55 (br s, 3H), 2.50-1.74 (m, 2H), 1.43 (s, 3H), 1.41-1.14 (m, 5H), 0.83 (t, J=6.8 Hz, 3H).

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

Where a conflict exists between the instant application and a reference provided herein, the instant application shall dominate.

What is claimed is:

1. A method for preparing a compound of Formula I:

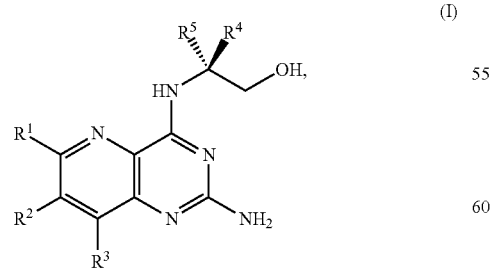

or a salt thereof, comprising:
a) forming a first reaction mixture comprising a compound of Formula III:

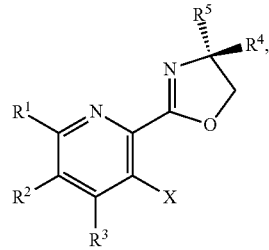

a compound having the Formula PG-NHC(=NH)NH$_2$ or a salt thereof, a first base, and a first solvent to form a compound of Formula II:

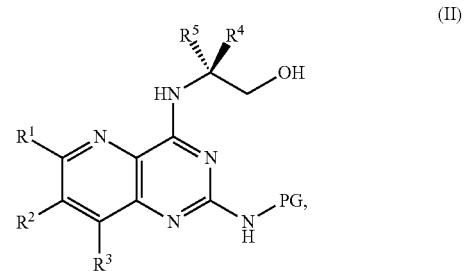

or a salt thereof; and b) forming a second reaction mixture comprising the compound of Formula II or the salt thereof, a deprotecting agent, and a second solvent to provide the compound of Formula I or the salt thereof, wherein R$^1$, R$^2$, and R$^3$ are each independently hydrogen, F, Cl, CN, CF$_3$, C$_{1-3}$ alkyl, or C$_{1-3}$ alkoxy;

R$^4$ is hydrogen or methyl;

R$^5$ is C$_{3-6}$ alkyl;

X is F, Cl, Br, I, or OTs; and

PG is an amino protecting group.

2. The method of claim 1, comprising
a) forming the first reaction mixture comprising the compound of Formula III:

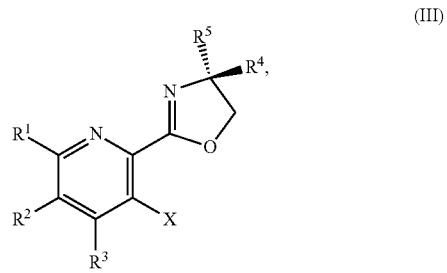

a compound having the Formula PG-NHC(=NH)NH$_2$ or the salt thereof, a first transition-metal catalyst, the first base, and the first solvent to form the compound of Formula II:

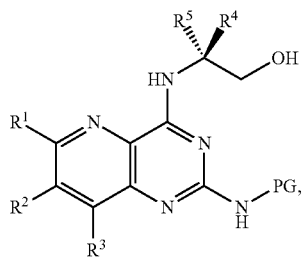

(II)

or the salt thereof; and b) forming the second reaction mixture comprising the compound of Formula II or the salt thereof, the deprotecting agent, and the second solvent to provide the compound of Formula I or the salt thereof, wherein $R^1$, $R^2$, and $R^3$ are each independently hydrogen, F, Cl, CN, $CF_3$, $C_{1-3}$ alkyl, or $C_{1-3}$ alkoxy;

$R^4$ is hydrogen or methyl;

$R^5$ is $C_{3-6}$ alkyl;

X is Cl, Br, I, or OTs; and

PG is an amino protecting group.

3. The method of claim 1, wherein the salt of the compound having the Formula PG-NHC(=NH)NH$_2$ is a hemisulfate, a sulfate, a chloride, a bromide, a carbonate, a nitrate, or an acetate salt.

4. The method of claim 1, wherein PG is 2,4-dimethoxybenzyl.

5. The method of claim 2, wherein the first transition-metal catalyst comprises a copper metal, a copper oxide, a copper (I) salt, a copper (II) salt, or combinations thereof.

6. The method of claim 2, wherein the first transition-metal catalyst is Cu(I) iodide, Cu(I) bromide, Cu(I) chloride, Cu(I) acetate, Cu(I) carbonate, Cu(I) nitrate, Cu(I) sulfate, Cu(I) phosphate, Cu(I) 3-methylsalicylate, Cu(I) thiophene-2-carboxylate, Cu(I) oxide, Cu(II) iodide, Cu(II) bromide, Cu(II) chloride, Cu(II) acetate, Cu(II) carbonate, Cu(II) nitrate, Cu(II) sulfate, Cu(II) pyrophosphate, Cu(II) phosphate, Cu(II) tartrate, Cu(II) oxide, or combinations thereof.

7. The method of claim 2, wherein the first transition-metal catalyst comprises Cu(II) acetate.

8. The method of claim 1, wherein the first base is lithium carbonate, sodium carbonate, potassium carbonate, cesium carbonate, lithium bicarbonate, sodium bicarbonate, potassium bicarbonate, sodium phosphate tribasic, potassium phosphate tribasic, potassium acetate, potassium trimethylacetate, tetrabutylphosphonium malonate, 1,8-diazabicyclo[5.4.0]undec-7-ene, 1,5-diazabicyclo[4.3.0]non-5-en, or combinations thereof.

9. The method of claim 2, wherein the first base comprises potassium phosphate tribasic.

10. The method of claim 1, wherein the first reaction mixture further comprises a first ligand.

11. The method of claim 10, wherein the first ligand is an amino acid, a polypyridyl ligand, or a tertiary amine.

12. The method of claim 10, wherein the first ligand is arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, α-(methylamino)isobutyric acid, (4-methyl-1-piperazinyl)acetic acid, N-acetyl-cysteine, 2,2'-bipyridine, 1,10-phenanthroline, 4,4'-dimethyl-2,2'-bipyridine, 6,6'-dimethyl-2,2'-bipyridine, 4,4'-di-tert-butyl-2,2-bipyridine, 2,2'-bipyridine-4, 4'-dicarboxylic acid, N,N,N',N'-tetramethylethylenediamine, or combinations thereof.

13. The method of claim 10, wherein the first ligand comprises cysteine.

14. The method of claim 1, wherein the deprotecting agent is an acid.

15. The method of claim 14, wherein the acid is trifluoroacetic acid, trichloroacetic acid, acetic acid, formic acid, hydrochloric acid, sulfuric acid, phosphoric acid, or combinations thereof.

16. The method of claim 14, wherein the acid comprises trifluoroacetic acid.

17. The method of claim 1, wherein the deprotecting agent is a hydrogen source and the second reaction mixture further comprises a second transition-metal catalyst.

18. The method of claim 17, wherein the hydrogen source is ammonium formate, formic acid, hydrogen gas, or combinations thereof.

19. The method of claim 17, wherein the second transition-metal catalyst is palladium hydroxide on carbon, palladium on carbon, or platinum oxide.

20. The method of claim 1, wherein the deprotecting agent is boron tribromide, 2,3-dichloro-5,6-dicyano-1,4-benzoquinone, eerie ammonium nitrate, or a combination of trifluoromethanesulfonic acid and 1,3-dimethoxybenzene.

21. The method of claim 1, further comprising prior to step a):

a1) forming a third reaction mixture comprising a compound of Formula IV:

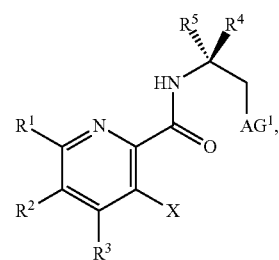

(IV)

or a salt thereof, a second base, and a third solvent to form the compound of Formula III, or the salt thereof, wherein $AG^1$ is Cl, Br, $OSO_3H$, $OSO_3^-$, OMs, OTs, or OTf.

22. The method of claim 21, further comprising prior to step a1):

a2) forming a fourth reaction mixture comprising a compound of Formula V:

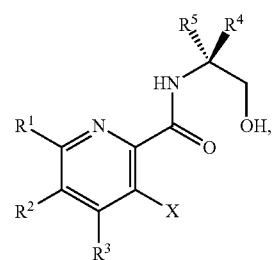

(V)

or a salt thereof, a first activating agent, and a fourth solvent to form the compound of Formula IV:

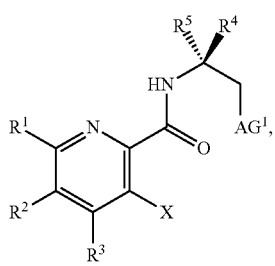

or the salt thereof.

23. The method of claim 1, further comprising prior to step a):

a1-2) forming a fifth reaction mixture comprising a compound of Formula V:

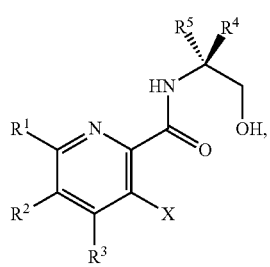

or a salt thereof, one or more cyclizing agents, and a fifth solvent to form the compound of Formula III or the salt thereof.

24. The method of claim 22, further comprising prior to step a2) or a1-2):

a3) forming a sixth reaction mixture comprising a compound of Formula VII:

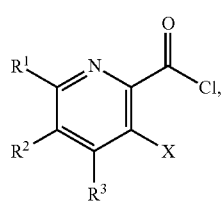

or a salt thereof, a compound of Formula VI:

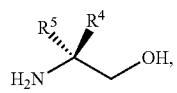

or a salt thereof, a third base, and a sixth solvent to form the compound of Formula V or the salt thereof.

25. The method of claim 24, further comprising prior to step a3):

a4) forming a seventh reaction mixture comprising a compound of Formula VIII:

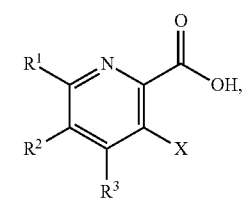

or a salt thereof, a second chlorinating agent, a promoter, and a seventh solvent to form the compound of Formula VII or the salt thereof.

26. The method of claim 22, further comprising prior to step a2) or a1-2):

a3-1) forming an eighth reaction mixture comprising a compound of Formula VIII:

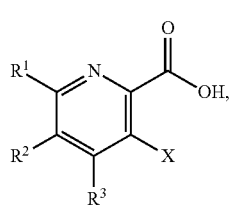

or a salt thereof, a compound of Formula VI:

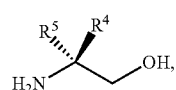

or a salt thereof, a second activating agent, a fourth base, and an eighth solvent to form the compound of Formula V or the salt thereof.

27. The method of claim 1, further comprising:

c) forming a ninth reaction mixture comprising the salt of the compound of Formula I, a fifth base, and a ninth solvent to provide the compound of Formula I in a neutral form.

28. The method of claim 1, wherein the compound of Formula I is of Formula Ia:

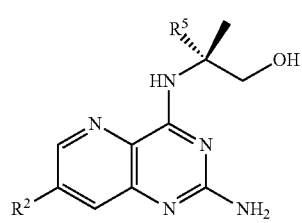

or a salt thereof.

29. The method of claim 1, wherein the compound of Formula I is of Formula Ib:

(Ib)

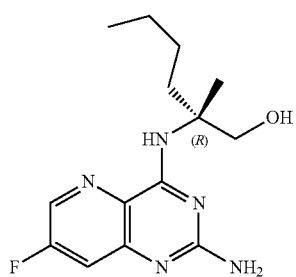

or a salt thereof.

30. A method for preparing a compound of Formula Ib:

(Ib)

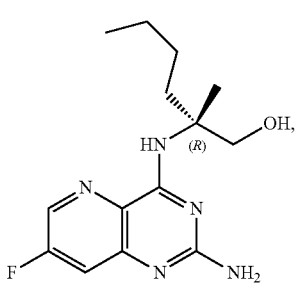

or a salt thereof, comprising:

a4) forming a seventh reaction mixture comprising a compound of Formula VIIIb:

(VIIIb)

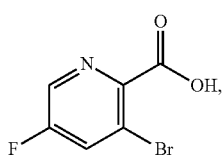

or a salt thereof, oxalyl chloride, N,N-dimethylformamide, 2-methyltetrahydrofuran to form a compound of Formula VIIb:

(VIIb)

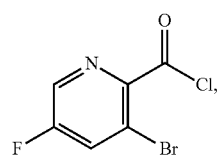

or a salt thereof;

a3) forming a sixth reaction mixture comprising the compound of Formula VIIb or the salt thereof, a compound of Formula VIb:

(VIb)

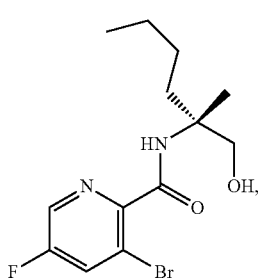

aqueous potassium carbonate, 2-methyltetrahydrofuran, and water to form a compound of Formula Vb:

(Vb)

or a salt thereof;

a2) forming a fourth reaction mixture comprising the compound of Formula Vb or the salt thereof, thionyl chloride, and 2-methyltetrahydrofuran to form a compound of Formula IVb:

(IVb-1)

or a salt thereof;

a1) forming a third reaction mixture comprising the compound of Formula IVb-1 or the salt thereof, aqueous sodium hydroxide, tetra-n-butylammonium hydrogensulfate, and 2-methyltetrahydrofuran to form a compound of Formula IIIb:

(IIIb)

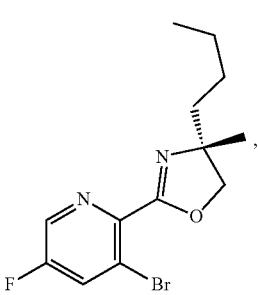

or a salt thereof;

a) forming a first reaction mixture comprising the compound of Formula IIIb or the salt thereof, a compound of Formula IXa wherein n is from 0 to 1:

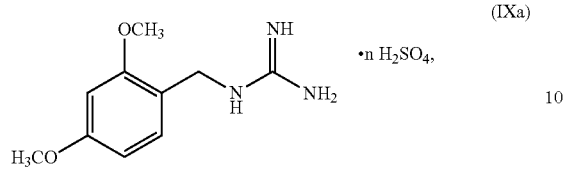

Cu(II) acetate, potassium phosphate tribasic, cysteine, 2-methyltetrahydrofuran, and acetonitrile to form a compound of Formula IIb:

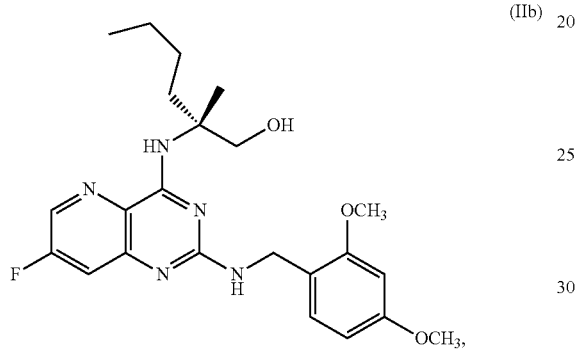

or a salt thereof;

b) forming a second reaction mixture comprising the compound of Formula IIb or the salt thereof, trifluoroacetic acid, and dichloromethane to prepare a trifluoroacetic acid salt of the compound of Formula Ib:

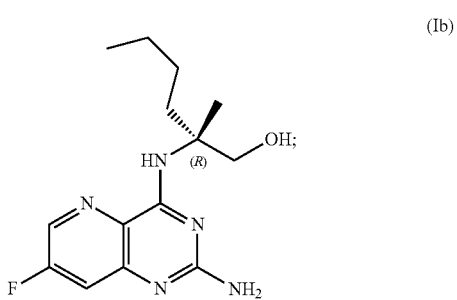

and c) forming a ninth reaction mixture comprising the trifluoroacetic acid salt of the compound of Formula Ib, sodium hydroxide, ethanol, and water to provide the compound of Formula Ib in a neutral form.

* * * * *